(12) United States Patent
Lehr et al.

(10) Patent No.: US 8,686,000 B2
(45) Date of Patent: Apr. 1, 2014

(54) HERBICIDALLY ACTIVE KETOSULTAMS AND DIKETOPYRIDINES

(75) Inventors: Stefan Lehr, Liederbach (DE); Christian Waldraff, Bad Vilbel (DE); Elmar Gatzweiler, Büdingen (DE); Isolde Häuser-Hahn, Leverkusen (DE); Ines Heinemann, Hofheim (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 99 days.

(21) Appl. No.: 13/223,275

(22) Filed: Aug. 31, 2011

(65) Prior Publication Data
US 2012/0058893 A1 Mar. 8, 2012

(30) Foreign Application Priority Data
Sep. 1, 2010 (EP) .................................... 10174905

(51) Int. Cl.
*A61K 31/4365* (2006.01)

(52) U.S. Cl.
USPC ........................................... 514/301; 546/114

(58) Field of Classification Search
USPC ........................................................ 546/114
See application file for complete search history.

(56) References Cited

FOREIGN PATENT DOCUMENTS

| CA | 2 741 138 | 5/2010 |
|---|---|---|
| EP | 1 754 483 | 2/2007 |
| WO | 2004/041813 | 5/2004 |
| WO | 2006/122200 | 11/2006 |
| WO | 2007/089634 | 8/2007 |
| WO | 2008/009908 | 1/2008 |
| WO | 2008/071918 | 6/2008 |
| WO | 2009/063180 | 5/2009 |
| WO | 2009/090401 | 7/2009 |
| WO | 2009/124636 | 10/2009 |
| WO | 2009/135580 | 11/2009 |
| WO | 2010/049269 | 5/2010 |
| WO | 2011/051212 | 5/2011 |

OTHER PUBLICATIONS

International Search Report Based on PCT/EP2011/064825 Mailed Nov. 14, 2011.
Schmidt et al., "Heilmittelchemische Studien in Der Heterocyclischen Reihe," Helvectica Chimica Acta, 45, 5, Jan. 1, 1962, pp. 1620-1627, XP000561887.
Rivkin et al., "Solvent-Free Microwave Synthesis of 4-Hydroxy-3-Phenylquinolin-2(1H)-Ones and Variants Using Activated Arylmalonates," Tetrahedron Letters, 47 (2006) pp. 2395-2398, XP 025003847.
Zhao et al., "Discovery and Sar Development of Thienopyridones: A Class of Small Molecule AMPK Activators," Bioorganic & Medical Chemistry Letters, 17 (2007) pp. 3254-3257.
Buchstaller et al., "Synthesis of Thieno[2,3-b]Pyridinones Acting as Cytoprotectants and as Inhibitors of [3H]Glycine Binding to the N-Methyl-D-Aspartate (NMDA) Receptor," Journal of Medicinal Chemistry, 2006, 49, 864-871, XP002616572.

*Primary Examiner* — Brian McDowell
(74) *Attorney, Agent, or Firm* — Miles & Stockbridge, P.C.

(57) ABSTRACT

Ketosultams and diketopyridines of the formula (I) and use thereof as herbicides are described.

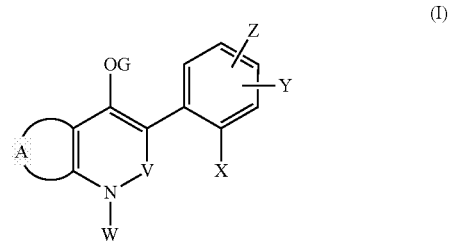

In this formula (I), G, X, Y and Z are each radicals such as hydrogen and organic radicals such as alkyl. W represents organic radicals such as alkyl. A represents a heterocycle.

7 Claims, No Drawings

HERBICIDALLY ACTIVE KETOSULTAMS AND DIKETOPYRIDINES

CROSS REFERENCE TO RELATED APPLICATIONS

This application claims priority to European Application 10174905.9 filed Sep. 1, 2010, the content of which is incorporated by reference in its entirety.

BACKGROUND

1. Field of the Invention

The invention relates to the technical field of the herbicides, especially to that of the herbicides for selective control of broad-leaved and gramineous weeds in crops of useful plants.

It especially relates to aryl-substituted ketosultam and diketopyridine derivatives, to processes for preparation thereof and to the use thereof as herbicides.

2. Description of Related Art

Various documents describe herbicidally active diketopyridines which form a fused ring system with 6-membered carbo- or heterocyclic rings. WO2008/009908 A1 and WO2008/071918 A1 describe diketopyridines with fused pyrazine. WO2009/090401 A1 and WO2010/049269 A1 mention diketopyridines fused to a pyridine ring. WO2009/063180 describes ketosultams fused to pyrazine rings.

However, the compounds known from these documents frequently exhibit inadequate herbicidal efficacy. It is therefore an object of the present invention to provide alternative herbicidally active compounds.

SUMMARY

It has been found that ketosultams and diketopyridines which have a fused-on saturated or unsaturated heterocyclic five-membered ring are particularly suitable as herbicides.

The present invention provides ketosultams and diketopyridines of the formula (I) or salts thereof i.

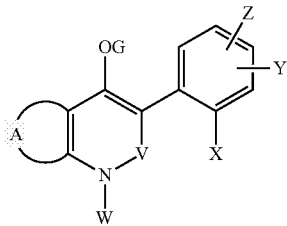

(I)

in which

A is a fused-on saturated or unsaturated five-membered heterocycle substituted by m radicals from the group consisting of $R^{10}$, $R^{11}$, $R^{12}$, $R^{13}$ and $R^{14}$;
V is $C(=O)$ or $S(O)_2$;
m is 0, 1 or 2;
n is 0, 1, 2 or 3;
G is hydrogen, $C(=O)R^1$, $C(=L)MR^2$, $SO_2R^3$, $P(=L)R^4R^5$, $C(=L)NR^6R^7$, E or $R^8$;
E is a metal ion equivalent or an ammonium ion;
L is oxygen or sulfur;
M is oxygen or sulfur;

$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl each substituted by n halogen atoms, a fully saturated 3- to 6-membered ring consisting of 3 to 5 carbon atoms and 1 to 3 heteroatoms from the group of oxygen, sulfur and nitrogen and substituted by n radicals from the group consisting of halogen, $(C_1-C_4)$-alkyl and $(C_1-C_4)$-alkoxy, $(C_3-C_6)$-cycloalkyl, phenyl, phenyl-$(C_1-C_4)$-alkyl, phenoxy-$(C_1-C_4)$-alkyl or heteroaryloxy-$(C_1-C_4)$-alkyl substituted by n radicals from the group consisting of halogen, $(C_1-C_4)$-alkyl and $(C_1-C_4)$-alkoxy;

$R^2$ is $(C_1-C_6)$-alkyl, $(C_2-C_6)$-alkenyl, $(C_1-C_4)$-alkoxy-$(C_1-C_6)$-alkyl or di-$(C_1-C_4)$-alkoxy-$(C_1-C_6)$-alkyl each substituted by n halogen atoms, or $(C_3-C_6)$-cycloalkyl, phenyl or benzyl substituted by n radicals in each case from the group consisting of halogen, $(C_1-C_4)$-alkyl and $(C_1-C_4)$-alkoxy;

$R^3$, $R^4$ and $R^5$ are each independently $(C_1-C_6)$-alkyl, $(C_1-C_4)$-alkoxy, $N-(C_1-C_6)$-alkylamino, $N,N$-di-$(C_1-C_6)$-alkylamino, $(C_1-C_4)$-alkylthio, $(C_2-C_4)$-alkenyl or $(C_3-C_6)$-cycloalkylthio each substituted by n halogen atoms, or phenyl, benzyl, phenoxy or phenylthio substituted by n radicals from the group consisting of halogen, $(C_1-C_4)$-alkyl and $(C_1-C_4)$-alkoxy;

$R^6$ and $R^7$ are each independently hydrogen, $(C_1-C_6)$-alkyl, $(C_3-C_6)$-cycloalkyl, $(C_2-C_6)$-alkenyl, $(C_1-C_6)$-alkoxy or $(C_1-C_4)$-alkoxy-$(C_1-C_6)$-alkyl substituted by n halogen atoms, phenyl or benzyl substituted by in each case n radicals from the group consisting of halogen, $(C_1-C_4)$-alkyl and $(C_1-C_4)$-alkoxy, or $R^6$ and $R^7$ form, together with the nitrogen atom to which they are bonded, a 3- to 6-membered ring containing 2 to 5 carbon atoms and 0 or 1 oxygen or sulfur atom;

$R^8$ is $(C_1-C_6)$-alkyl, $(C_2-C_6)$-alkenyl, $(C_2-C_6)$-alkynyl, $(C_1-C_4)$-alkoxy-$(C_1-C_6)$-alkyl, $(C_1-C_4)$-alkylthio-$(C_1-C_4)$-alkyl or di-$(C_1-C_4)$-alkoxy-$(C_1-C_6)$-alkyl substituted by n halogen atoms, $(C_3-C_6)$-cycloalkyl substituted by n radicals from the group consisting of halogen, $(C_1-C_4)$-alkyl and $(C_1-C_4)$-alkoxy, a fully saturated 3- to 6-membered ring consisting of 3 to 5 carbon atoms and 1 to 3 heteroatoms from the group of oxygen, sulfur and nitrogen and substituted by n radicals from the group consisting of halogen, $(C_1-C_4)$-alkyl and $(C_1-C_4)$-alkoxy, phenyl, phenyl-$(C_1-C_4)$-alkyl, heteroaryl, phenoxy-$(C_1-C_4)$-alkyl or heteroaryl-oxy-$(C_1-C_4)$-alkyl substituted by n radicals from the group consisting of halogen, $(C_1-C_4)$-alkyl and $(C_1-C_4)$-alkoxy;

$R^{10}$ is hydrogen, or $(C_1-C_6)$-alkyl, $(C_1-C_4)$-alkoxy, $(C_1-C_4)$-alkylthio, $(C_1-C_4)$-alkylsulfinyl or $(C_1-C_4)$-alkylsulfonyl substituted by n halogen atoms;

$R^{11}$, $R^{12}$ and $R^{13}$ are each independently hydrogen, halogen, or $(C_1-C_6)$-alkyl, $(C_2-C_6)$-alkenyl, $(C_2-C_6)$-alkynyl, $(C_1-C_4)$-alkoxy-$(C_1-C_6)$-alkyl, $(C_1-C_4)$-alkylthio-$(C_1-C_4)$-alkyl, di-$(C_1-C_4)$-alkoxy-$(C_1-C_6)$-alkyl, $(C_1-C_4)$-alkylthio, $(C_1-C_4)$-alkylsulfinyl or $(C_1-C_4)$-alkylsulfonyl substituted by n halogen atoms, or $(C_3-C_6)$-cycloalkyl substituted by n radicals from the group consisting of halogen, $(C_1-C_4)$-alkyl and $(C_1-C_4)$-alkoxy;

$R^{14}$ is hydrogen, or $(C_1-C_6)$-alkyl, $(C_2-C_6)$-alkenyl, $(C_2-C_6)$-alkynyl, $(C_1-C_4)$-alkoxy-$(C_1-C_6)$-alkyl, $(C_1-C_4)$-alkylthio-$(C_1-C_4)$-alkyl or di-$(C_1-C_4)$-alkoxy-$(C_1-C_6)$-alkyl substituted by n halogen atoms, or $(C_1-C_6)$-alkylcarbonyl, $(C_1-C_6)$-alkoxycarbonyl, $(C_1-C_6)$-alkylsulfonyl, or $(C_3-C_6)$-cycloalkyl, $(C_3-C_6)$-cycloalkylcarbonyl, $(C_3-C_6)$-cycloalkoxycarbonyl, $(C_3-C_6)$-cycloalkylsulfonyl substituted by n radicals from the group consisting of halogen, $(C_1-C_4)$-alkyl and $(C_1-C_4)$-alkoxy;

W is $(C_1-C_6)$-alkyl, $(C_2-C_6)$-alkenyl, $(C_3-C_6)$-alkynyl, $(C_3-C_6)$-cycloalkyl, $(C_1-C_4)$-alkoxy-$(C_1-C_6)$-alkyl, di-$(C_1-C_4)$-alkoxy-$(C_1-C_6)$-alkyl, $(C_1-C_4)$-alkylthio-$(C_1-C_6)$-alkyl, $(C_1-C_4)$-alkylsulfinyl-$(C_1-C_6)$-alkyl, $(C_1-C_4)$-alkylsulfonyl-$(C_1-C_6)$-alkyl or $(C_3-C_6)$-cycloalkyl-$(C_1-C_6)$-alkyl each substituted by n halogen atoms, and X, Y and Z are each independently hydrogen, $(C_1-C_6)$-alkyl, $(C_3-C_6)$-cycloalkyl, halogen, cyano, nitro, halo-$(C_1-C_6)$-alkyl, halo-$(C_1-C_6)$-alkoxy, $(C_3-C_6)$-cycloalkyl, $(C_1-C_6)$-alkoxy, $(C_1-C_6)$-alkoxy-$(C_1-C_6)$-alkyl, halo-$(C_1-C_6)$-alkoxy-$(C_1-C_6)$-alkyl.

DETAILED DESCRIPTION OF A PREFERRED EMBODIMENT

Alkyl denotes saturated straight-chain or branched hydrocarbyl radicals having 1 to 8 carbon atoms, for example $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Haloalkyl denotes straight-chain or branched alkyl groups having 1 to 8 carbon atoms, where some or all of the hydrogen atoms in these groups may be replaced by halogen atoms, for example $C_1-C_2$-haloalkyl such as chloromethyl, bromomethyl, dichloromethyl, trichloromethyl, fluoromethyl, difluoromethyl, trifluoro-methyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkenyl denotes unsaturated straight-chain or branched hydrocarbyl radicals having 2 to 8 carbon atoms and one double bond in any position, for example $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl denotes straight-chain or branched hydrocarbyl radicals having 2 to 8 carbon atoms and one triple bond in any position, for example $C_2-C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy denotes saturated straight-chain or branched alkoxy radicals having 1 to 8 carbon atoms, for example $C_1-C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethyl-propoxy, 1-ethyl-1-methylpropoxy and 1-ethyl-2-methylpropoxy; haloalkoxy denotes straight-chain or branched alkoxy groups having 1 to 8 carbon atoms (as specified above), where some or all of the hydrogen atoms in these groups may be replaced by halogen atoms as specified above, for example $C_1-C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

Alkylthio denotes saturated straight-chain or branched alkylthio radicals having 1 to 8 carbon atoms, for example $C_1-C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio; haloalkylthio denotes straight-chain or branched alkylthio groups having 1 to 8 carbon atoms (as specified above), where some or all of the hydrogen atoms in these groups may be replaced by halogen atoms as specified above, for example $C_1-C_2$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-di-fluoroethylthio, 2,2-dichloro-2-fluoroethylthio, 2,2,2-trichloroethylthio, pentafluoroethylthio and 1,1,1-trifluoroprop-2-ylthio.

Heteroaryl is especially 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl. This heteroaryl is—unless stated otherwise—in each case unsubstituted or in each case mono- or polysubstituted identically or differently by radicals selected from fluorine, chlorine, bromine, iodine, cyano, hydroxyl, mercapto, amino, methyl, ethyl, n-propyl, isopropyl, n-butyl, isobutyl, sec-butyl, tert-butyl, cyclopropyl, 1-chlorocyclopropyl, vinyl, ethynyl, methoxy, ethoxy, isopropoxy, methylthio, ethylthio, trifluoromethylthio, chlorodifluoromethyl, dichlorofluoromethyl, chlorofluoromethyl, chloromethyl, dichloromethyl, trichloromethyl, fluoromethyl, difluoromethyl, trifluoromethyl, 2,2,2-trifluoroethyl, trifluoromethoxy, trifluoromethylthio, 2,2,2-trifluoroethoxy, 2,2-dichloro-2-fluoroethyl, 2,2-difluoro-2-chloroethyl, 2-chloro-2-fluoroethyl, 2,2,2-trichloroethyl, 2,2,2-trifluoroethyl, 2-fluoroethyl, 2,2-difluoroethyl, 2-methoxyethoxy, acetyl, propionyl, methoxycarbonyl, ethoxycarbonyl, N-methylamino, N,N-dimethylamino, N-ethylamino, N,N-diethylamino, aminocarbonyl, methylaminocarbonyl, dimethylaminocarbonyl, dimethylcarbamoylamino, methoxycarbonylamino, methoxycarbonyloxy, ethoxycarbonylamino, ethoxycarbonyloxy, methylsulfamoyl, dimethylsulfamoyl, phenyl or phenoxy.

A saturated or unsaturated five-membered heterocycle is understood to mean a five-membered ring system which, apart from carbon atoms, contains 1 to 4 heteroatoms from the group of oxygen, sulfur and nitrogen. Examples of such a heterocycle are furan, thiophene, 1,2-oxazole, 1,3-oxazole, 1,2-thiazole, 1,3-thiaxazole, imidazole, pyrazole, 1,2-diazole, 1,2,5-oxadiazole and the unsaturated and partly saturated analogs of each.

The compounds of the formula (I) may, also depending on the type of substituents, be present as geometric and/or optical isomers or isomer mixtures, in different compositions which may be separated if appropriate by a customary manner. Both the pure isomers and the isomer mixtures, the preparation thereof and use thereof, and compositions comprising them, form part of the subject matter of this invention. Hereinafter, however, reference is made for the sake of simplicity always to compounds of the formula (I), even though what is meant is both the pure compounds and, if appropriate, mixtures with different proportions of isomeric compounds.

A metal ion equivalent is a metal ion with one positive charge, such as $Na^+$, $K^+$, $(Mg^{2+})_{1/2}$, $(Ca^{2+})_{1/2}$, $MgH^+$, $CaH^+$, $(Al^{3+})_{1/3}$ $(Fe^{2+})_{1/2}$ or $(Fe^{3+})_{1/3}$.

Halogen is fluorine, chlorine, bromine and iodine.

When a group is polysubstituted by radicals, this is understood to mean that this group is substituted by one or more identical or different radicals among those mentioned.

According to the nature of the substituents defined above, the compounds of the formula (I) have acidic or basic properties and can form salts with inorganic or organic acids or with bases or with metal ions, and in some cases also internal salts or adducts. When the compounds of the formula (I) bear amino, alkylamino or other groups which induce basic properties, these compounds can be reacted with acids to give salts or are obtained directly as salts by the synthesis.

Examples of inorganic acids are hydrohalic acids such as hydrogen fluoride, hydrogen chloride, hydrogen bromide and hydrogen iodide, sulfuric acid, phosphoric acid and nitric acid, and acidic salts such as $NaHSO_4$ and $KHSO_4$. Useful organic acids include, for example, formic acid, carbonic acid, and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids with straight-chain or branched alkyl radicals having 1 to 20 carbon atoms), arylsulfonic acids or -disulfonic acids (aromatic radicals such as phenyl and naphthyl which bear one or two sulfo groups), alkylphosphonic acids (phosphonic acids with straight-chain or branched alkyl radicals having 1 to 20 carbon atoms), arylphosphonic acids or -diphosphonic acids (aromatic radicals such as phenyl and naphthyl which bear one or two phosphonic acid radicals), where the alkyl or aryl radicals may bear further substituents, for example p-toluenesulfonic acid, salicylic acid, p-aminosalicylic acid, 2-phenoxybenzoic acid, 2-acetoxybenzoic acid etc.

Useful metal ions include especially the ions of the elements of the second main group, especially calcium and magnesium, of the third and fourth main groups, especially aluminum, tin and lead, and of the first to eighth transition groups, especially chromium, manganese, iron, cobalt, nickel, copper, zinc and others. Particular preference is given to the metal ions of the elements of the fourth period. These metals may be present in the different valences that they can adopt.

When the compounds of the formula (I) bear hydroxyl, carboxyl or other groups which induce acidic properties, these compounds can be reacted with bases to give salts. Suitable bases are, for example, hydroxides, carbonates, hydrogen-carbonates of the alkali metals and alkaline earth metals, especially those of sodium, potassium, magnesium and calcium, and also ammonia, primary, secondary and tertiary amines with $(C_1-C_4)$-alkyl groups, mono-, di- and trialkanolamines of $(C_1-C_4)$-alkanols, choline and chlorocholine.

The compounds of the formula (I) may, according to the nature and bonding of the substituents, be present as stereoisomers. When, for example, one or more asymmetrically substituted carbon atoms or sulfoxides are present, enantiomers and diastereomers may occur. Stereoisomers can be obtained by customary separation methods from the mixtures obtained in the preparation, for example by chromatographic separation processes. It is likewise possible to selectively prepare stereoisomers by use of stereoselective reactions employing optically active starting materials and/or auxiliaries. The invention also relates to all stereoisomers and mixtures thereof which are encompassed by the formula (I) but are not defined specifically.

In all formulae specified hereinafter, the substituents and symbols, unless defined differently, have the same definition as in formula (I).

Preference is given to ketosultams and diketopyridines of the formula (I) in which A is one of the five-membered heterocycles A1 to A12 shown below, in which the broken lines mean the bond to the adjacent pyridine or ketosultam ring,

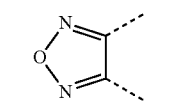
A1

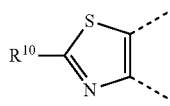
A2

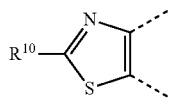
A3

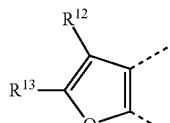
A4

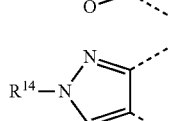
A5

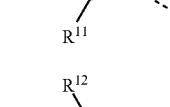
A6

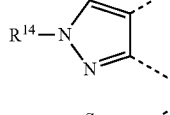
A7

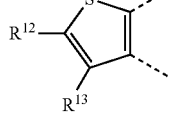
A8

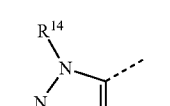
A9

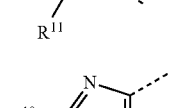
A10

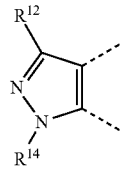
A11

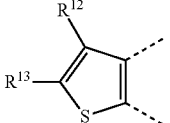
A12

V is C(=O) or S(O)$_2$;

n is 0, 1, 2 or 3;

G is hydrogen, C(=O)R$^1$, C(=L)MR$^2$, SO$_2$R$^3$, P(=L)R$^4$R$^5$, C(=L)NR$^6$R$^7$, E or R$^8$;

E is a metal ion equivalent or an ammonium ion;

L is oxygen or sulfur;

M is oxygen or sulfur;

R$^1$ is (C$_1$-C$_6$)-alkyl, (C$_2$-C$_6$)-alkenyl, (C$_1$-C$_4$)-alkoxy-(C$_1$-C$_6$)-alkyl, di-(C$_1$-C$_4$)-alkoxy-(C$_1$-C$_6$)-alkyl or (C$_1$-C$_4$)-alkylthio-(C$_1$-C$_6$)-alkyl each substituted by n halogen atoms, a fully saturated 3- to 6-membered ring consisting of 3 to 5 carbon atoms and 1 to 3 heteroatoms from the group of oxygen, sulfur and nitrogen and substituted by n radicals from the group consisting of halogen, (C$_1$-C$_4$)-alkyl and (C$_1$-C$_4$)-alkoxy, (C$_3$-C$_6$)-cycloalkyl, phenyl, phenyl-(C$_1$-C$_4$)-alkyl, heteroaryl, phenoxy-(C$_1$-C$_4$)-alkyl or heteroaryloxy-(C$_1$-C$_4$)-alkyl substituted by n radicals from the group consisting of halogen, (C$_1$-C$_4$)-alkyl and (C$_1$-C$_4$)-alkoxy;

R$^2$ is (C$_1$-C$_6$)-alkyl, (C$_2$-C$_6$)-alkenyl, (C$_1$-C$_4$)-alkoxy-(C$_1$-C$_6$)-alkyl or di-(C$_1$-C$_4$)-alkoxy-(C$_1$-C$_6$)-alkyl each substituted by n halogen atoms, or (C$_3$-C$_6$)-cycloalkyl, phenyl or benzyl substituted by n radicals in each case from the group consisting of halogen, (C$_1$-C$_4$)-alkyl and (C$_1$-C$_4$)-alkoxy;

R$^3$, R$^4$ and R$^5$ are each independently (C$_1$-C$_6$)-alkyl, (C$_1$-C$_4$)-alkoxy, N—(C$_1$-C$_6$)-alkylamino, N,N-di-(C$_1$-C$_6$)-alkylamino, (C$_1$-C$_4$)-alkylthio, (C$_2$-C$_4$)-alkenyl or (C$_3$-C$_6$)-cycloalkylthio each substituted by n halogen atoms, or phenyl, benzyl, phenoxy or phenylthio substituted by n radicals from the group consisting of halogen, (C$_1$-C$_4$)-alkyl and (C$_1$-C$_4$)-alkoxy;

R$^6$ and R$^7$ are each independently hydrogen, (C$_1$-C$_6$)-alkyl, (C$_3$-C$_6$)-cycloalkyl, (C$_2$-C$_6$)-alkenyl, (C$_1$-C$_6$)-alkoxy or (C$_1$-C$_4$)-alkoxy-(C$_1$-C$_6$)-alkyl substituted by n halogen atoms, phenyl or benzyl substituted by in each case n radicals from the group consisting of halogen, (C$_1$-C$_4$)-alkyl and (C$_1$-C$_4$)-alkoxy, or R$^6$ and R$^7$ form, together with the nitrogen atom to which they are bonded, a 3- to 6-membered ring containing 2 to 5 carbon atoms and 0 or 1 oxygen or sulfur atom;

R$^8$ is (C$_1$-C$_6$)-alkyl, (C$_2$-C$_6$)-alkenyl, (C$_2$-C$_6$)-alkynyl, (C$_1$-C$_4$)-alkoxy-(C$_1$-C$_6$)-alkyl, (C$_1$-C$_4$)-alkylthio-(C$_1$-C$_4$)-alkyl or di-(C$_1$-C$_4$)-alkoxy-(C$_1$-C$_6$)-alkyl substituted by n halogen atoms, (C$_3$-C$_6$)-cycloalkyl substituted by n radicals from the group consisting of halogen, (C$_1$-C$_4$)-alkyl and (C$_1$-C$_4$)-alkoxy, a fully saturated 3- to 6-membered ring consisting of 3 to 5 carbon atoms and 1 to 3 heteroatoms from the group of oxygen, sulfur and nitrogen and substituted by n radicals from the group consisting of halogen, (C$_1$-C$_4$)-alkyl and (C$_1$-C$_4$)-alkoxy, phenyl, phenyl-(C₁-C₄)-alkyl, heteroaryl, phenoxy-(C₁-C₄)-alkyl or heteroaryloxy-(C₁-C₄)-alkyl substituted by n radicals from the group consisting of halogen, (C₁-C₄)-alkyl and (C₁-C₄)-alkoxy;

W is (C₁-C₆)-alkyl, (C₂-C₆)-alkenyl, (C₃-C₆)-alkynyl, (C₃-C₆)-cycloalkyl, (C₁-C₄)-alkoxy-(C₁-C₆)-alkyl, di-(C₁-C₄)-alkoxy-(C₁-C₆)-alkyl, (C₁-C₄)-alkylthio-(C₁-C₆)-alkyl, (C₁-C₄)-alkylsulfinyl-(C₁-C₆)-alkyl, (C₁-C₄)-alkylsulfonyl-(C₁-C₆)-alkyl or (C₃-C₆)-cycloalkyl-(C₁-C₆)-alkyl each substituted by n halogen atoms;

X, Y and Z are each independently hydrogen, (C₁-C₆)-alkyl, (C₃-C₆)-cycloalkyl, halogen, cyano, nitro, halo-(C₁-C₆)-alkyl, halo-(C₁-C₆)-alkoxy, (C₃-C₆)-cycloalkyl, (C₁-C₆)-alkoxy, (C₁-C₆)-alkoxy-(C₁-C₆)-alkyl, halo-(C₁-C₆)-alkoxy-(C₁-C₆)-alkyl;

R¹⁰ is hydrogen, or (C₁-C₆)-alkyl, (C₁-C₄)-alkoxy, (C₁-C₄)-alkylthio, (C₁-C₄)-alkylsulfinyl or (C₁-C₄)-alkylsulfonyl substituted by n halogen atoms;

R¹¹, R¹² and R¹³ are each independently hydrogen, halogen, or (C₁-C₆)-alkyl, (C₂-C₆)-alkenyl, (C₂-C₆)-alkynyl, (C₁-C₄)-alkoxy-(C₁-C₆)-alkyl, (C₁-C₄)-alkylthio-(C₁-C₄)-alkyl, di-(C₁-C₄)-alkoxy-(C₁-C₆)-alkyl, (C₁-C₄)-alkylthio, (C₁-C₄)-alkylsulfinyl or (C₁-C₄)-alkylsulfonyl substituted by n halogen atoms, or (C₃-C₆)-cycloalkyl substituted by n radicals from the group consisting of halogen, (C₁-C₄)-alkyl and (C₁-C₄)-alkoxy; and R¹⁴ is hydrogen, or (C₁-C₆)-alkyl, (C₂-C₆)-alkenyl, (C₂-C₆)-alkynyl, (C₁-C₄)-alkoxy-(C₁-C₆)-alkyl, (C₁-C₄)-alkylthio-(C₁-C₄)-alkyl or di-(C₁-C₄)-alkoxy-(C₁-C₆)-alkyl substituted by n halogen atoms, or (C₁-C₆)-alkylcarbonyl, (C₁-C₆)-alkoxycarbonyl, (C₁-C₆)-alkylsulfonyl, or (C₃-C₆)-cycloalkyl, (C₃-C₆)-cycloalkylcarbonyl, (C₃-C₆)-cycloalkoxycarbonyl, (C₃-C₆)-cycloalkylsulfonyl substituted by n radicals from the group consisting of halogen, (C₁-C₄)-alkyl and (C₁-C₄)-alkoxy.

Particular preference is given to ketosultams and diketopyridines of the formula (I) in which A is one of the five-membered heterocycles A1 to A12 shown below, in which the broken lines mean the bond to the adjacent pyridine or ketosultam ring,

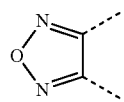

A1

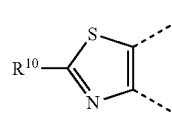

A2

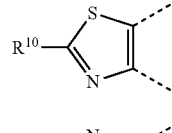

A3

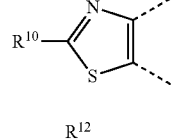

A4

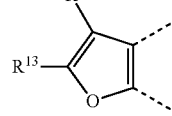

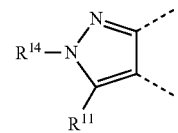

A5

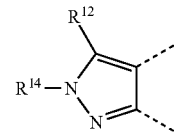

A6

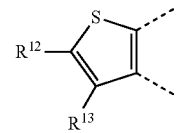

A7

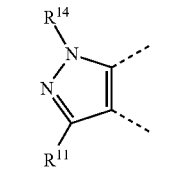

A8

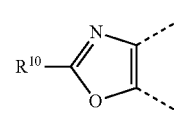

A9

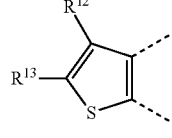

A10

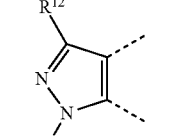

A11

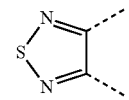

A12

V is C(=O) or S(O)₂;
n is 0, 1, 2 or 3;
G is hydrogen;

W is (C₁-C₆)-alkyl, (C₂-C₆)-alkenyl, (C₃-C₆)-alkynyl, (C₃-C₆)-cycloalkyl, (C₁-C₄)-alkoxy-(C₁-C₆)-alkyl, di-(C₁-C₄)-alkoxy-(C₁-C₆)-alkyl, (C₁-C₄)-alkylthio-(C₁-C₆)-alkyl, (C₁-C₄)-alkylsulfinyl-(C₁-C₆)-alkyl, (C₁-C₄)-alkylsulfonyl-(C₁-C₆)-alkyl or (C₃-C₆)-cycloalkyl-(C₁-C₆)-alkyl each substituted by n halogen atoms;

X, Y and Z are each independently hydrogen, (C₁-C₆)-alkyl, (C₃-C₆)-cycloalkyl, halogen, cyano, nitro, halo-(C₁-C₆)-alkyl, halo-(C₁-C₆)-alkoxy, (C₃-C₆)-cycloalkyl, (C₁-C₆)-alkoxy, (C₁-C₆)-alkoxy-(C₁-C₆)-alkyl, halo-(C₁-C₆)-alkoxy-(C₁-C₆)-alkyl;

R¹⁰ is hydrogen, or (C₁-C₆)-alkyl, (C₁-C₄)-alkoxy, (C₁-C₄)-alkylthio, (C₁-C₄)-alkylsulfinyl or (C₁-C₄)-alkylsulfonyl substituted by n halogen atoms;

R¹¹, R¹² and R¹³ are each independently hydrogen, halogen, or (C₁-C₆)-alkyl, (C₂-C₆)-alkenyl, (C₂-C₆)-alkynyl, (C₁-

$C_4$)-alkoxy-($C_1$-$C_6$)-alkyl, ($C_1$-$C_4$)-alkylthio-($C_1$-$C_4$)-alkyl, di-($C_1$-$C_4$)-alkoxy-($C_1$-$C_6$)-alkyl, ($C_1$-$C_4$)-alkylthio, ($C_1$-$C_4$)-alkylsulfinyl or ($C_1$-$C_4$)-alkylsulfonyl substituted by n halogen atoms or ($C_3$-$C_6$)-cycloalkyl substituted by n radicals from the group consisting of halogen, ($C_1$-$C_4$)-alkyl and ($C_1$-$C_4$)-alkoxy, and $R^{14}$ is hydrogen, or ($C_1$-$C_6$)-alkyl, ($C_2$-$C_6$)-alkenyl, ($C_2$-$C_6$)-alkynyl, ($C_1$-$C_4$)-alkoxy-($C_1$-$C_6$)-alkyl, ($C_1$-$C_4$)-alkylthio-($C_1$-$C_4$)-alkyl or di-($C_1$-$C_4$)-alkoxy-($C_1$-$C_6$)-alkyl substituted by n halogen atoms, or ($C_1$-$C_6$)-alkylcarbonyl, ($C_1$-$C_6$)-alkoxycarbonyl, ($C_1$-$C_6$)-alkylsulfonyl, or ($C_3$-$C_6$)-cycloalkyl, ($C_3$-$C_6$)-cycloalkylcarbonyl, ($C_3$-$C_6$)-cycloalkoxycarbonyl, ($C_3$-$C_6$)-cycloalkylsulfonyl substituted by n radicals from the group consisting of halogen, ($C_1$-$C_4$)-alkyl and ($C_1$-$C_4$)-alkoxy.

Particular preference is also given to ketosultams and diketopyridines of the formula (I) in which A is one of the five-membered heterocycles A1 to A12 shown below, in which the broken lines mean the bond to the adjacent pyridine or ketosultam ring,

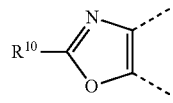
A9

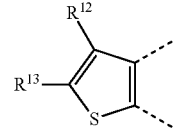
A10

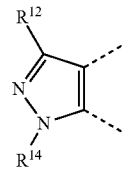
A11

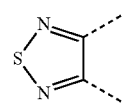
A12

V is C(=O) or S(O)$_2$;

n is 0, 1, 2 or 3;

G is C(=O)$R^1$;

$R^1$ is ($C_1$-$C_6$)-alkyl each substituted by n halogen atoms;

W is ($C_1$-$C_6$)-alkyl, ($C_2$-$C_6$)-alkenyl, ($C_3$-$C_6$)-alkynyl, ($C_3$-$C_6$)-cycloalkyl, ($C_1$-$C_4$)-alkoxy-($C_1$-$C_6$)-alkyl, di-($C_1$-$C_4$)-alkoxy-($C_1$-$C_6$)-alkyl, ($C_1$-$C_4$)-alkylthio-($C_1$-$C_6$)-alkyl, ($C_1$-$C_4$)-alkylsulfinyl-($C_1$-$C_6$)-alkyl, ($C_1$-$C_4$)-alkylsulfonyl-($C_1$-$C_6$)-alkyl or ($C_3$-$C_6$)-cycloalkyl-($C_1$-$C_6$)-alkyl each substituted by n halogen atoms;

X, Y and Z are each independently hydrogen, ($C_1$-$C_6$)-alkyl, ($C_3$-$C_6$)-cycloalkyl, halogen, cyano, nitro, halo-($C_1$-$C_6$)-alkyl, halo-($C_1$-$C_6$)-alkoxy, ($C_3$-$C_6$)-cycloalkyl, ($C_1$-$C_6$)-alkoxy, ($C_1$-$C_6$)-alkoxy-($C_1$-$C_6$)-alkyl, halo-($C_1$-$C_6$)-alkoxy-($C_1$-$C_6$)-alkyl;

$R^{10}$ is hydrogen, or ($C_1$-$C_6$)-alkyl, ($C_1$-$C_4$)-alkoxy, ($C_1$-$C_4$)-alkylthio, ($C_1$-$C_4$)-alkylsulfinyl or ($C_1$-$C_4$)-alkylsulfonyl substituted by n halogen atoms;

$R^{11}$, $R^{12}$ and $R^{13}$ are each independently hydrogen, halogen, or ($C_1$-$C_6$)-alkyl, ($C_2$-$C_6$)-alkenyl, ($C_2$-$C_6$)-alkynyl, ($C_1$-$C_4$)-alkoxy-($C_1$-$C_6$)-alkyl, ($C_1$-$C_4$)-alkylthio-($C_1$-$C_4$)-alkyl, di-($C_1$-$C_4$)-alkoxy-($C_1$-$C_6$)-alkyl, ($C_1$-$C_4$)-alkylthio, ($C_1$-$C_4$)-alkylsulfinyl or ($C_1$-$C_4$)-alkylsulfonyl substituted by n halogen atoms, or ($C_3$-$C_6$)-cycloalkyl substituted by n radicals from the group consisting of halogen, ($C_1$-$C_4$)-alkyl and ($C_1$-$C_4$)-alkoxy, and $R^{14}$ is hydrogen, or ($C_1$-$C_6$)-alkyl, ($C_2$-$C_6$)-alkenyl, ($C_2$-$C_6$)-alkynyl, ($C_1$-$C_4$)-alkoxy-($C_1$-$C_6$)-alkyl, ($C_1$-$C_4$)-alkylthio-($C_1$-$C_4$)-alkyl or di-($C_1$-$C_4$)-alkoxy-($C_1$-$C_6$)-alkyl substituted by n halogen atoms, or ($C_1$-$C_6$)-alkylcarbonyl, ($C_1$-$C_6$)-alkoxycarbonyl, ($C_1$-$C_6$)-alkylsulfonyl, or ($C_3$-$C_6$)-cycloalkyl, ($C_3$-$C_6$)-cycloalkylcarbonyl, ($C_3$-$C_6$)-cycloalkoxycarbonyl, ($C_3$-$C_6$)-cycloalkylsulfonyl substituted by n radicals from the group consisting of halogen, ($C_1$-$C_4$)-alkyl and ($C_1$-$C_4$)-alkoxy.

Particular preference is also given to ketosultams and diketopyridines of the formula (I) in which A is one of the five-membered heterocycles A1 to A12 shown below, in which the broken lines mean the bond to the adjacent pyridine or ketosultam ring, V is C(=O) or S(O)₂;
n is 0, 1, 2 or 3;
G is C(=L)MR²;
L is oxygen;
M is oxygen or sulfur;
R² is (C₁-C₆)-alkyl each substituted by n halogen atoms;
W is (C₁-C₆)-alkyl, (C₂-C₆)-alkenyl, (C₃-C₆)-alkynyl, (C₃-C₆)-cycloalkyl, (C₁-C₄)-alkoxy-(C₁-C₆)-alkyl, di-(C₁-C₄)-alkoxy-(C₁-C₆)-alkyl, (C₁-C₄)-alkylthio-(C₁-C₆)-alkyl, (C₁-C₄)-alkylsulfinyl-(C₁-C₆)-alkyl, (C₁-C₄)-alkylsulfonyl-(C₁-C₆)-alkyl or (C₃-C₆)-cycloalkyl-(C₁-C₆)-alkyl each substituted by n halogen atoms and
X, Y and Z are each independently hydrogen, (C₁-C₆)-alkyl, (C₃-C₆)-cycloalkyl, halogen, cyano, nitro, halo-(C₁-C₆)-alkyl, halo-(C₁-C₆)-alkoxy, (C₃-C₆)-cycloalkyl, (C₁-C₆)-alkoxy, (C₁-C₆)-alkoxy-(C₁-C₆)-alkyl, halo-(C₁-C₆)-alkoxy-(C₁-C₆)-alkyl;
R¹⁰ is hydrogen, or (C₁-C₆)-alkyl, (C₁-C₄)-alkoxy, (C₁-C₄)-alkylthio, (C₁-C₄)-alkylsulfinyl or (C₁-C₄)-alkylsulfonyl substituted by n halogen atoms;
R¹¹, R¹² and R¹³ are each independently hydrogen, halogen, or (C₁-C₆)-alkyl, (C₂-C₆)-alkenyl, (C₂-C₆)-alkynyl, (C₁-C₄)-alkoxy-(C₁-C₆)-alkyl, (C₁-C₄)-alkylthio-(C₁-C₄)-alkyl, di-(C₁-C₄)-alkoxy-(C₁-C₆)-alkyl, (C₁-C₄)-alkylthio, (C₁-C₄)-alkylsulfinyl or (C₁-C₄)-alkylsulfonyl substituted by n halogen atoms, or
(C₃-C₆)-cycloalkyl substituted by n radicals from the group consisting of halogen, (C₁-C₄)-alkyl and (C₁-C₄)-alkoxy, and
R¹⁴ is hydrogen, or (C₁-C₆)-alkyl, (C₂-C₆)-alkenyl, (C₂-C₆)-alkynyl, (C₁-C₄)-alkoxy-(C₁-C₆)-alkyl, (C₁-C₄)-alkylthio-(C₁-C₄)-alkyl or di-(C₁-C₄)-alkoxy-(C₁-C₆)-alkyl substituted by n halogen atoms, or (C₁-C₆)-alkylcarbonyl, (C₁-C₆)-alkoxycarbonyl, (C₁-C₆)-alkylsulfonyl, or (C₃-C₆)-cycloalkyl, (C₃-C₆)-cycloalkylcarbonyl, (C₃-C₆)-cycloalkoxycarbonyl, (C₃-C₆)-cycloalkylsulfonyl substituted by n radicals from the group consisting of halogen, (C₁-C₄)-alkyl and (C₁-C₄)-alkoxy.

Particular preference is also given to ketosultams and diketopyridines of the formula (I) in which
A is one of the five-membered heterocycles A1 to A12 shown below, in which the broken lines mean the bond to the adjacent pyridine or ketosultam ring, -continued

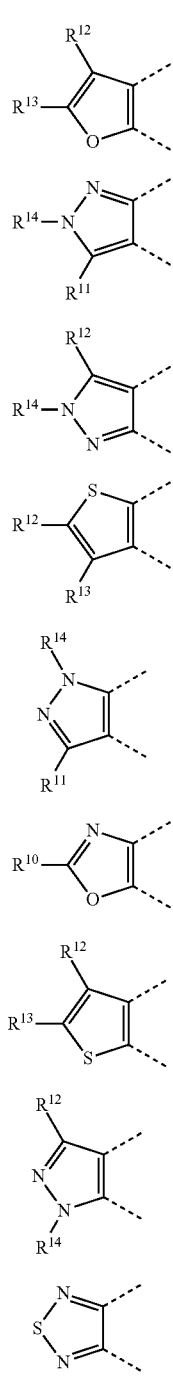

A4
A5
A6
A7
A8
A9
A10
A11
A12

V is C(=O) or S(O)$_2$;
n is 0, 1, 2 or 3;
G is R$^8$;
R$^8$ is (C$_1$-C$_6$)-alkyl, (C$_2$-C$_6$)-alkenyl, (C$_2$-C$_6$)-alkynyl substituted by n halogen atoms;
W is (C$_1$-C$_6$)-alkyl, (C$_2$-C$_6$)-alkenyl, (C$_3$-C$_6$)-alkynyl, (C$_3$-C$_6$)-cycloalkyl, (C$_1$-C$_4$)-alkoxy-(C$_1$-C$_6$)-alkyl, di-(C$_1$-C$_4$)-alkoxy-(C$_1$-C$_6$)-alkyl, (C$_1$-C$_4$)-alkylthio-(C$_1$-C$_6$)-alkyl, (C$_1$-C$_4$)-alkylsulfinyl-(C$_1$-C$_6$)-alkyl, (C$_1$-C$_4$)-alkylsulfonyl-(C$_1$-C$_6$)-alkyl or (C$_3$-C$_6$)-cycloalkyl-(C$_1$-C$_6$)-alkyl each substituted by n halogen atoms;
X, Y and Z are each independently hydrogen, (C$_1$-C$_6$)-alkyl, (C$_3$-C$_6$)-cycloalkyl, halogen, cyano, nitro, halo-(C$_1$-C$_6$)-alkyl, halo-(C$_1$-C$_6$)-alkoxy, (C$_3$-C$_6$)-cycloalkyl, (C$_1$-C$_6$)-alkoxy, (C$_1$-C$_6$)-alkoxy-(C$_1$-C$_6$)-alkyl, halo-(C$_1$-C$_6$)-alkoxy-(C$_1$-C$_6$)-alkyl;
R$^{10}$ is hydrogen, or (C$_1$-C$_6$)-alkyl, (C$_1$-C$_4$)-alkoxy, (C$_1$-C$_4$)-alkylthio, (C$_1$-C$_4$)-alkylsulfinyl or (C$_1$-C$_4$)-alkylsulfonyl substituted by n halogen atoms;
R$^{11}$, R$^{12}$ and R$^{13}$ are each independently hydrogen, halogen, or (C$_1$-C$_6$)-alkyl, (C$_2$-C$_6$)-alkenyl, (C$_2$-C$_6$)-alkynyl, (C$_1$-C$_4$)-alkoxy-(C$_1$-C$_6$)-alkyl, (C$_1$-C$_4$)-alkylthio-(C$_1$-C$_4$)-alkyl, di-(C$_1$-C$_4$)-alkoxy-(C$_1$-C$_6$)-alkyl, (C$_1$-C$_4$)-alkylthio, (C$_1$-C$_4$)-alkylsulfinyl or (C$_1$-C$_4$)-alkylsulfonyl substituted by n halogen atoms, or (C$_3$-C$_6$)-cycloalkyl substituted by n radicals from the group consisting of halogen, (C$_1$-C$_4$)-alkyl and (C$_1$-C$_4$)-alkoxy, and
R$^{14}$ is hydrogen, or (C$_1$-C$_6$)-alkyl, (C$_2$-C$_6$)-alkenyl, (C$_2$-C$_6$)-alkynyl, (C$_1$-C$_4$)-alkoxy-(C$_1$-C$_6$)-alkyl, (C$_1$-C$_4$)-alkylthio-(C$_1$-C$_4$)-alkyl or di-(C$_1$-C$_4$)-alkoxy-(C$_1$-C$_6$)-alkyl substituted by n halogen atoms, or (C$_1$-C$_6$)-alkylcarbonyl, (C$_1$-C$_6$)-alkoxycarbonyl, (C$_1$-C$_6$)-alkylsulfonyl, or (C$_3$-C$_6$)-cycloalkyl, (C$_3$-C$_6$)-cycloalkylcarbonyl, (C$_3$-C$_6$)-cycloalkoxycarbonyl, (C$_3$-C$_6$)-cycloalkylsulfonyl substituted by n radicals from the group consisting of halogen, (C$_1$-C$_4$)-alkyl and (C$_1$-C$_4$)-alkoxy.

Very particular preference is given to the compounds of the formula (I) specified in tables 1 to 124.

The abbreviations used mean:

| | | |
|---|---|---|
| Bz = benzyl | c-Pr = cyclopropyl | Et = ethyl |
| i-Bu = isobutyl | t-Bu = tert-butyl | i-Pr = isopropyl |
| Me = methyl | Ph = phenyl | c = cyclo |

TABLE 1

Inventive compounds of the formula (I) in which G is hydrogen, V is C=O, W is difluoroethyl, and A is A1:

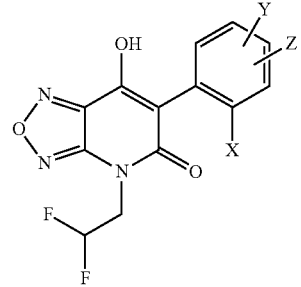

| No. | X | Y | Z |
|---|---|---|---|
| 1 | F | H | H |
| 2 | Cl | H | H |
| 3 | Br | H | H |
| 4 | I | H | H |
| 5 | OMe | H | H |
| 6 | EtO | H | H |
| 7 | CF$_3$ | H | H |
| 8 | CN | H | H |
| 9 | NO$_2$ | H | H |
| 10 | OCF$_3$ | H | H |
| 11 | H | 3-CF$_3$ | H |
| 12 | H | 3-Me | H |
| 13 | H | 3-F | H |
| 14 | H | 3-Cl | H |
| 15 | H | 3-CN | H |
| 16 | H | 3-Br | H |
| 17 | H | 3-I | H |

TABLE 1-continued

Inventive compounds of the formula (I) in which G is hydrogen, V is C=O, W is difluoroethyl, and A is A1:

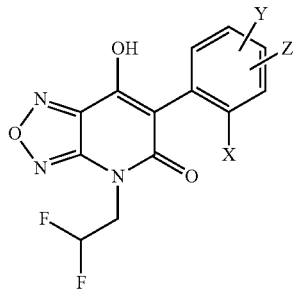

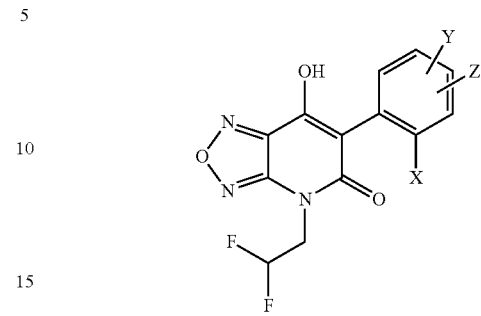

| No. | X | Y | Z |
|---|---|---|---|
| 18 | H | 3-NO$_2$ | H |
| 19 | H | 3-OCF$_3$ | H |
| 20 | H | 3-OMe | H |
| 21 | H | 3-EtO | H |
| 22 | H | 4-CF$_3$ | H |
| 23 | H | 4-Me | H |
| 24 | H | 4-F | H |
| 25 | H | 4-Cl | H |
| 26 | H | 4-CN | H |
| 27 | H | 4-Br | H |
| 28 | H | 4-I | H |
| 29 | H | 4-NO$_2$ | H |
| 30 | H | 4-OCF$_3$ | H |
| 31 | H | 4-OMe | H |
| 32 | H | 4-EtO | H |
| 33 | Cl | 4-Cl | H |
| 34 | H | 3-Cl | 4-Cl |
| 35 | Br | 4-Cl | H |
| 36 | Cl | H | 6-Cl |
| 37 | Cl | H | 6-F |
| 38 | F | H | 6-F |
| 39 | Me | 4-Cl | H |
| 40 | Me | 4-Br | H |
| 41 | Me | 4-I | H |
| 42 | Cl | 4-Cl | 6-Cl |
| 43 | Cl | 6-Me | 4-Br |
| 44 | Cl | 6-Me | 4-Cl |
| 45 | Br | 6-Me | 4-Cl |
| 46 | Br | 6-Me | 4-Br |
| 47 | OMe | 6-Me | 4-Cl |
| 48 | EtO | 6-Me | 4-Cl |
| 49 | Cl | 6-Me | 4-Br |
| 50 | Cl | 6-Et | 4-Cl |
| 51 | Br | 6-Et | 4-Cl |
| 52 | Br | 6-Et | 4-Br |
| 53 | OMe | 6-Et | 4-Cl |
| 54 | EtO | 6-Et | 4-Cl |
| 55 | Br | 4-Me | 6-Br |
| 56 | Cl | 4-Me | 6-Cl |
| 57 | OMe | 4-Me | 6-Me |
| 58 | EtO | 4-Me | 6-Me |
| 59 | OMe | 6-Et | 4-Me |
| 60 | EtO | 6-Et | 4-Me |
| 61 | Cl | 4-Me | 6-Et |
| 62 | Et | 6-Et | 4-Cl |
| 63 | Et | 6-Me | 4-Br |
| 64 | Et | 6-Et | 4-Br |
| 65 | Et | 6-Me | 4-Cl |
| 66 | Et | 6-Me | 4-Br |
| 67 | OMe | 4-Me | 6-Cl |
| 68 | EtO | 4-Me | 6-Cl |
| 69 | I | H | 4-Me |
| 70 | I | 6-Me | H |
| 71 | I | 6-Et | H |
| 72 | I | 4-Me | 6-Me |
| 73 | I | 6-Et | 4-Me |
| 74 | I | 6-Me | 4-Cl |
| 75 | I | 6-Et | 6-Cl |
| 76 | I | 6-Cl | 4-Me |
| 77 | Me | 4-I | H |
| 78 | Et | 4-I | H |
| 79 | Et | 4-I | 6-Me |
| 80 | Et | 4-I | 6-Et |
| 81 | Cl | 6-Me | 4-I |
| 82 | Cl | 6-Et | 4-I |
| 83 | c-Pr | H | H |
| 84 | c-Pr | 4-Me | H |
| 85 | c-Pr | H | 6-Me |
| 86 | c-Pr | 6-Et | H |
| 87 | c-Pr | 4-Me | 6-Me |
| 88 | c-Pr | 6-Et | 4-Me |
| 89 | c-Pr | 4-Me | 6-Cl |
| 90 | c-Pr | 6-Et | 4-Cl |
| 91 | c-Pr | 4-Cl | 6-Me |
| 92 | Me | 4-c-Pr | H |
| 93 | Et | 4-c-Pr | H |
| 94 | Me | 4-c-Pr | 6-Me |
| 95 | Et | 4-c-Pr | 6-Me |
| 96 | Et | 4-c-Pr | 6-Et |
| 97 | Cl | 6-Me | 4-c-Pr |
| 98 | Cl | 6-Et | 4-c-Pr |
| 99 | Et | 6-Et | 4-I |
| 100 | Cl | 6-F | 3-Me |
| 101 | F | 6-F | 3-F |
| 102 | EtO | 6-F | 3-F |
| 103 | F | 6-F | 3-EtO |
| 104 | F | H | 5-Cl |
| 105 | H | 3-CF$_3$ | 5-CF$_3$ |
| 106 | Me | 4-OCF$_3$ | H |
| 107 | OCF$_3$ | 4-Me | H |
| 108 | OCF3 | 5-Me | H |
| 109 | OCF3 | 6-Me | H |
| 110 | OCF3 | 6-Et | H |
| 111 | Me | 5-OCF3 | H |
| 112 | Me | 3-OCF3 | 6-Me |
| 113 | Br | 4-OCF$_3$ | 6-Cl |
| 114 | Br | 4-OCF$_3$ | 6-Br |
| 115 | OMe | 4-OCF$_3$ | 6-Br |
| 116 | OMe | 4-OCF$_3$ | 6-Cl |
| 117 | Cl | 4-OCF$_3$ | 6-Cl |
| 118 | OMe | 4-OCF$_3$ | 6-Cl |
| 119 | OMe | 4-OCF$_3$ | 6-Br |
| 120 | Me | 4-OCF$_3$ | 6-Me |
| 121 | Cl | 4-OCF$_3$ | 6-Me |
| 122 | OCF$_3$ | 6-Cl | 4-Br |
| 123 | OCF$_3$ | 6-Me | 4-Me |
| 124 | OCF$_3$ | 6-OMe | 4-Cl |
| 125 | OCF$_3$ | 6-Cl | 4-Me |
| 126 | Cl | 5-OCF$_3$ | H |
| 127 | Br | 5-OCF$_3$ | H |
| 128 | OCF$_3$ | 6-Et | 4-Cl |
| 129 | Br | 4-Cl | 6-Br |
| 130 | Br | 4-Cl | 6-Cl |
| 131 | Br | 4-Me | 6-Cl |
| 132 | Cl | 3-Me | 6-Cl |
| 133 | Cl | 3-F | 6-F |
| 134 | F | 3-Me | 6-F |
| 135 | F | 4-OMe | 6-F |

TABLE 1-continued

Inventive compounds of the formula (I) in which G is hydrogen, V is C=O, W is difluoroethyl, and A is A1:

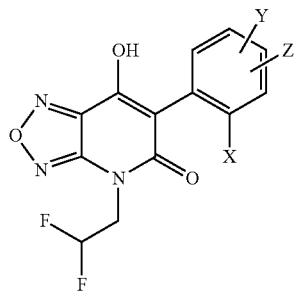

| No. | X | Y | Z |
|---|---|---|---|
| 136 | F | 3-OMe | 6-F |
| 137 | Cl | 3-Cl | 6-F |
| 138 | Cl | 4-Et | 6-Cl |
| 139 | Cl | 4-Et | 6-Br |
| 140 | Cl | 3-Br | 6-Cl |
| 141 | Cl | 4-CF$_3$ | 6-F |
| 142 | Cl | 4-CF$_3$ | 6-Cl |
| 143 | Cl | 3-Cl | 6-Cl |
| 144 | Cl | 3-CF$_3$ | 6-Cl |
| 145 | F | 3-F | 6-NO$_2$ |
| 146 | F | 4-NO$_2$ | 6-F |
| 147 | Cl | 4-CF$_3$ | 6-NO$_2$ |
| 148 | Br | 6-NO$_2$ | H |
| 149 | F | 4-CF$_3$ | 6-F |
| 150 | Br | 6-Br | H |
| 151 | Cl | 3-OMe | 6-F |
| 152 | F | 3-OMe | 6-Cl |
| 153 | F | 4-Cl | 6-F |
| 154 | F | 4-Br | 6-F |
| 155 | F | 4-Br | 6-Br |
| 156 | Cl | 4-Br | 6-Cl |
| 157 | F | 4-EtO | 6-F |
| 158 | F | 3-Cl | 6-F |
| 159 | Cl | 3-Cl | 6-Br |
| 160 | F | 3-F | 6-Cl |
| 161 | F | 3-F | 6-Br |
| 162 | F | 3-F | 6-I |
| 163 | Cl | 6-CF$_3$ | H |
| 164 | Cl | 3-Cl | 6-CF$_3$ |
| 165 | F | 3-Cl | 6-CF$_3$ |
| 166 | Cl | 3-CF$_3$ | 6-Cl |
| 167 | c-Pr | 4-Cl | 6-Cl |
| 168 | Me | 4-CF$_2$—CF$_3$ | 6-Me |
| 169 | Cl | 3-c-Pr | 6-Cl |
| 170 | Cl | 3-I | 6-Cl |
| 171 | Me | 4-c-Pr-(2'-c-Pr) | 6-Me |

TABLE 2

Inventive compounds of the formula (I) in which G is hydrogen, V is SO$_2$, W is difluoroethyl, A is A1, and X, Y and Z are each as defined in table 1:

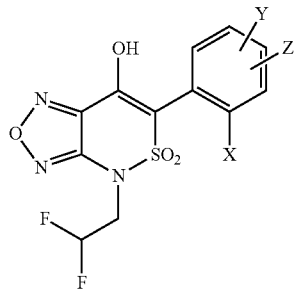

TABLE 3

Inventive compounds of the formula (I) in which G is hydrogen, V is C=O, W is trifluoroethyl, A is A1, and X, Y and Z are each as defined in table 1:

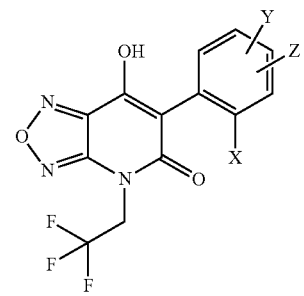

TABLE 4

Inventive compounds of the formula (I) in which G is hydrogen, V is SO$_2$, W is trifluoroethyl, A is A1, and X, Y and Z are each as defined in table 1:

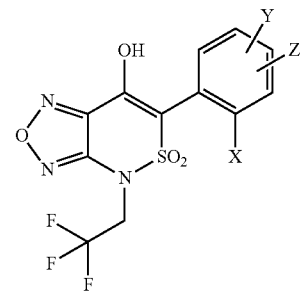

TABLE 5

Inventive compounds of the formula (I) in which G is hydrogen, V is C=O, W is propynyl, A is A1, and X, Y and Z are each as defined in table 1:

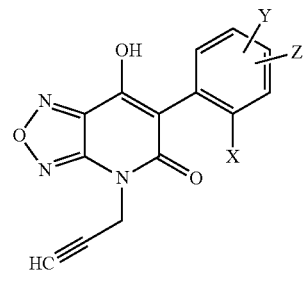

TABLE 6

Inventive compounds of the formula (I) in which G is hydrogen, V is SO$_2$, W is propynyl, A is A1, and X, Y and Z are each as defined in table 1:

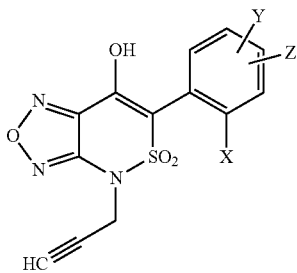

TABLE 7

Inventive compounds of the formula (I) in which G is hydrogen, V is C═O, W is difluoroethyl, A is A2, R$^{10}$ is hydrogen, and X, Y and Z are each as defined in table 1:

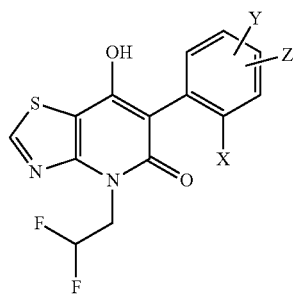

TABLE 8

Inventive compounds of the formula (I) in which G is hydrogen, V is SO$_2$, W is difluoroethyl, A is A2, R$^{10}$ is hydrogen, and X, Y and Z are each as defined in table 1:

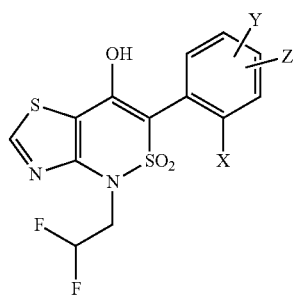

TABLE 9

Inventive compounds of the formula (I) in which G is hydrogen, V is C═O, W is trifluoroethyl, A is A2, R$^{10}$ is hydrogen, and X, Y and Z are each as defined in table 1:

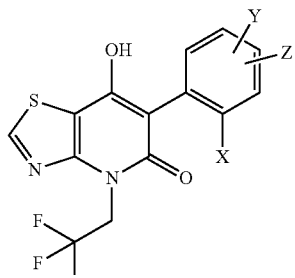

TABLE 10

Inventive compounds of the formula (I) in which G is hydrogen, V is SO$_2$, W is trifluoroethyl, A is A2, R$^{10}$ is hydrogen, and X, Y and Z are each as defined in table 1:

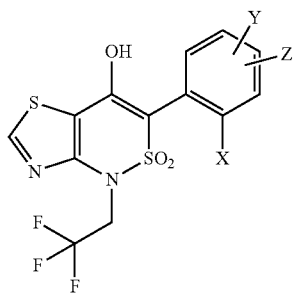

TABLE 11

Inventive compounds of the formula (I) in which G is hydrogen, V is C═O, W is propynyl, A is A2, R$^{10}$ is hydrogen, and X, Y and Z are each as defined in table 1:

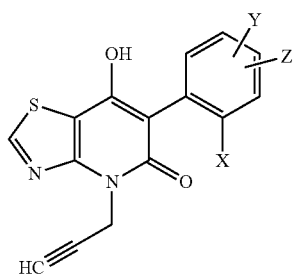

Table 12

Inventive compounds of the formula (I) in which G is hydrogen, V is $SO_2$, W is propynyl, $R^{10}$ is hydrogen, A is A2, and X, Y and Z are each as defined in table 1:

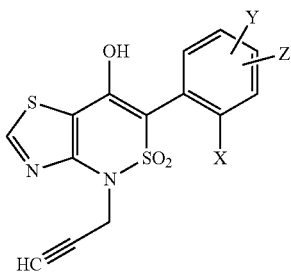

TABLE 13

Inventive compounds of the formula (I) in which G is hydrogen, V is C═O, W is difluoroethyl, A is A2, $R^{10}$ is methylthio, and X, Y and Z are each as defined in table 1:

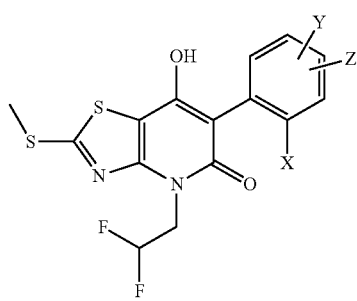

TABLE 14

Inventive compounds of the formula (I) in which G is hydrogen, V is $SO_2$, W is difluoroethyl, A is A2, $R^{10}$ is methylthio, and X, Y and Z are each as defined in table 1:

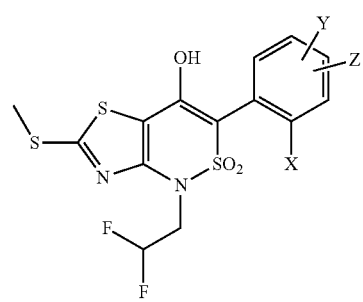

TABLE 15

Inventive compounds of the formula (I) in which G is hydrogen, V is C═O, W is trifluoroethyl, A is A2, $R^{10}$ is methylthio, and X, Y and Z are each as defined in table 1:

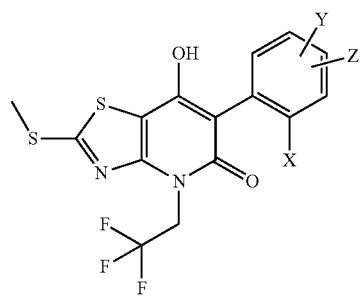

TABLE 16

Inventive compounds of the formula (I) in which G is hydrogen, V is $SO_2$, W is trifluoroethyl, A is A2, $R^{10}$ is methylthio, and X, Y and Z are each as defined in table 1:

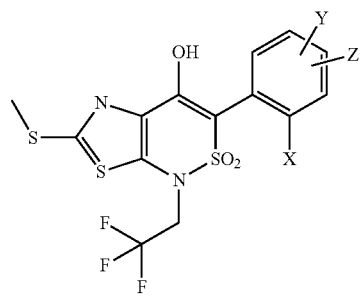

TABLE 17

Inventive compounds of the formula (I) in which G is hydrogen, V is C═O, W is propynyl, A is A2, $R^{10}$ is methylthio, and X, Y and Z are each as defined in table 1:

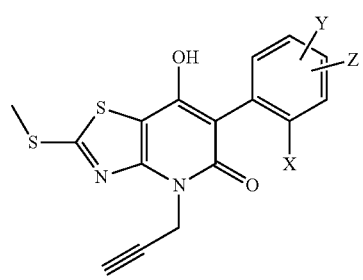

TABLE 18

Inventive compounds of the formula (I) in which G is hydrogen, V is $SO_2$, W is propynyl, A is A2, $R^{10}$ is methylthio, and X, Y and Z are each as defined in table 1:

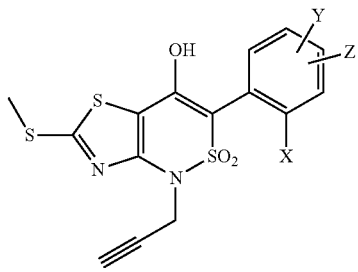

TABLE 19

Inventive compounds of the formula (I) in which G is hydrogen, V is C=O, W is difluoroethyl, A is A3, $R^{10}$ is hydrogen, and X, Y and Z are each as defined in table 1:

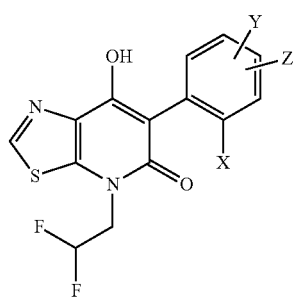

TABLE 20

Inventive compounds of the formula (I) in which G is hydrogen, V is $SO_2$, W is difluoroethyl, A is A3, $R^{10}$ is hydrogen, and X, Y and Z are each as defined in table 1:

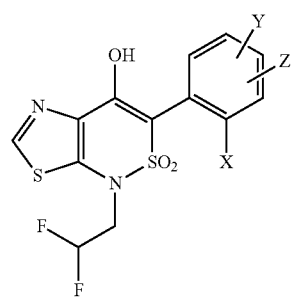

TABLE 21

Inventive compounds of the formula (I) in which G is hydrogen, V is C=O, W is trifluoroethyl, A is A3, $R^{10}$ is hydrogen, and X, Y and Z are each as defined in table 1:

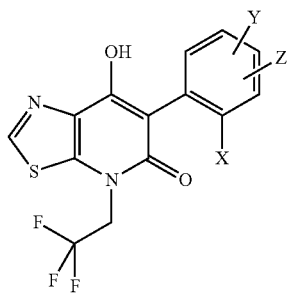

TABLE 22

Inventive compounds of the formula (I) in which G is hydrogen, V is $SO_2$, W is trifluoroethyl, A is A3, $R^{10}$ is hydrogen, and X, Y and Z are each as defined in table 1:

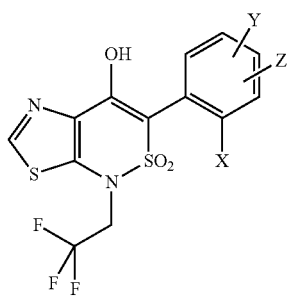

TABLE 23

Inventive compounds of the formula (I) in which G is hydrogen, V is C=O, W is propynyl, A is A3, $R^{10}$ is hydrogen, and X, Y and Z are each as defined in table 1:

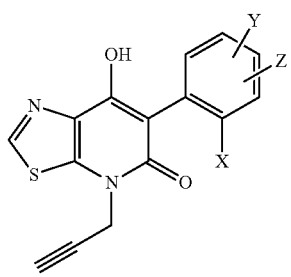

TABLE 24

Inventive compounds of the formula (I) in which G is hydrogen, V is SO$_2$, W is propynyl, A is A3, R$^{10}$ is hydrogen, and X, Y and Z are each as defined in table 1:

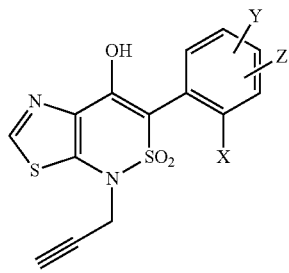

TABLE 25

Inventive compounds of the formula (I) in which G is hydrogen, V is C=O, W is difluoroethyl, A is A4, R$^{12}$ and R$^{13}$ are each hydrogen, and X, Y and Z are each as defined in table 1:

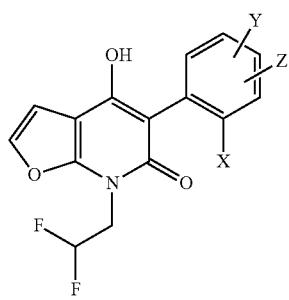

TABLE 26

Inventive compounds of the formula (I) in which G is hydrogen, V is SO$_2$, W is difluoroethyl, A is A4, R$^{12}$ and R$^{13}$ are each hydrogen, and X, Y and Z are each as defined in table 1:

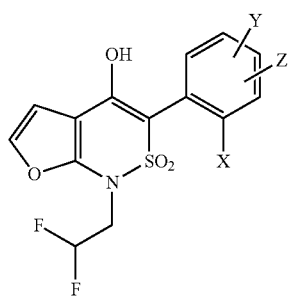

TABLE 27

Inventive compounds of the formula (I) in which G is hydrogen, V is C=O, W is trifluoroethyl, A is A4, R$^{12}$ and R$^{13}$ are each hydrogen, and X, Y and Z are each as defined in table 1:

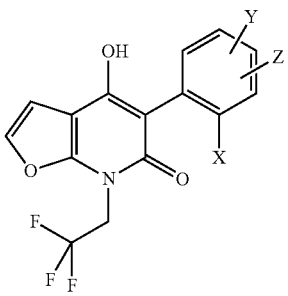

TABLE 28

Inventive compounds of the formula (I) in which G is hydrogen, V is SO$_2$, W is trifluoroethyl, A is A4, R$^{12}$ and R$^{13}$ are each hydrogen, and X, Y and Z are each as defined in table 1:

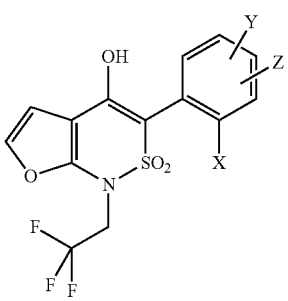

TABLE 29

Inventive compounds of the formula (I) in which G is hydrogen, V is C=O, W is propynyl, A is A4, R$^{12}$ and R$^{13}$ are each hydrogen, and X, Y and Z are each as defined in table 1:

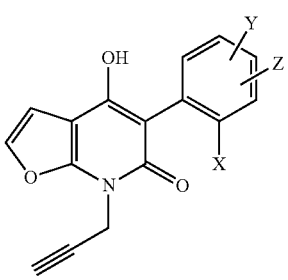

TABLE 30

Inventive compounds of the formula (I) in which G is hydrogen, V is SO$_2$, W is propynyl, A is A4, R$^{12}$ and R$^{13}$ are each hydrogen, and X, Y and Z are each as defined in table 1:

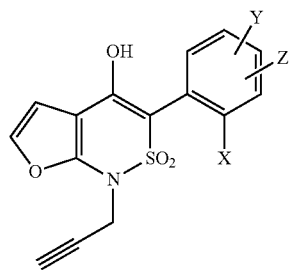

TABLE 31

Inventive compounds of the formula (I) in which G is hydrogen, V is C=O, W is difluoroethyl, A is A5, R$^{11}$ is hydrogen, R$^{14}$ is methyl, and X, Y and Z are each as defined in table 1:

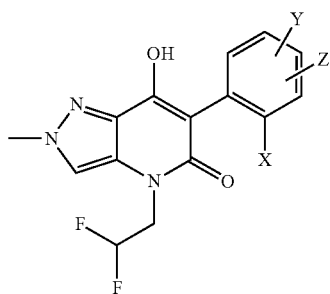

TABLE 32

Inventive compounds of the formula (I) in which G is hydrogen, V is SO$_2$, W is difluoroethyl, A is A5, R$^{11}$ is hydrogen, R$^{14}$ is methyl, and X, Y and Z are each as defined in table 1:

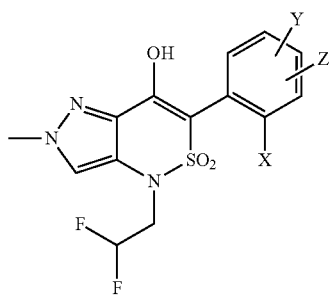

TABLE 33

Inventive compounds of the formula (I) in which G is hydrogen, V is C=O, W is trifluoroethyl, A is A5, R$^{11}$ is hydrogen, R$^{14}$ is methyl, and X, Y and Z are each as defined in table 1:

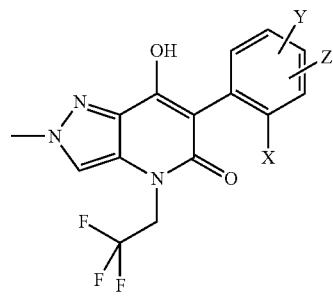

TABLE 34

Inventive compounds of the formula (I) in which G is hydrogen, V is SO2, W is trifluoroethyl, A is A5, R$^{11}$ is hydrogen, R$^{14}$ is methyl, and X, Y and Z are each as defined in table 1:

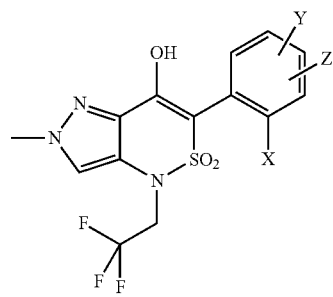

TABLE 35

Inventive compounds of the formula (I) in which G is hydrogen, V is C=O, W is propynyl, A is A5, R$^{11}$ is hydrogen, R$^{14}$ is methyl, and X, Y and Z are each as defined in table 1:

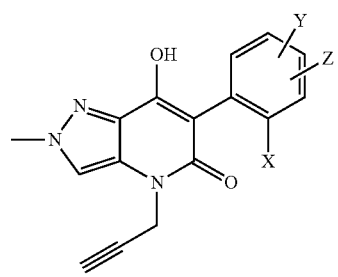

TABLE 36

Inventive compounds of the formula (I) in which G is hydrogen, V is C═O, W is propynyl, A is A5, $R^{11}$ is hydrogen, $R^{14}$ is methyl, and X, Y and Z are each as defined in table 1:

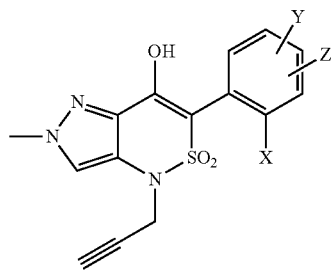

TABLE 37

Inventive compounds of the formula (I) in which G is hydrogen, V is C═O, W is difluoroethyl, A is A6, $R^{12}$ is hydrogen, $R^{14}$ is methyl, and X, Y and Z are each as defined in table 1:

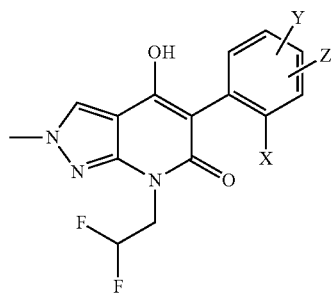

TABLE 38

Inventive compounds of the formula (I) in which G is hydrogen, V is SO2, W is difluoroethyl, A is A6, $R^{12}$ is hydrogen, $R^{14}$ is methyl, and X, Y and Z are each as defined in table 1:

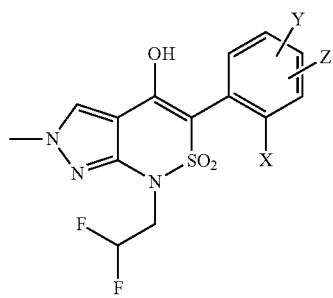

TABLE 39

Inventive compounds of the formula (I) in which G is hydrogen, V is C═O, W is trifluoroethyl, A is A6, $R^{12}$ is hydrogen, $R^{14}$ is methyl, and X, Y and Z are each as defined in table 1:

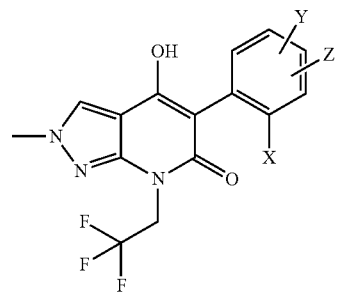

TABLE 40

Inventive compounds of the formula (I) in which G is hydrogen, V is $SO_2$, W is trifluoroethyl, A is A6, $R^{12}$ is hydrogen, $R^{14}$ is methyl, and X, Y and Z are each as defined in table 1:

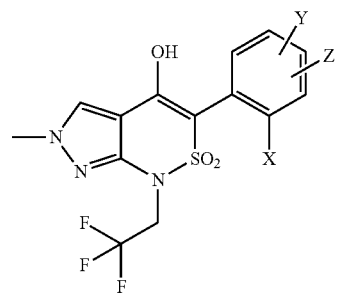

TABLE 41

Inventive compounds of the formula (I) in which G is hydrogen, V is C═O, W is propynyl, A is A6, $R^{12}$ is hydrogen, $R^{14}$ is methyl, and X, Y and Z are each as defined in table 1:

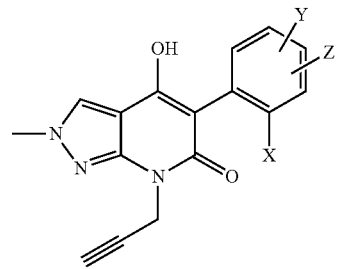

TABLE 42

Inventive compounds of the formula (I) in which G is hydrogen, V is C=O, W is propynyl, A is A6, $R^{12}$ is hydrogen, $R^{14}$ is methyl, and X, Y and Z are each as defined in table 1:

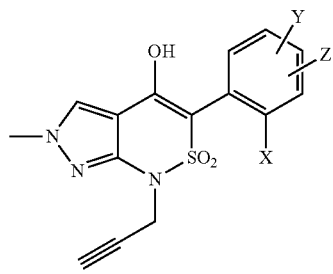

TABLE 43

Inventive compounds of the formula (I) in which G is hydrogen, V is C=O, W is difluoroethyl, A is A7, $R^{12}$ and $R^{13}$ are each hydrogen, and X, Y and Z are each as defined in table 1:

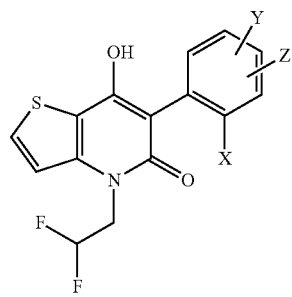

TABLE 44

Inventive compounds of the formula (I) in which G is hydrogen, V is $SO_2$, W is difluoroethyl, A is A7, $R^{12}$ and $R^{13}$ are each hydrogen, and X, Y and Z are each as defined in table 1:

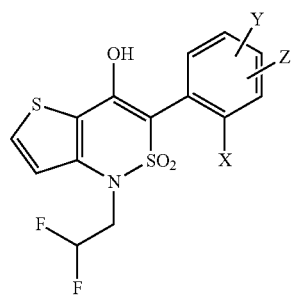

TABLE 45

Inventive compounds of the formula (I) in which G is hydrogen, V is C=O, W is trifluoroethyl, A is A7, $R^{12}$ and $R^{13}$ are each hydrogen, and X, Y and Z are each as defined in table 1:

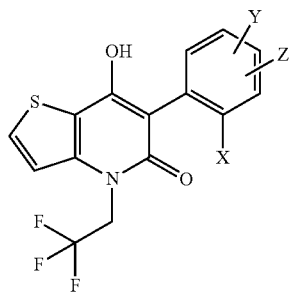

TABLE 46

Inventive compounds of the formula (I) in which G is hydrogen, V is $SO_2$, W is trifluoroethyl, A is A7, $R^{12}$ and $R^{13}$ are each hydrogen, and X, Y and Z are each as defined in table 1:

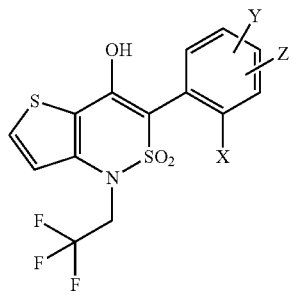

TABLE 47

Inventive compounds of the formula (I) in which G is hydrogen, V is C=O, W is propynyl, A is A7, $R^{12}$ and $R^{13}$ are each hydrogen, and X, Y and Z are each as defined in table 1:

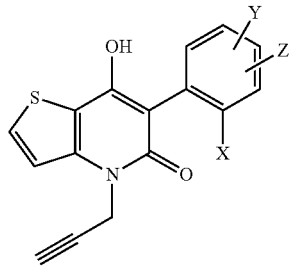

TABLE 48

Inventive compounds of the formula (I) in which G is hydrogen, V is SO$_2$, W is propynyl, A is A7, R$^{12}$ and R$^{13}$ are each hydrogen, and X, Y and Z are each as defined in table 1:

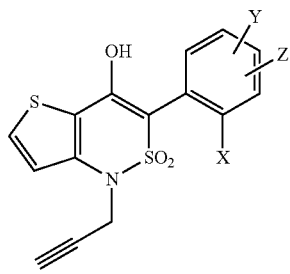

TABLE 49

Inventive compounds of the formula (I) in which G is hydrogen, V is C=O, W is difluoroethyl, A is A8, R$^{11}$ is hydrogen, R$^{14}$ is methyl, and X, Y and Z are each as defined in table 1:

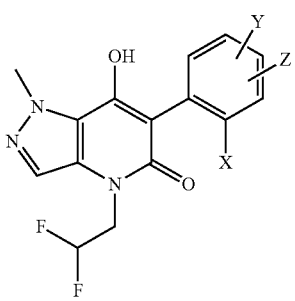

TABLE 50

Inventive compounds of the formula (I) in which G is hydrogen, V is SO$_2$, W is difluoroethyl, A is A8, R$^{11}$ is hydrogen, R$^{14}$ is methyl, and X, Y and Z are each as defined in table 1:

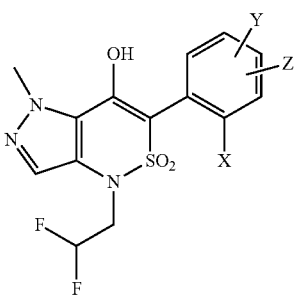

TABLE 51

Inventive compounds of the formula (I) in which G is hydrogen, V is C=O, W is trifluoroethyl, A is A8, R$^{11}$ is hydrogen, R$^{14}$ is methyl, and X, Y and Z are each as defined in table 1:

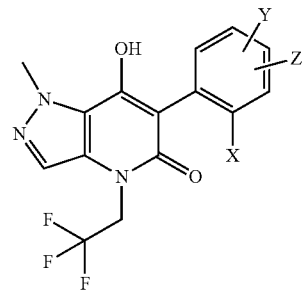

TABLE 52

Inventive compounds of the formula (I) in which G is hydrogen, V is SO$_2$, W is trifluoroethyl, A is A8, R$^{11}$ is hydrogen, R$^{14}$ is methyl, and X, Y and Z are each as defined in table 1:

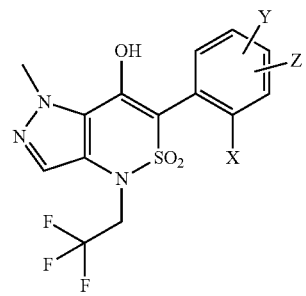

TABLE 53

Inventive compounds of the formula (I) in which G is hydrogen, V is C=O, W is propynyl, A is A8, R$^{11}$ is hydrogen, R$^{14}$ is methyl, and X, Y and Z are each as defined in table 1:

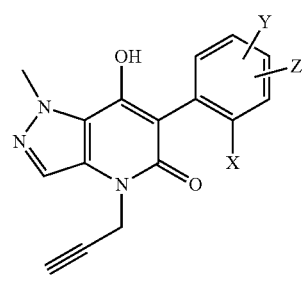

TABLE 54

Inventive compounds of the formula (I) in which G is hydrogen, V is SO$_2$, W is propynyl, A is A8, R$^{11}$ is hydrogen, R$^{14}$ is methyl, and X, Y and Z are each as defined in table 1:

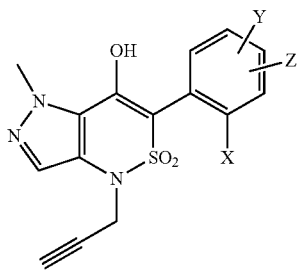

TABLE 55

Inventive compounds of the formula (I) in which G is hydrogen, V is C=O, W is difluoroethyl, A is A9, R$^{10}$ is hydrogen, and X, Y and Z are each as defined in table 1:

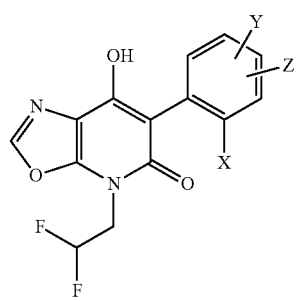

TABLE 56

Inventive compounds of the formula (I) in which G is hydrogen, V is SO$_2$, W is difluoroethyl, A is A9, R$^{10}$ is hydrogen, and X, Y and Z are each as defined in table 1:

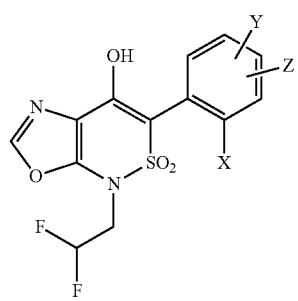

TABLE 57

Inventive compounds of the formula (I) in which G is hydrogen, V is C=O, W is trifluoroethyl, A is A9, R$^{10}$ is hydrogen, and X, Y and Z are each as defined in table 1:

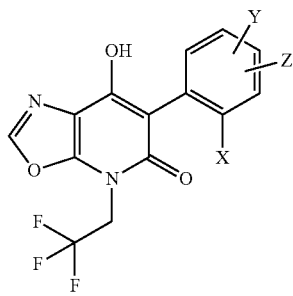

TABLE 58

Inventive compounds of the formula (I) in which G is hydrogen, V is SO$_2$, W is trifluoroethyl, A is A9, R$^{10}$ is hydrogen, and X, Y and Z are each as defined in table 1:

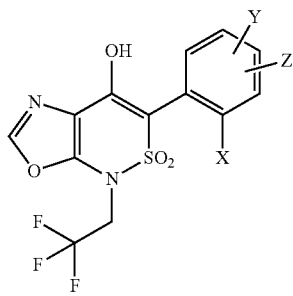

TABLE 59

Inventive compounds of the formula (I) in which G is hydrogen, V is C=O, W is propynyl, A is A9, R$^{10}$ is hydrogen, and X, Y and Z are each as defined in table 1:

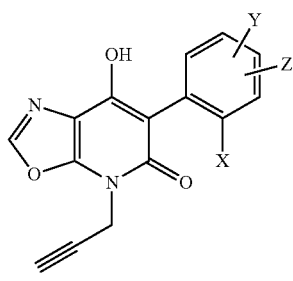

TABLE 60

Inventive compounds of the formula (I) in which G is hydrogen, V is SO$_2$, W is propynyl, A is A9, R$^{10}$ is hydrogen, and X, Y and Z are each as defined in table 1:

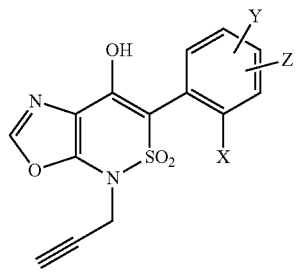

TABLE 61

Inventive compounds of the formula (I) in which G is hydrogen, V is C=O, W is difluorethyl, A is A10, R$^{12}$ and R$^{13}$ are each hydrogen, and X, Y and Z are each as defined in table 1:

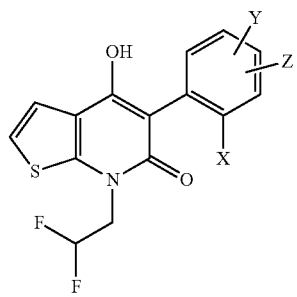

TABLE 62

Inventive compounds of the formula (I) in which G is hydrogen, V is SO$_2$, W is difluoroethyl, A is A10, R$^{12}$ and R$^{13}$ are each hydrogen, and X, Y and Z are each as defined in table 1:

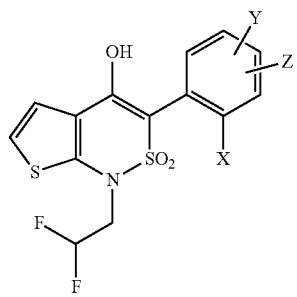

TABLE 63

Inventive compounds of the formula (I) in which G is hydrogen, V is C=O, W is trifluoroethyl, A is A10, R$^{12}$ and R$^{13}$ are each hydrogen, and X, Y and Z are each as defined in table 1:

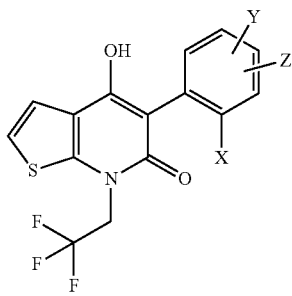

TABLE 64

Inventive compounds of the formula (I) in which G is hydrogen, V is SO$_2$, W is trifluoroethyl, A is A10, R$^{12}$ and R$^{13}$ are each hydrogen, and X, Y and Z are each as defined in table 1:

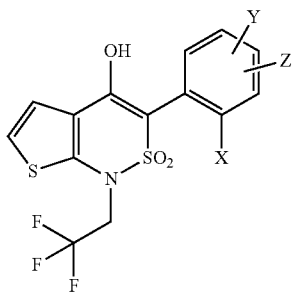

TABLE 65

Inventive compounds of the formula (I) in which G is hydrogen, V is C=O, W is propynyl, A is A10, R$^{12}$ and R$^{13}$ are each hydrogen, and X, Y and Z are each as defined in table 1:

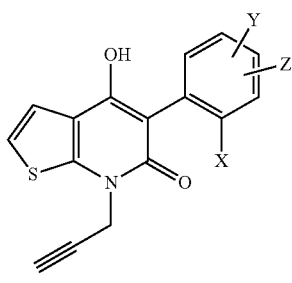

TABLE 66

Inventive compounds of the formula (I) in which G is hydrogen, V is SO$_2$, W is propynyl, A is A10, R$^{12}$ and R$^{13}$ are each hydrogen, and X, Y and Z are each as defined in table 1:

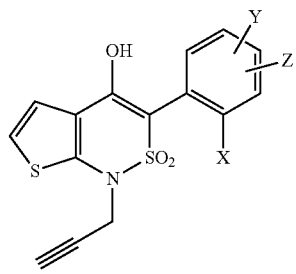

TABLE 67

Inventive compounds of the formula (I) in which G is hydrogen, V is C=O, W is difluoroethyl, A is A11, R$^{12}$ is hydrogen, R$^{14}$ is methyl, and X, Y and Z are each as defined in table 1:

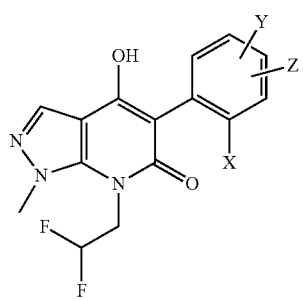

TABLE 68

Inventive compounds of the formula (I) in which G is hydrogen, V is SO$_2$, W is difluoroethyl, A is A11, R$^{12}$ is hydrogen, R$^{14}$ is methyl, and X, Y and Z are each as defined in table 1:

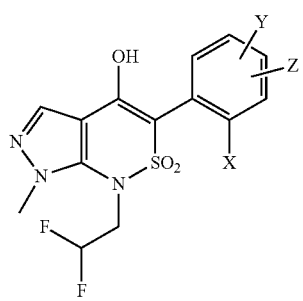

TABLE 69

Inventive compounds of the formula (I) in which G is hydrogen, V is C=O, W is trifluoroethyl, A is A11, R$^{12}$ is hydrogen, R$^{14}$ is methyl, and X, Y and Z are each as defined in table 1:

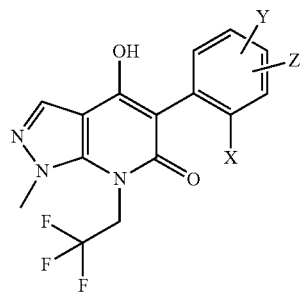

TABLE 70

Inventive compounds of the formula (I) in which G is hydrogen, V is SO$_2$, W is trifluoroethyl, A is A11, R$^{12}$ is hydrogen, R$^{14}$ is methyl, and X, Y and Z are each as defined in table 1:

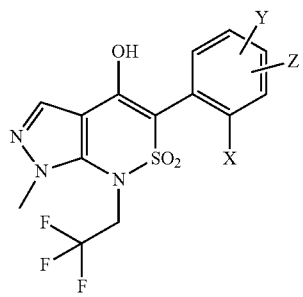

TABLE 71

Inventive compounds of the formula (I) in which G is hydrogen, V is C=O, W is propynyl, A is A11, R$^{12}$ is hydrogen, R$^{14}$ is methyl, and X, Y and Z are each as defined in table 1:

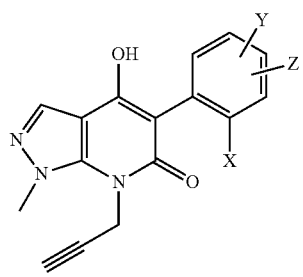

TABLE 72

Inventive compounds of the formula (I) in which G is hydrogen, V is SO₂, W is propynyl, A is A11, $R^{12}$ is hydrogen, $R^{14}$ is methyl, and X, Y and Z are each as defined in table 1:

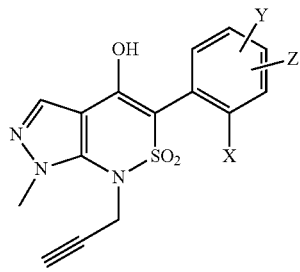

TABLE 73

Inventive compounds of the formula (I) in which G is hydrogen, V is SO₂, W is methyl, A is A1, and X, Y and Z are each as defined in table 1:

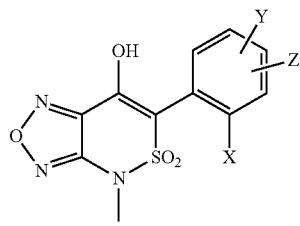

TABLE 74

Inventive compounds of the formula (I) in which G is hydrogen, V is C=O, W is methyl, A is A1, and X, Y and Z are each as defined in table 1:

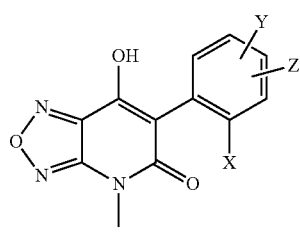

TABLE 75

Inventive compounds of the formula (I) in which G is hydrogen, V is SO₂, W is methyl, A is A2, $R^{10}$ is hydrogen, and X, Y and Z are each as defined in table 1:

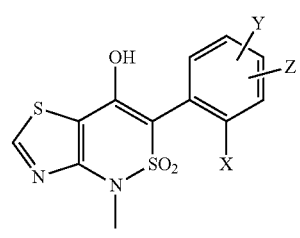

TABLE 76

Inventive compounds of the formula (I) in which G is hydrogen, V is C=O, W is methyl, A is A2, $R^{10}$ is hydrogen, and X, Y and Z are each as defined in table 1:

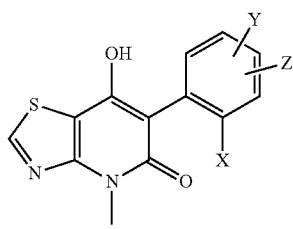

TABLE 77

Inventive compounds of the formula (I) in which G is hydrogen, V is SO₂, W is methyl, A is A2, $R^{10}$ is methylthio, and X, Y and Z are each as defined in table 1:

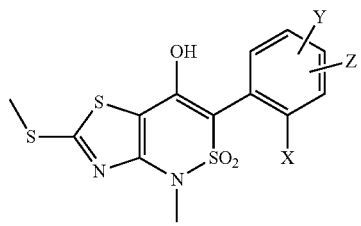

TABLE 78

Inventive compounds of the formula (I) in which G is hydrogen, V is C=O, W is methyl, A is A2, $R^{10}$ is methylthio, and X, Y and Z are each as defined in table 1:

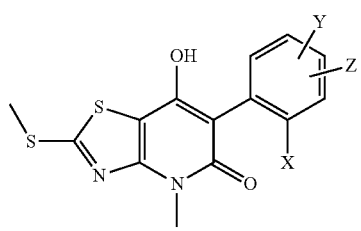

TABLE 79

Inventive compounds of the formula (I) in which G is hydrogen, V is SO₂, W is methyl, A is A3, $R^{10}$ is hydrogen, and X, Y and Z are each as defined in table 1:

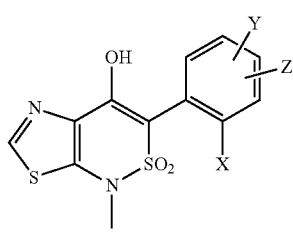

TABLE 80

Inventive compounds of the formula (I) in which G is hydrogen, V is C=O, W is methyl, A is A3, $R^{10}$ is hydrogen, and X, Y and Z are each as defined in table 1:

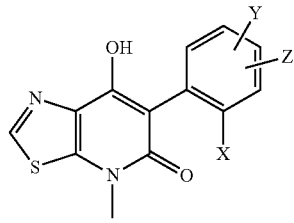

TABLE 81

Inventive compounds of the formula (I) in which G is hydrogen, V is $SO_2$, W is methyl, A is A4, $R^{12}$ and $R^{13}$ are each hydrogen, and X, Y and Z are each as defined in table 1:

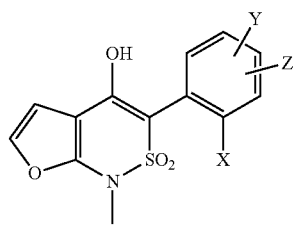

TABLE 82

Inventive compounds of the formula (I) in which G is hydrogen, V is C=O, W is methyl, A is A4, $R^{12}$ and $R^{13}$ are each hydrogen, and X, Y and Z are each as defined in table 1:

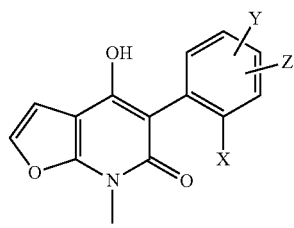

TABLE 83

Inventive compounds of the formula (I) in which G is hydrogen, V is $SO_2$, W is methyl, A is A5, $R^{11}$ is hydrogen, $R^{14}$ is methyl, and X, Y and Z are each as defined in table 1:

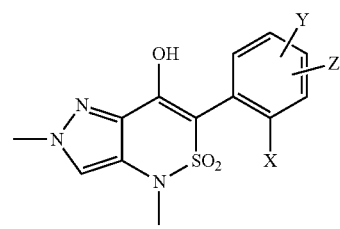

TABLE 84

Inventive compounds of the formula (I) in which G is hydrogen, V is C=O, W is methyl, A is A5, $R^{11}$ is hydrogen, $R^{14}$ is methyl, and X, Y and Z are each as defined in table 1:

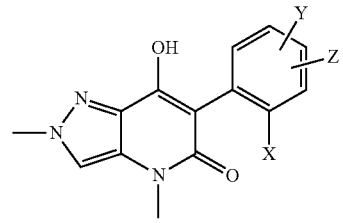

TABLE 85

Inventive compounds of the formula (I) in which G is hydrogen, V is $SO_2$, W is methyl, A is A6, $R^{12}$ is hydrogen, $R^{14}$ is methyl, and X, Y and Z are each as defined in table 1:

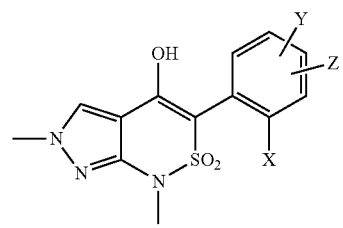

TABLE 86

Inventive compounds of the formula (I) in which G is hydrogen, V is C=O, W is methyl, A is A6, $R^{12}$ is hydrogen, $R^{14}$ is methyl, and X, Y and Z are each as defined in table 1:

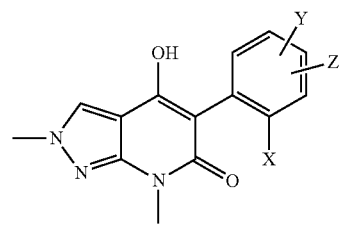

TABLE 87

Inventive compounds of the formula (I) in which G is hydrogen, V is $SO_2$, W is methyl, A is A7, $R^{12}$ and $R^{13}$ are each hydrogen, and X, Y and Z are each as defined in table 1:

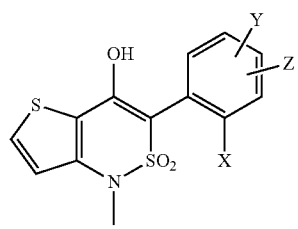

TABLE 88

Inventive compounds of the formula (I) in which G is hydrogen, V is C=O, W is methyl, A is A7, $R^{12}$ and $R^{13}$ are each hydrogen, and X, Y and Z are each as defined in table 1:

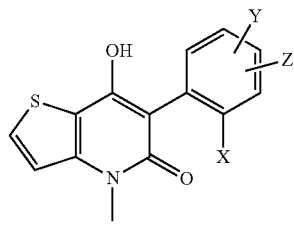

TABLE 89

Inventive compounds of the formula (I) in which G is hydrogen, V is $SO_2$, W is methyl, A is A8, $R^{11}$ is hydrogen, $R^{14}$ is methyl, and X, Y and Z are each as defined in table 1:

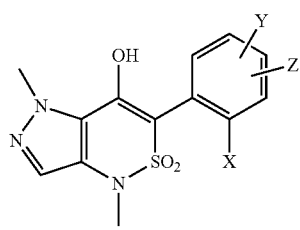

TABLE 90

Inventive compounds of the formula (I) in which G is hydrogen, V is C=O, W is methyl, A is A8, $R^{11}$ is hydrogen, $R^{14}$ is methyl, and X, Y and Z are each as defined in table 1:

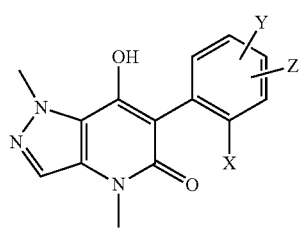

TABLE 91

Inventive compounds of the formula (I) in which G is hydrogen, V is $SO_2$, W is methyl, A is A9, $R^{10}$ is hydrogen, and X, Y and Z are each as defined in table 1:

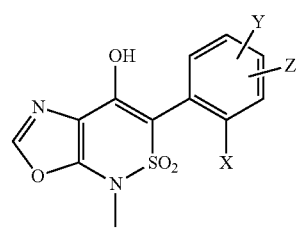

TABLE 92

Inventive compounds of the formula (I) in which G is hydrogen, V is C=O, W is methyl, A is A9, $R^{10}$ is hydrogen, and X, Y and Z are each as defined in table 1:

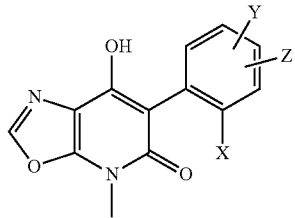

TABLE 93

Inventive compounds of the formula (I) in which G is hydrogen, V is $SO_2$, A is A10, $R^{12}$ and $R^{13}$ are each hydrogen, and X, Y and Z are each as defined in table 1:

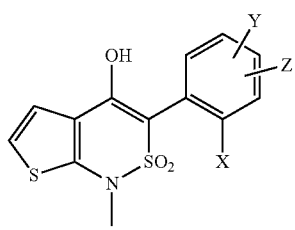

TABLE 94

Inventive compounds of the formula (I) in which G is hydrogen, V is C=O, W is methyl, A is A10, $R^{12}$ and $R^{13}$ are each hydrogen, and X, Y and Z are each as defined in table 1:

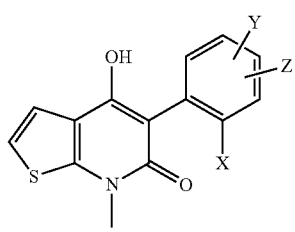

TABLE 95

Inventive compounds of the formula (I) in which G is hydrogen, V is $SO_2$, W is methyl, A is A11, $R^{12}$ is hydrogen, $R^{14}$ is methyl, and X, Y and Z are each as defined in table 1:

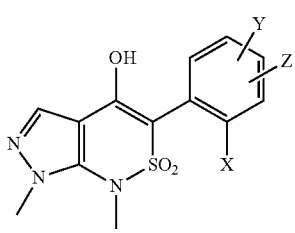

TABLE 96

Inventive compounds of the formula (I) in which G is hydrogen, V is C=O, W is methyl, A is A11, $R^{12}$ is hydrogen, $R^{14}$ is methyl, and X, Y and Z are each as defined in table 1:

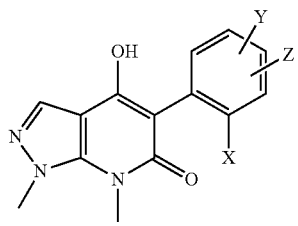

TABLE 97

Inventive compounds of the formula (I) in which G is hydrogen, V is $SO_2$, W is ethyl, A is A1, and X, Y and Z are each as defined in table 1:

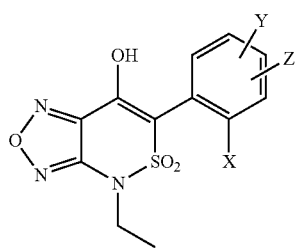

TABLE 98

Inventive compounds of the formula (I) in which G is hydrogen, V is C=O, W is ethyl, A is A1, and X, Y and Z are each as defined in table 1:

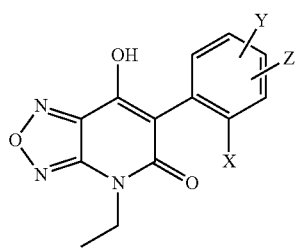

TABLE 99

Inventive compounds of the formula (I) in which G is hydrogen, V is $SO_2$, W is ethyl, A is A2, $R^{10}$ is hydrogen, and X, Y and Z are each as defined in table 1:

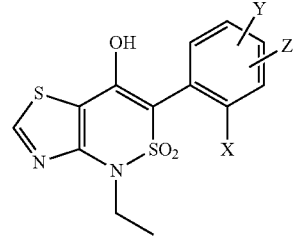

TABLE 100

Inventive compounds of the formula (I) in which G is hydrogen, V is C=O, W is ethyl, A is A2, $R^{10}$ is hydrogen, and X, Y and Z are each as defined in table 1:

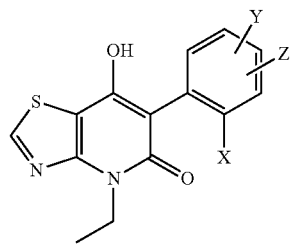

TABLE 101

Inventive compounds of the formula (I) in which G is hydrogen, V is $SO_2$, W is ethyl, A is A2, $R^{10}$ is methylthio, and X, Y and Z are each as defined in table 1:

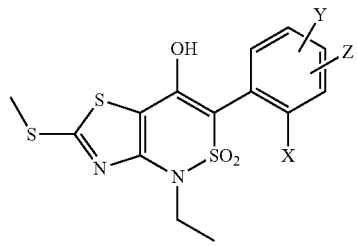

TABLE 102

Inventive compounds of the formula (I) in which G is hydrogen, V is C=O, W is ethyl, A is A2, $R^{10}$ is methylthio, and X, Y and Z are each as defined in table 1:

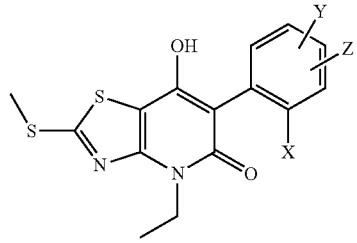

TABLE 103

Inventive compounds of the formula (I) in which G is hydrogen, V is $SO_2$, W is ethyl, A is A3, $R^{10}$ is hydrogen, and X, Y and Z are each as defined in table 1:

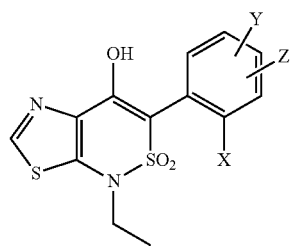

TABLE 104

Inventive compounds of the formula (I) in which G is hydrogen, V is C=O, W is ethyl, A is A3, $R^{10}$ is hydrogen, and X, Y and Z are each as defined in table 1:

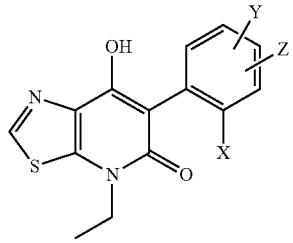

TABLE 105

Inventive compounds of the formula (I) in which G is hydrogen, V is $SO_2$, W is ethyl, A is A4, $R^{12}$ and $R^{13}$ are each hydrogen, and X, Y and Z are each as defined in table 1:

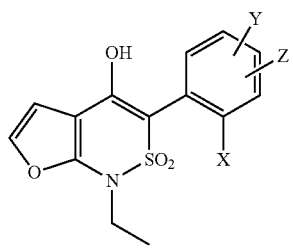

TABLE 106

Inventive compounds of the formula (I) in which G is hydrogen, V is C=O, W is ethyl, A is A4, $R^{12}$ and $R^{13}$ are each hydrogen, and X, Y and Z are each as defined in table 1:

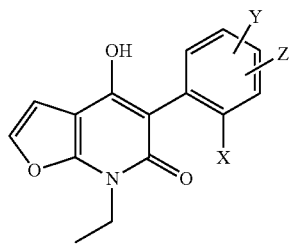

TABLE 107

Inventive compounds of the formula (I) in which G is hydrogen, V is SO2, W is ethyl, A is A5, $R^{11}$ is hydrogen, $R^{14}$ is methyl, and X, Y and Z are each as defined in table 1:

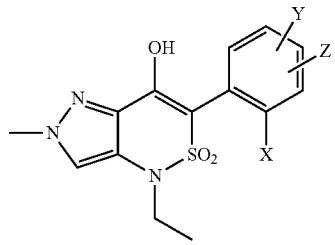

TABLE 108

Inventive compounds of the formula (I) in which G is hydrogen, V is C=O, W is ethyl, A is A5, $R^{11}$ is hydrogen, $R^{14}$ is methyl, and X, Y and Z are each as defined in table 1:

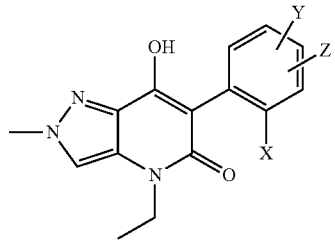

TABLE 109

Inventive compounds of the formula (I) in which G is hydrogen, V is $SO_2$, W is ethyl, A is A6, $R^{12}$ is hydrogen, $R^{14}$ is methyl, and X, Y and Z are each as defined in table 1:

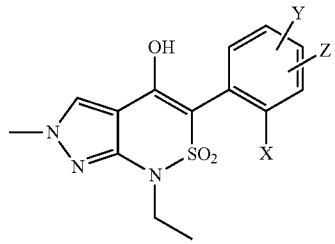

TABLE 110

Inventive compounds of the formula (I) in which G is hydrogen, V is C=O, W is ethyl, A is A6, $R^{12}$ is hydrogen, $R^{14}$ is methyl, and X, Y and Z are each as defined in table 1:

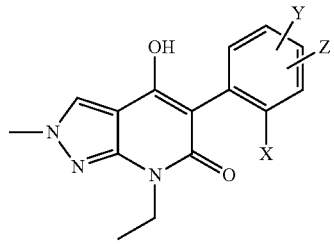

TABLE 111

Inventive compounds of the formula (I) in which G is hydrogen, V is $SO_2$, W is ethyl, A is A7, $R^{12}$ and $R^{13}$ are each hydrogen, and X, Y and Z are each as defined in table 1:

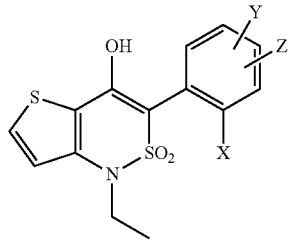

TABLE 112

Inventive compounds of the formula (I) in which G is hydrogen, V is C=O, W is ethyl, A is A7, $R^{12}$ and $R^{13}$ are each hydrogen, and X, Y and Z are each as defined in table 1:

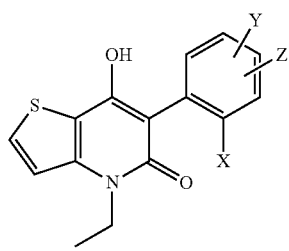

TABLE 113

Inventive compounds of the formula (I) in which G is hydrogen, V is $SO_2$, W is ethyl, A is A8, $R^{11}$ is hydrogen, $R^{14}$ is methyl, and X, Y and Z are each as defined in table 1:

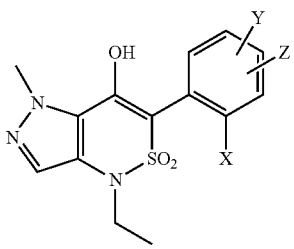

TABLE 114

Inventive compounds of the formula (I) in which G is hydrogen, V is C=O, W is ethyl, A is A8, $R^{11}$ is hydrogen, $R^{14}$ is methyl, and X, Y and Z are each as defined in table 1:

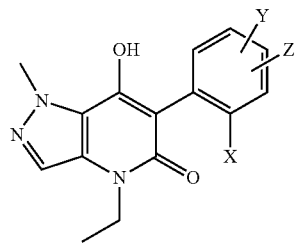

TABLE 115

Inventive compounds of the formula (I) in which G is hydrogen, V is $SO_2$, W is ethyl, A is A9, $R^{10}$ is hydrogen, and X, Y and Z are each as defined in table 1:

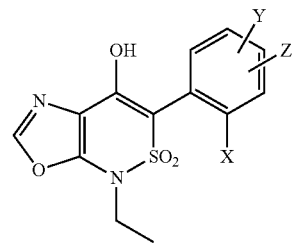

TABLE 116

Inventive compounds of the formula (I) in which G is hydrogen, V is C=O, W is ethyl, A is A9, $R^{10}$ is hydrogen, and X, Y and Z are each as defined in table 1:

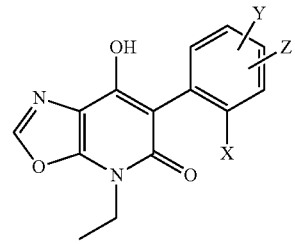

TABLE 117

Inventive compounds of the formula (I) in which G is hydrogen, V is $SO_2$, W is ethyl, A is A10, $R^{12}$ and $R^{13}$ are each hydrogen, and X, Y and Z are each as defined in table 1:

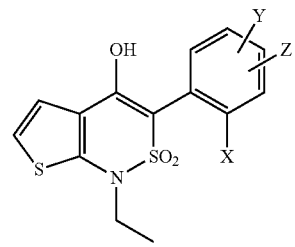

TABLE 118

Inventive compounds of the formula (I) in which G is hydrogen, V is C=O, W is ethyl, A is A10, $R^{12}$ and $R^{13}$ are each hydrogen, and X, Y and Z are each as defined in table 1:

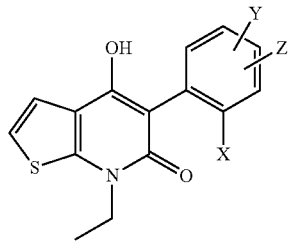

TABLE 119

Inventive compounds of the formula (I) in which G is hydrogen, V is $SO_2$, W is ethyl, A is A11, $R^{12}$ is hydrogen, $R^{14}$ is methyl, and X, Y and Z are each as defined in table 1:

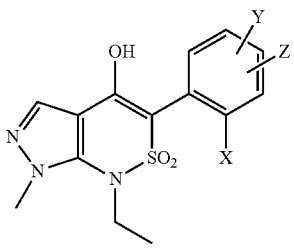

TABLE 120

Inventive compounds of the formula (I) in which G is hydrogen, V is C=O, W is ethyl, A is A11, $R^{12}$ is hydrogen, $R^{14}$ is methyl, and X, Y and Z are each as defined in table 1:

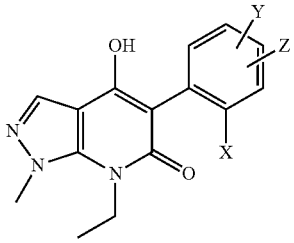

TABLE 121

Inventive compounds of the formula (I) in which G is hydrogen, V is $SO_2$, W is ethyl, A is A10, $R^{12}$ is ethyl and $R^{13}$ is methyl, and X, Y and Z are each as defined in table 1:

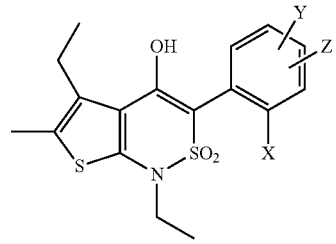

TABLE 122

Inventive compounds of the formula (I) in which G is hydrogen, V is C=O, W is ethyl, A is A10, $R^{12}$ is ethyl and $R^{13}$ is methyl, and X, Y and Z are each as defined in table 1:

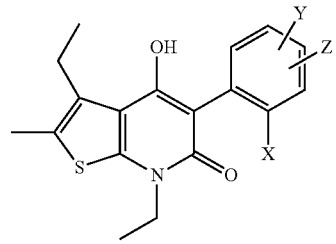

TABLE 123

Inventive compounds of the formula (I) in which G is hydrogen, V is $SO_2$, W is ethyl, A is A10, $R^{12}$ and $R^{13}$ are each methyl, and X, Y and Z are each as defined in table 1:

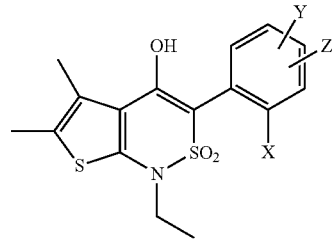

TABLE 124

Inventive compounds of the formula (I) in which G is hydrogen, V is C=O, W is ethyl, A is A10, $R^{12}$ and $R^{13}$ are each methyl, and X, Y and Z are each as defined in table 1:

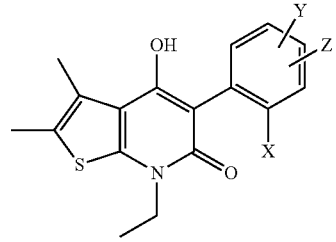

TABLE 125

Inventive compounds of the formula (I) in which G is hydrogen, V is SO$_2$, W is ethyl, A is A7, R$^{12}$ is phenyl and R$^{13}$ is hydrogen, and X, Y and Z are each as defined in table 1:

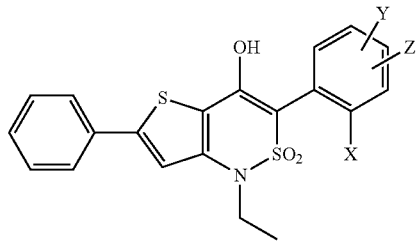

TABLE 126

Inventive compounds of the formula (I) in which G is hydrogen, V is C=O, W is ethyl, A is A10, R$^{12}$ is phenyl and R$^{13}$ is hydrogen, and X, Y and Z are each as defined in table 1:

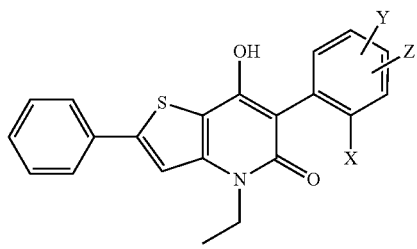

TABLE 127

Inventive compounds of the formula (I) in which G is hydrogen, V is SO$_2$, W is ethyl, A is A2, R$^{10}$ is methyl, and X, Y and Z are each as defined in table 1:

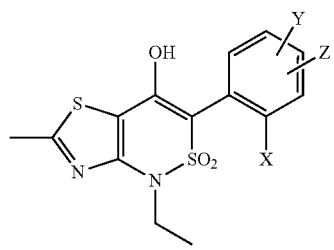

TABLE 128

Inventive compounds of the formula (I) in which G is hydrogen, V is C=O, W is ethyl, A is A2, R$^{10}$ is methyl, and X, Y and Z are each as defined in table 1:

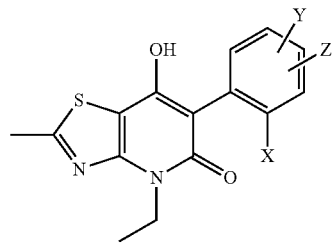

TABLE 129

Inventive compounds of the formula (I) in which G is hydrogen, V is SO$_2$, W is ethyl, A is A2, R$^{10}$ is ethyl, and X, Y and Z are each as defined in table 1:

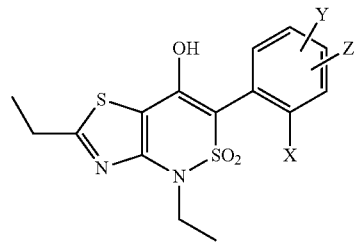

TABLE 130

Inventive compounds of the formula (I) in which G is hydrogen, V is C=O, W is ethyl, A is A2, R$^{10}$ is ethyl, and X, Y and Z are each as defined in table 1:

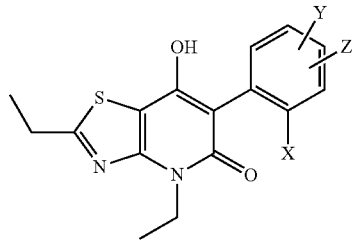

TABLE 131

Inventive compounds of the formula (I) in which G is hydrogen, V is SO$_2$, W is ethyl, A is A2, R$^{10}$ is n-propyl, and X, Y and Z are each as defined in table 1:

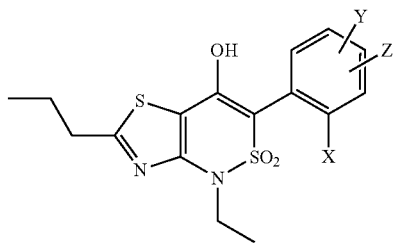

TABLE 132

Inventive compounds of the formula (I) in which G is hydrogen, V is C=O, W is ethyl, A is A2, R$^{10}$ is n-propyl, and X, Y and Z are each as defined in table 1:

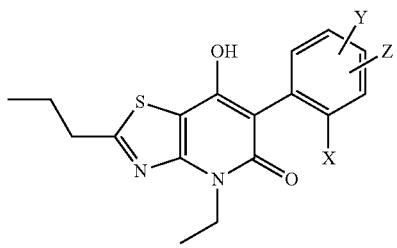

TABLE 133

Inventive compounds of the formula (I) in which G is hydrogen, V is SO$_2$, W is ethyl, A is A2, R$^{10}$ is i-propyl, and X, Y and Z are each as defined in table 1:

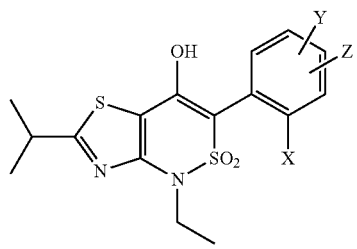

TABLE 134

Inventive compounds of the formula (I) in which G is hydrogen, V is C=O, W is ethyl, A is A2, R$^{10}$ is i-propyl, and X, Y and Z are each as defined in table 1:

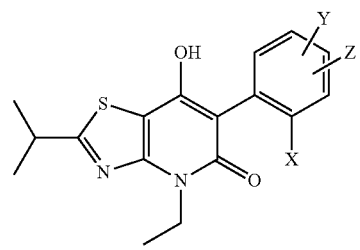

TABLE 135

Inventive compounds of the formula (I) in which G is hydrogen, V is SO$_2$, W is ethyl, A is A2, R$^{10}$ is c-propyl, and X, Y and Z are each as defined in table 1:

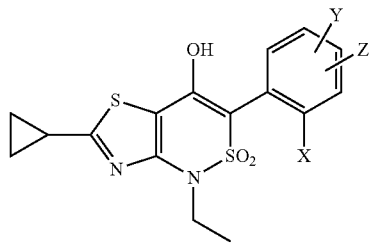

TABLE 136

Inventive compounds of the formula (I) in which G is hydrogen, V is C=O, W is ethyl, A is A2, R$^{10}$ is c-propyl, and X, Y and Z are each as defined in table 1:

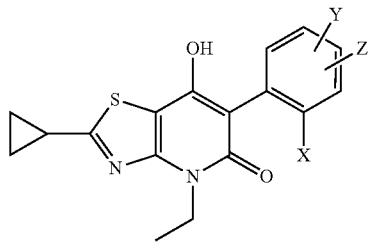

TABLE 137

Inventive compounds of the formula (I) in which G is hydrogen, V is SO$_2$, W is ethyl, A is A2, R$^{10}$ is methoxy, and X, Y and Z are each as defined in table 1:

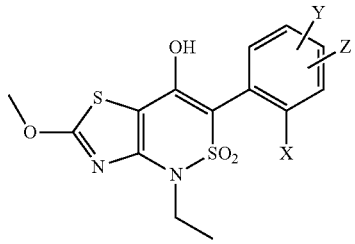

TABLE 138

Inventive compounds of the formula (I) in which G is hydrogen, V is C=O, W is ethyl, A is A2, R$^{10}$ is methoxy, and X, Y and Z are each as defined in table 1:

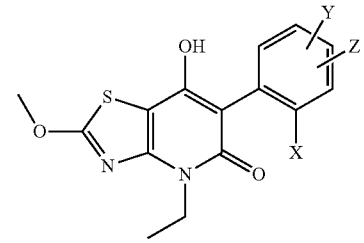

TABLE 139

Inventive compounds of the formula (I) in which G is hydrogen, V is $SO_2$, W is ethyl, A is A2, $R^{10}$ is ethoxy, and X, Y and Z are each as defined in table 1:

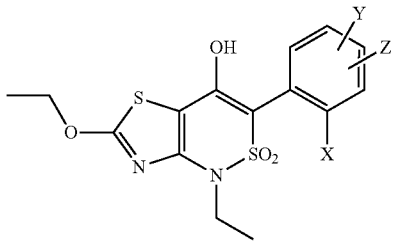

TABLE 140

Inventive compounds of the formula (I) in which G is hydrogen, V is C=O, W is ethyl, A is A2, $R^{10}$ is ethoxy, and X, Y and Z are each as defined in table 1:

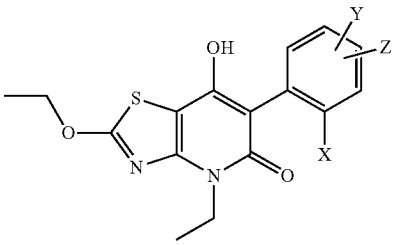

TABLE 141

Inventive compounds of the formula (I) in which G is hydrogen, V is $SO_2$, W is ethyl, A is A2, $R^{10}$ is methoxyethoxy, and X, Y and Z are each as defined in table 1:

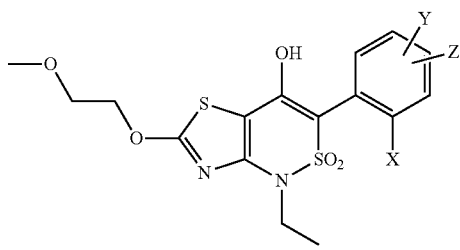

TABLE 142

Inventive compounds of the formula (I) in which G is hydrogen, V is C=O, W is ethyl, A is A2, $R^{10}$ is methoxyethoxy, and X, Y and Z are each as defined in table 1:

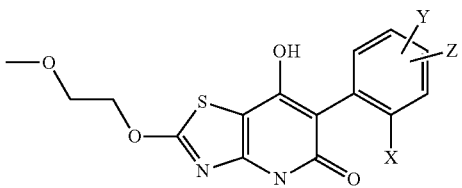

TABLE 143

Inventive compounds of the formula (I) in which G is hydrogen, V is $SO_2$, W is ethyl, A is A12, and X, Y and Z are each as defined in table 1:

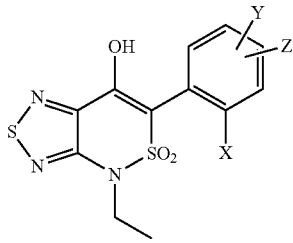

TABLE 144

Inventive compounds of the formula (I) in which G is hydrogen, V is C=O, W is ethyl, A is A12, and X, Y and Z are each as defined in table 1:

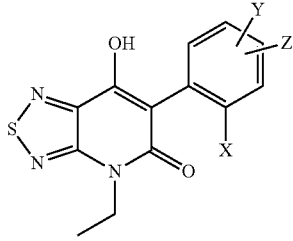

TABLE 145

Inventive compounds of the formula (I) in which G is hydrogen, V is $SO_2$, W is ethyl, A is A6, $R^{12}$ is hydrogen, $R^{14}$ is ethyl, and X, Y and Z are each as defined in table 1:

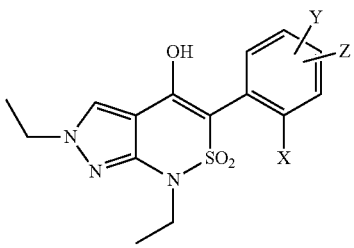

TABLE 146

Inventive compounds of the formula (I) in which G is hydrogen, V is C=O, W is ethyl, A is A6, $R^{12}$ is hydrogen, $R^{14}$ is ethyl, and X, Y and Z are each as defined in table 1:

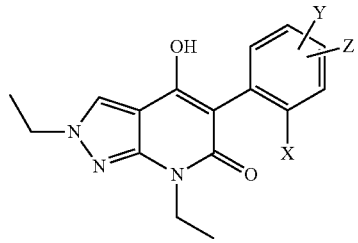

TABLE 147

Inventive compounds of the formula (I) in which G is hydrogen, V is SO$_2$, W is 2,2-difluoroethyl, A is A10, $R^{12}$ is ethyl and $R^{13}$ is methyl, and X, Y and Z are each as defined in table 1:

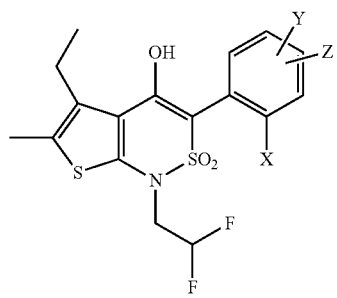

TABLE 148

Inventive compounds of the formula (I) in which G is hydrogen, V is C=O, W is 2,2-difluoroethyl, A is A10, $R^{12}$ is ethyl and $R^{13}$ is methyl, and X, Y and Z are each as defined in table 1:

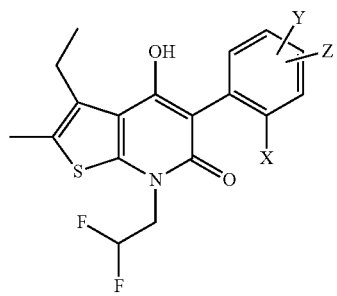

TABLE 149

Inventive compounds of the formula (I) in which G is hydrogen, V is SO$_2$, W is 2,2-difluoroethyl, A is A10, $R^{12}$ and $R^{13}$ are each methyl, and X, Y and Z are each as defined in table 1:

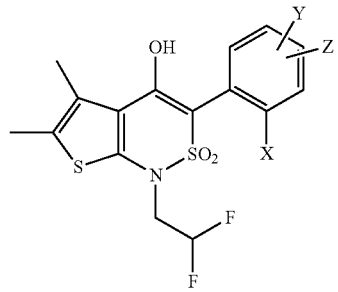

TABLE 150

Inventive compounds of the formula (I) in which G is hydrogen, V is C=O, W is 2,2-difluoroethyl, A is A10, $R^{12}$ and $R^{13}$ are each methyl, and X, Y and Z are each as defined in table 1:

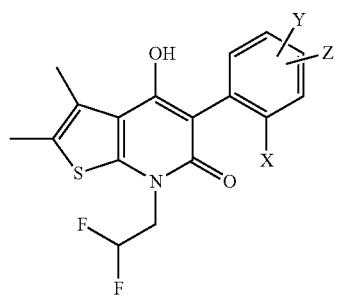

TABLE 151

Inventive compounds of the formula (I) in which G is hydrogen, V is SO$_2$, W is 2,2-difluoroethyl, A is A7, $R^{12}$ is phenyl and $R^{13}$ is hydrogen, and X, Y and Z are each as defined in table 1:

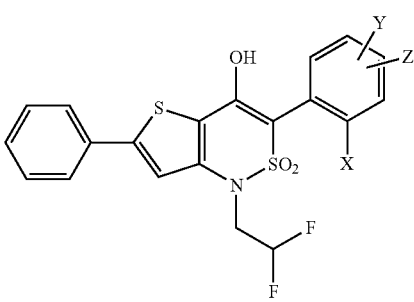

TABLE 152

Inventive compounds of the formula (I) in which G is hydrogen, V is C=O, W is 2,2-difluoroethyl, A is A10, R$^{12}$ is phenyl and R$^{13}$ is hydrogen, and X, Y and Z are each as defined in table 1:

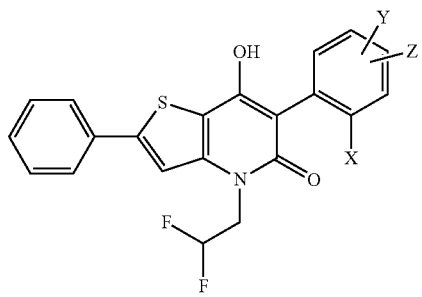

TABLE 153

Inventive compounds of the formula (I) in which G is hydrogen, V is SO$_2$, W is 2,2-difluoroethyl, A is A2, R$^{10}$ is methyl, and X, Y and Z are each as defined in table 1:

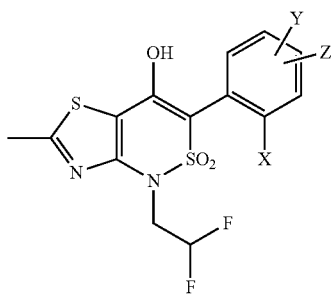

TABLE 154

Inventive compounds of the formula (I) in which G is hydrogen, V is C=O, W is 2,2-difluoroethyl, A is A2, R$^{10}$ is methyl, and X, Y and Z are each as defined in table 1:

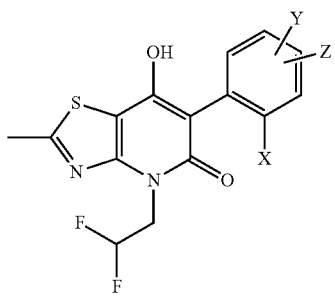

TABLE 155

Inventive compounds of the formula (I) in which G is hydrogen, V is SO$_2$, W is 2,2-difluoroethyl, A is A2, R$^{10}$ is ethyl, and X, Y and Z are each as defined in table 1:

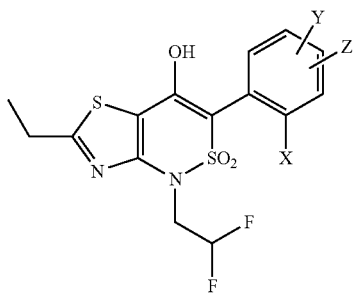

TABLE 156

Inventive compounds of the formula (I) in which G is hydrogen, V is C=O, W is 2,2-difluoroethyl, A is A2, R$^{10}$ is ethyl, and X, Y and Z are each as defined in table 1:

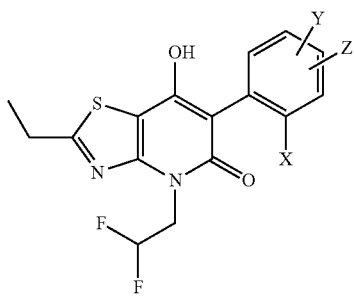

TABLE 157

Inventive compounds of the formula (I) in which G is hydrogen, V is SO$_2$, W is 2,2-difluoroethyl, A is A2, R$^{10}$ is n-propyl, and X, Y and Z are each as defined in table 1:

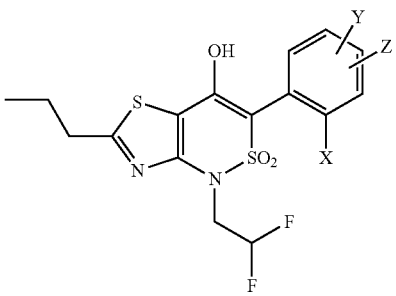

TABLE 158

Inventive compounds of the formula (I) in which G is hydrogen, V is C=O, W is 2,2-difluoroethyl, A is A2, R[10] is n-propyl, and X, Y and Z are each as defined in table 1:

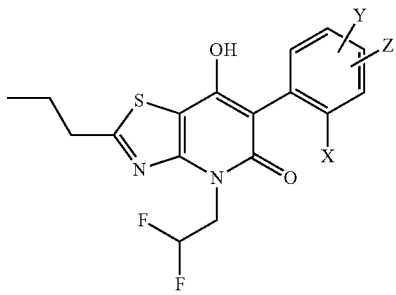

TABLE 159

Inventive compounds of the formula (I) in which G is hydrogen, V is SO$_2$, W is 2,2-difluoroethyl, A is A2, R[10] is i-propyl, and X, Y and Z are each as defined in table 1:

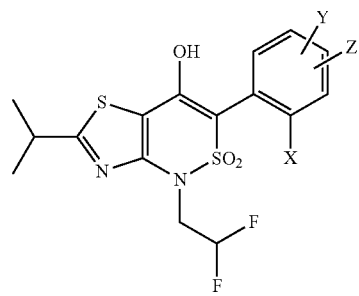

TABLE 160

Inventive compounds of the formula (I) in which G is hydrogen, V is C=O, W is 2,2-difluoroethyl, A is A2, R[10] is i-propyl, and X, Y and Z are each as defined in table 1:

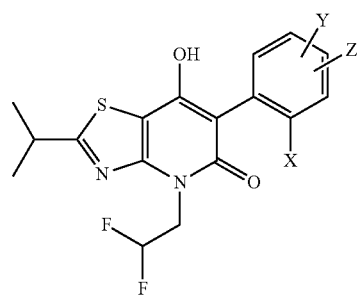

TABLE 161

Inventive compounds of the formula (I) in which G is hydrogen, V is SO$_2$, W is 2,2-difluoroethyl, A is A2, R[10] is c-propyl, and X, Y and Z are each as defined in table 1:

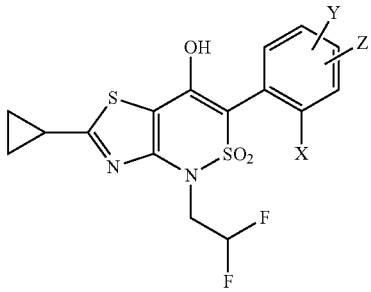

TABLE 162

Inventive compounds of the formula (I) in which G is hydrogen, V is C=O, W is 2,2-difluoroethyl, A is A2, R[10] is c-propyl, and X, Y and Z are each as defined in table 1:

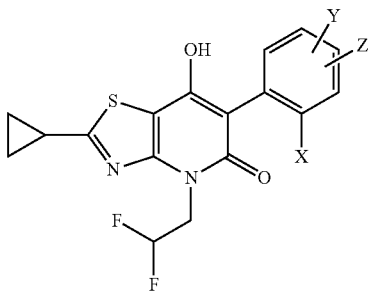

TABLE 163

Inventive compounds of the formula (I) in which G is hydrogen, V is SO$_2$, W is 2,2-difluoroethyl, A is A2, R[10] is methoxy, and X, Y and Z are each as defined in table 1:

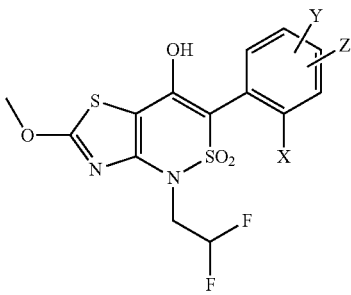

TABLE 164

Inventive compounds of the formula (I) in which G is hydrogen, V is C=O, W is 2,2-difluoroethyl, A is A2, $R^{10}$ is methoxy, and X, Y and Z are each as defined in table 1:

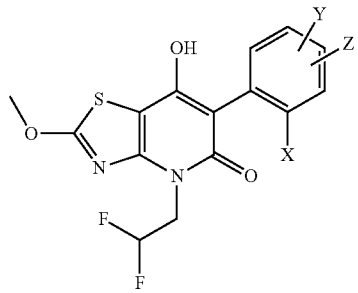

TABLE 165

Inventive compounds of the formula (I) in which G is hydrogen, V is $SO_2$, W is 2,2-difluoroethyl, A is A2, $R^{10}$ is ethoxy, and X, Y and Z are each as defined in table 1:

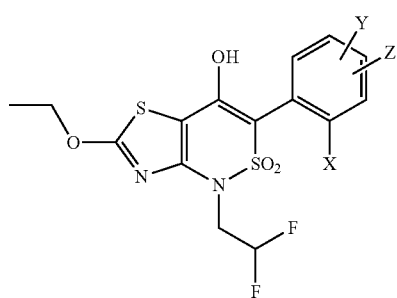

TABLE 166

Inventive compounds of the formula (I) in which G is hydrogen, V is C=O, W is 2,2-difluoroethyl, A is A2, $R^{10}$ is ethoxy, and X, Y and Z are each as defined in table 1:

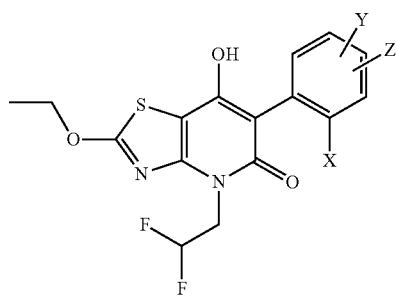

TABLE 167

Inventive compounds of the formula (I) in which G is hydrogen, V is $SO_2$, W is 2,2-difluoroethyl, A is A2, $R^{10}$ is methoxyethoxy, and X, Y and Z are each as defined in table 1:

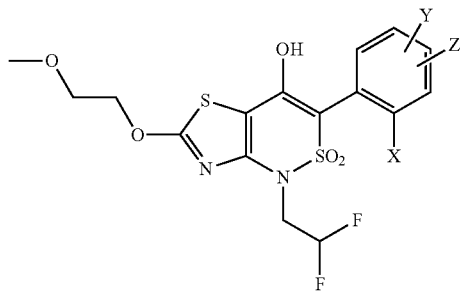

TABLE 168

Inventive compounds of the formula (I) in which G is hydrogen, V is C=O, W is 2,2-difluoroethyl, A is A2, $R^{10}$ is methoxyethoxy, and X, Y and Z are each as defined in table 1:

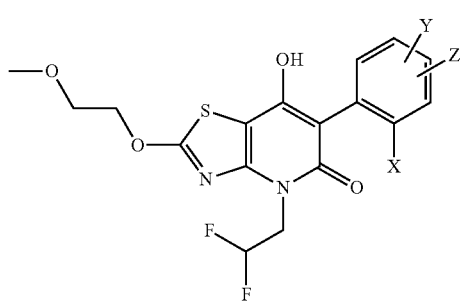

TABLE 169

Inventive compounds of the formula (I) in which G is hydrogen, V is $SO_2$, W is 2,2-difluoroethyl, A is A12, and X, Y and Z are each as defined in table 1:

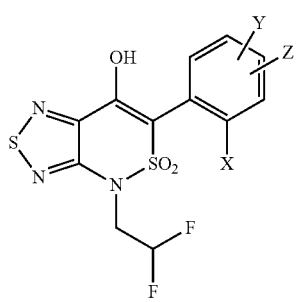

TABLE 170

Inventive compounds of the formula (I) in which G is hydrogen, V is C=O, W is 2,2-difluoroethyl, A is A12, and X, Y and Z are each as defined in table 1:

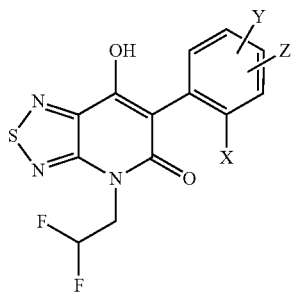

TABLE 171

Inventive compounds of the formula (I) in which G is hydrogen, V is SO$_2$, W is 2,2-difluoroethyl, A is A6, R$^{12}$ is hydrogen, R$^{14}$ is ethyl, and X, Y and Z are each as defined in table 1:

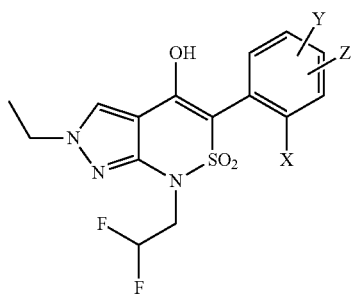

TABLE 172

Inventive compounds of the formula (I) in which G is hydrogen, V is C=O, W is 2,2-difluoroethyl, A is A6, R$^{12}$ is hydrogen, R$^{14}$ is ethyl, and X, Y and Z are each as defined in table 1:

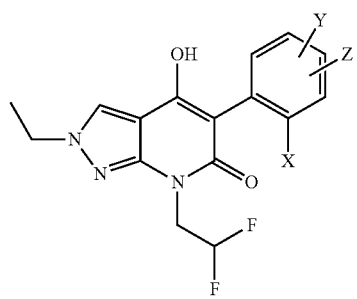

TABLE 173

Inventive compounds of the formula (I) in which G is hydrogen, V is SO$_2$, W is propynyl, A is A10, R$^{12}$ is ethyl and R$^{13}$ is methyl, and X, Y and Z are each as defined in table 1:

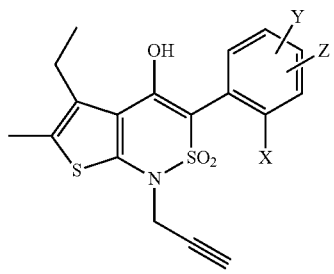

TABLE 174

Inventive compounds of the formula (I) in which G is hydrogen, V is C=O, W is propynyl, A is A10, R$^{12}$ is ethyl and R$^{13}$ is methyl, and X, Y and Z are each as defined in table 1:

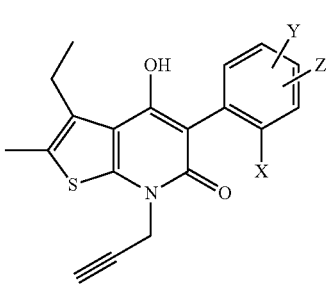

TABLE 175

Inventive compounds of the formula (I) in which G is hydrogen, V is SO$_2$, W is propynyl, A is A10, R$^{12}$ and R$^{13}$ are each methyl, and X, Y and Z are each as defined in table 1:

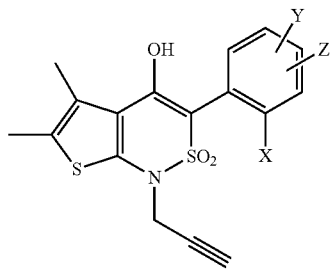

TABLE 176

Inventive compounds of the formula (I) in which G is hydrogen, V is C=O, W is propynyl, A is A10, $R^{12}$ and $R^{13}$ are each methyl, and X, Y and Z are each as defined in table 1:

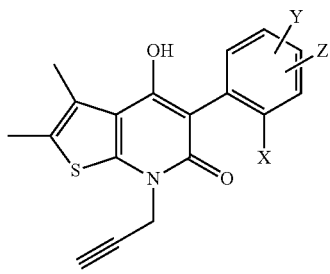

TABLE 177

Inventive compounds of the formula (I) in which G is hydrogen, V is $SO_2$, W is propynyl, A is A7, $R^{12}$ is phenyl and $R^{13}$ is hydrogen, and X, Y and Z are each as defined in table 1:

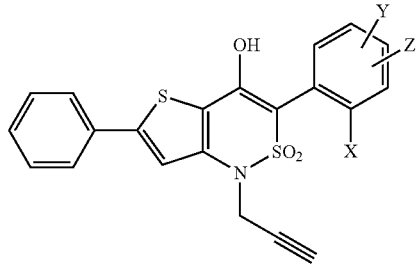

TABLE 178

Inventive compounds of the formula (I) in which G is hydrogen, V is C=O, W is propynyl, A is A10, $R^{12}$ is phenyl and $R^{13}$ is hydrogen, and X, Y and Z are each as defined in table 1:

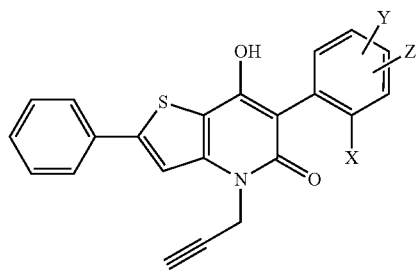

TABLE 179

Inventive compounds of the formula (I) in which G is hydrogen, V is $SO_2$, W is propynyl, A is A2, $R^{10}$ is methyl, and X, Y and Z are each as defined in table 1:

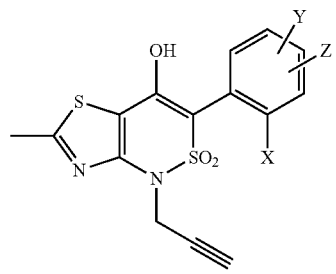

TABLE 180

Inventive compounds of the formula (I) in which G is hydrogen, V is C=O, W is propynyl, A is A2, $R^{10}$ is methyl, and X, Y and Z are each as defined in table 1:

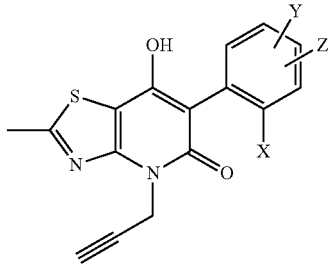

TABLE 181

Inventive compounds of the formula (I) in which G is hydrogen, V is $SO_2$, W is propynyl, A is A2, $R^{10}$ is ethyl, and X, Y and Z are each as defined in table 1:

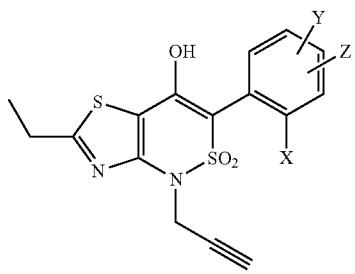

TABLE 182

Inventive compounds of the formula (I) in which G is hydrogen, V is C=O, W is propynyl, A is A2, $R^{10}$ is ethyl, and X, Y and Z are each as defined in table 1:

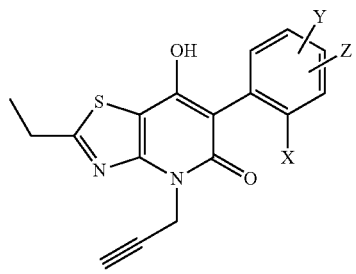

TABLE 183

Inventive compounds of the formula (I) in which G is hydrogen, V is $SO_2$, W is propynyl, A is A2, $R^{10}$ is n-propyl, and X, Y and Z are each as defined in table 1:

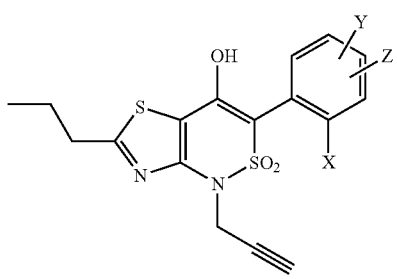

TABLE 184

Inventive compounds of the formula (I) in which G is hydrogen, V is C=O, W is propynyl, A is A2, $R^{10}$ is n-propyl, and X, Y and Z are each as defined in table 1:

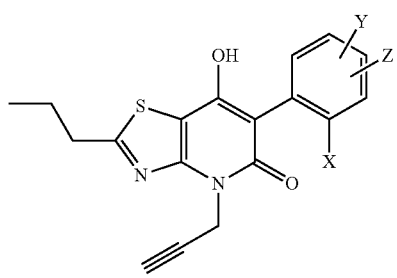

TABLE 185

Inventive compounds of the formula (I) in which G is hydrogen, V is $SO_2$, W is propynyl, A is A2, $R^{10}$ is i-propyl, and X, Y and Z are each as defined in table 1:

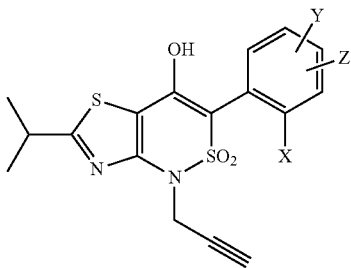

TABLE 186

Inventive compounds of the formula (I) in which G is hydrogen, V is C=O, W is propynyl, A is A2, $R^{10}$ is i-propyl, and X, Y and Z are each as defined in table 1:

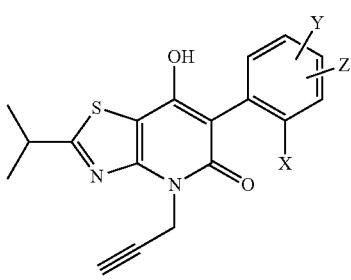

TABLE 187

Inventive compounds of the formula (I) in which G is hydrogen, V is $SO_2$, W is propynyl, A is A2, $R^{10}$ is c-propyl, and X, Y and Z are each as defined in table 1:

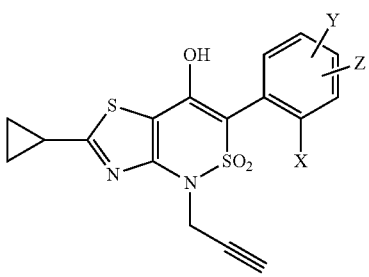

TABLE 188

Inventive compounds of the formula (I) in which G is hydrogen, V is C=O, W is propynyl, A is A2, $R^{10}$ is c-propyl, and X, Y and Z are each as defined in table 1:

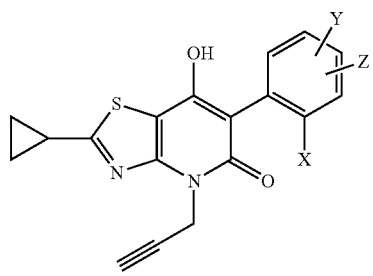

TABLE 189

Inventive compounds of the formula (I) in which G is hydrogen, V is $SO_2$, W is propynyl, A is A2, $R^{10}$ is methoxy, and X, Y and Z are each as defined in table 1:

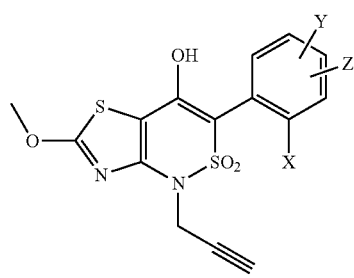

TABLE 190

Inventive compounds of the formula (I) in which G is hydrogen, V is C=O, W is propynyl, A is A2, $R^{10}$ is methoxy, and X, Y and Z are each as defined in table 1:

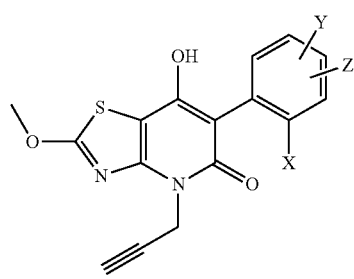

TABLE 191

Inventive compounds of the formula (I) in which G is hydrogen, V is $SO_2$, W is propynyl, A is A2, $R^{10}$ is ethoxy, and X, Y and Z are each as defined in table 1:

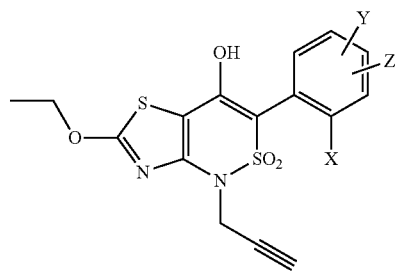

TABLE 191

Inventive compounds of the formula (I) in which G is hydrogen, V is C=O, W is propynyl, A is A2, $R^{10}$ is ethoxy, and X, Y and Z are each as defined in table 1:

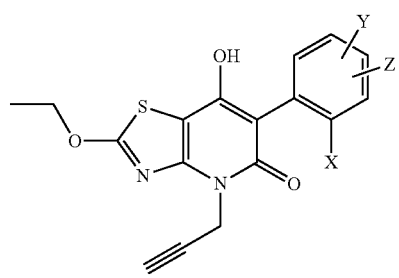

TABLE 193

Inventive compounds of the formula (I) in which G is hydrogen, V is $SO_2$, W is propynyl, A is A2, $R^{10}$ is methoxyethoxy, and X, Y and Z are each as defined in table 1:

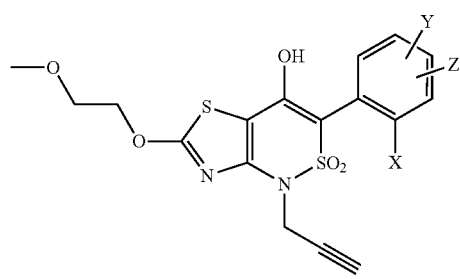

TABLE 194

Inventive compounds of the formula (I) in which G is hydrogen, V is C=O, W is propynyl, A is A2, $R^{10}$ is methoxyethoxy, and X, Y and Z are each as defined in table 1:

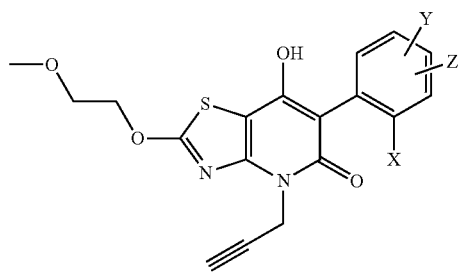

TABLE 195

Inventive compounds of the formula (I) in which G is hydrogen, V is SO$_2$, W is propynyl, A is A12, and X, Y and Z are each as defined in table 1:

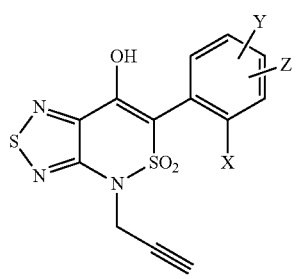

TABLE 196

Inventive compounds of the formula (I) in which G is hydrogen, V is C=O, W is propynyl, A is A12, and X, Y and Z are each as defined in table 1:

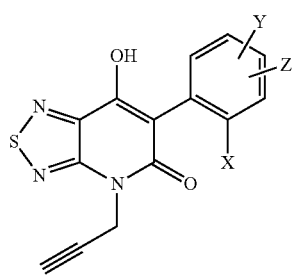

TABLE 197

Inventive compounds of the formula (I) in which G is hydrogen, V is SO$_2$, W is propynyl, A is A6, $R^{12}$ is hydrogen, $R^{14}$ is ethyl, and X, Y and Z are each as defined in table 1:

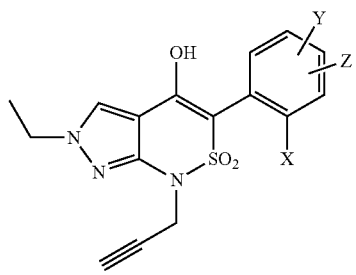

TABLE 198

Inventive compounds of the formula (I) in which G is hydrogen, V is C=O, W is propynyl, A is A6, $R^{12}$ is hydrogen, $R^{14}$ is ethyl, and X, Y and Z are each as defined in table 1:

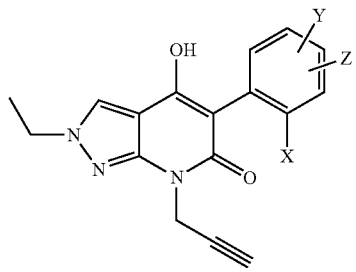

TABLE 199

Inventive compounds of the formula (I) in which G is hydrogen, V is SO$_2$, W is methyl, A is A10, $R^{12}$ is ethyl and $R^{13}$ is methyl, and X, Y and Z are each as defined in table 1:

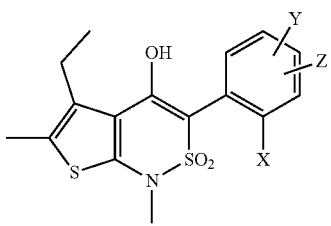

TABLE 200

Inventive compounds of the formula (I) in which G is hydrogen, V is C=O, W is methyl, A is A10, $R^{12}$ is ethyl and $R^{13}$ is methyl, and X, Y and Z are each as defined in table 1:

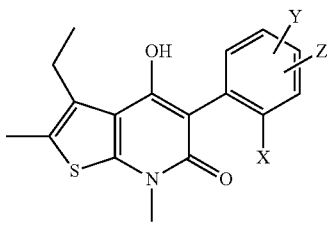

TABLE 201

Inventive compounds of the formula (I) in which G is hydrogen, V is SO$_2$, W is methyl, A is A10, R$^{12}$ and R$^{13}$ are each methyl, and X, Y and Z are each as defined in table 1:

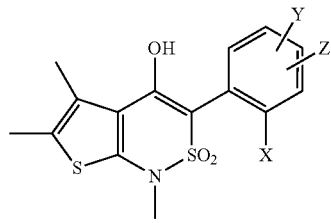

TABLE 202

Inventive compounds of the formula (I) in which G is hydrogen, V is C=O, W is methyl, A is A10, R$^{12}$ and R$^{13}$ are each methyl, and X, Y and Z are each as defined in table 1:

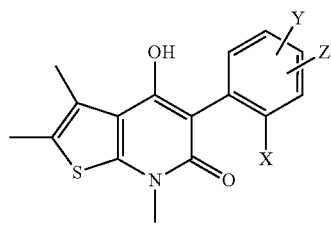

TABLE 203

Inventive compounds of the formula (I) in which G is hydrogen, V is SO$_2$, W is methyl, A is A7, R$^{12}$ is phenyl and R$^{13}$ is hydrogen, and X, Y and Z are each as defined in table 1:

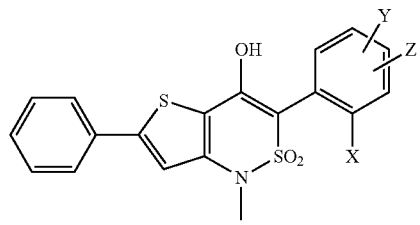

TABLE 204

Inventive compounds of the formula (I) in which G is hydrogen, V is C=O, W is methyl, A is A10, R$^{12}$ is phenyl and R$^{13}$ is hydrogen, and X, Y and Z are each as defined in table 1:

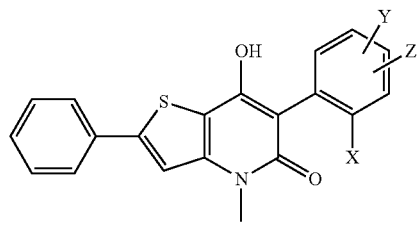

TABLE 205

Inventive compounds of the formula (I) in which G is hydrogen, V is SO$_2$, W is methyl, A is A2, R$^{10}$ is methyl, and X, Y and Z are each as defined in table 1:

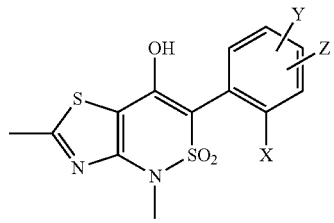

TABLE 206

Inventive compounds of the formula (I) in which G is hydrogen, V is C=O, W is methyl, A is A2, R$^{10}$ is methyl, and X, Y and Z are each as defined in table 1:

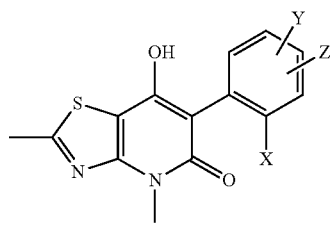

TABLE 207

Inventive compounds of the formula (I) in which G is hydrogen, V is SO$_2$, W is methyl, A is A2, R$^{10}$ is ethyl, and X, Y and Z are each as defined in table 1:

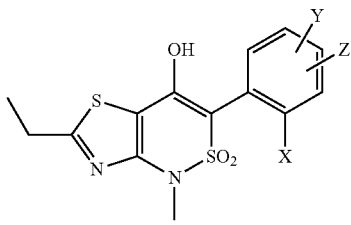

TABLE 208

Inventive compounds of the formula (I) in which G is hydrogen, V is C=O, W is methyl, A is A2, R$^{10}$ is ethyl, and X, Y and Z are each as defined in table 1:

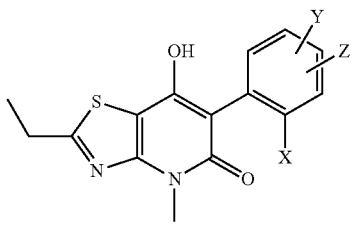

TABLE 209

Inventive compounds of the formula (I) in which G is hydrogen, V is SO₂, W is methyl, A is A2, R¹⁰ is n-propyl, and X, Y and Z are each as defined in table 1:

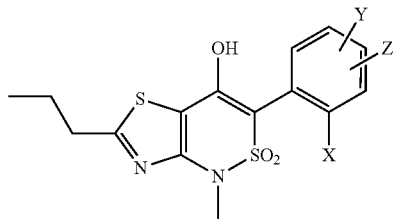

TABLE 210

Inventive compounds of the formula (I) in which G is hydrogen, V is C=O, W is methyl, A is A2, R¹⁰ is n-propyl, and X, Y and Z are each as defined in table 1:

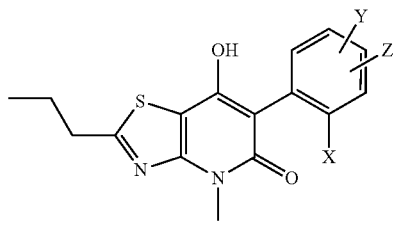

TABLE 211

Inventive compounds of the formula (I) in which G is hydrogen, V is SO₂, W is methyl, A is A2, R¹⁰ is i-propyl, and X, Y and Z are each as defined in table 1:

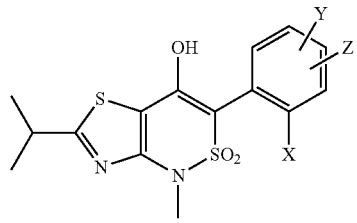

TABLE 212

Inventive compounds of the formula (I) in which G is hydrogen, V is C=O, W is methyl, A is A2, R¹⁰ is i-propyl, and X, Y and Z are each as defined in table 1:

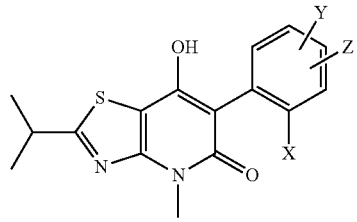

TABLE 213

Inventive compounds of the formula (I) in which G is hydrogen, V is SO₂, W is methyl, A is A2, R¹⁰ is c-propyl, and X, Y and Z are each as defined in table 1:

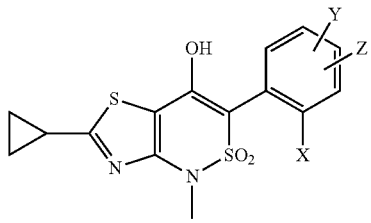

TABLE 214

Inventive compounds of the formula (I) in which G is hydrogen, V is C=O, W is methyl, A is A2, R¹⁰ is c-propyl, and X, Y and Z are each as defined in table 1:

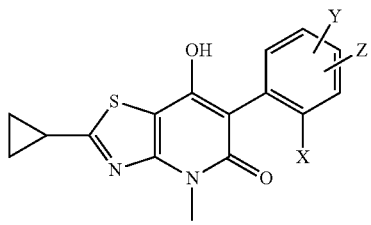

TABLE 215

Inventive compounds of the formula (I) in which G is hydrogen, V is SO₂, W is methyl, A is A2, R¹⁰ is methoxy, and X, Y and Z are each as defined in table 1:

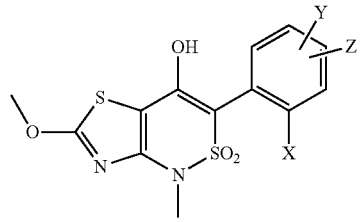

TABLE 216

Inventive compounds of the formula (I) in which G is hydrogen, V is C=O, W is methyl, A is A2, R¹⁰ is methoxy, and X, Y and Z are each as defined in table 1:

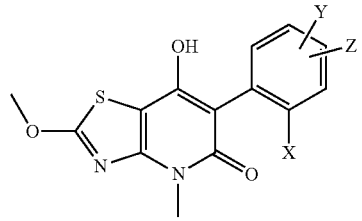

TABLE 217

Inventive compounds of the formula (I) in which G is hydrogen, V is $SO_2$, W is methyl, A is A2, $R^{10}$ is ethoxy, and X, Y and Z are each as defined in table 1:

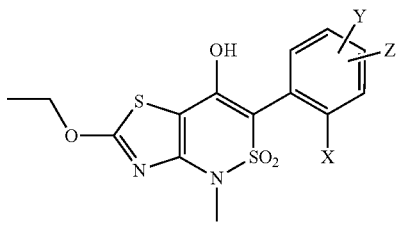

TABLE 218

Inventive compounds of the formula (I) in which G is hydrogen, V is C=O, W is methyl, A is A2, $R^{10}$ is ethoxy, and X, Y and Z are each as defined in table 1:

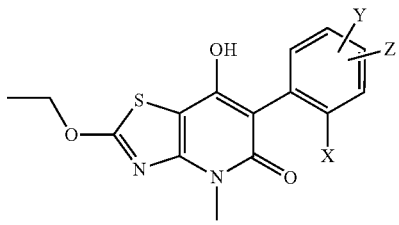

TABLE 219

Inventive compounds of the formula (I) in which G is hydrogen, V is $SO_2$, W is methyl, A is A2, $R^{10}$ is methoxyethoxy, and X, Y and Z are each as defined in table 1:

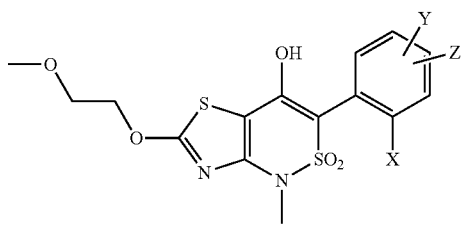

TABLE 220

Inventive compounds of the formula (I) in which G is hydrogen, V is C=O, W is methyl, A is A2, $R^{10}$ is methoxyethoxy, and X, Y and Z are each as defined in table 1:

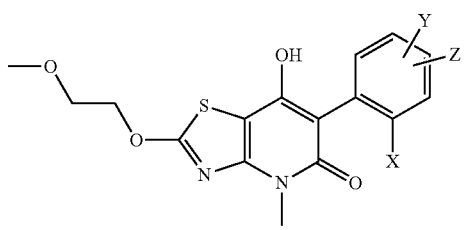

TABLE 221

Inventive compounds of the formula (I) in which G is hydrogen, V is $SO_2$, W is methyl, A is A12, and X, Y and Z are each as defined in table 1:

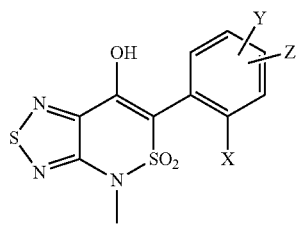

TABLE 222

Inventive compounds of the formula (I) in which G is hydrogen, V is C=O, W is methyl, A is A12, and X, Y and Z are each as defined in table 1:

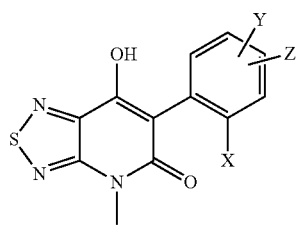

TABLE 223

Inventive compounds of the formula (I) in which G is hydrogen, V is $SO_2$, W is methyl, A is A6, $R^{12}$ is hydrogen, $R^{14}$ is ethyl, and X, Y and Z are each as defined in table 1:

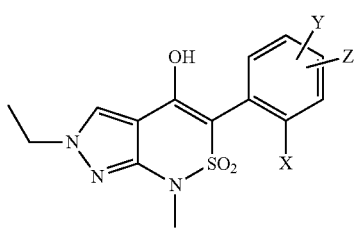

TABLE 224

Inventive compounds of the formula (I) in which G is hydrogen, V is C=O, W is methyl, A is A6, $R^{12}$ is hydrogen, $R^{14}$ is ethyl, and X, Y and Z are each as defined in table 1:

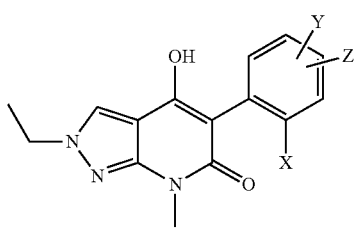

TABLE 225

Inventive compounds of the formula (I) in which G is hydrogen, V is SO₂, W is methoxyethyl, A is A2, $R^{10}$ is hydrogen, and X, Y and Z are each as defined in table 1:

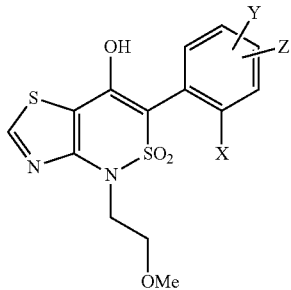

TABLE 226

Inventive compounds of the formula (I) in which G is hydrogen, V is C=O, W is methoxyethyl, A is A2, $R^{10}$ is hydrogen, and X, Y and Z are each as defined in table 1:

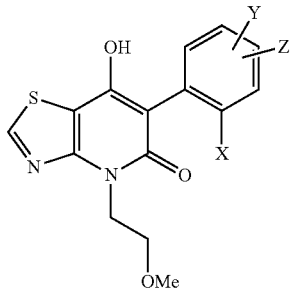

TABLE 227

Inventive compounds of the formula (I) in which G is hydrogen, V is SO₂, W is methylthioethyl, A is A2, $R^{10}$ is hydrogen, and X, Y and Z are each as defined in table 1:

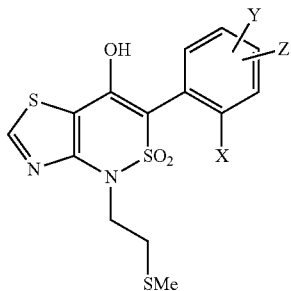

TABLE 228

Inventive compounds of the formula (I) in which G is hydrogen, V is C=O, W is methylthioethyl, A is A2, $R^{10}$ is hydrogen, and X, Y and Z are each as defined in table 1:

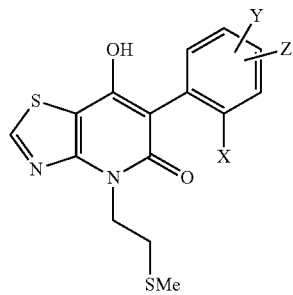

Inventive compounds of the formula (I) in which G is hydrogen, V is C=O or SO₂, can be prepared, for example, by the method specified in scheme 1, by base-induced condensation reaction of compounds of the formula (II). $R^9$ therein is ($C_1$-$C_6$)-alkyl, especially methyl or ethyl.

Scheme 1

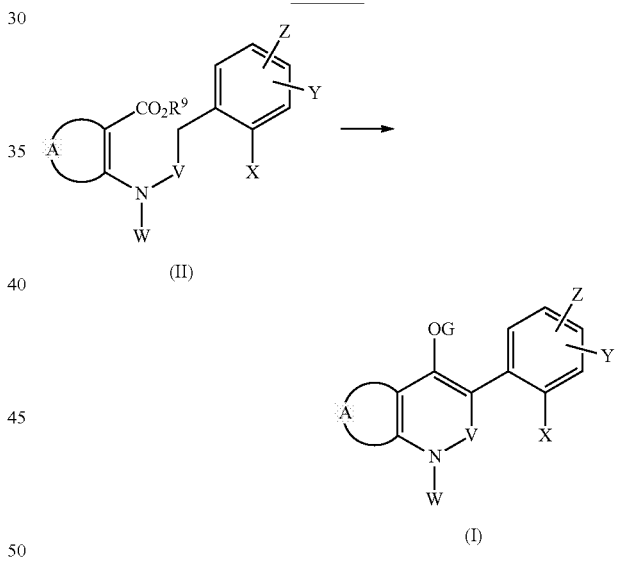

Compounds of the formula (II) can be prepared, for example, by the methods specified in scheme 1a, by reaction of aminocarboxylic acid derivatives with phenylacetic acid derivatives or benzylsulfonic acid derivatives. U therein is a leaving group introduced by carboxylic acid activation reagents, such as carbonyldiimidazole, carbonyldiimides (for example dicyclohexylcarbodiimide), phosphorylating reagents (for example POCl₃, BOP-Cl), halogenating agents, for example thionyl chloride, oxalyl chloride, phosgene or chloroformic esters. Such methods are also known to the person skilled in the art from WO2008/009908 A1 and WO2008/071918 A1 or WO2009/063180 and documents cited therein. Compounds of the formula (II) are novel and likewise form part of the subject matter of the present invention.

Scheme 1a

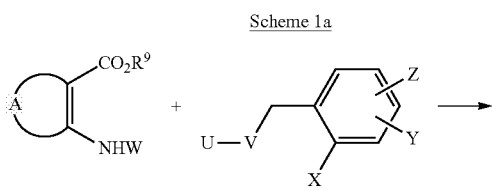

It is additionally known that reactions of W' halides or else corresponding sulfonates with appropriate amino acid esters lead to the desired precursors. Alternatively, it is correspondingly also possible, on completion of condensation of the amino acid ester with the appropriate phenylacetic acid or benzylsulfonic acid, to effect the alkylation with W' halides or sulfonates (see scheme 1b), which then likewise leads to the inventive intermediates II.

Scheme 1b

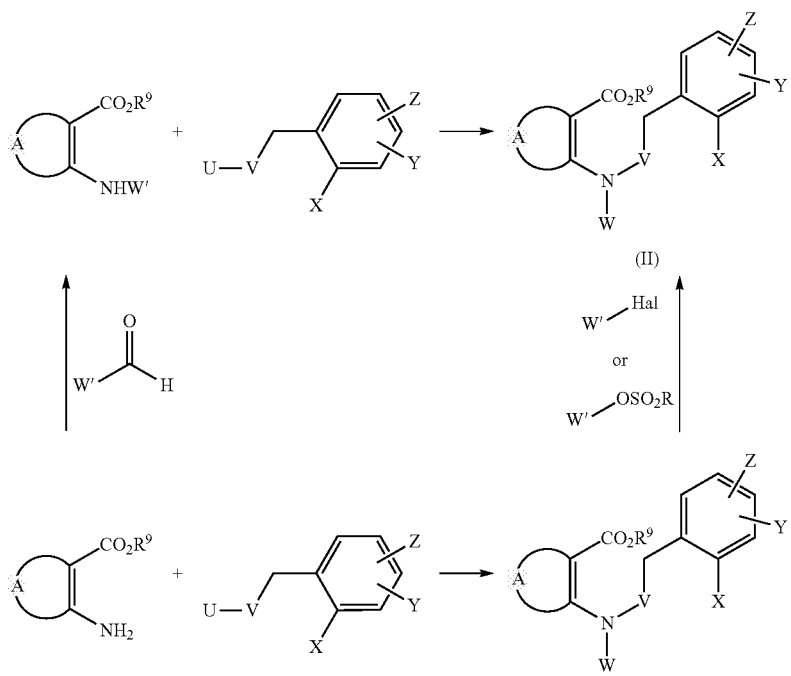

-continued

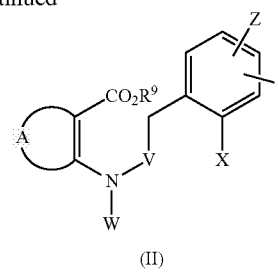

(II)

The free phenylacetic acids needed to prepare the phenylacetic acid derivatives specified in scheme 1a, i.e. those in which U is hydroxyl and V is C=O, are known or can be prepared by processes known per se and known, for example, from WO 2005/075401, WO 2001/96277, WO 1996/35664 and WO 1996/25395. In the case that W is to be any radical other than hydrogen, a W' radical can be introduced by methods known from the literature, for example by means of reductive amination of a corresponding amino acid ester with an aldehyde, followed by a reduction, for example with sodium cyanoborohydride. W' is $(C_1-C_6)$-alkyl, $(C_2-C_6)$-alkenyl, $(C_3-C_6)$-alkynyl, $(C_3-C_6)$-cycloalkyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, $(C_3-C_6)$-cycloalkyl-$(C_1-C_6)$-alkyl each substituted by n halogen atoms.

Particular phenylacetic acid derivatives can also be prepared using acetic ester enolates in the presence of palladium catalysts, for example formed from a palladium source (e.g. $Pd_2(dba)_3$ or $Pd(Oac)_2$) and a ligand (e.g. $(t-Bu)_3P$, iMes*HCl or 2'-(N,N-dimethylamino)-2-(dicyclohexylphosphanyl)biphenyl) (WO 2005/048710, J. Am. Chem. Soc 2002. 124, 12557, J. Am. Chem. Soc 2003. 125, 11176 or J. Am. Chem. Soc. 2001, 123, 799). In addition, it is possible to convert particular substituted aryl halides under copper catalysis to the corresponding substituted malonic esters (for example described in Org. Lett. 2002, 2, 269, WO 2004/108727), which can be converted to phenylacetic acids by known methods.

The free benzylsulfonic acids needed for preparation of the benzylsulfonic acid derivatives specified in scheme 1a, i.e. those in which U is hydroxyl and V is SO2, are known or can be prepared by processes known per se and known, for example, from WO2009/063180.

Inventive compounds of the formula (I) in which G is hydrogen can also be prepared, for example, by the method specified in scheme 2, by reaction of compounds of the formula (I) in which G is alkyl, preferably methyl, with strong mineral bases such as sodium hydroxide or potassium hydroxide, or in concentrated mineral acids such as hydrobromic acid.

Scheme 2

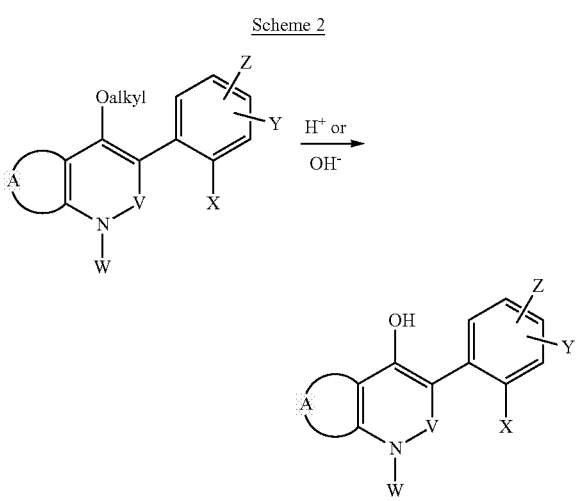

Inventive compounds of the formula (I) in which G is C(=O)R¹, can be prepared, for example, by reactions, known to those skilled in the art, of compounds of the formula (I) in which G is hydrogen with carbonyl halides of the formula Hal-CO—R¹ or with carboxylic anhydrides of the formula R¹—CO—O—CO—R¹.

Inventive compounds of the formula (I) in which G is C(=L)MR² can be prepared, for example, by reactions, known to those skilled in the art, of compounds of the formula (I) in which G is hydrogen with a) chloroformic esters or chloroformic thioesters of the formula R²—M-COOR¹ or b) with chloroformyl halides or chlorothioformyl halides.

Inventive compounds of the formula (I) in which G is SO₂R³ can be prepared, for example, by reactions, known to those skilled in the art, of compounds of the formula (I) in which G is hydrogen, with sulfonyl chlorides of the formula R³—SO₂—Cl.

Inventive compounds of the formula (I) in which G is P(=L)R⁴R⁵ can be prepared, for example, by reactions, known to those skilled in the art, of compounds of the formula (I) in which G is hydrogen with phosphoryl chlorides of the formula Hal-P(=L)R⁴R⁶.

Inventive compounds of the formula (I) in which G is E can be prepared, for example, by reactions, known to those skilled in the art, of compounds of the formula (I) in which G is hydrogen with metal compounds of the formula Me(OR¹⁰)ₜ or with amines. Me therein is a mono- or divalent metal ion, preferably an alkali metal or alkaline earth metal such as lithium, sodium, potassium, magnesium or calcium. The index t is 1 or 2. An ammonium ion is the NH₄⁺ or R¹³R¹⁴R¹⁵R¹⁶N⁺ group in which R¹³, R¹⁴, R¹⁵ and R¹⁶ are preferably each independently (C₁-C₆)-alkyl or benzyl.

Inventive compounds of the formula (I) in which G is C(=L)NR⁶R⁷ can be prepared, for example, by reactions, known to those skilled in the art, of compounds of the formula (I) in which G is hydrogen with isocyanates or isothiocyanates of the formula R⁶—N=C=L or with carbamoyl chlorides or thiocarbamoyl chlorides of the formula R⁶R⁷N—C(=L)Cl.

Inventive compounds of the formula (I) in which G is alkyl, preferably methyl, can also be prepared, for example, according to scheme 3, by reactions, known to those skilled in the art, of compounds of the formula (III) with compounds of the formula (IV). Z' therein is bromine or iodine, and Q is a trialkyltin group, a magnesium halide group or preferably a boronic acid or ester thereof. These reactions are typically performed in the presence of a catalyst (e.g. Pd salts or Pd complexes) and in the presence of a base (e.g. sodium carbonate, potassium phosphate).

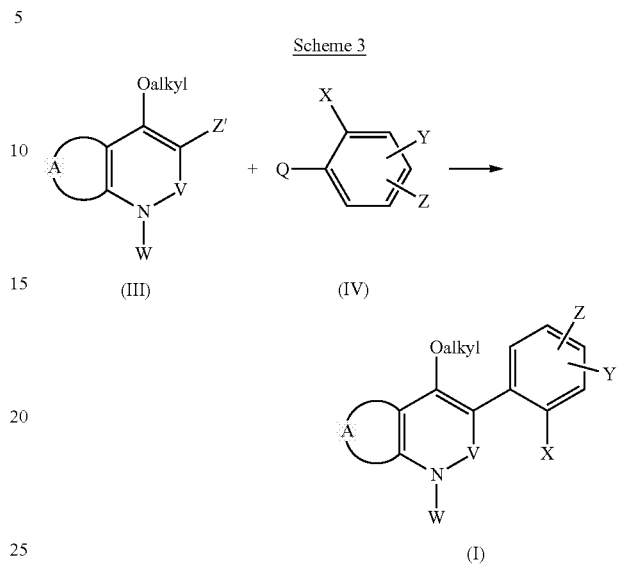

Libraries of compounds of the formula (I) and/or salts thereof which can be synthesized by the abovementioned reactions can also be prepared in a parallelized manner, which can be done in a manual, semiautomated or fully automated manner. It is possible, for example, to automate the performance of the reaction, the workup or the purification of the products or intermediates. This is understood overall to mean a procedure as described, for example, by D. Tiebes in Combinatorial Chemistry—Synthesis, Analysis, Screening (editor: Gunther Jung), Wiley publishers 1999, on pages 1 to 34.

For parallelized reaction performance and workup, it is possible to use a range of commercially available equipment, for example Calypso reaction blocks from Barnstead International, Dubuque, Iowa 52004-0797, USA or reaction stations from Radleys, Shire Hill, Saffron Walden, Essex, CB11 3AZ, England, or MuItiPROBE Automated Workstations from Perkin Elmer, Waltham, Mass. 02451, USA. For the parallelized purification of compounds of the formula (I) and salts thereof, or of intermediates obtained in the preparation, apparatus available includes chromatography apparatus, for example from ISCO, Inc., 4700 Superior Street, Lincoln, Nebr. 68504, USA.

The apparatus detailed leads to a modular procedure, in which the individual steps are automated, but manual operations have to be conducted between the steps. This can be avoided by the use of partly or fully integrated automation systems, in which the particular automation modules are operated, for example, by robots. Such automation systems can be purchased, for example, from Caliper, Hopkinton, Mass. 01748, USA.

The performance of individual or several synthesis steps can be supported by the use of polymer-supported reagents/scavenger resins. The specialist literature describes a multitude of experimental protocols, for example ChemFiles, Vol. 4, No. 1, Polymer-Supported Scavengers and Reagents for Solution-Phase Synthesis (Sigma-Aldrich).

In addition to the methods described here, compounds of the formula (I) and salts thereof can be prepared completely or partially by solid phase-supported methods. For this purpose, individual intermediates or all intermediates of the synthesis or of a synthesis matched to the appropriate procedure are bound to a synthesis resin. Solid phase-supported synthesis methods have been described sufficiently in the specialist literature, for example Barry A. Bunin in "The Combinatorial Index", Academic Press publishers, 1998 and Combinatorial Chemistry—Synthesis, Analysis, Screening (editor: Gunther Jung), Wiley publishers, 1999. The use of solid phase-supported synthesis methods allows a range of protocols known from the literature, which can in turn be executed in a manual or automated manner. The reactions can be performed, for example, by means of IRORI technology in microreactors from Nexus Biosystems, 12140 Community Road, Poway, Calif. 92064, USA.

Both on the solid phase and in the liquid phase, the performance of individual or several synthesis steps can be supported by the use of microwave technology. The specialist literature describes a range of experimental protocols, for example Microwaves in Organic and Medicinal Chemistry (editors: C. O. Kappe and A. Stadler), Wiley publishers, 2005.

The preparation by the process described herein affords compounds of the formula (I) and salts thereof in the form of substance libraries. The present invention also provides libraries containing at least two compounds of the formula (I) and salts thereof.

The inventive compounds of the formula (I) (and/or salts thereof), referred to hereinafter collectively as "inventive compounds", have excellent herbicidal efficacy against a broad spectrum of economically important mono- and dicotyledonous annual weed plants. The active ingredients also have good control over perennial weed plants which are difficult to control, which produce shoots from rhizomes, rootstocks or other permanent organs.

The present invention therefore also provides a method for controlling unwanted plants or for regulating the growth of plants, preferably in crops of plants, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). In this context, the inventive compounds can be applied for example pre-planting (if appropriate also by incorporation into the soil), pre-emergence or post-emergence. Examples of individual representatives of the monocotyledonous and dicotyledonous weed flora which can be controlled by the inventive compounds will be mentioned, though there is no intention to impose a restriction to particular species mentioned.

Monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the emergence of the weed seedlings is prevented completely or the weeds grow until they have reached the cotyledon stage, but then stop growing and, ultimately, die completely after three to four weeks have passed.

When the active ingredients are applied post-emergence to the green plant parts, growth stops after the treatment, and the weed plants remain in the growth stage of the time of application or die fully after a certain period of time, so that competition by weeds, which is harmful to the crop plants, is thus eliminated at a very early stage and in a sustained manner.

Although the inventive compounds display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the particular inventive compound and its application rate. For these reasons, the present compounds are highly suitable for the selective control of unwanted vegetation in plant crops such as agriculturally useful plants or ornamentals.

Moreover, the inventive compounds (depending on their particular structure and the application rate applied) have outstanding growth-regulating properties in crop plants. They engage in the plant's own metabolism in a regulatory manner and can therefore be used for controlled influence of plant constituents and to facilitate harvesting, for example by triggering desiccation and stunted growth. In addition, they are also suitable for general control and inhibition of unwanted vegetative growth without destroying the plants in the process. Inhibition of vegetative growth plays an important role in many monocotyledonous and dicotyledonous crops since, for example, this can reduce or completely prevent lodging.

Owing to their herbicidal and plant growth-regulating properties, the active ingredients can also be used to control weed plants in crops of known genetically modified plants or genetically modified plants which are yet to be developed. The transgenic plants generally feature special advantageous properties, for example resistances to certain pesticides, mainly certain herbicides, resistances to plant diseases or causative organisms of plant diseases, such as certain insects or microorganisms such as fungi, bacteria or viruses. Other special properties relate, for example, to the harvested material with regard to quantity, quality, storability, composition and specific constituents. Thus, transgenic plants with an increased starch content or a modified starch quality or those with a different fatty acid composition of the harvested material are known. Further special properties may be tolerance or resistance to abiotic stressors, for example heat, cold, drought, salt and ultraviolet radiation.

Preference is given to employing the inventive compounds of the formula (I) or salts thereof in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

The compounds of the formula (I) can preferably be used as herbicides in crops of useful plants which are resistant, or have been made resistant by recombinant means, to the phytotoxic effects of the herbicides.

Conventional ways of generating novel plants which have modified properties compared to existing plants are, for example, traditional breeding methods and the generation of mutants. Alternatively, novel plants with modified properties can be generated with the aid of recombinant methods (see, for example, EP 0221044, EP 0131624). For example, the following have been described in several cases:

recombinant modifications of crop plants for the purpose of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377 A) or of the sulfonylurea type (EP 0257993 A, U.S. Pat. No. 5,013,659), or are resistant to combinations or mixtures of these herbicides by virtue of "gene stacking", such as transgenic crop plants, for example maize or soya with the trade name or the designation Optimum™ GAT™ (Glyphosate ALS Tolerant), transgenic crop plants, for example cotton which is capable of producing

*Bacillus thuringiensis* toxins (Bt toxins), which make the plants resistant to certain pests (EP 0142924 A, EP 0193259 A), transgenic crop plants with a modified fatty acid composition (WO 91/013972 A), genetically modified crop plants with novel constituents or secondary metabolites, for example novel phytoalexins, which bring about an increased disease resistance (EP 0309862 A, EP 0464461 A), genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular biology techniques by means of which novel transgenic plants with modified properties can be produced are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. For the bonding of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

The production of plant cells with a reduced activity for a gene product can be achieved for example by the expression of at least one corresponding antisense RNA, or of a sense RNA for achieving a cosuppression effect, or by the expression of at least one correspondingly constructed ribozyme which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, it is possible to obtain transgenic plants which feature modified properties as the result of overexpression, suppression or inhibition of homologous (=natural) genes or gene sequences or expression of heterologous (=foreign) genes or gene sequences.

The inventive compounds (I) can preferably be used in transgenic crops which are resistant to growth regulators, for example 2, 4 D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, glyphosates, glufosinates or benzoylisoxazoles and analogous active ingredients, or to any combinations of these active ingredients.

The inventive compounds can more preferably be used in transgenic crop plants which are resistant to a combination of glyphosates and glufosinates, glyphosates and sulfonylureas or imidazolinones. It is very particularly preferred to employ the inventive compounds in transgenic crop plants, for example maize or soya, with the trade name or the designation Optimum™ GAT™ (Glyphosate ALS Tolerant).

When the inventive active ingredients are employed in transgenic crops, effects are frequently observed—in addition to the effects on weed plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also provides for the use of the inventive compounds of the formula (I) as herbicides for controlling weed plants in transgenic crop plants.

The inventive compounds can be used in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Kuchler, "Chemische Technologie" [Chemical Technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry", 2nd Ed., J. Wiley & Sons, N.Y; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-Active Ethylene Oxide Adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active substances, for example, insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the production of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 if; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight; the remainder to 100% by weight consists of customary formulation constituents. In the case of emulsifiable concentrates, the active ingredient concentration may be about 1 to 90% by weight, preferably 5 to 80% by weight. Dust-type formulations contain 1 to 30% by weight of active ingredient, preferably usually 5 to 20% by weight of active ingredient; sprayable solutions contain about 0.05 to 80% by weight, preferably 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreezes and solvents, fillers, carriers and dyes, defoamers, evaporation inhibitors and agents which influence the pH and the viscosity.

Based on these formulations, it is also possible to prepare combinations with other pesticidally active substances, for example insecticides, acaricides, herbicides, fungicides, and also with safeners, fertilizers and/or growth regulators, for example in the form of a finished formulation or as a tankmix.

Usable combination partners for the inventive compounds in mixture formulations or in tankmixes are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Known herbicides or plant growth regulators which can be combined with the inventive compounds include, for example, the following active ingredients (the compounds are referred to by the common name according to the International Organization for Standardization (ISO) or by the chemical name or by the code number) and always include all use forms, such as acids, salts, esters and isomers such as stereoisomers and optical isomers. By way of example, one and in some cases even several use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammoniumsulfamat, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl] phenyl]-ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl] methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

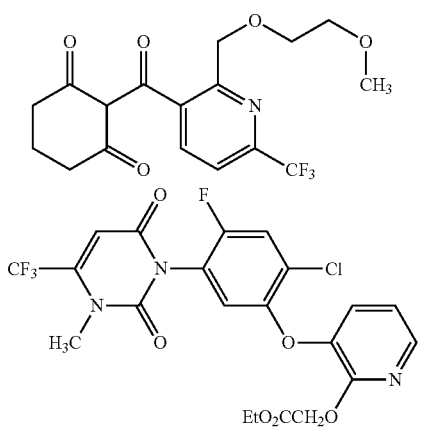

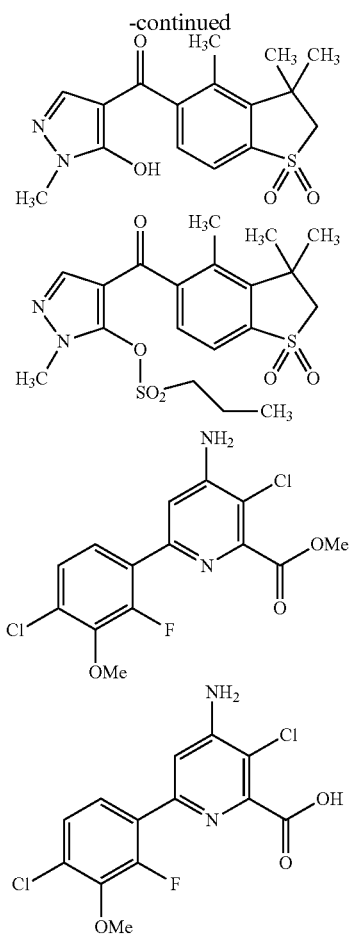

For use, the formulations present in commercially available form are optionally diluted in a customary manner, for example in the case of wettable powders, emulsifiable concentrates, dispersions and water-dispersible granules by means of water. Dust formulations, soil granules and granules for broadcasting, and also sprayable solutions, are typically not diluted with any further inert substances before use.

The required application rate of the compounds of the formula (I) varies with the outside conditions, such as temperature, humidity, the type of herbicide used, among other factors. It can vary within wide limits, for example between 0.001 and 1.0 kg/ha or more of active substance, but is preferably between 0.005 and 750 g/ha.

The examples which follow illustrate the invention in detail.

Chemical Examples

Preparation of 4-allyl-7-hydroxy-6-mesityl[1,3]thiazolo[4,5-b]pyridin-5(4H)-one (compound No. I-a-2)

1.8 g (5 mmol) of methyl 4-[allyl(mesitylacetyl)amino]-1,3-thiazole-5-carboxylate were initially charged in 5 ml of N,N-dimethylformamide and cooled to 0° C. 1.5 eq of sodium hydride (60%) were added and allowed to warm up gradually to room temperature (RT). After stirring at RT for one hour, 5 ml of water were added and the mixture was acidified to pH 1-2. The precipitate formed was filtered off with suction. 1.5 g of inventive compound I-a-2 were thus obtained.

Preparation of 1-(2,2-difluoroethyl)-3-(2-iodophenyl)-1H-[1,3]thiazolo[4,5-c][1,2]thiazin-4-ol 2,2-dioxide (compound No. I-a-14)

2.0 g (4 mmol) of methyl 4-{(2,2-difluoroethyl)[(2-iodobenzyl)sulfonyl]amino}-1,3-thiazole-5-carboxylate were dissolved in 25 ml of dimethylformamide and cooled to 0° C., and 143.3 mg (6 mmol) of sodium hydride were added. After addition, the mixture was warmed to RT and stirred for 12 h. Thereafter, the reaction mixture was poured onto 100 ml of water and brought to pH 4-5 with 2N HCl. The precipitate formed was filtered off and washed with water. This gave 1.7 g of compound I-a-14.

In analogy to the preparation of compounds No. I-a-2 and No. I-a-14 and according to the general details regarding the preparation, the following compounds of the formula (I-a) are obtained:

TABLE 229

Inventive compounds of the formula (I) in which G is hydrogen:

(I-a)

| No. | A | V | W | X | Y | Z | Analytical data |
|---|---|---|---|---|---|---|---|
| I-a-1 | thiazole | SO₂ | CH₂CHF₂ | Cl | 4-Cl | H | ¹H NMR (400 MHz, CDCl₃): 9.06 (s, 1H); 7.57 (d, 1H); 7.39 (d, 1H); 7.36 (dd, 1H); 6.14 (tt, 1H); 6.00 (s, 1H); 4.53 (m, 2H) |
| I-a-2 | thiazole | C=O | CH₂—CH=CH₂ | Me | 4-Me | 6-Me | ¹H NMR (400 MHz, d6-DMSO): 10.6 (bs, 1H), 9.31 (s, 1H), 6.90 (s, 2H), 5.96 (m, 1H), 5.07 (m, 1H), 4.90 (m, 3H), 2.27 (s, 3H), 1.97 (s, 6H) |
| I-a-3 | oxadiazole | SO₂ | CH₂CHF₂ | Cl | 6-Cl | H | ¹H NMR (400 MHz, CDCl₃): 7.48 (m, 2H); 7.38 (dd, 1H); 7.19 (s, 1H); 6.12 (tt, 1H); 3.94 (m, 2H) |
| I-a-4 | methylthio-thiazole | C=O | CH₂CHF₂ | Br | 4-Cl | 6-Et | ¹H NMR (400 MHz, d6-DMSO): 11.34 (bs, 1H), 7.63 (d, 1H), 7.38 (d, 1H), 6.32 (m, 1H), 4.67 (m, 2H), 2.81 (s, 3H), 2.38 (m, 2H), 1.00 (t, 3H) |
| I-a-5 | N-methylpyrazole | SO₂ | CH₂CHF₂ | CF₃ | H | H | ¹H NMR (400 MHz, CDCl₃): 7.95 (s, 1H); 7.80 (d, 1H); 7.60 (m, 2H); 7.26 (s, 1H); 6.16 (tt, 1H); 5.61 (s, 1H); 4.27 (m, 2H); 3.93 (s, 3H) |
| I-a-6 | oxadiazole | SO₂ | CH₂CHF₂ | CF₃ | H | H | ¹H NMR (400 MHz, CDCl₃): 7.84 (d, 1H); 7.66 (m, 3H); 7.24 (s, 1H); 6.11 (tt, 1H); 3.93 (m, 2H) |
| I-a-7 | N-methylpyrazole | SO₂ | CH₂CHF₂ | Cl | 4-Cl | H | ¹H NMR (400 MHz, CDCl₃): 7.96 (s, 1H); 7.55 (d, 1H); 7.33 (m, 2H); 6.15 (tt, 1H); 5.84 (s, 1H); 4.25 (m, 2H); 3.93 (s, 3H) |
| I-a-8 | thiophene | C=O | CH₃ | Cl | 6-Cl | H | ¹H NMR (400 MHz, d6-DMSO): 10.8 (bs, 1H), 7.53 (m, 3H), 7.38 (t, 1H), 7.28 (d, 1H), 3.53 (s, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-9 | thiazole | SO$_2$ | CH$_2$CHF$_2$ | Cl | 6-Cl | H | $^1$H NMR (400 MHz, CDCl$_3$): 9.05 (s, 1H); 7.50 (d, 1H); 7.43 (d, 1H); 7.37 (t, 1H); 6.24 (s, 1H); 6.20 (tt, 1H); 4.49 (m, 2H) |
| I-a-10 | thiazole | SO$_2$ | CH$_2$CF$_3$ | CF$_3$ | H | H | $^1$H NMR (400 MHz, CDCl$_3$): 9.07 (s, 1H); 7.83 (d, 1H); 7.65 (m, 3H); 5.79 (s, 1H); 4.83 (m, 2H) |
| I-a-11 | thiazole | SO$_2$ | CH$_2$CHF$_2$ | CF$_3$ | H | H | $^1$H NMR (400 MHz, CDCl$_3$): 9.06 (s, 1H); 7.83 (d, 1H); 7.64 (m, 3H); 6.15 (tt, 1H); 5.75 (s, 1H); 4.52 (m, 2H) |
| I-a-12 | N-methylpyrazole | SO$_2$ | CH$_2$CHF$_2$ | I | H | H | $^1$H NMR (400 MHz, CDCl$_3$): 7.97 (m, 2H); 7.39 (m, 2H); 7.14 (m, 1H); 6.15 (tt, 1H); 5.88 (s, 1H); 4.25 (m, 2H); 3.92 (s, 3H) |
| I-a-13 | N-methylpyrazole | SO$_2$ | CH$_2$CF$_3$ | I | H | H | $^1$H NMR (400 MHz, CDCl$_3$): 7.98 (m, 2H); 7.39 (m, 2H); 7.13 (m, 1H); 5.92 (s, 1H); 4.54 (q, 2H); 3.94 (s, 3H) |
| I-a-14 | thiazole | SO$_2$ | CH$_2$CHF$_2$ | I | H | H | $^1$H NMR (400 MHz, CDCl$_3$): 9.06 (s, 1H); 7.99 (d, 1H); 7.42 (m, 2H); 7.18 (m, 1H); 6.14 (tt, 1H); 6.04 (s, 1H); 4.53 (m, 2H) |
| I-a-15 | thiazole | SO$_2$ | CH$_2$CF$_3$ | I | H | H | $^1$H NMR(400 MHz, CDCl$_3$): 9.06 (s, 1H); 7.99 (d, 1H); 7.43 (m, 2H); 7.18 (m, 1H); 6.09 (s, 1H); 4.82 (m, 2H) |
| I-a-16 | oxadiazole | C=O | CH$_3$ | Cl | 6-Cl | H | $^1$H NMR (400 MHz, CDCl$_3$): 7.48 (m, 2H), 7.38 (t, 1H), 3.58 (s, 3H) |
| I-a-17 | oxadiazole | SO$_2$ | CH$_2$CHF$_2$ | Cl | 4-Cl | H | $^1$H NMR (400 MHz, CDCl$_3$): 12.00 (s, 1H); 7.80 (d, 1H); 7.55 (dd, 1H); 7.51 (d, 1H); 6.25 (tt, 1H); 3.88 (m, 2H) |
| I-a-18 | thiophene | C=O | CH$_2$—CH=CH$_2$ | Cl | 6-Cl | H | $^1$H NMR (400 MHz, CDCl$_3$): 7.48 (m, 2H), 7.34 (m, 2H), 6.98 (d, 1H), 5.93 (m, 1H), 5.27 (m, 2H), 4.78 (m, 2H), |
| I-a-19 | thiazole | C=O | CH$_3$ | Cl | 6-Cl | H | $^1$H NMR(400 MHz, d6-DMSO): 11.3 (bs, 1H), 9.42 (s, 1H), 7.53 (m, 2H), 7.38 (t, 1H), 3.72 (s, 3H) |

TABLE 229-continued

Inventive compounds of the formula (I) in which G is hydrogen:

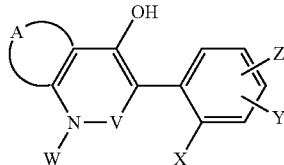

(I-a)

| No. | A | V | W | X | Y | Z | Analytical data |
|---|---|---|---|---|---|---|---|
| I-a-20 | thiophen-3-yl | C=O | $CH_2$—CH=$CH_2$ | Me | 4-Me | 6-Me | $^1$H NMR (400 MHz, d6-DMSO): 10.1 (bs, 1H), 7.45 (d, 1H), 7.24 (d, 1H), 6.88 (s, 2H), 5.89 (m, 1H), 5.19 (m, 1H), 5.05 (m, 1H), 4.68 (m, 2H), 2.26 (s, 3H), 1.96 (s, 6H) |
| I-a-21 | thiazol-5-yl | C=O | $CH_2CF_3$ | Br | 4-Cl | 6-Et | $^1$H NMR (400 MHz, d6-DMSO): 11.7 (bs, 1H), 9.38 (s, 1H), 7.63 (d, 1H), 7.38 (d, 1H), 5.12 (m, 2H), 2.39 (m, 2H), 1.02 (dt, 3H) |
| I-a-22 | thiophen-3-yl | C=O | $CH_2$—CH=$CH_2$ | Cl | 4-Cl | H | $^1$H NMR (400 MHz, d6-DMSO): 10.7 (bs, 1H), 7.65 (m, 1H), 7.45 (m, 1H), 7.42 (m, 1H), 7.32 (d, 1H), 7.28 (d, 1H), 5.87 (m, 1H), 5.19 (m, 2H), 4.68 (m, 2H) |
| I-a-23 | thiophen-3-yl | C=O | $CH_2$—CH=$CH_2$ | Br | 4-Cl | 6-Et | $^1$H NMR (400 MHz, d6-DMSO): 10.6 (bs, 1H), 7.62 (m, 1H), 7.47 (m, 1H), 7.38 (m, 1H), 7.27 (d, 1H), 5.87 (m, 1H), 5.19 (m, 1H), 5.05 (m, 1H), 4.68 (m, 2H), 2.39 (m, 2H), 1.01 (t, 3H) |
| I-a-24 | thiazol-5-yl | C=O | $CH_2$—CH=$CH_2$ | Br | 4-Cl | 6-Et | $^1$H NMR (400 MHz, d6-DMSO): 11.2 (bs, 1H), 9.36 (s, 1H), 7.64 (d, 1H), 7.40 (d, 1H), 5.95 (m, 1H), 5.08 (m, 1H), 4.94 (m, 3H), 2.38 (q, 2H), 1.01 (t, 3H) |
| I-a-25 | thiazol-5-yl | C=O | $CH_2$—CH=$CH_2$ | Cl | 6-Cl | H | $^1$H NMR (400 MHz, d6-DMSO): 11.4 (bs, 1H), 9.38 (s, 1H), 7.52 (m, 2H), 7.40 (m, 1H), 5.95 (m, 1H), 5.09 (m, 1H), 4.95 (m, 3H) |
| I-a-26 | 1-methylpyrazol-4-yl | $SO_2$ | $CH_2CHF_2$ | Cl | 6-Cl | H | $^1$H NMR (400 MHz, $CDCl_3$): 7.99 (s, 1H); 7.48 (dd, 1H); 7.40 (dd, 1H); 7.33 (t, 1H); 6.22 (tt, 1H); 6.09 (s, 1H); 4.25 (m, 2H); 3.92 (s, 3H) |
| I-a-27 | 1-methylpyrazol-4-yl | C=O | $CH_2$—CH=$CH_2$ | Cl | 4-Cl | H | $^1$H NMR (400 MHz, d6-DMSO): 8.18 (s, 1H), 7.62 (d, 1H), 7.38 (dd, 1H), 7.27 (d, 2H), 5.89 (m, 1H), 5.07 (m, 2H), 4.58 (m, 2H), 3.94 (s, 3H) |

TABLE 229-continued

Inventive compounds of the formula (I) in which G is hydrogen:

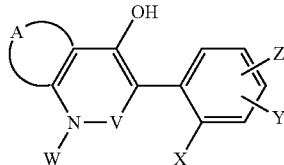

(I-a)

| No. | A | V | W | X | Y | Z | Analytical data |
|---|---|---|---|---|---|---|---|
| I-a-28 | N-methylpyrazol-4-yl | C=O | CH$_2$—CH=CH$_2$ | Br | 4-Cl | Et | $^1$H NMR (400 MHz, d6-DMSO): 8.17 (s, 1H), 7.58 (d, 1H), 7.34 (d, 1H), 5.89 (m, 1H), 5.05 (m, 1H), 4.95 (m, 1H), 4.58 (m, 2H), 3.94 (s, 3H), 2.38 (m, 2H), 0.99 (t, 3H) |
| I-a-29 | N-methylpyrazol-4-yl | C=O | CH$_2$—CH=CH$_2$ | Me | 4-Me | 6-Me | $^1$H NMR (400 MHz, d6-DMSO): 10.4 (bs, 1H), 8.13 (s, 1H), 6.84 (d, 2H), 5.89 (m, 1H), 5.05 (m, 1H), 4.94 (m, 1H), 4.60 (m, 2H), 3.93 (s, 3H) |
| I-a-30 | N-methylpyrazol-4-yl | C=O | CH$_2$—CH=CH$_2$ | Cl | 6-Cl | H | $^1$H NMR (400 MHz, d6-DMSO): 11.1 (bs, 1H), 8.18 (s, 1H), 7.48 (dd, 2H), 7.34 (dd, 1H), 5.90 (m, 1H), 5.07 (m, 1H), 4.99 (m, 1H), 4.59 (m, 2H), 3.95 (s, 3H) |
| I-a-31 | thien-2-yl | C=O | CH=CH—OCH$_3$ | Cl | 6-Cl | H | $^1$H NMR (400 MHz, CDCl$_3$): 7.44 (m, 2H), 7.28 (m, 2H), 6.93 (d, 1H), 6.27 (d, 1H), 5.84 (d, 1H), 3.71 (s, 3H) |
| I-a-32 | thien-2-yl | C=O | CH=CH—F (Z isomer) | Cl | 6-Cl | H | $^1$H NMR (400 MHz, CDCl$_3$): 7.85 (dd, 1H), 7.47 (m, 2H), 7.33 (m, 2H), 6.93 (d, 1H), 6.27 (d, 1H) |
| I-a-33 | thien-2-yl | C=O | CH=CH—F (E isomer) | Cl | 6-Cl | H | $^1$H NMR (400 MHz, CDCl$_3$): 7.42 (m, 2H), 7.32 (m, 2H), 6.95 (d, 1H), 6.80 (dd, 1H), 6.32 (dd, 1H), |
| I-a-34 | thiazol-5-yl | C=O | CH$_2$CHF$_2$ | Cl | 4-Cl | H | $^1$H NMR (400 MHz, d6-DMSO): 11.5 (bs, 1H), 9.41 (s, 1H), 7.67 (d, 1H), 7.46 (dd, 1H), 7.33 (d, 1H), 6.34 (m, 1H), 4.72 (m, 2H) |
| I-a-35 | N-methylpyrazol-4-yl | C=O | CH$_2$CHF$_2$ | Cl | 6-Cl | H | $^1$H NMR (400 MHz, d6-DMSO): 11.3 (bs, 1H), 8.22 (s, 1H), 7.49 (dd, 2H), 7.36 (dd, 1H), 6.31 (m, 1H), 4.42 (m, 2H), 3.97 (s, 3H) |
| I-a-36 | thiazol-5-yl | C=O | CH$_2$CHF$_2$ | Br | 4-Cl | 6-Et | $^1$H NMR (400 MHz, d6-DMSO): 11.5 (bs, 1H), 9.41 (s, 1H), 7.64 (d, 1H), 7.40 (d, 1H), 6.33 (m, 1H), 4.75 (m, 2H), 2.39 (m, 2H), 1.03 (t, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-37 | thiazole | C=O | CH₂CHF₂ | Me | 4-Me | 6-Me | ¹H NMR (400 MHz, d6-DMSO): 10.8 (bs, 1H), 9.36 (s, 1H), 6.90 (s, 2H), 6.35 (m, 1H), 4.75 (m, 2H), 2.18 (s, 3H), 1.97 (s, 6H) |
| I-a-38 | thiazole | C=O | CH₂CHF₂ | Cl | 6-Cl | H | ¹H NMR (400 MHz, d6-DMSO): 11.7 (bs, 1H), 9.42 (s, 1H), 7.53 (d, 2H) 7.41 (t, 1H), 6.34 (m, 1H), 4.75 (m, 2H) |
| I-a-39 | 2-methylthio-thiazole | C=O | CH₂CHF₂ | Cl | 6-Cl | H | ¹H NMR (400 MHz, d6-DMSO): 11.8 (bs, 1H), 7.51 (d, 2H) 7.41 (t, 1H), 6.33 (m, 1H), 4.67 (m, 2H), 2.81 (s, 3H) |
| I-a-40 | thiophene | C=O | CH₂CHF₂ | Cl | 6-Cl | H | ¹H NMR (400 MHz, CDCl₃): 7.49 (d, 2H) 7.33 (m, 2H), 7.00 (d, 1H), 6.23 (m, 1H), 4.44 (m, 2H) |
| I-a-41 | thiazole | C=O | CH₂CF₃ | Me | 4-Me | 6-Me | ¹H NMR (400 MHz, d6-DMSO): 11.0 (bs, 1H), 9.37 (s, 1H), 6.91 (s, 2H), 5.13 (m, 2H), 2.27 (s, 3H), 1.98 (s, 6H) |
| I-a-42 | N-methylpyrazole | C=O | CH₂CHF₂ | Me | 4-Me | 6-Me | ¹H NMR (400 MHz, d6-DMSO): 10.7 (bs, 1H), 8.18 (s, 1H), 6.85 (s, 2H), 6.31 (m, 1H), 4.41 (m, 2H), 3.95 (s, 3H) |
| I-a-43 | N-methylpyrazole | C=O | CH₂CHF₂ | Br | 4-Cl | 6-Et | ¹H NMR (400 MHz, d6-DMSO): 11.1 (bs, 1H), 8.19 (s, 1H), 7.60 (d, 1H), 7.35 (d, 1H), 6.30 (m, 1H), 4.42 (m, 2H), 3.97 (s, 3H) |
| I-a-44 | thiazole | C=O | CH₂C≡CH | Cl | 6-Cl | H | ¹H NMR (400 MHz, d6-DMSO): 11.6 (bs, 1H), 9.42 (s, 1H), 7.50 (d, 2H) 7.40 (t, 1H), 5.04 (d, 2H), 3.15 (t, 1H) |
| I-a-45 | thiazole | C=O | CH₂CF₃ | Cl | 6-Cl | H | ¹H NMR (400 MHz, d6-DMSO): 11.8 (bs, 1H), 9.43 (s, 1H), 7.54 (d, 2H) 7.42 (t, 1H), 5.13 (m, 2H) |
| I-a-46 | thiazole | C=O | CH₂C≡CH | Br | 4-Cl | 6-Et | ¹H NMR (400 MHz, d6-DMSO): 11.7 (bs, 1H), 9.42 (s, 1H), 7.64 (d, 1H), 7.40 (d, 1H), 5.04 (d, 2H), 3.13 (t, 1H), 2.39 (m, 2H), 1.01 (dt, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-47 | 1-methylpyrazol-4-yl | C=O | $CH_2CF_3$ | Br | 4-Cl | 6-Et | $^1$H NMR (400 MHz, d6-DMSO): 11.2 (bs, 1H), 8.20 (s, 1H), 7.60 (d, 1H), 7.36 (d, 1H), 4.80 (m, 2H), 3.96 (s, 3H), 2.38 (m, 2H), 0.99 (t, 3H) |
| I-a-48 | 1-methylpyrazol-4-yl | C=O | $CH_2CF_3$ | Cl | 6-Cl | H | $^1$H NMR (400 MHz, d6-DMSO): 11.4 (bs, 1H), 8.22 (s, 1H), 7.49 (d, 2H), 7.36 (t, 1H), 4.80 (m, 2H), 3.97 (s, 3H) |
| I-a-49 | 1-methylpyrazol-4-yl | C=O | $CH_2CF_3$ | Me | 4-Me | 6-Me | $^1$H NMR (400 MHz, d6-DMSO): 10.7 (bs, 1H), 8.16 (s, 1H), 6.86 (d, 2H), 4.80 (m, 2H), 3.95 (s, 3H), 2.18 (s, 3H), 1.95 (s, 6H) |
| I-a-50 | 2-methylthiothiazol-4,5-diyl | C=O | $CH_2C{\equiv}CH$ | Cl | 6-Cl | H | $^1$H NMR (400 MHz, d6-DMSO): 11.5 (bs, 1H), 7.51 (d, 2H), 7.39 (t, 1H), 4.97 (d, 2H), 3.16 (t, 1H), 2.85 (s, 3H) |
| I-a-51 | thiazol-4,5-diyl | C=O | $CH_2CH_3$ | Cl | 6-Cl | H | $^1$H NMR (400 MHz, d6-DMSO): 11.3 (bs, 1H), 9.41 (s, 1H), 7.52 (d, 2H) 7.40 (t, 1H), 4.35 (m, 2H), 1.24 (m, 3H) |
| I-a-52 | 2-methylthiazol-4,5-diyl | C=O | $CH_2C{\equiv}CH$ | Cl | 6-Cl | H | $^1$H NMR (400 MHz, d6-DMSO): 11.5 (bs, 1H), 7.52 (d, 2H), 7.40 (t, 1H), 4.98 (d, 2H), 3.14 (t, 1H), 2.83 (s, 3H) |
| I-a-53 | thiazol-4,5-diyl | C=O | $CH_2$—c-Pr | Cl | 6-Cl | H | $^1$H NMR (400 MHz, $CDCl_3$): 8.91 (s, 1H), 7.41 (d, 2H) 7.23 (t, 1H), 4.35 (d, 2H), 1.43 (m, 1H), 0.47 (m, 4H) |
| I-a-54 | 1-methylpyrazol-4-yl | C=O | $CH_2CHF_2$ | Cl | 6-Cl | H | $^1$H NMR (400 MHz, d6-DMSO): 11.6 (bs, 1H), 8.08 (s, 1H), 7.49 (d, 2H), 7.36 (t, 1H), 6.25 (m, 1H), 4.35 (m, 2H), 4.05 (s, 3H) |
| I-a-55 | thiazol-4,5-diyl | C=O | $CH_2C{\equiv}CH$ | Me | 3-Br | 6-Me | $^1$H NMR (400 MHz, d6-DMSO): 11.1 (bs, 1H), 9.40 (s, 1H), 7.48 (d, 1H), 7.06 (d, 1H), 5.04 (d, 2H), 3.12 (t, 1H), 2.22 (s, 3H), 1.98 (s, 3H) |
| I-a-56 | thiazol-4,5-diyl | C=O | $CH_2CHF_2$ | Cl | 4-Cl | 6-Et | $^1$H NMR (400 MHz, d6-DMSO): 11.6 (bs, 1H), 9.39 (s, 1H), 7.49 (d, 1H), 7.35 (d, 1H), 6.33 (m, 1H), 4.74 (m, 2H), 2.39 (m, 2H), 1.03 (m, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-57 | thiazole | C=O | $CH_2CHF_2$ | Me | 3-Br | Me | $^1$H NMR (400 MHz, d6-DMSO): 11.2 (bs, 1H), 9.39 (s, 1H). 7.48 (d, 1H), 7.06 (d, 1H), 6.35 (m, 1H), 4.74 (m, 2H), 2.10 (s, 3H), 1.98 (s, 3H) |
| I-a-58 | thiazole | C=O | $CH_2CHF_2$ | Cl | 4-Cl | 6-Me | $^1$H NMR (400 MHz, d6-DMSO): 11.6 (bs, 1H), 9.40 (s, 1H). 7.49 (d, 1H), 7.38 (d, 1H), 6.34 (m, 1H), 4.74 (m, 2H), 2.08 (s, 3H) |
| I-a-59 | thiazole | C=O | $CH_2C\equiv CH$ | Cl | 4-Cl | 6-Me | $^1$H NMR (400 MHz, d6-DMSO): 11.4 (bs, 1H), 9.42 (s, 1H). 7.49 (d, 1H), 7.38 (d, 1H), 5.04 (d, 2H), 3.14 (t, 1H), 2.08 (s, 3H) |
| I-a-60 | thiazole | C=O | $CH_2CHF_2$ | Et | 4-Cl | 6-OMe | $^1$H NMR (400 MHz, d6-DMSO): 10.9 (bs, 1H), 9.36 (s, 1H). 6.95 (d, 2H), 6.32 (m, 1H), 4.72 (m, 2H), 3.66 (s, 3H), 2.31 (m, 2H), 0.86 (m, 3H) |
| I-a-61 | thiazole | C=O | $CH_2CHF_2$ | Cl | 4-Br | 6-Et | $^1$H NMR (400 MHz, d6-DMSO): 11.4 (bs, 1H), 9.41 (s, 1H). 7.62 (d, 1H), 7.50 (d, 1H), 6.33 (m, 1H), 4.74 (m, 2H), 2.38 (m, 2H), 1.01 (m, 3H) |
| I-a-62 | thiazole | C=O | $CH_2CHF_2$ | Me | 4-Cl | 6-$CF_3$ | $^1$H NMR (400 MHz, d6-DMSO): 11.4 (bs, 1H), 9.40 (s, 1H). 7.75 (d, 1H), 7.67 (d, 1H), 6.31 (m, 1H), 4.73 (m, 2H), 2.08 (s, 3H) |
| I-a-63 | N-methylpyrazole | C=O | $CH_2CHF_2$ | Cl | 4-Cl | 6-Et | $^1$H NMR (400 MHz, CDCl$_3$): 7.75 (s, 1H). 7.35 (d, 1H), 7.23 (d, 1H), 6.25 (m, 1H), 4.53 (m, 2H), 4.01 (s, 3H), 2.43 (m, 2H), 1.08 (m, 3H) |
| I-a-64 | N-methylpyrazole | C=O | $CH_2CF_3$ | Cl | 4-Cl | 6-Et | $^1$H NMR (400 MHz, CDCl$_3$): 7.78 (s, 1H). 7.31 (d, 1H), 7.20 (d, 1H), 4.82 (m, 2H), 3.98 (s, 3H), 2.40 (m, 2H), 1.06 (m, 3H) |
| I-a-65 | N-methylpyrazole | C=O | $CH_2CF_3$ | Cl | 4-Cl | 6-Me | $^1$H NMR (400 MHz, d6-DMSO): 11.3 (bs, 1H), 8.22 (s, 1H). 7.46 (d, 1H), 7.36 (d, 1H), 4.80 (m, 2H), 3.97 (s, 3H), 2.06 (s, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-66 | pyrazole | C=O | CH$_2$CHF$_2$ | Cl | 4-Cl | 6-Me | $^1$H NMR (400 MHz, d6-DMSO): 11.2 (bs, 1H), 8.21 (s, 1H). 7.45 (d, 1H), 7.35 (d, 1H), 6.32 (m, 1H), 4.43 (m, 2H), 3.97 (s, 3H), 2.06 (s, 3H) |
| I-a-67 | pyrazole | C=O | CH$_3$ | Cl | 4-Cl | 6-Me | $^1$H NMR (400 MHz, d6-DMSO): 10.9 (bs, 1H), 8.17 (s, 1H). 7.44 (d, 1H), 7.34 (d, 1H), 3.97 (s, 3H), 3.41 (s, 3H), 2.06 (s, 3H) |
| I-a-68 | pyrazole | C=O | CH$_2$CF$_3$ | Cl | 3-Br | 6-Cl | $^1$H NMR (400 MHz, d6-DMSO): 11.6 (bs, 1H), 8.23 (s, 1H). 7.78 (d, 1H), 7.48 (d, 1H), 4.80 (m, 2H), 3.97 (s, 3H) |
| I-a-69 | pyrazole | C=O | CH$_3$ | Me | 4-CF$_2$—CF$_3$ | 6-Me | $^1$H NMR (400 MHz, d6-DMSO): 10.8 (bs, 1H), 8.18 (s, 1H). 7.37 (s, 2H), 3.97 (s, 3H), 3.42 (s, 3H), 2.09 (s, 6H) |
| I-a-70 | pyrazole | C=O | CH$_3$ | Cl | 3-Br | 6-Cl | $^1$H NMR (400 MHz, d6-DMSO): 11.1 (bs, 1H), 8.18 (s, 1H). 7.75 (d, 1H), 7.45 (d, 1H), 3.97 (s, 3H), 3.41 (s, 3H) |
| I-a-71 | pyrazole | C=O | CH$_2$CF$_3$ | Me | 4-CF$_2$—CF$_3$ | 6-Me | $^1$H NMR (400 MHz, d6-DMSO): 11.3 (bs, 1H), 8.22 (s, 1H). 7.38 (s, 2H), 4.82 (m, 2H), 3.97 (s, 3H), 2.09 (s, 6H) |
| I-a-72 | pyrazole | C=O | CH$_2$CHF$_2$ | Me | 4-CF$_2$—CF$_3$ | 6-Me | $^1$H NMR (400 MHz, d6-DMSO): 11.1 (bs, 1H), 8.22 (s, 1H). 7.37 (s, 2H), 6.33 (m, 1H), 4.42 (m, 2H), 3.98 (s, 3H), 2.09 (s, 6H) |
| I-a-73 | pyrazole | C=O | CH$_2$CHF$_2$ | Cl | 3-Br | 6-Cl | $^1$H NMR (400 MHz, d6-DMSO): 11.4 (bs, 1H), 8.22 (s, 1H). 7.77 (d, 1H), 7.46 (d, 1H), 6.31 (m, 1H), 4.41 (m, 2H), 3.97 (s, 3H) |
| I-a-74 | pyrazole | C=O | CH$_3$ | Cl | 4-Cl | 6-Et | $^1$H NMR (400 MHz, d6-DMSO): 10.9 (bs, 1H), 8.16 (s, 1H). 7.45 (d, 1H), 7.32 (d, 1H), 3.97 (s, 3H), 3.41 (s, 3H), 2.35 (m, 2H), 1.00 (m, 3H) |
| I-a-75 | thiazole | C=O | CH$_2$CHF$_2$ | Cl | 3-Br | 6-Cl | $^1$H NMR (400 MHz, d6-DMSO): 11.8 (bs, 1H), 9.41 (s, 1H). 7.82 (d, 1H), 7.53 (d, 1H), 6.33 (m, 1H), 4.72 (m, 2H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-76 | pyrazole | C=O | CH$_3$ | F | 3-Me | 6-Cl | $^1$H NMR (400 MHz, d6-DMSO): 11.1 (bs, 1H), 8.17 (s, 1H). 7.25 (m, 2H), 3.97 (s, 3H), 3.40 (s, 3H), 2.22 (s, 3H) |
| I-a-77 | pyrazole | C=O | CH$_2$CHF$_2$ | F | 3-Me | 6-Cl | $^1$H NMR (400 MHz, d6-DMSO): 11.5 (bs, 1H), 8.19 (s, 1H). 7.24 (m, 2H), 6.33 (m, 1H), 4.39 (m, 2H), 3.97 (s, 3H), 2.22 (s, 3H) |
| I-a-78 | pyrazole | C=O | CH$_2$CF$_3$ | F | 3-Me | 6-Cl | $^1$H NMR (400 MHz, d6-DMSO): 8.22 (s, 1H). 7.26 (m, 2H), 6.33 (m, 1H), 4.79 (m, 2H), 3.97 (s, 3H), 2.22 (s, 3H) |
| I-a-79 | pyrazole | C=O | CH$_2$C≡CH | Me | 4-CF$_2$—CF$_3$ | 6-Me | $^1$H NMR (400 MHz, CDCl$_3$): 7.77 (s, 1H). 7.34 (s, 2H), 4.94 (d, 2H), 4.02 (s, 3H), 2.18 (t, 1H), 2.16 (s, 6H) |
| I-a-80 | thiazole | C=O | CH$_2$CHF$_2$ | CF$_3$ | H | H | $^1$H NMR (400 MHz, d6-DMSO): 9.42 (s, 1H). 7.76 (d, 1H), 7.69 (t, 1H), 7.57 (t, 1H), 7.32 (d, 1H), 6.30 (m, 1H), 4.71 (m, 2H) |
| I-a-81 | pyrazole | C=O | CH$_2$C≡CH | F | 3-Me | 6-Cl | $^1$H NMR (400 MHz, d6-DMSO): 11.2 (bs, 1H), 8.20 (s, 1H). 7.25 (m, 2H), 4.73 (m, 2H), 3.99 (s, 3H), 3.10 (t, 1H), 2.22 (s, 3H) |
| I-a-82 | thiazole | C=O | CH$_3$ | I | H | H | $^1$H NMR (400 MHz, d6-DMSO): 11.0 (bs, 1H), 9.37 (s, 1H). 7.91 (d, 1H), 7.42 (t, 1H), 7.21 (d, 1H), 7.09 (t, 1H), 3.69 (s, 3H) |
| I-a-83 | thiazole | C=O | CH$_2$CHF$_2$ | Cl | 3-c-Pr | 6-Cl | $^1$H NMR (400 MHz, d6-DMSO): 11.6 (bs, 1H), 9.38 (s, 1H). 7.40 (d, 1H), 7.05 (d, 1H), 6.33 (m, 1H), 4.73 (m, 2H), 2.13 (m, 1H), 0.74 (m, 2H), 0.65 (m, 2H) |
| I-a-84 | thiazole | C=O | CH$_2$CHF$_2$ | I | H | H | $^1$H NMR (400 MHz, d6-DMSO): 11.3 (bs, 1H), 9.40 (s, 1H). 7.92 (d, 1H), 7.43 (t, 1H), 7.24 (d, 1H), 7.10 (t, 1H), 6.33 (m, 1H), 4.74 (m, 2H), |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-85 | thiazole | C=O | CH$_3$ | CF$_3$ | H | H | $^1$H NMR (400 MHz, d6-DMSO): 11.0 (bs, 1H), 9.37 (s, 1H). 7.78 (d, 1H), 7.68 (t, 1H), 7.58 (t, 1H), 7.30 (d, 1H), 3.68 (s, 3H) |
| I-a-86 | thiazole | C=O | CH$_2$CF$_3$ | Cl | 3-Me | 6-Cl | $^1$H NMR (400 MHz, d6-DMSO): 11.7 (bs, 1H), 9.42 (s, 1H). 7.40 (m, 2H), 5.12 (m, 2H), 2.37 (s, 3H) |
| I-a-87 | thiazole | C=O | CH$_2$CHF$_2$ | Br | 4-Br | 6-OCF$_3$ | $^1$H NMR (400 MHz, d6-DMSO): 11.8 (bs, 1H), 9.44 (s, 1H). 8.06 (d, 1H), 7.73 (d, 1H), 6.31 (m, 1H), 4.74 (m, 2H) |
| I-a-88 | thiazole | C=O | CH$_2$CHF$_2$ | Cl | 3-I | 6-Cl | $^1$H NMR (400 MHz, d6-DMSO): 11.7 (bs, 1H), 9.42 (s, 1H). 7.98 (d, 1H), 7.31 (d, 1H), 6.33 (m, 1H), 4.73 (m, 2H) |
| I-a-89 | thiazole | C=O | CH$_2$CHF$_2$ | Cl | 3-Me | 6-Cl | $^1$H NMR (400 MHz, d6-DMSO): 9.41 (s, 1H). 7.40 (m, 2H), 6.33 (m, 1H), 4.73 (m, 2H), 2.33 (s, 3H) |
| I-a-90 | thiazole | C=O | CH$_3$ | Cl | 3-Me | 6-Cl | $^1$H NMR (400 MHz, d6-DMSO): 11.2 (bs, 1H), 9.39 (s, 1H). 7.40 (m, 2H), 3.70 (s, 3H), 2.36 (s, 3H) |
| I-a-91 | thiazole | C=O | CH$_2$CF$_3$ | Me | 3-Br | 6-Cl | $^1$H NMR (400 MHz, d6-DMSO): 9.43 (s, 1H). 7.65 (d, 1H), 7.34 (d, 1H), 5.13 (m, 2H), 2.16 (s, 3H) |
| I-a-92 | thiazole | C=O | CH$_3$ | Cl | 3-I | 6-Cl | $^1$H NMR (400 MHz, d6-DMSO): 11.5 (bs, 1H), 9.41 (s, 1H). 7.96 (d, 1H), 7.31 (d, 1H), 3.70 (s, 3H) |
| I-a-93 | thiazole | C=O | CH$_3$ | Me | 3-Br | 6-Cl | $^1$H NMR (400 MHz, d6-DMSO): 9.38 (s, 1H). 7.63 (d, 1H), 7.31 (d, 1H), 3.70 (s, 3H), 2.15 (s, 3H) |
| I-a-94 | thiazole | C=O | CH$_2$CHF$_2$ | Me | 3-Br | 6-Cl | $^1$H NMR (400 MHz, d6-DMSO): 11.5 (bs, 1H), 9.41 (s, 1H). 7.63 (d, 1H), 7.32 (d, 1H), 6.34 (m, 1H), 4.74 (m, 2H), 2.16 (s, 3H) |
| I-a-95 | thiazole | C=O | CH$_2$CF$_3$ | Cl | 3-I | 6-Cl | $^1$H NMR (400 MHz, CDCl$_3$): 8.96 (s, 1H). 7.82 (d, 1H), 7.14 (t, 1H), 5.13 (m, 2H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-96 | thiazole | C=O | CH₂CHF₂ | Me | 4-Br | 6-Et | ¹H NMR (400 MHz, d6-DMSO): 9.39 (s, 1H). 7.33 (d, 1H), 7.30 (d, 1H), 6.34 (m, 1H), 4.74 (m, 2H), 2.31 (m, 2H), 2.10 (s, 3H), 0.99 (m, 3H) |
| I-a-97 | thiazole | C=O | CH₂CHF₂ | Me | 4-Br | 6-Me | ¹H NMR (400 MHz, d6-DMSO): 11.2 (bs, 1H), 9.39 (s, 1H). 7.32 (d, 2H), 6.35 (m, 1H), 4.74 (m, 2H), 2.01 (s, 6H) |
| I-a-98 | 2-SMe-thiazole | C=O | CH₃ | Cl | 6-Cl | H | ¹H NMR (400 MHz, d6-DMSO): 11.3 (bs, 1H), 7.49 (d, 2H), 7.39 (t, 1H), 3.68 (s, 3H), 2.86 (s, 3H) |
| I-a-99 | 2-SO₂Me-thiazole | C=O | CH₂CHF₂ | Cl | 6-Cl | H | ¹H NMR (400 MHz, CDCl₃): 7.48 (d, 2H), 7.37 (t, 1H), 6.22 (m, 1H), 4.81 (m, 2H); 3.41 (s, 3H) |
| I-a-100 | 2-SO₂Me-thiazole | C=O | CH₃ | Cl | 6-Cl | H | ¹H NMR (400 MHz, d6-DMSO): 7.36 (d, 2H), 7.19 (t, 1H), 3.50 (s, 3H), 3.36 (s, 3H) |
| I-a-101 | thiazole | C=O | CH₃ | Me | 4-O—CH₂—CF₃ | 6-Et | ¹H NMR (400 MHz, CDCl₃): 8.90 (s, 1H), 6.80 (d, 1H), 6.76 (d, 1H), 4.38 (m, 2H); 3.90 (s, 3H), 2.44 (m, 2H), 1.09 (m, 3H) |
| I-a-102 | 2-S(O)Me-thiazole | C=O | CH₂CHF₂ | Cl | 6-Cl | H | ¹H NMR (400 MHz, d6-DMSO): 12.0 (bs, 1H), 7.54 (d, 2H), 7.43 (t, 1H), 6.36 (m, 1H), 4.70 (m, 2H); 3.12 (s, 3H) |
| I-a-103 | thiazole | C=O | CH₃ | Me | 4-Br | 6-Et | ¹H NMR (400 MHz, d6-DMSO): 10.8 (bs, 1H), 9.36 (s, 1H). 7.32 (d, 1H), 7.29 (d, 1H), 3.70 (s, 3H), 2.31 (m, 2H), 1.98 (s, 3H), 0.98 (t, 3H) |
| I-a-104 | thiazole | C=O | CH₂CHF₂ | Me | 4-CF₂—CF₃ | 6-Me | ¹H NMR (400 MHz, d6-DMSO): 11.3 (bs, 1H), 9.40 (s, 1H). 7.41 (s, 2H), 6.36 (m, 1H), 4.75 (m, 2H); 2.11 (s, 6H) |
| I-a-105 | thiazole | C=O | CH₂C≡CH | Me | 4-CF₂—CF₃ | 6-Me | ¹H NMR (400 MHz, d6-DMSO): 11.3 (bs, 1H), 9.42 (s, 1H). 7.41 (s, 2H), 5.05 (d, 2H), 3.14 (t, 1H); 2.11 (s, 6H) |

TABLE 229-continued

Inventive compounds of the formula (I) in which G is hydrogen:

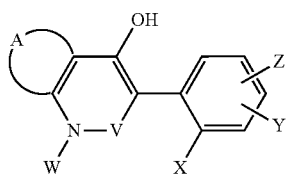

(I-a)

| No. | A | V | W | X | Y | Z | Analytical data |
|---|---|---|---|---|---|---|---|
| I-a-106 | (methylsulfinyl-thiazolyl) | C=O | CH$_3$ | Cl | 6-Cl | H | $^1$H NMR (400 MHz, d6-DMSO): 11.7 (bs, 1H), 7.53 (d, 2H), 7.42 (t, 1H), 3.67 (s, 3H), 3.12 (s, 3H) |
| I-a-107 | (thiazolyl) | C=O | CH$_3$ | Me | 4-O—CH$_2$—CF$_3$ | 6-Me | $^1$H NMR (400 MHz, CDCl$_3$): 8.91 (s, 1H), 6.78 (s, 2H), 4.37 (m, 2H); 3.90 (s, 3H), 2.13 (s, 6H) |
| I-a-108 | (thiazolyl) | C=O | CH$_3$ | Me | 4-CF$_2$—CF$_3$ | 6-Me | $^1$H NMR (400 MHz, d6-DMSO): 11.0 (bs, 1H), 9.38 (s, 1H). 7.40 (s, 2H), 3.71 (s, 3H); 2.10 (s, 6H) |
| I-a-109 | (thiazolyl) | C=O | CH$_2$C≡CH | I | 4-Cl | 6-Et | $^1$H NMR (400 MHz, d6-DMSO): 11.3 (bs, 1H), 9.42 (s, 1H). 7.81 (d, 1H), 7.39 (d, 1H), 5.04 (d, 2H), 3.12 (t, 1H); 2.37 (m, 2H), 0.99 (m, 3H) |
| I-a-110 | (thiazolyl) | C=O | CH$_2$CHF$_2$ | I | 4-Cl | 6-Et | $^1$H NMR (400 MHz, d6-DMSO): 11.3 (bs, 1H), 9.41 (s, 1H). 7.81 (d, 1H), 7.40 (d, 1H), 6.32 (m, 1H), 4.75 (m, 2H), 2.36 (m, 2H), 0.97 (m, 3H) |
| I-a-111 | (thiazolyl) | C=O | CH$_3$ | I | 4-Cl | 6-Et | $^1$H NMR (400 MHz, d6-DMSO): 11.1 (bs, 1H), 9.38 (s, 1H). 7.80 (d, 1H), 7.39 (d, 1H), 3.70 (s, 3H), 2.36 (m, 2H), 0.99 (m, 3H) |
| I-a-112 | (thiazolyl) | C=O | CH$_2$CHF$_2$ | F | 4-Me | 6-Me | $^1$H NMR (400 MHz, d6-DMSO): 11.3 (bs, 1H), 9.39 (s, 1H). 6.94 (d, 1H), 6.86 (dd, 1H), 6.35 (m, 1H), 4.73 (m, 2H), 2.32 (s, 3H), 2.06 (s, 3H) |
| I-a-113 | (thiazolyl) | C=O | CH$_2$CHF$_2$ | Br | 4-Br | 6-Me | $^1$H NMR (400 MHz, d6-DMSO): 11.4 (bs, 1H), 9.40 (s, 1H). 7.74 (d, 1H), 7.55 (d, 1H), 6.34 (m, 1H), 4.74 (m, 2H), 2.09 (s, 3H) |
| I-a-114 | (thiazolyl) | C=O | CH$_3$ | F | 4-Me | 6-Me | $^1$H NMR (400 MHz, d6-DMSO): 10.9 (bs, 1H), 9.36 (s, 1H). 6.93 (d, 1H), 6.84 (dd, 1H), 3.69 (s, 3H), 2.32 (s, 3H), 2.04 (s, 3H) |

TABLE 229-continued

Inventive compounds of the formula (I) in which G is hydrogen:

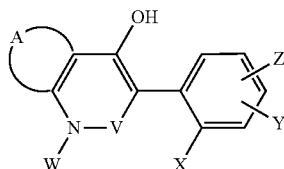
(I-a)

| No. | A | V | W | X | Y | Z | Analytical data |
|---|---|---|---|---|---|---|---|
| I-a-115 | thiazole | C=O | CH₂CHF₂ | Br | 4-Br | 6-Et | ¹H NMR (400 MHz, d6-DMSO): 11.4 (bs, 1H), 9.40 (s, 1H). 7.75 (d, 1H), 7.52 (d, 1H), 6.33 (m, 1H), 4.74 (m, 2H), 2.39 (m, 2H), 0.98 (m, 3H) |
| I-a-116 | thiazole | C=O | CH₂C≡CH | Br | 4-Br | 6-Et | ¹H NMR (400 MHz, d6-DMSO): 11.3 (bs, 1H), 9.42 (s, 1H). 7.76 (d, 1H), 7.52 (d, 1H), 5.04 (d, 2H), 3.13 (t, 1H), 2.36 (m, 2H), 1.00 (m, 3H) |
| I-a-117 | thiazole | C=O | CH₂C≡CH | Br | 4-Br | 6-Me | ¹H NMR (400 MHz, d6-DMSO): 11.3 (bs, 1H), 9.42 (s, 1H). 7.75 (d, 1H), 7.55 (d, 1H), 5.04 (d, 2H), 3.13 (t, 1H), 2.08 (s, 3H) |
| I-a-118 | thiazole | C=O | CH₃ | Br | 4-Br | 6-Me | ¹H NMR (400 MHz, d6-DMSO): 11.1 (bs, 1H), 9.38 (s, 1H). 7.73 (d, 1H), 7.54 (d, 1H), 3.70 (s, 3H), 2.08 (s, 3H) |
| I-a-119 | thiazole | C=O | CH₃ | Br | 4-Br | 6-Et | ¹H NMR (400 MHz, d6-DMSO): 11.1 (bs, 1H), 9.38 (s, 1H). 7.74 (d, 1H), 7.51 (d, 1H), 3.70 (s, 3H), 2.37 (m, 2H), 1.00 (t, 3H) |
| I-a-120 | thiazole | C=O | CH₂C≡CH | F | 4-Me | 6-Me | ¹H NMR (400MHz, d6-DMSO): 11.3 (bs, 1H), 9.41 (s, 1H). 6.94 (d, 1H), 6.86 (dd, 1H), 5.04 (d, 2H), 3.17 (t, 1H), 2.32 (s, 3H), 2.04 (s, 3H) |
| I-a-121 | thiazole | C=O | CH₂CHF₂ | Me | 4-(2'-c-Pr)—c-Pr | Me | ¹H NMR (400 MHz, CDCl₃): 8.91 (s, 1H). 6.84 (d, 2H), 6.28 (m, 1H), 4.86 (m, 2H), 2.08 (s, 6H), 1.60 (m, 1H), 1.10 (m, 1H) 0.90 (m, 1H), 0.75 (m, 2H), 0.40 (m, 2H), 0.15 (m, 2H) |
| I-a-122 | thiazole | C=O | CH₃ | Me | 4-(2'-c-Pr)—c-Pr | Me | ¹H NMR (400 MHz, d6-DMSO): 10.6 (bs, 1H), 9.33 (s, 1H). 6.74 (d, 2H), 3.69 (s, 3H), 1.94 (s, 6H), 1.60 (m, 1H), 1.10 (m, 1H) 0.90 (m, 1H), 0.75 (m, 2H), 0.40 (m, 2H), 0.15 (m, 2H) |
| I-a-123 | 2-methylthiazole | C=O | CH₃ | Cl | 6-Cl | H | ¹H NMR (400 MHz, d6-DMSO): 11.2 (bs, 1H), 7.52 (d, 2H), 7.39 (t, 1H), 3.65 (s, 3H), 2.81 (s, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-124 | 2-methyl-thiazol-5,4-diyl | C=O | CH$_2$CHF$_2$ | Cl | 6-Cl | H | $^1$H NMR (400 MHz, d6-DMSO): 11.5 (bs, 1H), 7.52 (d, 2H), 7.40 (t, 1H), 6.33 (m, 1H), 4.69 (m, 2H), 2.82 (s, 3H) |
| I-a-125 | 3-ethyl-2-methyl-thien-4,5-diyl | C=O | CH$_2$CHF$_2$ | Cl | 4-Br | 6-Et | $^1$H NMR (400 MHz, CDCl$_3$): 7.58 (d, 1H); 7.45 (d, 1H); 6.21 (tt, 1H); 5.39 (s, 1H); 4.38 (m, 2H); 2.82 (m, 2H); 2.47 (m, 2H); 2.39 (s, 3H); 1.15 (t, 3H); 1.11 (t, 3H) |
| I-a-126 | 2,3-dimethyl-thien-4,5-diyl | C=O | CH$_2$CHF$_2$ | Cl | 4-Br | 6-Et | $^1$H NMR (400 MHz, CDCl$_3$): 7.37 (d, 1H); 7.23 (d, 1H); 6.05 (tt, 1H); 4.33 (m, 2H); 4.18 (m, 1H); 3.73 (s, 2H); 3.69 (m, 1H); 2.54 (q, 2H); 2.37 (s, 3H); 2.30 (s, 3H); 1.36 (t, 3H); 1.17 (t, 3H) |
| I-a-127 | 2-phenyl-thien-4,5-diyl | C=O | CH$_2$CHF$_2$ | Br | 4-Cl | 6-Et | $^1$H NMR (400 MHz, CDCl$_3$): 7.71 (d, 1H); 7.69 (m, 1H); 7.62 (d, 1H); 7.46 (m, 3H); 7.35 (m, 2H); 6.16 (tt, 1H); 5.64 (s, 1H); 4.57 (m, 2H); 2.51 (m, 2H); 1.13 (t, 3H) |
| I-a-128 | thien-2,3-diyl | C=O | CH$_2$CHF$_2$ | Cl | 4-BrI | 6-Et | $^1$H NMR (400 MHz, CDCl$_3$): 7.47 (d, 1H); 7.40 (d, 1H); 7.33 (d, 1H); 6.92 (d, 1H); 6.12 (tt, 1H); 4.15 (m, 2H); 2.55 (m, 2H); 1.04 (t, 3H) |
| I-a-129 | 5-methyl-thien-2,3-diyl | C=O | CH$_2$CHF$_2$ | Br | 4-Cl | 6-Et | $^1$H NMR (400 MHz, CDCl$_3$): 7.59 (d, 1H); 7.32 (d, 1H); 6.94 (q, 1H); 6.20 (tt, 1H); 5.54 (s, 1H); 4.37 (m, 2H); 2.52 (d, 3H); 2.47 (m, 2H); 1.10 (t, 3H) |
| I-a-130 | 1-ethyl-pyrazol-3,4-diyl | C=O | CH$_2$CHF$_2$ | Br | 4-Cl | 6-Et | $^1$H NMR (400 MHz, d$_6$-DMSO): 11.11 (s, 1H); 8.24 (s, 1H); 7.60 (d, 1H); 7.36 (d, 1H); 6.31 (tt, 1H); 4.42 (m, 2H); 4.26 (q, 2H); 2.38 (m, 2H); 1.44 (t, 3H); 0.99 (t, 3H) |
| I-a-131 | thiazol-5,4-diyl | C=O | CH$_3$ | Br | 4-Br | 6-OCF$_3$ | $^1$H NMR (400 MHz, d6-DMSO): 11.5 (bs, 1H), 9.41 (s, 1H). 8.05 (d, 1H), 7.71 (d, 1H), 3.69 (s, 3H) |

TABLE 229-continued

Inventive compounds of the formula (I) in which G is hydrogen:

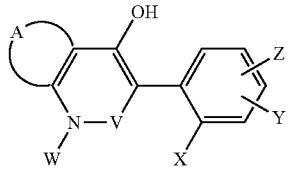

(I-a)

| No. | A | V | W | X | Y | Z | Analytical data |
|---|---|---|---|---|---|---|---|
| I-a-132 | thiadiazole | C=O | $CH_2CHF_2$ | Cl | 6-Cl | H | $^1$H NMR (400 MHz, d6-DMSO): 12.3 (bs, 1H), 7.59 (m, 2H), 7.45 (m, 1H), 6.38 (m, 1H), 4.65 (m, 2H) |
| I-a-133 | thiadiazole | C=O | $CH_3$ | Cl | 6-Cl | H | $^1$H NMR (400 MHz, d6-DMSO): 12.3 (bs, 1H), 7.55 (d, 2H), 7.44 (t, 1H), 3.61 (s, 3H) |
| I-a-134 | thiadiazole | C=O | $CH_3$ | Br | 4-Cl | 6-Et | $^1$H NMR (400 MHz, d6-DMSO): 12.0 (bs, 1H), 7.66 (d, 1H), 7.42 (d, 1H), 3.60 (s, 3H), 2.40 (m, 2H), 1.02 (t, 3H) |
| I-a-135 | thiadiazole | C=O | $CH_2CHF_2$ | Br | 4-Cl | 6-Et | $^1$H NMR (400 MHz, $CDCl_3$): 7.58 (d, 1H), 7.31 (m, 1H), 6.22 (m, 1H), 4.70 (m, 2H), 2.47 (m, 2H), 1.12 (m, 3H) |
| I-a-136 | thiazole | C=O | $CH_2CHF_2$ | Cl | 4-Br | 6-$OCF_3$ | $^1$H NMR (400 MHz, d6-DMSO): 11.9 (bs, 1H), 9.44 (s, 1H). 7.94 (d, 1H), 7.70 (d, 1H), 6.31 (m, 1H), 4.74 (m, 2H) |
| I-a-137 | thiazole | C=O | $CH_3$ | Cl | 4-Br | 6-$OCF_3$ | $^1$H NMR (400 MHz, d6-DMSO): 11.5 (bs, 1H), 9.42 (s, 1H). 7.93 (d, 1H), 7.69 (d, 1H), 3.69 (s, 3H) |
| I-a-138 | thiazole | C=O | $CH_2C\equiv CH$ | Br | 4-Br | 6-$OCF_3$ | $^1$H NMR (400 MHz, d6-DMSO): 11.7 (bs, 1H), 9.45 (s, 1H). 8.06 (d, 1H), 7.72 (d, 1H), 5.03 (d, 2H), 3.13 (t, 1H) |
| I-a-139 | thiazole | C=O | $CH_2C\equiv CH$ | Cl | 4-Br | 6-$OCF_3$ | $^1$H NMR (400 MHz, d6-DMSO): 11.8 (bs, 1H), 9.45 (s, 1H). 7.93 (d, 1H), 7.69 (d, 1H), 5.03 (d, 2H), 3.14 (t, 1H) |
| I-a-140 | thiazole | C=O | $CH_2CHF_2$ | Br | 4-Cl | 6-$OCF_3$ | $^1$H NMR (400 MHz, d6-DMSO): 11.9 (bs, 1H), 9.44 (s, 1H). 7.94 (d, 1H), 7.63 (d, 1H), 6.31 (m, 1H), 4.74 (m, 2H) |
| I-a-141 | thiazole | C=O | $CH_3$ | Br | 4-Cl | 6-$OCF_3$ | $^1$H NMR (400 MHz, d6-DMSO): 11.5 (bs, 1H), 9.41 (s, 1H), 7.94 (d, 1H), 7.62 (d, 1H), 3.69 (s, 3H) |
| I-a-142 | thiazole | C=O | $CH_2CHF_2$ | $CF_3$ | 6-F | H | $^1$H NMR (400 MHz, d6-DMSO): 11.7 (bs, 1H), 9.43 (s, 1H). 7.66 (m, 2H), 7.60 (m, 1H), 6.31 (m, 1H), 4.73 (m, 2H) |

TABLE 229-continued

Inventive compounds of the formula (I) in which G is hydrogen:

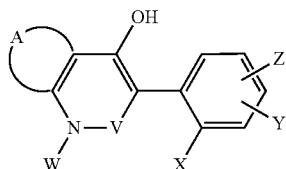

(I-a)

| No. | A | V | W | X | Y | Z | Analytical data |
|---|---|---|---|---|---|---|---|
| I-a-143 | thiazole | C=O | $CH_2C\equiv CH$ | Br | 4-Cl | 6-$OCF_3$ | $^1$H NMR (400 MHz, d6-DMSO): 11.7 (bs, 1H), 9.45 (s, 1H). 7.95 (d, 1H), 7.63 (d, 1H), 5.04 (d, 2H), 3.13 (t, 1H) |
| I-a-144 | thiazole | C=O | $CH_3$ | $CF_3$ | 6-F | H | $^1$H NMR (400 MHz, d6-DMSO): 11.4 (bs, 1H), 9.41 (s, 1H). 7.65 (m, 2H), 7.59 (m, 1H), 3.69 (s, 3H) |
| I-a-145 | thiazole | C=O | $CH_2CHF_2$ | $CF_3$ | 6-Cl | H | $^1$H NMR (400 MHz, d6-DMSO): 11.8 (bs, 1H), 9.42 (s, 1H). 7.86 (dd, 1H), 7.80 (dd, 1H), 7.63 (t, 1H), 6.30 (m, 1H), 4.73 (m, 2H) |
| I-a-146 | thiazole | C=O | $CH_2C\equiv CH$ | $CF_3$ | 6-F | H | $^1$H NMR (400 MHz, $CDCl_3$): 8.96 (s, 1H). 7.57 (dd, 1H), 7.49 (m, 1H), 7.34 (m, 1H), 5.17 (d, 2H), 2.21 (d, 1H) |
| I-a-147 | thiazole | C=O | $CH_3$ | $CF_3$ | 6-Cl | H | $^1$H NMR (400 MHz, d6-DMSO): 11.3 (bs, 1H), 9.40 (s, 1H). 7.87 (dd, 1H), 7.78 (dd, 1H), 7.62 (m, 1H), 3.68 (s, 3H) |
| I-a-148 | 2-Me-thiazole | C=O | $CH_2CHF_2$ | Cl | 4-Cl | 6-Et | $^1$H NMR (400 MHz, d6-DMSO): 11.3 (bs, 1H), 7.49 (d, 1H), 7.35 (d, 1H), 6.33 (m, 1H), 4.69 (m, 2H), 2.81 (s, 3H), 2.37 (m, 2H), 1.00 (t, 3H) |
| I-a-149 | thiazole | C=O | $CH_2C\equiv CH$ | $CF_3$ | 6-Cl | H | $^1$H NMR (400 MHz, $CDCl_3$): 8.98 (s, 1H). 7.66 (m, 2H), 7.43 (m, 1H), 7.34 (m, 1H), 5.16 (d, 2H), 2.21 (d, 1H) |
| I-a-150 | 2-Me-thiazole | C=O | $CH_2C\equiv CH$ | Cl | 4-Cl | 6-Et | $^1$H NMR (400 MHz, $CDCl_3$): 7.36 (d, 1H), 7.25 (d, 1H), 5.17 (dd, 2H), 2.82 (s, 3H), 2.50 (m, 2H), 2.16 (t, 1H), 1.09 (t, 3H) |
| I-a-151 | 2-Me-thiazole | C=O | $CH_3$ | Cl | 4-Cl | 6-Et | $^1$H NMR (400 MHz, $CDCl_3$): 7.40 (d, 1H), 7.26 (s, 1H), 3.82 (s, 3H), 2.82 (s, 3H), 2.44 (m, 2H), 1.09 (t, 3H) |
| I-a-152 | 2-Me-thiazole | C=O | $CH_2CHF_2$ | Br | 4-Cl | 6-Et | $^1$H NMR (400 MHz, d6-DMSO): 11.3 (bs, 1H), 7.63 (d, 1H), 7.39 (d, 1H), 6.32 (m, 1H), 4.69 (m, 2H), 2.81 (s, 3H), 2.40 (m, 2H), 1.00 (t, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-153 | 2-methylthiazol-4,5-diyl | C=O | CH$_2$C≡CH | Br | 4-Cl | 6-Et | $^1$H NMR (400 MHz, d6-DMSO): 11.2 (bs, 1H), 7.63 (d, 1H), 7.39 (d, 1H), 4.98 (d, 2H), 2.82 (s, 3H), 3.13 (t, 1H), 2.36 (dq, 2H), 1.00 (dt, 3H) |
| I-a-154 | 2-methylthiazol-4,5-diyl | C=O | CH$_3$ | Br | 4-Cl | 6-Et | $^1$H NMR (400 MHz, d6-DMSO): 10.9 (bs, 1H), 7.62 (d, 1H), 7.38 (s, 1H), 3.65 (s, 3H), 2.80 (s, 3H), 2.36 (m, 2H), 1.00 (m, 3H) |
| I-a-155 | 2-ethylthiazol-4,5-diyl | C=O | CH$_2$CHF$_2$ | Cl | 6-Cl | H | $^1$H NMR (400 MHz, d6-DMSO): 11.4 (bs, 1H), 7.51 (d, 2H), 7.40 (t, 1H), 6.33 (m, 1H), 4.69 (m, 2H), 3.12 (q, 2H), 1.37 (t, 3H) |
| I-a-156 | 2-ethylthiazol-4,5-diyl | C=O | CH$_2$C≡CH | Cl | 6-Cl | H | $^1$H NMR (400 MHz, d6-DMSO): 11.4 (bs, 1H), 7.52 (d, 2H), 7.40 (t, 1H), 5.00 (d, 2H), 3.14 (m, 2H + 1H), 1.38 (t, 3H) |
| I-a-157 | 2-ethylthiazol-4,5-diyl | C=O | CH$_2$CHF$_2$ | Cl | 4-Cl | 6-Et | $^1$H NMR (400 MHz, d6-DMSO): 11.4 (bs, 1H), 7.49 (d, 1H), 7.35 (d, 1H), 6.33 (m, 1H), 4.70 (m, 2H), 3.12 (q, 2H), 2.36 (m, 2H), 1.37 (t, 3H), 0.99 (t, 3H) |
| I-a-158 | 2-ethylthiazol-4,5-diyl | C=O | CH$_3$ | Cl | 6-Cl | H | $^1$H NMR (400 MHz, d6-DMSO): 11.3 (bs, 1H), 7.51 (d, 2H), 7.40 (t, 1H), 3.66 (s, 3H), 3.11 (q, 2H), 1.35 (t, 3H) |
| I-a-159 | 2-ethylthiazol-4,5-diyl | C=O | CH$_3$ | Cl | 4-Cl | 6-Et | $^1$H NMR (400 MHz, d6-DMSO): 10.9 (bs, 1H), 7.49 (d, 1H), 7.36 (d, 1H), 3.67 (s, 3H), 3.12 (q, 2H), 2.38 (m, 2H), 1.35 (t, 3H), 0.99 (t, 3H) |
| I-a-160 | 2-ethylthiazol-4,5-diyl | C=O | CH$_2$CHF$_2$ | Br | 4-Cl | 6-Et | $^1$H NMR (400 MHz, d6-DMSO): 11.3 (bs, 1H), 7.63 (d, 1H), 7.39 (d, 1H), 6.32 (m, 1H), 4.69 (m, 2H), 3.12 (q, 2H), 2.38 (m, 2H), 1.37 (t, 3H), 0.99 (t, 3H) |
| I-a-161 | 2-ethylthiazol-4,5-diyl | C=O | CH$_3$ | Br | 4-Cl | 6-Et | $^1$H NMR (400 MHz, d6-DMSO): 10.9 (bs, 1H), 7.63 (d, 1H), 7.39 (d, 1H), 3.64 (s, 3H), 3.12 (q, 2H), 2.38 (m, 2H), 1.37 (t, 3H), 1.01 (t, 3H) |

TABLE 229-continued

Inventive compounds of the formula (I) in which G is hydrogen:

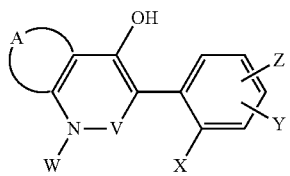
(I-a)

| No. | A | V | W | X | Y | Z | Analytical data |
|---|---|---|---|---|---|---|---|
| I-a-162 | thiazole-ethyl | C=O | CH₂CHF₂ | Cl | 6-Cl | H | ¹H NMR (400 MHz, d6-DMSO): 11.6 (bs, 1H), 7.52 (d, 2H), 7.40 (t, 1H), 6.33 (m, 1H), 4.69 (m, 2H), 3.08 (t, 2H), 1.77 (q, 2H), 0.97 (t, 3H) |
| I-a-163 | thiazole-ethyl | C=O | CH₃ | Cl | 6-Cl | H | ¹H NMR (400 MHz, d6-DMSO): 11.2 (bs, 1H), 7.51 (d, 2H), 7.40 (t, 1H), 3.66 (s, 3H), 3.07 (t, 2H), 1.78 (q, 2H), 0.99 (t, 3H) |
| I-a-164 | thiazole-ethyl | C=O | CH₂CHF₂ | Cl | 4-Cl | 6-Et | ¹H NMR (400 MHz, d6-DMSO): 11.4 (bs, 1H), 7.48 (d, 1H), 7.35 (d, 1H), 6.32 (m, 1H), 4.69 (m, 2H), 3.07 (t, 2H), 2.37 (m, 2H), 1.80 (m, 2H), 0.99 (m, 6H) |
| I-a-165 | thiazole-ethyl | C=O | CH₃ | Cl | 4-Cl | 6-Et | ¹H NMR (400 MHz, d6-DMSO): 11.0 (bs, 1H), 7.48 (d, 1H), 7.34 (d, 1H), 3.66 (s, 3H), 3.07 (t, 2H), 2.37 (m, 2H), 1.79 (m, 2H), 1.00 (m, 6H) |
| I-a-166 | thiazole-ethyl | C=O | CH₂CHF₂ | Br | 4-Cl | 6-Et | ¹H NMR (400 MHz, d6-DMSO): 11.3 (bs, 1H), 7.63 (d, 1H), 7.39 (d, 1H), 6.32 (m, 1H), 4.70 (m, 2H), 3.07 (t, 2H), 2.38 (m, 2H), 1.79 (m, 2H), 0.98 (m, 6H) |
| I-a-167 | thiazole-ethyl | C=O | CH₃ | Br | 4-Cl | 6-Et | ¹H NMR (400 MHz, d6-DMSO): 11.0 (bs, 1H), 7.62 (d, 1H), 7.38 (d, 1H), 3.70 (s, 3H), 3.07 (t, 2H), 2.37 (m, 2H), 1.79 (m, 2H), 1.00 (m, 6H) |
| I-a-168 | thiazole-ethyl | C=O | CH₂C≡CH | Cl | 6-Cl | H | ¹H NMR (400 MHz, CDCl₃): 7.33 (d, 1H), 7.14 (m, 1H), 5.17 (dd, 2H), 3.01 (m, 2H), 2.14 (t, 1H), 1.86 (m, 2H), 1.09 (t, 3H) |
| I-a-169 | thiazole-ethyl | C=O | CH₂C≡CH | Cl | 4-Cl | 6-Et | ¹H NMR (400 MHz, CDCl₃): 7.39 (d, 1H), 7.26 (d, 1H), 5.18 (dd, 2H), 3.08 (s, 3H), 2.48 (m, 2H), 2.17 (t, 1H), 1.90 (m, 2H), 1.09 (m, 3H) |

TABLE 229-continued

Inventive compounds of the formula (I) in which G is hydrogen:

(I-a)

| No. | A | V | W | X | Y | Z | Analytical data |
|---|---|---|---|---|---|---|---|
| I-a-170 | (2-ethyl-thiazol-2-yl) | C=O | $CH_2C{\equiv}CH$ | Br | 4-Cl | 6-Et | $^1$H NMR (400 MHz, CDCl$_3$): 7.58 (d, 1H), 7.31 (d, 1H), 5.18 (dd, 2H), 3.09 (s, 3H), 2.48 (m, 2H), 2.17 (t, 1H), 1.92 (m, 2H), 1.10 (m, 3H) |
| I-a-171 | thiazol-2-yl | C=O | $CH_2CH_2{-}OCH_3$ | Cl | 6-Cl | H | $^1$H NMR (400 MHz, d6-DMSO): 11.4 (bs, 1H), 9.40 (s, 1H), 7.53 (d, 2H), 7.41 (t, 1H), 4.50 (t, 2H), 3.64 (t, 2H), 3.25 (s, 3H) |
| I-a-172 | thiazol-2-yl | C=O | $CH_2CH_2{-}SCH_3$ | Cl | 6-Cl | H | $^1$H NMR (400 MHz, d6-DMSO): 11.4 (bs, 1H), 9.42 (s, 1H), 7.53 (d, 2H), 7.42 (t, 1H), 4.51 (m, 2H), 2.82 (m, 2H), 2.13 (s, 3H) |
| I-a-173 | furan-2-yl | C=O | $CH_2CHF_2$ | Cl | 6-Cl | H | $^1$H NMR (400 MHz, d6-DMSO): 11.7 (bs, 1H), 8.12 (d, 1H), 7.52 (d, 2H), 7.38 (t, 1H), 7.12 (d, 1H), 6.32 (m, 1H), 4.51 (m, 2H), |
| I-a-174 | furan-2-yl | C=O | $CH_2CHF_2$ | Br | 4-Cl | Et | $^1$H NMR (400 MHz, d6-DMSO): 11.6 (bs, 1H), 8.12 (d, 1H), 7.62 (d, 1H), 7.37 (d, 1H), 7.12 (d, 1H), 6.32 (m, 1H), 4.51 (m, 2H), 2.38 (m, 2H), 1.00 (t, 3H) |
| I-a-175 | furan-2-yl | C=O | $CH_2C{\equiv}CH$ | Cl | 6-Cl | H | $^1$H NMR (400 MHz, d6-DMSO): 11.7 (bs, 1H), 8.12 (d, 1H), 7.52 (d, 2H), 7.38 (t, 1H), 7.07 (d, 1H), 4.91 (d, 2H), 3.29 (t, 1H), |
| I-a-176 | 2-EtO-thiazol-5-yl | C=O | $CH_2CHF_2$ | Cl | 6-Cl | H | $^1$H NMR (400 MHz, d6-DMSO): 11.4 (bs, 1H), 7.52 (d, 2H), 7.39 (t, 1H), 6.32 (m, 1H), 4.60 (m, 4H), 1.42 (t, 3H) |

Preparation of 7-allyl-5-mesityl-6-oxo-6,7-dihydrothieno[2,3-b]pyridin-4-yl 2-methylpropanoate (compound No. I-b-8):

g (3.4 mmol) of inventive compound I-a-20 were initially charged in 10 ml of dichloromethane. 1.1 eq of 2-methylpropionyl chloride and 1.3 eq of triethylamine were added and the mixture was left to stir at RT for 1 h. Subsequently, the mixture was added to water and the phases were separated by means of an extraction cartridge. The organic phase thus obtained was concentrated and separated by column chromatography on silica gel (gradient n-heptane/EtOAc 100:0 to 50:50). This gave 1.1 g of inventive compound I-b-8.

Preparation of 3-(2-iodophenyl)-2,2-dioxido-1-(2,2,2-trifluoroethyl)-1H-[1,3]thiazolo[4,5-c][1,2]thiazin-4-yl2-methylpropanoate (compound No. I-b-32)

150 mg (0.31 mmol) of 3-(2-iodophenyl)-1-(2,2,2-trifluoroethyl)-1H-[1,3]thiazolo[4,5-c][1,2]thiazin-4-ol 2,2-dioxide (compound I-a-15) were dissolved in 5 ml of dichloromethane, and 0.04 ml (0.46 mmol) of pyridine was added at RT. The reaction mixture was stirred at RT for 5 min, and then 0.04 ml (0.4 mmol) of 2-methylpropionyl chloride was added and the mixture was stirred at room temperature for a further 4 h. Thereafter, the solvent was removed under reduced pres sure and the residue was purified by means of preparative HPLC(C$_{18}$—SiO$_2$, gradient acetonitrile/water 20:80 to 100:0). This gave 47 mg of compound I-b-32.

In analogy to the examples mentioned (1-b-8 and 1-b-32) and according to the general details regarding the preparation, the following compounds of the formula (I-b) are obtained:

TABLE 148

Inventive compounds of the formula (I) in which G is C(=O)R$^1$:

(I-b)

| No. | A | V | W | X | Y | Z | R$^1$ | Analytical data |
|---|---|---|---|---|---|---|---|---|
| I-b-1 | N-methylpyrazol-3,4-diyl | SO$_2$ | CH$_2$CHF$_2$ | Cl | 6-Cl | H | i-Pr | $^1$H NMR (400 MHz, CDCl$_3$): 7.47 (s, 1H); 7.41 (d, 2H); 7.30 (dd, 1H); 6.25 (tt, 1H); 4.30 (td, 2H); 3.93 (s, 3H); 2.57 (m, 1H); 0.98 (d, 6H) |
| I-b-2 | thiazol-4,5-diyl | SO$_2$ | CH$_2$CHF$_2$ | Cl | 4-Cl | H | i-Bu | $^1$H NMR (400 MHz, d6-DMSO): 10.6 (bs, 1H), 9.31 (s, 1H), 6.90 (s, 2H), 5.96 (m, 1H), 5.07 (m, 1H), 4.90 (m, 3H), 2.27 (s, 3H), 1.97 (s, 6H) |
| I-b-3 | thiazol-4,5-diyl | SO$_2$ | CH$_2$CHF$_2$ | Cl | 6-Cl | H | i-Pr | $^1$H NMR (400 MHz, CDCl$_3$): 8.88 (s, 1H); 7.45 (m, 2H); 7.34 (m, 1H); 6.24 (tt, 1H); 4.55 (m, 2H); 2.59 (m, 1H); 1.00 (d, 6H) |
| I-b-4 | thiazol-4,5-diyl | SO$_2$ | CH$_2$CHF$_2$ | I | H | H | i-Pr | $^1$H NMR (400 MHz, CDCl$_3$): 8.86 (s, 1H); 7.95 (d, 1H); 7.51 (dd, 1H); 7.44 (td, 1H); 7.14 (td, 1H); 6.27 (m, 1H); 4.66 (m, 1H); 4.51 (m, 1H); 2.55 (m, 1H); 0.99 (d, 3H); 0.89 (d, 3H) |
| I-b-5 | 1,2,5-oxadiazol-3,4-diyl | SO$_2$ | CH$_2$CHF$_2$ | CF$_3$ | H | H | i-Pr | $^1$H NMR (400 MHz, CDCl$_3$): 7.86 (d, 1H); 7.69 (m, 3H); 6.24 (tt, 1H); 4.04 (m, 2H); 2.76 (m, 1H); 1.28 (d, 6H) |
| I-b-6 | thiazol-4,5-diyl | SO$_2$ | CH$_2$CHF$_2$ | I | H | H | i-Pr | $^1$H NMR (400 MHz, CDCl$_3$): 8.86 (s, 1H); 7.95 (d, 1H); 7.51 (dd, 1H); 7.44 (td, 1H); 7.14 (td, 1H); 6.27 (m, 1H); 4.66 (m, 1H); 4.51 (m, 1H); 2.55 (m, 1H); 0.99 (d, 3H); 0.89 (d, 3H) |
| I-b-7 | thiazol-4,5-diyl | C=O | CH$_2$-c-Pr | Cl | 6-Cl | H | Et | $^1$H NMR (400 MHz, CDCl$_3$): 8.93 (s, 1H), 7.41 (d, 2H), 7.26 (m, 1H), 4.40 (d, 2H), 2.38 (q, 2H), 1.45 (m, 1H); 1.02 (t, 3H), 0.50 (m, 4H) |

TABLE 148-continued

Inventive compounds of the formula (I) in which G is C(=O)R¹:

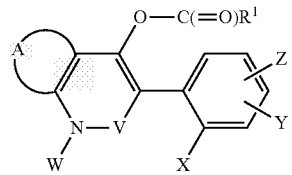

(I-b)

| No. | A | V | W | X | Y | Z | R¹ | Analytical data |
|---|---|---|---|---|---|---|---|---|
| I-b-8 | thiophene (3-yl) | C=O | CH₂—CH=CH₂ | Me | 4-Me | 6-Me | i-Bu | ¹H NMR (400 MHz, CDCl₃): 6.95 (m, 2H), 6.87 (s, 2H), 5.96 (m, 1H), 5.30 (m, 2H), 4.83 (m, 2H), 2.50 (m, 1H), 2.26 (s, 3H), 2.07 (s, 6H), 0.92 (d, 6H) |
| I-b-9 | thiophene (3-yl) | C=O | CH₂—CH=CH₂ | Br | 4-Cl | 6-Et | i-Bu | ¹H NMR (400 MHz, CDCl₃): 7.51 (d, 1H), 7.25 (s, 1H), 7.00 (d, 1H), 6.93 (d, 1H), 5.94 (m, 1H), 5.33 (m, 2H), 4.84 (m, 2H), 2.60 (m, 1H), 2.48 (m, 2H), 1.12 (t, 3H), 0.99 (d, 6H) |
| I-b-10 | thiophene (3-yl) | C=O | CH₂—CH=CH₂ | Cl | 6-Cl | H | i-Bu | ¹H NMR (400 MHz, CDCl₃): 7.39 (d, 2H), 7.22 (m, 1H), 7.00 (d, 1H), 6.97 (d, 1H), 5.96 (m, 1H), 5.33 (m, 2H), 4.84 (m, 2H), 2.63 (m, 1H), 0.99 (d, 6H) |
| I-b-11 | thiophene (3-yl) | C=O | CH₂—CH=CH₂ | Cl | 4-Cl | H | i-Bu | ¹H NMR (400 MHz, CDCl₃): 7.39 (d, 2H), 7.22 (m, 1H), 7.00 (d, 1H), 6.97 (d, 1H), 5.96 (m, 1H), 5.33 (m, 2H), 4.84 (m, 2H), 2.63 (m, 1H), 0.99 (d, 6H) |
| I-b-12 | oxadiazole | SO₂ | CH₂CHF₂ | Cl | 4-Cl | H | i-Pr | ¹H NMR (400 MHz, CDCl₃): 7.60 (d, 1H); 7.59 (d, 1H); 7.40 (dd, 1H); 6.23 (tt, 1H); 4.03 (m, 2H); 2.78 (m, 1H); 1.28 (d, 6H) |
| I-b-13 | thiazole | C=O | CH₂—CH=CH₂ | Cl | 6-Cl | H | i-Bu | ¹H NMR (400 MHz, CDCl₃): 8.94 (s, 1H), 7.40 (d, 2H), 7.26 (m, 1H), 6.07 (m, 1H), 5.28 (m, 1H), 5.23 (m, 1H), 5.15 (m, 2H), 2.62 (m, 1H), 1.03 (d, 6H) |
| I-b-14 | thiazole | C=O | CH₂—CH=CH₂ | Br | 4-Cl | 6-Et | i-Bu | ¹H NMR (400 MHz, CDCl₃): 8.93 (s, 1H), 7.52 (d, 1H), 7.26 (d, 1H), 6.05 (m, 1H), 5.28 (m, 1H), 5.22 (m, 1H), 5.14 (m, 2H), 2.59 (m, 1H), 2.46 (m, 2H), 1.12 (t, 3H), 1.00 (d, 6H) |

TABLE 148-continued

Inventive compounds of the formula (I) in which G is C(=O)R¹:

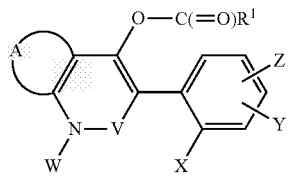

(I-b)

| No. | A | V | W | X | Y | Z | R¹ | Analytical data |
|---|---|---|---|---|---|---|---|---|
| I-b-15 | thiazole | C=O | CH₂—CH=CH₂ | Cl | 4-Cl | H | i-Bu | ¹H NMR (400 MHz, CDCl₃): 8.92 (s, 1H), 7.50 (d, 1H), 7.34 (dd, 1H), 7.22 (d, 1H), 6.06 (m, 1H), 5.30 (m, 1H), 5.24 (m, 1H), 5.10 (m, 2H), 2.61 (m, 1H), 1.07 (dd, 6H) |
| I-b-16 | thiazole | C=O | CH₂—CH=CH₂ | Me | 4-Me | 6-Me | i-Bu | ¹H NMR (400 MHz, CDCl₃): 8.88 (s, 1H), 6.87 (d, 2H), 6.07 (m, 1H), 5.24 (m, 2H), 5.13 (m, 2H), 2.50 (m, 1H), 2.27 (s, 3H), 2.07 (s, 6H), 0.92 (d, 6H) |
| I-b-17 | thiophene | C=O | CH₂CHF₂ | Me | 4-Me | 6-Me | i-Bu | ¹H NMR (400 MHz, CDCl₃): 7.02 (d, 1H), 6.98 (d, 1H), 6.88 (d, 2H), 6.26 (m, 1H), 4.48 (m, 2H), 2.51 (m, 1H), 2.27 (s, 3H), 2.06 (s, 3H), 0.92 (d, 6H) |
| I-b-18 | thiophene | C=O | CH₂CF₃ | Me | 4-Me | 6-Me | i-Bu | ¹H NMR (400 MHz, CDCl₃): 7.02 (d, 1H), 6.95 (d, 1H), 6.87 (d, 2H), 4.85 (m, 2H), 2.52 (m, 1H), 2.26 (s, 3H), 2.06 (s, 3H), 0.92 (d, 6H) |
| I-b-19 | pyrazole | C=O | CH₂—CH=CH₂ | Cl | 4-Cl | H | t-Bu | ¹H NMR (400 MHz, CDCl₃): 7.49 (d, 1H), 7.47 (s, 1H), 7.26 (dd, 1H), 7.19 (d, 1H), 6.07 (m, 1H), 5.30 (m, 1H), 5.04 (m, 3H), 4.18 (s, 3H), 1.12 (s, 9H) |
| I-b-20 | pyrazole | C=O | CH₂—CH=CH₂ | Cl | 6-Cl | H | Et | ¹H NMR (400 MHz, CDCl₃): 7.52 (s, 1H), 7.38 (d, 2H), 7.23 (m, 1H), 6.04 (m, 1H), 5.21 (m, 2H), 4.85 (m, 2H), 3.99 (s, 3H), 2.37 (q, 2H), 1.02 (t, 3H) |
| I-b-21 | thiazole | C=O | CH=CH(CH₃) | Cl | 6-Cl | H | t-Bu | ¹H NMR (400 MHz, CDCl₃): 8.94 (s, 1H), 7.39 (d, 2H), 7.26 (m, 1H), 6.64 (m, 1H), 6.10 (m, 1H), 1.62 (dd, 3H), 1.09 (d, 9H) |

TABLE 148-continued

Inventive compounds of the formula (I) in which G is C(=O)R¹:

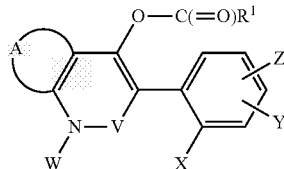

(I-b)

| No. | A | V | W | X | Y | Z | R¹ | Analytical data |
|---|---|---|---|---|---|---|---|---|
| I-b-22 | thiazole | C=O | CH₂—CH=CH₂ | Br | 4-Cl | Et | t-Bu | ¹H NMR (400 MHz, CDCl₃): 8.93 (s, 1H), 7.51 (d, 1H), 7.26 (d, 1H), 6.05 (m, 1H), 5.22 (m, 2H), 5.14 (m, 2H), 2.47 (m, 2H), 1.12 (t, 3H), 0.88 (d, 9H) |
| I-b-23 | thiophene | C=O | CH₂—CH=CH₂ | Cl | 4-Cl | H | t-Bu | ¹H NMR (400 MHz, CDCl₃): 7.49 (d, 1H), 7.27 (m, 1H), 7.24 (m, 1H), 7.00 (d, 1H), 6.93 (d, 1H), 5.98 (m, 1H), 5.35 (m, 2H), 4.82 (m, 2H), 1.11 (d, 9H) |
| I-b-24 | thiazole | C=O | CH₂—CH=CH₂ | Cl | 6-Cl | H | t-Bu | ¹H NMR (400 MHz, CDCl₃): 8.94 (s, 1H), 7.39 (d, 2H), 7.25 (m, 1H), 6.08 (m, 1H), 5.24 (m, 2H), 5.15 (d, 2H), 1.09 (d, 9H) |
| I-b-25 | N-methylpyrazole | C=O | CH₂CHF₂ | Me | 4-Me | 6-Me | Et | ¹H NMR (400 MHz, CDCl₃): 7.49 (s, 1H), 6.87 (s, 2H), 6.30 (m, 1H), 4.58 (m, 2H), 3.99 (s, 3H), 2.27 (s, 3H), 2.25 (q, 2H), 2.05 (s, 6H), 0.90 (t, 3H) |
| I-b-26 | thiazole | C=O | CH₂CHF₂ | Cl | 4-Cl | H | Et | ¹H NMR (400 MHz, CDCl₃): 8.97 (s, 1H), 7.52 (d, 1H), 7.32 (d, 1H), 7.23 (dd, 1H), 6.30 (m, 1H), 4.91 (m, 2H), 2.40 (m, 2H), 1.06 (t, 3H) |
| I-b-27 | thiazole | C=O | CH₂—CH=CH₂ | Cl | 6-Cl | H | Et | ¹H NMR (400 MHz, CDCl₃): 8.97 (s, 1H), 7.37 (d, 2H), 7.25 (t, 1H), 6.06 (m, 1H), 5.24 (m, 2H), 5.17 (m, 2H), 2.37 (m, 2H), 1.01 (t, 3H) |
| I-b-28 | oxadiazole | SO₂ | CH₂CHF₂ | Cl | 6-Cl | H | i-Pr | ¹H NMR (400 MHz, CDCl₃): 7.48 (m, 2H); 7.40 (dd, 1H); 6.24 (tt, 1H); 4.05 (m, 2H); 2.78 (m, 1H); 1.28 (d, 6H) |
| I-b-29 | phenylthiophene | C=O | CH₂CHF₂ | Br | 4-Cl | 6-Et | i-Pr | ¹H NMR (400 MHz, CDCl₃): 7.66 (m, 2H); 7.52 (d, 1H); 7.45 (m, 3H); 7.36 (s, 1H); 7.27 (s, 1H); 6.19 (tt, 1H); 4.62 (m, 2H); 2.62 (m, 1H); 2.51 (m, 2H); 1.15 (t, 3H); 1.04 (d, 3H); 1.02 (d, 3H) |

TABLE 148-continued

Inventive compounds of the formula (I) in which G is C(=O)R[1]:

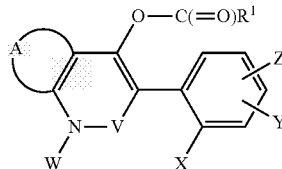

(I-b)

| No. | A | V | W | X | Y | Z | R[1] | Analytical data |
|---|---|---|---|---|---|---|---|---|
| I-b-30 | (dimethylthiophene) | C=O | $CH_2CHF_2$ | Cl | 4-Br | 6-Et | i-Pr | $^1$H NMR (400 MHz, $CDCl_3$): 7.48 (d, 1H); 7.36 (d, 1H); 6.22 (tt, 1H); 4.43 (m, 2H); 2.49 (m, 3H); 2.37 (s, 3H); 2.19 (s, 3H); 1.14 (t, 3H); 0.91 (s, 3H); 0.87 (d, 3H) |

Preparation of 5-(2,6-dichlorophenyl)-7-(2,2-difluoroethyl)-6-oxo-6,7-dihydrothieno[2,3-b]pyridin-4-yl ethyl carbonate (compound No. I-c-27)

0.134 g (0.35 mmol) of inventive compound I-a-40 were initially charged in 5 ml of dichloromethane. 1.3 eq of triethylamine and then 1.1 eq of ethyl chloroformate were added and the mixture was left to stir at RT for 1 h. Subsequently, the mixture was added to water and the phases were separated by means of an extraction cartridge. The organic phase was concentrated and separated by column chromatography on silica gel (gradient n-heptane/EtOAc 100:0 to 50:50). This gave 0.1 g of inventive compound I-c-27.

Preparation of O-[1-(2,2-difluoroethyl)-3-(2-iodophenyl)-2,2-dioxido-1H-[1,3]thiazolo[4,5-c][1,2]thiazin-4-yl] S-methyl thiocarbonate (compound I-c-16)

150 mg (0.3 mmol) of 1-(2,2-difluoroethyl)-3-(2-iodophenyl)-1H-[1,3]thiazolo[4,5-c][1,2]thiazin-4-ol 2,2-dioxide (compound I-a-14) were dissolved in 5 ml of dichloromethane, and 0.04 ml (0.48 mmol) of pyridine was added at RT. The reaction mixture was stirred at RT for 5 min, and then 0.03 ml (0.38 mmol) of methyl chlorothioformate was added and the mixture was stirred at RT for a further 4 h. After removing the solvent under reduced pressure, the residue was purified by column chromatography ($SiO_2$, gradient ethyl acetate/n-heptane 10:90 to 75:25). This gave 144 mg of compound I-c-16.

In analogy to the examples mentioned (I-c-16 and I-c-27) and according to the general details regarding the preparation, the following compounds of the formula (I-c) are obtained.

TABLE 149

Inventive compounds of the formula (I) in which G is C(=L)MR[2]:

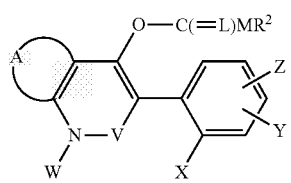

(I-c)

| No. | A | V | W | X | Y | Z | L | M | R[2] | Analytical data |
|---|---|---|---|---|---|---|---|---|---|---|
| I-c-1 | (pyrazole) | $SO_2$ | $CH_2CHF_2$ | Cl | 6-Cl | H | O | S | Et | $^1$H NMR (400 MHz, $CDCl_3$): 7.56 (s, 1H); 7.43 (d, 2H); 7.31 (dd, 1H); 6.24 (tt, 1H); 4.28 (td, 2H); 3.94 (s, 3H); 2.81 (q, 2H); 1.22 (t, 3H) |
| I-c-2 | (thiazole) | $SO_2$ | $CH_2CHF_2$ | Cl | 4-Cl | H | O | S | Me | $^1$H NMR (400 MHz, $CDCl_3$): 8.89 (s, 1H); 7.55 (d, 1H); 7.45 (d, 1H); 7.35 (dd, 1H); 6.17 (tt, 1H); 4.56 (m, 2H); 2.30 (s, 3H) |

TABLE 149-continued

Inventive compounds of the formula (I) in which G is C(=L)MR²:

(I-c)

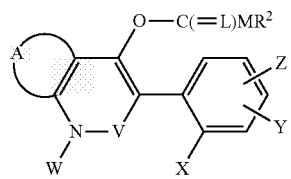

| No. | A | V | W | X | Y | Z | L | M | R² | Analytical data |
|---|---|---|---|---|---|---|---|---|---|---|
| I-c-3 | furazan | SO₂ | CH₂CHF₂ | Cl | 6-Cl | H | O | S | Me | ¹H NMR (400 MHz, CDCl₃): 7.49 (m, 2H); 7.41 (dd, 1H); 6.21 (tt, 1H); 4.03 (m, 2H); 2.42 (s, 3H) |
| I-c-4 | thiazole | SO₂ | CH₂CHF₂ | Cl | 4-Cl | H | O | S | Et | ¹H NMR (400 MHz, CDCl₃): 8.89 (s, 1H); 7.54 (d, 1H); 7.45 (d, 1H); 7.35 (dd, 1H); 6.16 (tt, 1H); 4.54 (m, 2H); 2.79 (m, 2H); 1.20 (t, 3H) |
| I-c-5 | N-Me pyrazole | SO₂ | CH₂CHF₂ | Cl | 4-Cl | H | O | S | Me | ¹H NMR (400 MHz, CDCl₃): 7.53 (m, 2H); 7.44 (d, 1H); 7.32 (dd, 1H); 6.20 (tt, 1H); 4.30 (m, 2H); 3.93 (s, 3H); 2.30 (s, 3H) |
| I-c-6 | N-Me pyrazole | SO₂ | CH₂CHF₂ | Cl | 4-Cl | H | O | S | Et | ¹H NMR (400 MHz, CDCl₃): 7.53 (m, 2H); 7.44 (d, 1H); 7.32 (dd, 1H); 6.21 (tt, 1H); 4.30 (m, 2H); 3.93 (s, 3H); 2.79 (q, 2H); 1.22 (t, 3H) |
| I-c-7 | thiazole | SO₂ | CH₂CHF₂ | Cl | 6-Cl | H | O | S | Me | ¹H NMR (400 MHz, CDCl₃): 8.91 (s, 1H); 7.46 (dd, 2H); 7.35 (dd, 1H); 6.23 (tt, 1H); 4.55 (m, 2H); 2.31 (s, 3H) |
| I-c-8 | furazan | SO₂ | CH₂CHF₂ | CF3 | H | H | O | S | Me | ¹H NMR (400 MHz, CDCl₃): 7.87 (d, 1H); 7.69 (m, 3H); 6.21 (tt, 1H); 4.02 (m, 2H); 2.42 (s, 3H) |
| I-c-9 | N-Me pyrazole | SO₂ | CH₂CHF₂ | CF3 | H | H | O | O | Et | ¹H NMR (400 MHz, CDCl₃): 7.78 (d, 1H); 7.63 (m, 3H); 7.53 (s, 1H); 6.20 (m, 1H); 4.37 (m, 1H); 4.20 (m, 1H); 4.12 (m, 2H); 3.93 (s, 3H); 1.17 (t, 3H) |
| I-c-10 | thiazole | SO₂ | CH₂CF₃ | CF3 | H | H | O | S | Et | ¹H NMR (400 MHz, CDCl₃): 8.89 (s, 1H); 7.80 (d, 1H); 7.64 (m, 3H); 4.78 (m, 2H); 2.76 (m, 2H); 1.16 (t, 3H) |
| I-c-11 | thiazole | SO₂ | CH₂CHF₂ | CF3 | H | H | O | S | Me | ¹H NMR (400 MHz, CDCl₃): 8.88 (s, 1H); 7.80 (d, 1H); 7.64 (m, 3H); 6.17 (m, 1H); 4.62 (m, 1H); 4.44 (m, 1H); 2.25 (s, 3H) |

TABLE 149-continued

Inventive compounds of the formula (I) in which G is C(=L)MR²:

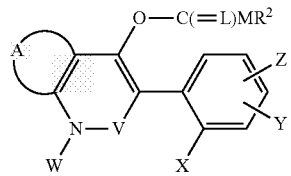

(I-c)

| No. | A | V | W | X | Y | Z | L | M | R² | Analytical data |
|---|---|---|---|---|---|---|---|---|---|---|
| I-c-12 | thiazole | SO₂ | CH₂CHF₂ | CF₃ | H | H | O | S | Et | ¹H NMR (400 MHz, CDCl₃): 8.87 (s, 1H); 7.81 (m, 1H); 7.65 (m, 3H); 6.17 (m, 1H); 4.63 (m, 1H); 4.44 (m, 1H); 2.75 (m, 2H); 1.16 (t, 3H) |
| I-c-13 | N-methylpyrazole | SO₂ | CH₂CHF₂ | CF₃ | H | H | O | S | Et | ¹H NMR (400 MHz, CDCl₃): 7.93 (dd, 1H); 7.48 (dd, 1H); 7.45 (s, 1H); 7.41 (td, 1H); 7.11 (td, 1H); 6.27 (tt, 1H); 4.39 (m, 1H); 4.26 (m, 1H); 3.92 (s, 3H); 2.53 (m, 1H); 0.97 (d, 3H); 9.88 (d, 3H) |
| I-c-14 | thiazole | C=O | CH₂—CH=CH₂ | Cl | 4-Cl | H | O | O | Et | ¹H NMR (400 MHz, CDCl₃): 8.93 (s, 1H), 7.52 (d, 1H), 7.26 (d, 1H), 6.05 (m, 1H), 5.28 (m, 1H), 5.22 (m, 1H), 5.14 (m, 2H), 2.59 (m, 1H), 2.46 (m, 2H), 1.12 (t, 3H), 1.00 (d, 6H) |
| I-c-15 | thiophene | C=O | CH₂—CH=CH₂ | Cl | 6-Cl | H | O | O | Et | ¹H NMR (400 MHz, CDCl₃): 8.92 (s, 1H), 7.50 (d, 1H), 7.34 (dd, 1H), 7.22 (d, 1H), 6.06 (m, 1H), 5.30 (m, 1H), 5.24 (m, 1H), 5.10 (m, 2H), 2.61 (m, 1H), 1.07 (dd, 6H) |
| I-c-16 | thiazole | SO₂ | CH₂CHF₂ | I | H | H | O | S | Me | ¹H NMR (400 MHz, CDCl₃): 8.88 (s, 1H); 7.96 (d, 1H); 7.52 (dd, 1H); 7.46 (td, 1H); 7.17 (td, 1H); 6.27 (m, 1H); 4.66 (m, 1H); 4.49 (m, 1H); 2.27 (s, 3H) |
| I-c-17 | thiazole | SO₂ | CH₂CHF₂ | I | H | H | O | S | Et | ¹H NMR (400 MHz, CDCl₃): 8.88 (s, 1H); 7.96 (d, 1H); 7.53 (dd, 1H); 7.45 (td, 1H); 7.16 (td, 1H); 6.26 (m, 1H); 4.67 (m, 1H); 4.49 (m, 1H); 2.77 (m, 2H); 1.17 (t, 3H) |
| I-c-18 | thiazole | SO₂ | CH₂CF₃ | I | H | H | O | S | Me | ¹H NMR (400 MHz, CDCl₃): 8.90 (s, 1H); 7.97 (d, 1H); 7.47 (m, 2H); 7.16 (m, 1H); 4.80 (m, 2H); 2.77 (s, 3H) |
| I-c-19 | thiazole | SO₂ | CH₂CF₃ | I | H | H | O | S | Et | ¹H NMR (400 MHz, CDCl₃): 8.89 (s, 1H); 7.95 (d, 1H); 7.49 (dd, 1H); 7.45 (t, 1H); 7.15 (td, 1H); 4.80 (m, 2H); 2.77 (m, 2H); 1.17 (t, 3H) |

TABLE 149-continued

Inventive compounds of the formula (I) in which G is C(=L)MR²:

(I-c)

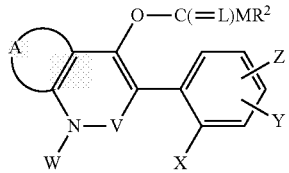

| No. | A | V | W | X | Y | Z | L | M | R² | Analytical data |
|---|---|---|---|---|---|---|---|---|---|---|
| I-c-20 | furazanyl | SO₂ | CH₂CHF₂ | CF₃ | H | H | O | S | Et | ¹H NMR (400 MHz, CDCl₃): 7.87 (d, 1H); 7.69 (m, 3H); 6.21 (tt, 1H); 4.01 (m, 2H); 2.96 (q, 2H); 1.38 (t, 3H) |
| I-c-21 | furazanyl | C=O | CH₃ | Cl | 6-Cl | H | O | O | Et | ¹H NMR (400 MHz, CDCl₃): 7.42 (m, 2H), 7.33 (m, 1H), 7.10 (m, 2H), 4.29 (q, 2H), 3.72 (s, 3H), 1.32 (m, 3H) |
| I-c-22 | 2-MeS-thiazolyl | C=O | CH₃ | Me | 4-Me | 6-Me | O | O | Et | ¹H NMR (400 MHz, CDCl₃): 6.89 (s, 2H), 4.06 (q, 2H), 3.88 (s, 3H), 2.78 (s, 3H), 2.28 (s, 3H), 2.08 (s, 6H), 1.11 (t, 3H) |
| I-c-23 | furazanyl | SO₂ | CH₂CHF₂ | Cl | 4-Cl | H | O | S | Me | ¹H NMR (400 MHz, CDCl₃): 7.60 (m, 2H); 7.40 (dd, 1H); 6.20 (tt, 1H); 4.00 (m, 2H); 2.42 (s, 3H) |
| I-c-24 | furazanyl | SO₂ | CH₂CHF₂ | Cl | 4-Cl | H | O | S | Et | ¹H NMR (400 MHz, CDCl₃): 7.59 (m, 2H); 7.40 (dd, 1H); 6.20 (tt, 1H); 4.00 (m, 2H); 2.95 (q, 2H); 1.38 (t, 3H) |
| I-c-25 | thiazolyl | C=O | CH₂CHF₂ | Cl | 6-Cl | H | O | O | Et | ¹H NMR (400 MHz, CDCl₃): 8.99 (s, 1H), 7.42 (dd, 2H), 7.32 (m, 1H), 6.30 (m, 1H), 4.93 (m, 2H), 4.24 (m, 2H), 1.26 (m, 3H) |
| I-c-26 | 2-MeS-thiazolyl | C=O | CH₂CHF₂ | Me | 4-Me | 6-Me | O | O | Et | ¹H NMR (400 MHz, CDCl₃): 6.90 (s, 2H), 6.30 (m, 1H), 4.84 (m, 2H), 4.06 (m, 2H), 2.78 (s, 3H), 2.28 (s, 3H), 2.07 (s, 6H), 1.11 (t, 3H) |
| I-c-27 | thienyl | C=O | CH₂CHF₂ | Cl | 6-Cl | H | O | O | Et | ¹H NMR (400 MHz, CDCl₃): 7.42 (m, 2H), 7.31 (m, 1H), 7.10 (m, 2H), 6.28 (m, 1H), 4.49 (m, 2H), 4.19 (q, 2H), 1.22 (m, 3H) |
| I-c-28 | thiazolyl | C=O | CH₂CF₃ | Cl | 6-Cl | H | O | O | Et | ¹H NMR (400 MHz, CDCl₃): 8.98 (s, 1H), 7.42 (dd, 2H), 7.30 (m, 1H), 5.21 (m, 2H), 4.22 (m, 2H), 1.25 (m, 3H) |
| I-c-29 | 2-MeS-thiazolyl | C=O | CH₂CHF₂ | Br | 4-Cl | 6-Et | O | O | Et | ¹H NMR (400 MHz, CDCl₃): 7.53 (d, 1H), 7.26 (d, 1H), 6.28 (m, 1H), 4.84 (m, 2H), 4.19 (m, 2H), 2.79 (s, 3H), 2.46 (m, 2H), 1.23 (m, 3H), 1.12 (t, 3H) |

TABLE 149-continued

Inventive compounds of the formula (I) in which G is C(=L)MR²:

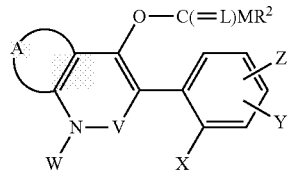

(I-c)

| No. | A | V | W | X | Y | Z | L | M | R² | Analytical data |
|---|---|---|---|---|---|---|---|---|---|---|
| I-c-30 | pyrazolyl (N-Me) | C=O | CH₂CHF₂ | Br | 4-Cl | 6-Et | O | O | Et | ¹H NMR (400 MHz, CDCl₃): 7.59 (s, 1H), 7.51 (d, 1H), 7.26 (d, 1H), 6.28 (m, 1H), 4.58 (m, 2H), 4.22 (m, 2H), 2.45 (m, 2H), 1.26 (m, 3H), 1.10 (t, 3H) |
| I-c-31 | pyrazolyl (N-Me) | C=O | CH₂CHF₂ | Me | 4-Me | 6-Me | O | O | Et | ¹H NMR (400 MHz, CDCl₃): 7.59 (s, 1H), 6.89 (s, 2H), 6.29 (m, 1H), 4.58 (m, 2H), 4.08 (m, 2H), 2.28 (s, 3H), 2.07 (s, 6H), 1.15 (t, 3H) |
| I-c-32 | oxadiazolyl | SO₂ | CH₂CHF₂ | Cl | 6-Cl | H | O | S | Me | ¹H NMR (400 MHz, CDCl₃): 7.49 (m, 2H); 7.41 (dd, 1H); 6.21 (tt, 1H); 4.03 (m, 2H); 2.42 (s, 3H) |
| I-c-33 | pyrazolyl (N-Me) | SO₂ | CH₂CHF₂ | Cl | 6-Cl | H | O | S | Me | ¹H NMR (400 MHz, CDCl₃): 7.56 (s, 1H); 7.43 (m, 2H); 7.32 (dd, 1H); 6.24 (tt, 1H); 4.29 (td, 2H); 3.94 (s, 3H); 2.31 (s, 3H) |
| I-c-34 | thienyl | C=O | CH₂CHF₂ | Br | 4-Cl | 6-Et | O | O | Et | ¹H NMR (400 MHz, CDCl₃): 7.52 (d, 1H), 7.28 (d, 1H), 7.10 (m, 2H), 6.25 (m, 1H), 4.50 (m, 2H), 4.18 (q, 2H), 2.48 (q, 2H), 1.23 (m, 3H), 1.14 (t, 3H) |
| I-c-35 | thiazolyl (SMe) | C=O | CH₂CF₃ | Cl | 6-Cl | H | O | O | Et | ¹H NMR (400 MHz, CDCl₃): 7.41 (d, 2H), 7.27 (t, 1H), 5.14 (m, 2H), 4.21 (m, 2H), 2.77 (s, 3H), 1.23 (s, 3H) |
| I-c-36 | thiazolyl | C=O | CH₂C≡CH | Br | 4-Cl | 6-Et | O | O | Et | ¹H NMR (400 MHz, CDCl₃): 9.01 (s, 1H), 7.52 (d, 1H), 7.28 (d, 1H), 5.28 (m, 2H), 4.21 (m, 2H), 2.47 (m, 2H), 2.24 (t, 1H), 1.23 (m, 3H), 1.12 (t, 3H) |
| I-c-37 | thiazolyl | C=O | CH₂CH₃ | Cl | 6-Cl | H | O | O | Et | ¹H NMR (400 MHz, CDCl₃): 8.97 (s, 1H), 7.41 (dd, 2H), 7.27 (m, 1H), 4.59 (m, 2H), 4.21 (m, 2H), 1.42 (t, 3H), 1.25 (m, 3H) |
| I-c-38 | thiazolyl | C=O | CH₃ | Me | 4-Br | 6-Et | O | O | Et | ¹H NMR (400 MHz, CDCl₃): 8.95 (s, 1H), 7.29 (d, 1H), 7.27 (d, 1H), 4.12 (q, 2H), 3.95 (s, 3H), 2.40 (m, 2H), 2.10 (s, 3H), 1.18 (m, 3H), 1.11 (t, 3H) |

TABLE 149-continued

Inventive compounds of the formula (I) in which G is C(=L)MR²:

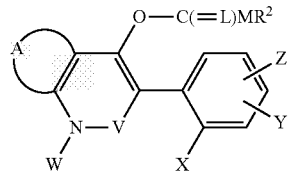

(I-c)

| No. | A | V | W | X | Y | Z | L | M | R² | Analytical data |
|---|---|---|---|---|---|---|---|---|---|---|
| I-c-39 | ![pyrazole] | SO₂ | CH₂CHF₂ | I | H | H | O | S | Me | ¹H NMR (400 MHz, CDCl₃): 7.94 (m, 1H); 7.55 (s, 1H); 7.50 (dd, 1H); 7.43 (td, 1H); 7.14 (td, 1H); 6.27 (tdd, 1H); 4.40 (m, 1H); 4.25 (m, 1H); 3.93 (s, 3H); 2.27 (s, 3H) |
| I-c-40 | ![dimethylthiophene] | C=O | CH₂CHF₂ | Cl | 4-Br | 6-Et | O | S | Me | ¹H NMR (400 MHz, CDCl₃): 7.48 (br s, 1H); 7.37 (br s, 1H); 6.22 (tt, 1H); 4.42 (m, 2H); 2.45 (m, 2H); 2.38 (s, 3H); 2.24 (s, 6H); 1.14 (t, 3H) |
| I-c-41 | ![phenylthiophene] | C=O | CH₂CHF₂ | Br | 4-Cl | 6-Et | O | S | Me | ¹H NMR (400 MHz, CDCl₃): 7.67 (m, 2H); 7.53 (d, 1H); 7.46 (m, 3H); 7.36 (s, 1H); 7.28 (d, 1H); 6.19 (tt, 1H); 4.62 (m, 2H); 2.49 (m, 2H); 2.32 (s, 3H); 1.15 (t, 3H) |

Preparation of 4-(2,2-difluoroethyl)-6-mesityl-5-oxo-4,5-dihydro[1,3]-thiazolo[4,5-b]pyridin-7-yl-methanesulfonate (I-d-1)

0.2 g (0.57 mmol) of inventive compound I-a-37 was dissolved in 5 ml of dichloromethane, and first 0.075 g (1.3 eq, 0.1 ml) of triethylamine and then 0.05 g (1.1 eq, 0.5 ml) of methanesulfonyl chloride were added. The mixture was left to stir at room temperature for one hour, 10 ml of water were added, and the organic phase was removed and concentrated under reduced pressure. This gave 0.221 g of compound I-d-1 as a solid.

In analogy to the example mentioned and according to the general details regarding the preparation, the following compounds of the formula (I-d) are obtained.

TABLE 150

Inventive compounds of the formula (I) in which G is SO₂R³:

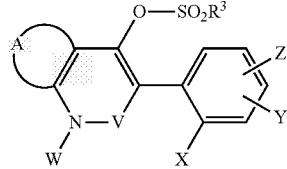

(I-d)

| No. | A | V | W | X | Y | Z | R³ | Analytical data |
|---|---|---|---|---|---|---|---|---|
| I-d-1 | ![thiazole] | C=O | CH₂CHF₂ | Me | 4-Me | 6-Me | Me | ¹H NMR (400 MHz, CDCl₃): 8.97 (s, 1H), 6.88 (s, 2H), 6.30 (m, 1H), 4.91 (m, 2H), 2.43 (s, 3H), 2.30 (s, 3H), 2.14 (s, 6H) |
| I-d-2 | ![thiazole] | C=O | CH₂C≡CH | Me | 3-Br | 6-Me | 4-Me-phenyl | ¹H NMR (400 MHz, CDCl₃): 9.04 (s, 1H), 7.36 (d, 1H), 7.21 (d, 2H), 7.13 (d, 2H), 5.27 (d, 2H), 2.44 (s, 3H), 2.24 (t, 1H), 2.04 (s, 3H), 2.02 (s, 3H) |

TABLE 150-continued

Inventive compounds of the formula (I) in which G is SO₂R³:

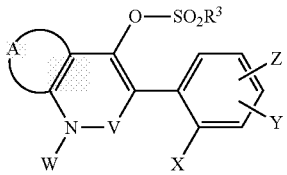

(I-d)

| No. | A | V | W | X | Y | Z | R³ | Analytical data |
|---|---|---|---|---|---|---|---|---|
| I-d-3 | pyrazole | C=O | CH₂—CH=CH₂ | Br | 4-Cl | 6-Et | Me | ¹H NMR (400 MHz, CDCl₃): 7.87 (s, 1H), 7.54 (d, 1H), 7.29 (d, 1H), 6.01 (m, 1H), 5.21 (m, 2H), 4.82 (m, 2H), 4.02 (s, 3H), 2.81 (s, 3H), 2.49 (m, 2H), 1.14 (m, 3H), |
| I-d-4 | thiazole | C=O | CH₂CHF₂ | Br | 4-Cl | 6-Et | Me | ¹H NMR (400 MHz, CDCl₃): 9.02 (s, 1H), 7.58 (d, 1H), 7.34 (d, 1H), 6.28 (m, 1H), 4.92 (m, 2H), 2.78 (s, 3H), 2.52 (m, 2H), 1.12 (m, 3H) |
| I-d-5 | pyrazole | C=O | CH₂CF₃ | Br | 4-Cl | 6-Et | Me | ¹H NMR (400 MHz, CDCl₃): 7.89 (s, 1H), 7.54 (d, 1H), 7.30 (d, 1H), 4.87 (m, 2H), 4.02 (s, 3H), 2.81 (s, 3H), 2.48 (m, 2H), 1.15 (m, 3H), |
| I-d-6 | Me-S-thiazole | C=O | CH₂C≡CH | Cl | 6-Cl | H | 4-Me-phenyl | ¹H NMR (400 MHz, CDCl₃): 7.42 (d, 1H), 7.18 (d, 2H), 7.12 (m, 3H), 5.21 (d, 2H), 2.81 (s, 3H), 2.43 (s, 3H), 2.23 (t, 1H), |
| I-d-7 | pyrazole | C=O | CH₂CF₃ | Cl | 6-Cl | H | 4-Me-phenyl | ¹H NMR (400 MHz, CDCl₃): 8.00 (s, 1H), 7.42 (d, 2H), 7.19 (d, 2H), 7.12 (m, 3H), 4.87 (m, 2H), 4.04 (s, 3H), 2.41 (s, 3H) |

7. Preparation of sodium 6-(2,6-dichlorophenyl)-4-(2,2-difluoroethyl)-5-oxo-4,5-dihydro[1,3]thiazolo[4,5-b]pyridin-7-olate (compound I-g-1)

9.14 mg of sodium (0.39 mmol) were dissolved in 2 ml of MeOH, and a solution of 0.15 g (1.0 eq) of inventive compound I-a-38 in 5 ml of MeOH was added. The mixture was left to stir for 10 min and concentrated to dryness under reduced pressure. This gave compound I-g-1.

In analogy to the example mentioned and according to the general details regarding the preparation, the following compounds of the formula (I-g) are obtained.

TABLE 151

Inventive compounds of the formula (I) in which G is E:

(I-g)

| No. | A | V | W | X | Y | Z | E | Analytical data |
|-----|---|---|---|---|---|---|---|---|
| I-g-1 | thiazole | C=O | CH$_2$CHF$_2$ | Cl | 6-Cl | H | Na$^+$ | $^1$H NMR (400 MHz, d6-DMSO): 7.35 (d, 2H) 7.18 (t, 1H), 6.22 (m, 1H), 4.53 (m, 2H) |
| I-g-2 | pyrazole | C=O | CH$_2$CH=CH$_2$ | Cl | 4-Cl | H | Na$^+$ | $^1$H NMR (400 MHz, d6-DMSO): 7.67 (s, 1H), 7.33 (d, 1H), 7.21 (d, 2H), 7.16 (dd, 1H), 5.86 (m, 1H), 4.99 (m, 2H), 4.44 (m, 2H), 3.78 (s, 3H) |
| I-g-3 | thiazole | C=O | CH$_2$CH$_3$ | Cl | 6-Cl | H | K$^+$ | $^1$H NMR (400 MHz, d6-DMSO): 8.97 (s, 1H), 7.33 (d, 2H) 7.13 (t, 1H), 4.16 (q, 2H), 1.12 (t, 3H) |
| I-g-4 | pyrazole | C=O | CH$_2$CH=CH$_2$ | Cl | 6-Cl | H | N(Me)$_4^+$ | $^1$H NMR (400 MHz, d6-DMSO): 7.63 (s, 1H), 7.28 (d, 1H), 7.09 (d, 2H), 5.85 (m, 1H), 4.97 (m, 2H), 4.43 (m, 2H), 3.78 (s, 3H), 3.19 (s, 12H) |
| I-g-5 | thiazole | C=O | CH$_2$CHF$_2$ | Me | 4-Me | 6-Me | N(Me)$_4^+$ | $^1$H NMR (400 MHz, d6-DMSO): 6.72 (s, 2H), 4.53 (m, 2H), 3.17 (s, 12H), 2.21 (s, 3H), 1.98 (s, 6H) |
| I-g-6 | pyrazole | C=O | CH$_2$CHF$_2$ | Br | 4-Cl | 6-Et | K$^+$ | $^1$H NMR (400 MHz, d6-DMSO): 7.70 (s, 1H), 7.39 (s, 1H), 7.14 (s, 1H), 6.21 (m, 1H), 4.22 (m, 2H), 3.80 (s, 3H), 2.42 (q, 2H), 0.95 (t, 3H) |
| I-g-7 | thiazole | C=O | CH$_2$CHF$_2$ | OMe | 4-Cl | 6-Et | Na$^+$ | $^1$H NMR (400 MHz, d6-DMSO): 6.77 (d, 1H) 6.73 (d, 1H), 6.21 (m, 1H), 4.52 (m, 2H), 3.56 (s, 3H), 2.35 (q, 2H), 0.96 (t, 3H) |

Preparation of 1-(2,2-difluoroethyl)-3-(2-iodophenyl)-4-(prop-2-yn-1-yloxy)-1H-[1,3]thiazolo[4,5-c][1,2]thiazine 2,2-dioxide (compound No. I-h-2)

150 mg (0.3 mmol) of 1-(2,2-difluoroethyl)-3-(2-iodophenyl)-1H-[1,3]thiazolo[4,5-c][1,2]thiazin-4-ol 2,2-dioxide (compound I-a-14) were dissolved in 3 ml of DMF, and 85 mg of potassium carbonate were added at RT. The reaction mixture was stirred at RT for 5 min, and then 0.035 ml (0.46 mmol) of propargyl bromide was added dropwise. The reaction mixture was stirred at 90° C. for 4 h, then poured onto water and extracted repeatedly with ethyl acetate. The combined organic phases were dried (sodium sulfate) and concentrated to dryness. The residue was purified by means of preparative HPLC(C$_{18}$—SiO$_2$, gradient acetonitrile/water 20:80 to 100:0). This gave 51 mg of compound I-h-3.

In analogy to example (1-h-2) and according to the general details regarding the preparation, the following compounds of the formula (I-h) are obtained:

TABLE 152

Inventive compounds of the formula (I) in which G is R⁸:

(I-h)

| No. | A | V | W | X | Y | Z | R⁸ | Analytical data |
|---|---|---|---|---|---|---|---|---|
| I-h-1 | thiazole | SO₂ | CH₂CF₃ | I | H | H | CH₂—C≡CH | ¹H NMR (400 MHz, CDCl₃): 8.88 (s, 1H); 7.97 (dd, 1H); 7.67 (dd, 1H); 7.48 (td, 1H); 7.18 (td, 1H); 4.74 (m, 2H); 4.40 (dd, 1H); 4.22 (dd, 1H); 2.56 (t, 1H) |
| I-h-2 | thiazole | SO₂ | CH₂CHF₂ | I | H | H | CH₂—C≡CH | ¹H NMR (400 MHz, CDCl₃): 8.87 (s, 1H); 7.96 (dd, 1H); 7.72 (dd, 1H); 7.49 (td, 1H); 7.18 (td, 1H); 6.21 (m, 1H); 4.62 (m, 1H); 4.42 (m, 1H); 4.38 (dd, 1H); 4.22 (dd, 1H); 2.56 (t, 1H) |
| I-h-3 | pyrazole | SO₂ | CH₂CHF₂ | I | H | H | CH₂—C≡CH | ¹H NMR (400 MHz, CDCl₃): 7.94 (dd, 1H); 7.77 (s, 1H); 7.66 (dd, 1H); 7.44 (td, 1H); 7.14 (td, 1H); 6.22 (tt, 1H); 4.32 (m, 1H); 4.33 (m, 1H); 4.19 (m, 1H); 3.94 (s, 3H); 2.55 (t, 1H) |
| I-h-4 | pyrazole | SO₂ | CH₂CF₃ | I | H | H | CH₂—C≡CH | ¹H NMR (400 MHz, CDCl₃): 7.94 (dd, 1H); 7.78 (s, 1H); 7.64 (dd, 1H); 7.44 (td, 1H); 7.13 (td, 1H); 4.56 (m, 1H); 4.40 (m, 1H); 4.38 (dd, 1H); 4.28 (dd, 1H); 3.95 (s, 3H); 2.55 (t, 1H) |
| I-h-5 | furazan | C=O | CH₂—CH=CH₂ | Cl | 6-Cl | H | CH₂—CH=CH₂ | ¹H NMR (400 MHz, CDCl₃): 7.42 (d, 2H), 7.30 (m, 1H), 5.94 (m, 2H), 5.27 (m, 6H), 4.76 (m, 2H) |
| I-h-6 | thiazole | C=O | CH₂CHF₂ | Cl | 4-Cl | H | CH₂CHF₂ | ¹H NMR (400 MHz, CDCl₃): 8.97 (s, 1H), 7.56 (d, 1H), 7.37 (dd, 1H), 7.26 (d, 1H), 6.27 (m, 1H), 5.84 (m, 1H), 4.86 (m, 2H), 3.90 (m, 2H) |
| I-h-7 | pyrazole | SO₂ | CH₂CHF₂ | Cl | 6-Cl | H | CH₂—C≡CH | ¹H NMR (400 MHz, CDCl₃): 7.79 (s, 1H); 7.44 (d, 2H); 7.33, (dd, 1H); 6.17 (tt, 1H); 4.41 (d, 2H); 4.21 (td, 2H); 3.95 (s, 3H); 2.53 (t, 1H) |
| I-h-8 | thiazole | C=O | CH₂CHF₂ | CF₃ | H | H | CH₂CHF₂ | ¹H NMR (400 MHz, CDCl₃): 8.95 (s, 1H), 7.82 (d, 1H), 7.67 (t, 1H), 7.58 (t, 1H), 7.41 (d, 1H), 6.25 (m, 1H), 5.77 (m, 1H), 4.85 (m, 2H), 3.88 (m, 2H) |

TABLE 152-continued

Inventive compounds of the formula (I) in which G is $R^8$:

(I-h)

| No. | A | V | W | X | Y | Z | $R^8$ | Analytical data |
|---|---|---|---|---|---|---|---|---|
| I-h-9 | thiazole | C=O | $CH_3$ | I | H | H | $CH_3$ | $^1$H NMR (400 MHz, $CDCl_3$): 8.91 (s, 1H), 7.94 (d, 1H), 7.41 (t, 1H), 7.32 (d, 1H), 7.07 (t, 1H), 3.89 (s, 3H), 3.69 (s, 3H), |
| I-h-10 | thiazole | C=O | $CH_3$ | $CF_3$ | H | H | $CH_3$ | $^1$H NMR (400 MHz, $CDCl_3$): 8.91 (s, 1H), 7.78 (d, 1H), 7.62 (t, 1H), 7.51 (t, 1H), 7.36 (d, 1H), 3.88 (s, 3H), 3.71 (s, 3H) |
| I-h-11 | thiazole | C=O | $CH_2C \equiv CH$ | $CF_3$ | H | H | $CH_2C \equiv CH$ | $^1$H NMR (400 MHz, $CDCl_3$): 8.98 (s, 1H), 7.78 (d, 1H), 7.65 (t, 1H), 7.54 (t, 1H), 7.46 (d, 1H), 5.23 (m, 2H), 4.43 (m, 2H), 2.51 (m, 1H), 2.22 (m, 1H) |
| I-h-12 | thiazole | C=O | $CH_2CF_3$ | $CF_3$ | H | H | $CH_2CF_3$ | $^1$H NMR (400 MHz, $CDCl_3$): 8.96 (s, 1H), 7.83 (d, 1H), 7.69 (t, 1H), 7.60 (t, 1H), 7.41 (d, 1H), 5.13 (m, 2H), 3.93 (m, 2H) |
| I-h-13 | isothiazole | C=O | $CH_3$ | Cl | 6-Cl | H | $CH_3$ | $^1$H NMR (400 MHz, $CDCl_3$): 7.42 (d, 2H), 7.29 (t, 1H), 4.27 (s, 3H), 3.78 (s, 3H) |
| I-h-14 | isothiazole | C=O | $CH_2CHF_2$ | Cl | 6-Cl | H | $CH_2CHF_2$ | $^1$H NMR (400 MHz, $CDCl_3$): 7.44 (d, 2H), 7.32 (t, 1H), 6.23 (m, 1H), 5.95 (m, 1H), 4.94 (m, 2H), 4.73 (m, 2H) |
| I-h-15 | thiazole | C=O | $CH_2-CH_2-SCH_3$ | Cl | 6-Cl | H | $CH_2-CH_2-SCH_3$ | $^1$H NMR (400 MHz, $CDCl_3$): 8.92 (s, 1H), 7.42 (d, 2H), 7.27 (4, 1H), 4.69 (t, 2H), 4.04 (t, 2H), 2.93 (t, 2H), 2.67 (t, 2H), 2.21 (s, 3H), 2.01 (s, 3H) |

Preparation of compound No. II-1

0.5 g (1.45 mmol) of methyl 4-{[(2,6-dichlorophenyl)acetyl]amino}-1,3-thiazole-5-carboxylate were dissolved in 10 ml of acetonitrile, and 0.46 g (2.5 eq) of dimethyl sulfate and 0.44 g of potassium carbonate were added. The mixture was heated to boiling under reflux for 2.5 h and freed of the solvent under reduced pressure, and the residue was taken up in 10 ml of water. After addition of 10 ml of dichloromethane, the phases were separated using an extraction cartridge and the organic phase was concentrated. Chromatographic purification on silica gel (gradient EtOAc: n-heptane 1:9 to 1:1) gave 0.40 g of inventive compound II-1.

Preparation of Compound No. II-25

0.75 g (2.17 mmol) of methyl 2-{[(2,6-dichlorophenyl)acetyl]amino}thiophene-3-carboxylate was dissolved in 7 ml of THF, and 0.1 g of sodium hydride (60%) was added. The mixture was left to stir for 10 min and then 0.7 g (1.5 eq) of 2,2-trifluoromethyl difluoromethanesulfonate in 3 ml of THF was added dropwise within 10 min. Subsequently, the mixture was heated to boiling for 2 h and freed of the solvent. The residue formed was partitioned between 10 ml of water and 10 ml of dichloromethane, and the two phases were separated using an extraction cartridge. The organic phase was concentrated. Chromatographic purification on silica gel (gradient EtOAc:n-heptane 1:9 to 1:1) gave 0.74 g of inventive compound II-25.

Preparation of Compound No. II-42

2.0 g (9.16 mmol) of methyl 4-amino-2-methylthio-1,3-thiazole-5-carboxylate were initially charged in 40 ml of dioxane and, at 70° C., a solution of 1.98 g (1.1 eq) of mesitylacetyl chloride in 10 ml of dioxane was added dropwise. The mixture was heated to boiling under reflux until no further evolution of gas was observed. After removing the solvent under reduced pressure, the mixture was taken up in 50 ml of dichloromethane and washed with 5% $NaHCO_3$ solution, and the organic phase was removed and dried with sodium sulfate. After removing the solvent, the mixture was taken up in 1:10 ethyl acetate/n-heptane and the precipitate formed was filtered off. This gave 2.7 g of inventive compound II-42.

In analogy to the above examples and according to the general details regarding the preparation, the following compounds of the formula (II) are obtained:

TABLE 153

Inventive compounds of the formula (II)

| No. | A | V | W | X | Y | Z | $R^9$ | Analytical data |
|---|---|---|---|---|---|---|---|---|
| II-1 | thiazole | C=O | | Me | Cl | 6-Cl | H | Me | $^1$H NMR (400 MHz, $CDCl_3$): 8.87 (s, 1H), 7.32 (m, 2H), 7.10 (m, 1H), 3.93 (s, 3H), 3.82 (bs, 2H), 3.31 (bs, 3H) |
| II-2 | oxadiazole | C=O | | Me | Cl | 6-Cl | H | Me | m.p.: 121-124° C. |
| II-3 | thiophene | C=O | $CH_2$—CH=$CH_2$ | Cl | 6-Cl | H | Me | $^1$H NMR (400 MHz, $CDCl_3$): 7.47 (d, 1H), 7.22 (d, 3H), 7.10 (m, 1H), 5.87 (m, 1H), 5.12 (m, 2H), 4.60 (m, 1H), 4.05 (m, 1H), 3.89 (s, 3H), 3.87 (dd, 2H) |
| II-4 | thiophene | C=O | $CH_2$—CH=$CH_2$ | Me | 4-Me | 6-Me | Me | $^1$H NMR (400 MHz, $CDCl_3$): 7.43 (d, 1H), 7.22 (d, 1H), 6.82 (s, 2H), 5.87 (m, 1H), 5.09 (m, 2H), 4.60 (m, 1H), 4.03 (m, 1H), 3.87 (s, 3H), 3.48 (dd, 2H) |
| II-5 | thiazole | C=O | $CH_2$—CH=$CH_2$ | Cl | 6-Cl | H | Me | $^1$H NMR (400 MHz, $CDCl_3$): 8.87 (s, 1H), 7.27 (m, 2H), 7.10 (m, 1H), 5.87 (m, 1H), 5.07 (m, 2H), 4.43 (m, 2H), 3.94 (s, 3H), 3.81 (bs, 2H) |
| II-6 | thiazole | C=O | $CH_2$—CH=$CH_2$ | Br | 4-Cl | 6-Et | Me | $^1$H NMR (400 MHz, $CDCl_3$): 8.89 (s, 1H), 7.38 (d, 1H), 7.12 (d, 1H), 5.85 (m, 1H), 5.07 (m, 2H), 4.43 (m, 2H), 3.94 (s, 3H), 3.65 (bs, 2H) |

TABLE 153-continued

Inventive compounds of the formula (II)

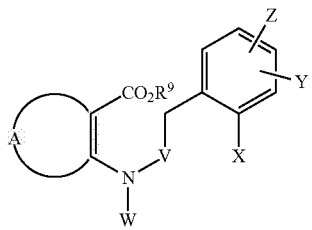

(II)

| No. | A | V | W | X | Y | Z | R⁹ | Analytical data |
|---|---|---|---|---|---|---|---|---|
| II-7 | thiophene | C=O | CH$_2$—CH=CH$_2$ | Br | 4-Cl | 6-Et | Me | $^1$H NMR (400 MHz, CDCl$_3$): 7.45 (d, 1H), 7.40 (d, 1H), 7.23 (d, 1H), 7.12 (m, 1H), 5.86 (m, 1H), 5.13 (m, 2H), 4.58 (m, 1H), 4.04 (m, 1H), 3.89 (s, 3H), 3.71 (d, 2H) |
| II-8 | thiophene | C=O | CH$_2$—CH=CH$_2$ | Cl | 4-Cl | H | Me | $^1$H NMR (400 MHz, CDCl$_3$): 7.40 (d, 1H), 7.32 (d, 1H), 7.18 (m, 3H), 5.84 (m, 1H), 5.10 (m, 2H), 4.59 (m, 1H), 4.03 (m, 1H), 3.83 (s, 3H), 3.63 (dd, 2H) |
| II-9 | thiazole | C=O | CH$_2$—CH=CH$_2$ | Me | 4-Me | 6-Me | Me | $^1$H NMR (400 MHz, CDCl$_3$): 8.86 (s, 1H), 6.79 (s, 2H), 5.85 (m, 1H), 5.07 (m, 2H), 4.41 (m, 2H), 3.92 (s, 3H), 3.42 (bs, 2H) |
| II-10 | pyrazole | C=O | CH$_2$—CH=CH$_2$ | Cl | 4-Cl | H | Et | $^1$H NMR (400 MHz, CDCl$_3$): 7.96 (s, 1H), 7.35 (d, 1H), 7.19 (dd, 1H), 7.14 (d, 1H), 5.82 (m, 1H), 5.11 (m, 2H), 4.39 (m, 1H), 4.28 (m, 2H), 4.12 (m, 1H), 3.67 (s, 3H), 3.47 (dd, 2H), 1.33 (m, 3H) |
| II-11 | pyrazole | C=O | CH$_2$—CH=CH$_2$ | Cl | 6-Cl | H | Me | $^1$H NMR (400 MHz, CDCl$_3$): 8.01 (s, 1H), 7.29 (d, 2H), 7.15 (t, 1H), 5.83 (m, 1H), 5.13 (m, 2H), 4.44 (m, 1H), 4.15 (m, 1H), 3.87 (s, 3H), 3.87 (d, 1H), 3.49 (d, 1H) |
| II-12 | pyrazole | C=O | CH$_2$—CH=CH$_2$ | Br | 4-Cl | 6-Et | Et | $^1$H NMR (400 MHz, CDCl$_3$): 8.01 (s, 1H), 7.41 (d, 1H), 7.15 (dd, 1H), 7.14 (d, 1H), 5.85 (m, 1H), 5.11 (m, 2H), 4.44 (m, 1H), 4.38 (m, 1H), 4.27 (m, 1H), 4.12 (m, 1H), 3.88 (s, 3H), 3.64 (d, 1H), 3.40 (d, 1H), 2.59 (m, 2H), 1.36 (t, 3H), 1.15 (t, 3H) |

TABLE 153-continued

Inventive compounds of the formula (II)

| No. | A | V | W | X | Y | Z | R⁹ | Analytical data |
|---|---|---|---|---|---|---|---|---|
| II-13 | N-methylpyrazole (1,4-linked) | C=O | CH₂—CH=CH₂ | Me | 4-Me | 6-Me | Et | ¹H NMR (400 MHz, CDCl₃): 8.00 (s, 1H), 6.82 (s, 2H), 5.84 (m, 1H), 5.10 (m, 2H), 4.54 (m, 1H), 4.38 (m, 1H), 4.27 (m, 1H), 4.02 (m, 1H), 3.72 (s, 3H), 3.42 (d, 1H), 3.17 (d, 1H), 2.24 (s, 3H), 2.14 (s, 6H) |
| II-14 | N-methylpyrazole (1,3-linked) | C=O | CH₂—CH=CH₂ | Cl | 4-Cl | H | Et | ¹H NMR (400 MHz, CDCl₃): 7.86 (s, 1H), 7.28 (d, 1H), 7.20 (dd, 1H), 7.14 (d, 1H), 5.85 (m, 1H), 5.09 (m, 2H), 4.31 (m, 2H), 4.22 (m, 2H), 3.89 (s, 3H), 3.62 (s, 2H), 1.31 (t, 3H) |
| II-15 | N-methylpyrazole (1,3-linked) | C=O | CH₂—CH=CH₂ | Cl | 6-Cl | H | Et | ¹H NMR (400 MHz, CDCl₃): 7.93 (s, 1H), 7.26 (d, 2H), 7.09 (dd, 1H), 5.87 (m, 1H), 5.11 (m, 2H), 4.31 (m, 4H), 3.93 (s, 3H), 3.81 (s, 2H), 1.35 (t, 3H) |
| II-16 | N-methylpyrazole (1,3-linked) | C=O | CH₂—CH=CH₂ | Br | 4-Cl | 6-Et | Et | ¹H NMR (400 MHz, CDCl₃): 7.93 (s, 1H), 7.38 (d, 1H), 7.10 (d, 1H), 5.86 (m, 1H), 5.11 (m, 2H), 4.29 (m, 4H), 3.93 (s, 3H), 3.66 (s, 2H), 2.60 (m, 2H), 1.34 (dt, 3H), 1.14 (t, 3H) |
| II-17 | N-methylpyrazole (1,3-linked) | C=O | CH₂—CH=CH₂ | Me | 4-Me | 6-Me | Et | ¹H NMR (400 MHz, CDCl₃): 7.90 (s, 1H), 6.78 (s, 2H), 5.87 (m, 1H), 5.10 (m, 2H), 4.29 (m, 4H), 3.92 (s, 3H), 3.43 (s, 2H), 2.21 (s, 3H), 2.16 (s, 6H), 1.34 (dt, 3H) |
| II-18 | thiazole | C=O | CH₂—CHF₂ | Cl | 6-Cl | H | Me | ¹H NMR (400 MHz, CDCl₃): 8.86 (s, 1H), 7.27 (d, 2H), 7.11 (t, 1H), 6.10 (m, 1H), 4.11 (m, 2H), 3.95 (s, 3H), 3.86 (s, 2H) |
| II-19 | thiazole | C=O | CH₂—CHF₂ | Me | 4-Me | 6-Me | Me | ¹H NMR (400 MHz, CDCl₃): 8.87 (s, 1H), 6.80 (s, 2H), 6.09 (m, 1H), 4.09 (m, 2H), 3.93 (s, 3H), 3.46 (s, 2H), 2.22 (s, 3H), 2.16 (s, 6H) |

TABLE 153-continued

Inventive compounds of the formula (II)

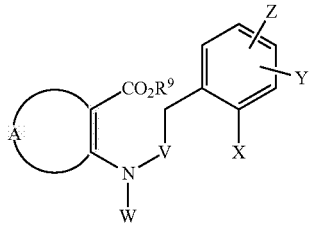
(II)

| No. | A | V | W | X | Y | Z | R⁹ | Analytical data |
|---|---|---|---|---|---|---|---|---|
| II-20 | thiazole | C=O | CH₂—CHF₂ | Cl | 4-Cl | H | Me | ¹H NMR (400 MHz, CDCl₃): 8.85 (s, 1H), 7.31 (d, 1H), 7.17 (d, 2H), 6.08 (m, 1H), 4.09 (m, 2H), 3.88 (s, 3H), 3.64 (s, 2H) |
| II-21 | thiazole | C=O | CH₂—CHF₂ | Br | 4-Cl | 6-Et | Me | ¹H NMR (400 MHz, CDCl₃): 8.90 (s, 1H), 7.39 (d, 1H), 7.13 (d, 2H), 6.08 (m, 1H), 4.11 (m, 2H), 3.94 (s, 3H), 3.68 (s, 2H), 2.60 (m, 2H), 1.16 (t, 3H) |
| II-22 | MeS-thiazole | C=O | CH₂—CHF₂ | Cl | 6-Cl | H | Et | ¹H NMR (400 MHz, CDCl₃): 7.27 (d, 2H), 7.11 (t, 1H), 6.08 (m, 1H), 4.36 (m, 2H), 4.07 (m, 2H), 3.94 (s, 2H), 2.68 (s, 3H), 1.36 (t, 3H) |
| II-23 | N-Me pyrazole | C=O | CH₂—CHF₂ | Cl | 6-Cl | H | Et | ¹H NMR (400 MHz, CDCl₃): 7.94 (s, 1H), 7.26 (d, 2H), 7.11 (dd, 1H), 6.08 (m, 1H), 4.31 (m, 2H), 4.05 (m, 2H), 3.94 (s, 3H), 3.85 (s, 2H), 1.34 (t, 3H) |
| II-24 | N-Me pyrazole | C=O | CH₂—CHF₂ | Cl | 6-Cl | H | Et | ¹H NMR (400 MHz, d6-DMSO): 8.04 (s, 1H), 7.48 (d, 2H), 7.32 (t, 1H), 6.23 (m, 1H), 5.13 (m, 2H), 4.23 (m, 4H), 3.89 (s, 3H), 3.87 (d, 1H), 3.54 (d, 1H), 1.28 (t, 3H) |
| II-25 | thiophene | C=O | CH₂—CHF₂ | Cl | 6-Cl | H | Me | ¹H NMR (400 MHz, CDCl₃): 7.45 (d, 1H), 7.28 (m, 3H), 7.14 (m, 1H), 6.11 (m, 1H), 4.23 (m, 2H), 3.90 (s, 3H), 3.87 (m, 2H) |
| II-26 | N-Me pyrazole | C=O | CH₂—CHF₂ | Me | 4-Me | 6-Me | Et | ¹H NMR (400 MHz, CDCl₃): 7.91 (s, 1H), 6.75 (s, 2H), 6.07 (m, 1H), 4.29 (m, 2H), 4.01 (broad, 3H), 3.94 (s, 3H), 3.46 (s, 2H), 1.34 (t, 3H) |
| II-27 | thiazole | C=O | CH₂—C≡CH | Cl | 6-Cl | H | Me | ¹H NMR (400 MHz, CDCl₃): 8.91 (s, 1H), 7.27 (d, 2H), 7.11 (t, 1H), 4.67 (d, 2H), 3.95 (s, 3H), 3.84 (s, 2H), 2.14 (t, 1H) |

TABLE 153-continued

Inventive compounds of the formula (II)

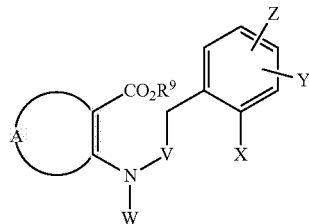

(II)

| No. | A | V | W | X | Y | Z | R⁹ | Analytical data |
|---|---|---|---|---|---|---|---|---|
| II-28 | thiazole | C=O | CH₂—CF₃ | Cl | 6-Cl | H | Me | $^1$H NMR (400 MHz, CDCl$_3$): 8.91 (s, 1H), 7.28 (d, 2H), 7.13 (t, 1H), 4.51 (q, 2H), 3.96 (s, 3H), 3.86 (s, 2H) |
| II-29 | thiazole | C=O | CH₂—CF₃ | Me | 4-Me | 6-Me | Me | $^1$H NMR (400 MHz, CDCl$_3$): 8.91 (s, 1H), 6.80 (s, 2H), 4.48 (q, 2H), 3.94 (s, 3H), 3.47 (s, 2H), 2.26 (s, 3H), 2.14 (s, 6H) |
| II-30 | N-methylpyrazole | C=O | CH₂—CHF₂ | Br | 4-Cl | 6-Et | Et | $^1$H NMR (400 MHz, CDCl$_3$): 7.94 (s, 1H), 7.39 (d, 1H), 7.12 (d, 1H), 6.06 (m, 1H), 4.31 (m, 2H), 4.05 (m, 2H), 3.96 (s, 3H), 3.69 (s, 2H), 2.58 (q, 2H), 1.35 (t, 3H), 1.14 (t, 3H) |
| II-31 | thiazole | C=O | CH₂—CF₃ | Br | 4-Cl | 6-Et | Me | $^1$H NMR (400 MHz, CDCl$_3$): 8.94 (s, 1H), 7.39 (d, 1H), 7.13 (d, 1H), 4.51 (q, 2H), 3.95 (s, 3H), 3.65 (s, 2H), 2.60 (m, 2H), 1.20 (m, 3H) |
| II-32 | 2-methylthio-thiazole | C=O | CH₂—CHF₂ | Br | 4-Cl | 6-Et | Et | $^1$H NMR (400 MHz, CDCl$_3$): 7.39 (d, 1H), 7.12 (d, 1H), 6.06 (m, 1H), 4.35 (m, 2H), 4.07 (m, 2H), 3.77 (s, 2H), 2.70 (s, 3H), 2.61 (m, 2H), 1.37 (t, 3H), 1.16 (t, 3H) |
| II-33 | 2-methylthio-thiazole | C=O | CH₂—CHF₂ | Me | 4-Me | 6-Me | Et | $^1$H NMR (400 MHz, CDCl$_3$): 6.79 (s, 2H), 6.07 (m, 1H), 4.35 (m, 2H), 4.05 (m, 2H), 3.54 (s, 2H), 2.70 (s, 3H), 2.27 (s, 3H), 2.17 (s, 6H), 1.39 (m, 3H) |
| II-34 | thiazole | C=O | CH₂—C≡CH | Br | 4-Cl | 6-Et | Me | $^1$H NMR (400 MHz, CDCl$_3$): 8.93 (s, 1H), 7.38 (d, 1H), 7.12 (d, 1H), 4.68 (s, 2H), 3.94 (s, 3H), 3.67 (s, 2H), 2.61 (m, 2H), 2.14 (s, 1H), 1.16 (m, 3H) |
| II-35 | thiazole | C=O | CH₂—C≡CH | Me | 4-Me | 6-Me | Me | $^1$H NMR (400 MHz, CDCl$_3$): 8.90 (s, 1H), 6.79 (s, 2H), 4.64 (s, 2H), 3.92 (s, 3H), 3.46 (s, 2H), 2.22 (s, 3H), 2.16 (s, 1H), 2.13 (s, 6H) |

TABLE 153-continued

Inventive compounds of the formula (II)

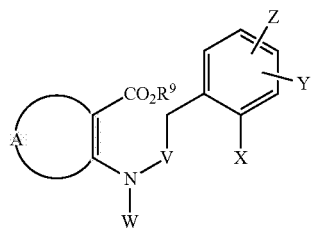

(II)

| No. | A | V | W | X | Y | Z | R⁹ | Analytical data |
|---|---|---|---|---|---|---|---|---|
| II-36 | 2-(methylthio)thiazole | C=O | CH$_2$—CF$_3$ | Cl | 6-Cl | H | Et | $^1$H NMR (400 MHz, CDCl$_3$): 7.27 (d, 2H), 7.11 (t, 1H), 4.46 (q, 2H), 4.37 (m, 2H), 3.95 (s, 2H), 2.71 (s, 3H), 1.37 (t, 3H) |
| II-37 | 2-(methylthio)thiazole | C=O | CH$_2$—CF$_3$ | Br | 4-Cl | 6-Et | Et | $^1$H NMR (400 MHz, CDCl$_3$): 7.39 (d, 1H), 7.12 (d, 1H), 4.45 (q, 2H), 4.36 (m, 2H), 3.78 (s, 2H), 2.71 (s, 3H), 2.61 (m, 2H), 1.37 (t, 3H), 1.16 (t, 3H) |
| II-38 | 2-(methylthio)thiazole | C=O | CH$_2$—CF$_3$ | Me | 4-Me | 6-Me | Et | $^1$H NMR (400 MHz, CDCl$_3$): 6.79 (s, 2H), 4.43 (q, 2H), 4.35 (m, 2H), 3.58 (s, 2H), 2.71 (s, 3H), 2.22 (s, 3H), 2.17 (s, 6H), 1.36 (t, 3H) |
| II-39 | 1-methylpyrazole | C=O | CH$_2$—CF$_3$ | Cl | 6-Cl | H | Et | $^1$H NMR (400 MHz, CDCl$_3$): 7.96 (s, 1H), 7.27 (d, 2H), 7.12 (dd, 1H), 4.42 (q, 2H), 4.31 (m, 2H), 3.96 (s, 3H), 3.86 (s, 2H), 1.34 (t, 3H) |
| II-40 | 1-methylpyrazole | C=O | CH$_2$—CF$_3$ | Br | 4-Cl | 6-Et | Et | $^1$H NMR (400 MHz, CDCl$_3$): 7.96 (s, 1H), 7.38 (d, 1H), 7.12 (d, 1H), 4.41 (q, 2H), 4.30 (m, 2H), 3.96 (s, 3H), 3.70 (s, 2H), 2.58 (q, 2H), 1.34 (t, 3H), 1.15 (t, 3H) |
| II-41 | 1-methylpyrazole | C=O | CH$_2$—CF$_3$ | Me | 4-Me | 6-Me | Et | $^1$H NMR (400 MHz, CDCl$_3$): 7.93 (s, 1H), 6.79 (s, 2H), 4.40 (m, 2H), 4.29 (m, 2H), 3.96 (s, 3H), 3.46 (s, 2H), 2.22 (s, 3H), 2.14 (s, 6H), 1.33 (t, 3H) |
| II-42 | 2-(methylthio)thiazole | C=O | CH$_2$—C≡CH | Cl | 6-Cl | H | Et | $^1$H NMR (400 MHz, CDCl$_3$): 7.26 (m, 2H); 7.10 (dd, 1H); 4.63 (d, 2H); 4.35 (q, 2H); 3.92 (br s, 2H); 2.70 (s, 3H); 2.14 (br s, 1H); 1.37 (t, 3H) |

TABLE 153-continued

Inventive compounds of the formula (II)

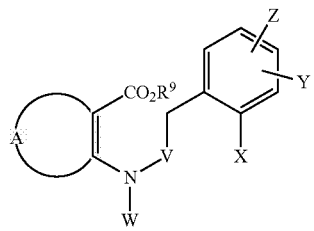

(II)

| No. | A | V | W | X | Y | Z | R⁹ | Analytical data |
|---|---|---|---|---|---|---|---|---|
| II-43 | 2-MeS-thiazol-4,5-diyl | C=O | CH₂—C≡CH | Br | 4-Cl | 6-Et | Et | ¹H NMR (400 MHz, CDCl₃): 7.38 (d, 1H); 7.12 (d, 1H); 4.61 (d, 2H); 4.35 (q, 2H); 3.76 (br s, 2H); 2.71 (s, 3H); 2.62 (q, 2H); 2.14 (br s, 1H); 1.37 (t, 3H); 1.16 (t, 3H) |
| II-44 | 2-MeS-thiazol-4,5-diyl | C=O | CH₂—C≡CH | Me | 4-Me | 6-Me | Et | ¹H NMR (400 MHz, CDCl₃): 6.78 (s, 2H); 4.60 (d, 2H); 4.34 (q, 2H); 3.54 (br s, 2H); 2.71 (s, 3H); 2.22 (s, 3H); 2.17 (s, 6H); 2.13 (br s, 1H); 1.36 (t, 3H) |
| II-45 | 1-Me-pyrazol-4,5-diyl | C=O | CH₂—C≡CH | Cl | 6-Cl | H | Et | ¹H NMR (400 MHz, CDCl₃): 7.95 (s, 1H); 7.25 (m, 2H); 7.14 (t, 1H); 4.59 (d, 2H); 4.29 (q, 2H); 3.96 (s, 3H); 3.84 (s, 2H); 2.15 (t, 1H); 1.34 (t, 3H) |
| II-46 | 1-Me-pyrazol-4,5-diyl | C=O | CH₂—C≡CH | Br | 4-Cl | 6-Et | Et | ¹H NMR(400 MHz, CDCl₃): 7.96 (s, 1H); 7.37 (d, 1H); 7.11 (d, 1H); 4.59 (d, 2H); 4.29 (q, 2H); 3.97 (s, 3H); 3.69 (s, 2H); 2.60 (q, 2H); 2.15 (t, 1H); 1.34 (t, 3H); 1.14 (t, 3H) |
| II-47 | 1-Me-pyrazol-4,5-diyl | C=O | CH₂—C≡CH | Me | 4-Me | 6-Me | Et | ¹H NMR (400 MHz, CDCl₃): 7.92 (s, 1H); 6.77 (s, 2H); 4.57 (br s, 2H); 4.28 (q, 2H); 3.95 (s, 3H); 3.46 (s, 2H); 2.21 (s, 3H); 2.15 (s, 6H); 2.14 (t, 1H); 1.33 (t, 3H) |
| II-48 | thiazol-4,5-diyl | C=O | CH₂—c-Pr | Cl | 6-Cl | H | Me | ¹H NMR (400 MHz, CDCl₃): 8.88 (s, 1H); 7.26 (m, 2H); 7.10 (t, 1H); 3.94 (s, 3H); 3.81 (s, 2H); 3.71 (d, 2H); 0.98 (m, 1H); 0.37 (m, 2H); 0.03 (m, 2H) |
| II-49 | thiazol-4,5-diyl | C=O | CH₂—C≡CH | Cl | 4-Cl | 6-Me | Me | ¹H NMR (400 MHz, CDCl₃): 8.91 (s, 1H); 7.18 (s, 1H); 7.06 (d, 1H); 4.65 (d, 2H); 3.93 (s, 3H); 3.64 (s, 2H); 2.27 (s, 3H); 2.15 (br s, 1H) |

TABLE 153-continued

Inventive compounds of the formula (II)

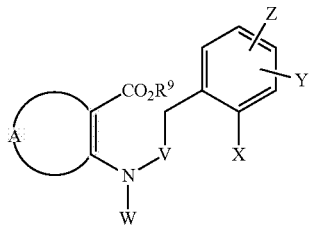

(II)

| No. | A | V | W | X | Y | Z | R⁹ | Analytical data |
|---|---|---|---|---|---|---|---|---|
| II-50 | thiazole | C=O | CH$_2$—C≡CH | Me | 3-Br | 6-Me | Me | $^1$H NMR (400 MHz, CDCl$_3$): 8.92 (s, 1H); 7.32 (d, 1H); 6.83 (d, 1H); 4.64 (s, 2H); 3.94 (s, 3H); 3.56 (s, 2H); 2.30 (s, 3H); 2.16 (s, 4H) |
| II-51 | thiazole | C=O | CH$_2$—CHF$_2$ | Cl | 4-Cl | 6-Et | Me | $^1$H NMR (400 MHz, CDCl$_3$): 8.90 (s, 1H); 7.20 (br s, 1H); 7.09 (d, 1H); 6.07 (tt, 1H); 4.10 (td, 2H); 3.94 (s, 3H); 3.65 (s, 2H); 2.59 (q, 2H); 1.16 (t, 3H) |
| II-52 | thiazole | C=O | CH$_2$—CHF$_2$ | Cl | 4-Cl | 6-Me | Me | $^1$H NMR (400 MHz, CDCl$_3$): 8.88 (s, 1H); 7.19 (s, 1H); 7.07 (s, 1H); 6.08 (tt, 1H); 4.10 (m, 2H); 3.94 (s, 3H); 3.65 (s, 2H); 2.27 (s, 3H) |
| II-53 | thiazole | C=O | CH$_2$—CHF$_2$ | Me | 3-Br | 6-Me | Me | $^1$H NMR (400 MHz, CDCl$_3$): 8.90 (s, 1H); 7.33 (d, 1H); 6.84 (d, 1H); 6.08 (tt, 1H); 4.09 (td, 2H); 3.95 (s, 3H); 3.57 (s, 2H); 2.29 (s, 3H); 2.15 (s, 3H) |
| II-54 | thiazole | C=O | CH$_2$—C≡CH | Cl | 4-Cl | 6-Et | Me | $^1$H NMR (400 MHz, CDCl$_3$): 8.93 (s, 1H); 7.20 (d, 1H); 7.08 (d, 1H); 4.66 (d, 2H); 3.94 (s, 3H); 3.63 (s, 2H); 2.60 (q, 2H); 2.14 (br s, 1H); 1.16 (t, 3H) |
| II-55 | thiazole | C=O | CH$_2$—C≡CH | Me | 4-Cl | 6-CF$_3$ | Me | $^1$H NMR (400 MHz, CDCl$_3$): 8.96 (s, 1H); 7.46 (s, 1H); 7.36 (s, 1H); 4.64 (d, 2H); 3.95 (s, 3H); 3.58 (s, 2H); 2.31 (s, 3H); 2.14 (br s, 1H) |
| II-56 | thiazole | C=O | CH$_2$—CHF$_2$ | Me | 4-Cl | 6-CF$_3$ | Me | $^1$H NMR (400 MHz, CDCl$_3$): 8.94 (s, 1H); 7.47 (d, 1H); 7.37 (s, 1H); 6.05 (tt, 1H); 4.10 (td, 2H); 3.95 (s, 3H); 3.60 (s, 2H); 2.30 (s, 3H) |
| II-57 | thiazole | C=O | CH$_2$—C≡CH | Et | 4-Cl | 6-OMe | Me | $^1$H NMR (400 MHz, CDCl$_3$): 8.82 (s, 1H); 6.77 (d, 1H); 6.60 (d, 1H); 4.63 (d, 2H); 3.92 (s, 3H); 3.70 (s, 3H); 3.52 (s, 2H); 2.54 (q, 2H); 2.12 (br s, 1H); 1.14 (t, 3H) |

TABLE 153-continued

Inventive compounds of the formula (II)

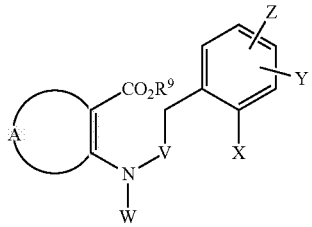

| No. | A | V | W | X | Y | Z | R⁹ | Analytical data |
|---|---|---|---|---|---|---|---|---|
| II-58 | thiazole | C=O | CH₂—CHF₂ | Et | 4-Cl | 6-OMe | Me | $^1$H NMR (400 MHz, CDCl$_3$): 8.78 (s, 1H); 6.77 (d, 1H); 6.60 (d, 1H); 6.08 (tt, 1H); 4.07 (td, 2H); 3.93 (s, 3H); 3.70 (s, 3H); 3.53 (s, 2H); 2.53 (q, 2H); 1.14 (t, 3H) |
| II-59 | thiazole | C=O | CH₂—C≡CH | Cl | 4-Br | 6-Et | Me | $^1$H NMR (400 MHz, CDCl$_3$): 8.92 (s, 1H); 7.35 (d, 1H); 7.23 (d, 1H); 4.65 (d, 2H); 3.93 (s, 3H); 3.63 (s, 2H); 2.60 (q, 2H); 2.14 (br s, 1H); 1.16 (t, 3H) |
| II-60 | pyrazole | C=O | CH₂—C≡CH | Cl | 4-Cl | 6-Et | Et | $^1$H NMR (400 MHz, CDCl$_3$): 7.96 (s, 1H); 7.19 (d, 1H); 7.06 (d, 1H); 4.58 (s, 2H); 4.29 (q, 2H); 3.97 (s, 3H); 3.64 (s, 2H); 2.58 (q, 2H); 2.16 (t, 1H); 1.34 (t, 3H); 1.15 (t, 3H) |
| II-61 | pyrazole | C=O | CH₂—CHF₂ | Cl | 4-Cl | 6-Et | Et | $^1$H NMR (400 MHz, CDCl$_3$): 7.94 (s, 1H); 7.21 (d, 1H); 7.07 (d, 1H); 6.06 (tt, 1H); 4.31 (q, 2H); 4.02 (td, 2H); 3.95 (s, 3H); 3.65 (s, 2H); 2.57 (q, 2H); 1.34 (t, 3H); 1.15 (t, 3H) |
| II-62 | pyrazole | C=O | CH₃ | Cl | 4-Cl | 6-Me | Et | $^1$H NMR (400 MHz, CDCl$_3$): 7.92 (s, 1H); 7.17 (d, 1H); 7.04 (s, 1H); 4.28 (q, 2H); 3.93 (s, 3H); 3.62 (s, 2H); 3.24 (s, 3H); 2.25 (s, 3H); 1.33 (t, 3H) |
| II-63 | pyrazole | C=O | CH₂—CF₃ | Cl | 4-Cl | 6-Me | Et | $^1$H NMR (400 MHz, CDCl$_3$): 7.93 (s, 1H); 7.19 (s, 1H); 7.05 (s, 1H); 6.06 (tt, 1H); 4.29 (q, 2H); 4.02 (br s, 2H); 3.95 (s, 3H); 3.66 (s, 2H); 2.24 (s, 3H); 1.34 (t, 3H) |
| II-64 | pyrazole | C=O | CH₃ | Cl | 4-Cl | 6-Et | Et | $^1$H NMR (400 MHz, CDCl$_3$): 7.95 (s, 1H); 7.19 (d, 1H); 7.06 (d, 1H); 4.40 (br s, 1H); 4.30 (q, 2H); 3.96 (s, 3H); 3.67 (s, 2H); 2.24 (s, 3H); 1.34 (t, 3H) |

TABLE 153-continued

Inventive compounds of the formula (II)

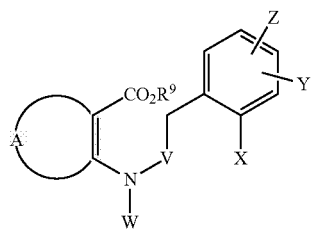

(II)

| No. | A | V | W | X | Y | Z | $R^9$ | Analytical data |
|---|---|---|---|---|---|---|---|---|
| II-65 | pyrazole | C=O | $CH_2-C\equiv CH$ | Cl | 4-Cl | 6-Me | Et | $^1$H NMR (400 MHz, $CDCl_3$): 7.94 (s, 1H); 7.18 (d, 1H); 7.04 (s, 1H); 4.57 (br s, 2H); 4.28 (q, 2H); 3.96 (s, 3H); 3.65 (s, 2H); 2.25 (s, 3H); 2.16 (t, 1H); 1.33 (t, 3H) |
| II-66 | pyrazole | C=O | $CH_2-CHF_2$ | Cl | 4-Cl | 6-Me | Et | $^1$H NMR (400 MHz, $CDCl_3$): 7.94 (s, 1H); 7.19 (d, 1H); 7.06 (d, 1H); 4.29 (q, 2H); 3.94 (s, 3H); 3.62 (s, 2H); 3.24 (s, 3H); 2.58 (q, 2H); 1.34 (t, 3H); 1.15 (t, 3H) |
| II-67 | pyrazole | C=O | $CH_2-CHF_2$ | Me | $4-CF_2-CF_3$ | 6-Me | Et | $^1$H NMR (400 MHz, $CDCl_3$): 7.92 (s, 1H); 7.19 (s, 2H); 6.07 (tt, 1H); 4.31 (q, 2H); 4.02 (br s, 1H); 3.95 (s, 3H); 3.56 (s, 2H); 2.26 (s, 6H); 1.35 (t, 3H) |
| II-68 | pyrazole | C=O | $CH_2-CHF_2$ | Cl | 3-Br | 6-Cl | Et | $^1$H NMR (400 MHz, $CDCl_3$): 7.95 (s, 1H); 7.47 (d, 1H); 7.16 (d, 1H); 6.08 (tt, 1H); 4.31 (q, 2H); 4.03 (br t, 2H); 3.96 (s, 3H); 3.92 (s, 2H); 3.41 (br t, 1H); 1.35 (t, 3H) |
| II-69 | pyrazole | C=O | $CH_2-CF_3$ | Me | $4-CF_2-CF_3$ | 6-Me | Et | $^1$H NMR (400 MHz, $CDCl_3$): 7.94 (s, 1H); 7.19 (s, 2H); 4.40 (br s, 2H); 4.31 (q, 2H); 3.96 (s, 3H); 3.57 (s, 2H); 2.25 (s, 6H); 1.34 (t, 3H) |
| II-70 | pyrazole | C=O | $CH_3$ | Me | $4-CF_2-CF_3$ | 6-Me | Et | $^1$H NMR (400 MHz, $CDCl_3$): 7.91 (s, 1H); 7.17 (s, 2H); 4.30 (q, 2H); 3.93 (s, 3H); 3.52 (s, 2H); 3.24 (s, 3H); 2.26 (s, 6H); 1.34 (t, 3H) |
| II-71 | pyrazole | C=O | $CH_2-CF_3$ | Cl | 3-Br | 6-Cl | Et | $^1$H NMR (400 MHz, $CDCl_3$): 7.97 (s, 1H); 7.47 (d, 1H); 7.16 (d, 1H); 4.42 (br s, 2H); 4.31 (q, 2H); 3.97 (s, 3H); 3.93 (s, 2H); 1.35 (t, 3H) |

TABLE 153-continued

Inventive compounds of the formula (II)

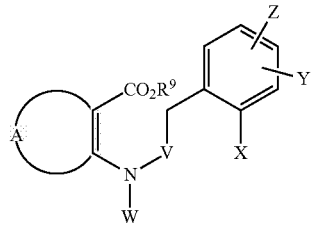

(II)

| No. | A | V | W | X | Y | Z | R⁹ | Analytical data |
|---|---|---|---|---|---|---|---|---|
| II-72 | pyrazole | C=O | $CH_3$ | Cl | 3-Br | 6-Cl | Et | $^1$H NMR (400 MHz, $CDCl_3$): 7.95 (s, 1H); 7.44 (d, 1H); 7.14 (d, 1H); 4.30 (q, 2H); 3.94 (s, 3H); 3.88 (s, 2H); 3.25 (s, 3H); 1.34 (t, 3H) |
| II-73 | pyrazole | C=O | $CH_2$—C≡CH | Cl | 3-Br | 6-Cl | Et | $^1$H NMR (400 MHz, $CDCl_3$): 7.96 (s, 1H); 7.45 (d, 1H); 7.14 (d, 1H); 4.59 (br s, 2H); 4.30 (q, 2H); 3.97 (s, 3H); 3.91 (s, 2H); 2.17 (t, 1H); 1.34 (t, 3H) |
| II-74 | pyrazole | C=O | $CH_3$ | F | 3-Me | 6-Cl | Et | $^1$H NMR (400 MHz, $CDCl_3$): 7.90 (s, 1H); 6.98 (m, 2H); 4.29 (q, 2H); 3.92 (s, 3H); 3.64 (s, 2H); 3.24 (s, 3H); 2.20 (s, 3H); 1.33 (t, 3H) |
| II-75 | pyrazole | C=O | $CH_2$—C≡CH | F | 3-Me | 6-Cl | Et | $^1$H NMR (400 MHz, $CDCl_3$): 7.92 (s, 1H); 6.99 (m, 2H); 4.57 (d, 2H); 4.28 (q, 2H); 3.95 (s, 3H); 3.68 (s, 2H); 2.20 (d, 3H); 2.15 (t, 1H); 1.33 (t, 3H) |
| II-76 | pyrazole | C=O | $CH_2$—$CF_3$ | F | 3-Me | 6-Cl | Et | $^1$H NMR (400 MHz, $CDCl_3$): 7.93 (s, 1H); 7.00 (m, 2H); 4.41 (br q, 2H); 4.30 (q, 2H); 3.95 (s, 3H); 3.70 (s, 2H); 2.20 (d, 3H); 1.34 (t, 3H) |
| II-77 | thiazole | C=O | $CH_3$ | I | H | H | Me | $^1$H NMR (400 MHz, $CDCl_3$): 8.82 (s, 1H); 7.74 (d, 1H); 7.28 (m, 2H); 6.88 (t, 1H); 3.85 (s, 3H); 3.68 (br s, 2H); 3.32 (s, 3H) |
| II-78 | thiazole | C=O | $CH_2$—$CHF_2$ | Cl | 3-c-Pr | 6-Cl | Me | $^1$H NMR (400 MHz, $CDCl_3$): 8.86 (s, 1H); 7.16 (d, 1H); 6.80 (d, 1H); 6.11 (tt, 1H); 4.12 (td, 2H); 3.95 (s, 3H); 3.89 (s, 2H); 2.10 (m, 1H); 0.99 (m, 2H); 0.63 (m, 2H) |
| II-79 | thiazole | C=O | $CH_2$—$CHF_2$ | Cl | 3-Br | 6-Cl | Me | $^1$H NMR (400 MHz, $CDCl_3$): 8.88 (s, 1H); 7.47 (d, 1H); 7.16 (d, 1H); 6.09 (tt, 1H); 4.11 (td, 2H); 3.95 (s, 3H); 3.91 (s, 2H) |

TABLE 153-continued

Inventive compounds of the formula (II)

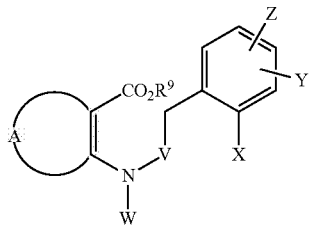

(II)

| No. | A | V | W | X | Y | Z | R⁹ | Analytical data |
|---|---|---|---|---|---|---|---|---|
| II-80 | thiazole | C=O | CH₂—C≡CH | CF₃ | H | H | Me | ¹H NMR (400 MHz, CDCl₃): 8.89 (s, 1H); 7.58 (d, 1H); 7.49 (t, 1H); 7.41 (d, 1H); 7.33 (t, 1H); 4.65 (d, 2H); 3.90 (s, 3H); 3.68 (br s, 2H); 2.16 (br s, 1H) |
| II-81 | thiazole | C=O | CH₃ | Cl | 3-Me | 6-Cl | Me | ¹H NMR (400 MHz, CDCl₃): 8.86 (s, 1H); 7.16 (d, 1H); 7.05 (d, 1H); 3.94 (s, 3H); 3.82 (s, 2H); 3.32 (s, 3H); 2.32 (s, 3H) |
| II-82 | thiazole | C=O | CH₂—CHF₂ | Cl | 3-Me | 6-Cl | Me | ¹H NMR (400 MHz, CDCl₃): 8.86 (s, 1H); 7.17 (d, 1H); 7.06 (d, 1H); 6.10 (tt, 1H); 4.11 (td, 2H); 3.95 (s, 3H); 3.87 (s, 2H); 2.32 (s, 3H) |
| II-83 | thiazole | C=O | CH₂—CHF₂ | Cl | 3-I | 6-Cl | Me | ¹H NMR (400 MHz, CDCl₃): 8.87 (s, 1H); 7.69 (d, 1H); 7.01 (d, 1H); 6.09 (tt, 1H); 4.11 (td, 2H); 3.95 (s, 5H) |
| II-84 | thiazole | C=O | CH₂—CF₃ | Me | 3-Br | 6-Cl | Me | ¹H NMR (400 MHz, CDCl₃): 8.92 (s, 1H); 7.38 (d, 1H); 7.05 (d, 1H); 4.49 (q, 2H); 3.95 (s, 3H); 3.79 (s, 2H); 2.38 (s, 3H) |
| II-85 | thiazole | C=O | CH₂—CHF₂ | Me | 3-Br | 6-Cl | Me | ¹H NMR (400 MHz, CDCl₃): 8.88 (s, 1H); 7.38 (d, 1H); 7.04 (d, 1H); 6.08 (tt, 1H); 4.10 (td, 2H); 3.94 (s, 3H); 3.78 (s, 2H); 2.38 (s, 3H) |
| II-86 | thiazole | C=O | CH₂—CHF₂ | Me | 4-Br | 6-Et | Me | ¹H NMR (400 MHz, CDCl₃): 8.91 (s, 1H); 7.14 (s, 2H); 6.08 (tt, 1H); 4.08 (td, 2H); 3.95 (s, 3H); 3.45 (s, 2H); 2.48 (q, 2H); 2.17 (s, 3H); 1.10 (t, 3H) |
| II-87 | thiazole | C=O | CH₃ | Me | 4-Br | 6-Me | Me | ¹H NMR (400 MHz, CDCl₃): 8.89 (s, 1H); 7.12 (s, 2H); 3.93 (s, 3H); 3.40 (s, 2H); 3.29 (s, 3H); 2.17 (s, 6H) |
| II-88 | thiazole | C=O | CH₃ | Me | 4-Br | 6-Et | Me | ¹H NMR (400 MHz, CDCl₃): 8.89 (s, 1H); 7.13 (s, 2H); 3.94 (s, 3H); 3.41 (s, 2H); 3.29 (s, 3H); 2.49 (m, 2H); 2.18 (s, 3H); 1.11 (t, 3H) |

TABLE 153-continued

Inventive compounds of the formula (II)

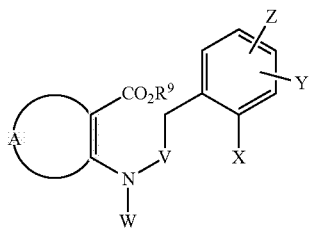

(II)

| No. | A | V | W | X | Y | Z | R⁹ | Analytical data |
|---|---|---|---|---|---|---|---|---|
| II-89 | thiazolyl | C=O | $CH_2$—$CHF_2$ | Me | 4-Br | 6-Me | Me | $^1$H NMR (400 MHz, $CDCl_3$): 8.90 (s, 1H); 7.13 (s, 2H); 6.08 (tt, 1H); 4.08 (td, 2H); 3.94 (s, 3H); 3.45 (s, 2H); 2.16 (s, 6H) |
| II-90 | 2-(methylthio)thiazolyl | C=O | $CH_3$ | Cl | 6-Cl | H | Et | $^1$H NMR (400 MHz, $CDCl_3$): 7.26 (m, 2H); 7.10 (t, 1H); 4.35 (q, 2H); 3.88 (s, 2H); 3.27 (s, 3H); 2.70 (s, 3H); 1.36 (t, 3H) |
| II-91 | thiazolyl | C=O | $CH_2$—$CHF_2$ | Me | 4-$CF_2$—$CF_3$ | 6-Me | Me | $^1$H NMR (400 MHz, $CDCl_3$): 8.89 (s, 1H); 7.19 (s, 2H); 6.08 (tt, 1H); 4.09 (td, 2H); 3.94 (s, 3H); 3.56 (s, 2H); 2.25 (s, 6H) |
| II-92 | thiazolyl | C=O | $CH_3$ | I | 4-Cl | 6-Et | Me | $^1$H NMR (400 MHz, $CDCl_3$): 8.90 (s, 1H); 7.65 (d, 1H); 7.15 (d, 1H); 3.94 (s, 3H); 3.68 (s, 2H); 3.32 (s, 3H); 2.61 (q, 2H); 1.15 (t, 3H) |
| II-93 | thiazolyl | C=O | $CH_2$—$CHF_2$ | I | 4-Cl | 6-Et | Me | $^1$H NMR (400 MHz, $CDCl_3$): 8.92 (s, 1H); 7.65 (d, 1H); 7.16 (d, 1H); 6.08 (tt, 1H); 4.12 (td, 2H); 3.95 (s, 3H); 3.72 (s, 2H); 2.61 (q, 2H); 1.15 (t, 3H) |
| II-94 | thiazolyl | C=O | $CH_2$—C≡CH | Me | 4-$CF_2$—$CF_3$ | 6-Me | Me | $^1$H NMR (400 MHz, $CDCl_3$): 8.91 (s, 1H); 7.19 (s, 2H); 4.65 (d, 2H); 3.93 (s, 3H); 3.55 (s, 2H); 2.27 (s, 6H); 2.15 (br s, 1H) |
| II-95 | thiazolyl | C=O | $CH_3$ | Me | 4-$CF_2$—$CF_3$ | 6-Me | Me | $^1$H NMR (400 MHz, $CDCl_3$): 8.87 (s, 1H); 7.18 (s, 2H); 3.93 (s, 3H); 3.52 (s, 2H); 3.31 (s, 3H); 2.27 (s, 6H) |
| II-96 | thiazolyl | C=O | $CH_2$—C≡CH | I | 4-Cl | 6-Et | Me | $^1$H NMR (400 MHz, $CDCl_3$): 8.94 (s, 1H); 7.65 (d, 1H); 7.15 (d, 1H); 4.67 (d, 2H); 3.94 (s, 3H); 3.71 (s, 2H); 2.62 (q, 2H); 2.14 (br s, 1H); 1.15 (t, 3H) |

TABLE 153-continued

Inventive compounds of the formula (II)

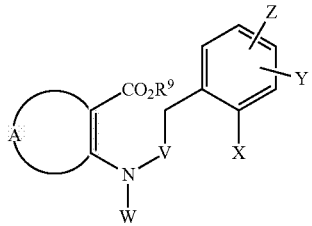

(II)

| No. | A | V | W | X | Y | Z | R⁹ | Analytical data |
|---|---|---|---|---|---|---|---|---|
| II-97 | thiazole | C=O | CH$_3$ | F | 4-Me | 6-Me | Me | $^1$H NMR (400 MHz, CDCl$_3$): 8.81 (s, 1H); 6.73 (s, 1H); 6.59 (d, 1H); 3.89 (s, 3H); 3.51 (s, 2H); 3.28 (s, 3H); 2.24 (s, 3H); 2.20 (s, 3H) |
| II-98 | thiazole | C=O | CH$_2$—CHF$_2$ | F | 4-Me | 6-Me | Me | $^1$H NMR (400 MHz, CDCl$_3$): 8.81 (s, 1H); 6.74 (s, 1H); 6.60 (d, 1H); 6.09 (tt, 1H); 4.07 (td, 2H); 3.91 (s, 3H); 3.54 (s, 2H); 2.24 (s, 3H); 2.20 (s, 3H) |
| II-99 | thiazole | C=O | CH$_2$—CHF$_2$ | Br | 4-Br | 6-Me | Me | $^1$H NMR (400 MHz, CDCl$_3$): 8.89 (s, 1H); 7.54 (d, 1H); 7.26 (m, 1H); 6.08 (tt, 1H); 4.10 (td, 2H); 3.94 (s, 3H); 3.68 (s, 2H); 2.28 (s, 3H) |
| II-100 | thiazole | C=O | CH$_3$ | Br | 4-Br | 6-Me | Me | $^1$H NMR (400 MHz, CDCl$_3$): 8.88 (s, 1H); 7.52 (br s, 1H); 7.25 (d, 1H); 3.93 (s, 3H); 3.64 (s, 2H); 3.30 (s, 3H); 2.29 (s, 3H) |
| II-101 | thiazole | C=O | CH$_3$ | Br | 4-Br | 6-Et | Me | $^1$H NMR (400 MHz, CDCl$_3$): 8.89 (s, 1H); 7.53 (m, 1H); 7.26 (m, 1H); 3.93 (s, 3H); 3.64 (s, 2H); 3.31 (s, 3H); 2.61 (q, 2H); 1.16 (s, 3H) |
| II-102 | thiazole | C=O | CH$_2$—CHF$_2$ | Br | 4-Br | 6-Et | Me | $^1$H NMR (400 MHz, CDCl$_3$): 8.91 (s, 1H); 7.53 (d, 1H); 7.27 (d, 1H); 6.08 (tt, 1H); 4.11 (td, 2H); 3.94 (s, 3H); 3.67 (s, 2H); 2.60 (q, 2H); 1.16 (t, 3H) |
| II-103 | thiazole | C=O | CH$_2$—C≡CH | Br | 4-Br | 6-Et | Me | $^1$H NMR (400 MHz, CDCl$_3$): 8.93 (s, 1H); 7.53 (d, 1H); 7.27 (d, 1H); 4.66 (d, 2H); 3.94 (s, 3H); 3.66 (s, 2H); 2.61 (q, 2H); 2.14 (br s, 1H); 1.16 (t, 3H) |
| II-104 | thiazole | C=O | CH$_2$—C≡CH | Br | 4-Br | 6-Me | Me | $^1$H NMR (400 MHz, CDCl$_3$): 8.92 (s, 1H); 7.51 (m, 1H); 7.25 (m, 1H); 4.65 (d, 2H); 3.93 (s, 3H); 3.66 (s, 2H); 2.29 (s, 3H); 2.15 (br s, 1H) |

TABLE 153-continued

Inventive compounds of the formula (II)

| No. | A | V | W | X | Y | Z | R⁹ | Analytical data |
|---|---|---|---|---|---|---|---|---|
| II-105 | thiazole | C=O | CH₂—CHF₂ | Me | 4-(2'-c-Pr)—c-Pr | 6-Me | Me | ¹H NMR (400 MHz, CDCl₃): 8.88 (s, 1H); 6.64 (br s, 2H); 6.09 (br t, 1H); 4.07 (br t, 2H); 3.93 (s, 3H); 3.44 (s, 2H); 2.14 (s, 6H); 1.53 (m, 1H); 1.07 (m, 1H); 0.89 (m, 1H); 0.73 (m, 1H); 0.67 (m, 1H); 0.38 (m, 2H); 0.12 (m, 2H) |
| II-106 | thiazole | C=O | CH₃ | Me | 4-(2'-c-Pr)—c-Pr | 6-Me | Me | ¹H NMR (400 MHz, CDCl₃): 8.86 (s, 1H); 6.63 (br s, 2H); 3.92 (s, 3H); 3.41 (br s, 2H); 3.28 (s, 3H); 2.15 (s, 6H); 1.53 (m, 1H); 1.07 (m, 1H); 0.89 (m, 1H); 0.73 (m, 1H); 0.66 (m, 1H); 0.38 (m, 2H); 0.12 (m, 2H) |
| II-107 | thiadiazole | C=O | CH₃ | Cl | 6-Cl | H | Me | ¹H NMR (400 MHz, CDCl₃): 7.30 (m, 2H); 7.16 (m, 1H); 4.29-3.27 (m, 8H) |
| II-108 | thiadiazole | C=O | CH₃ | Br | 4-Cl | 6-Et | Me | ¹H NMR (400 MHz, CDCl₃): 7.42 (br s, 1H); 7.15 (br s, 1H); 4.11-3.26 (m, 8H); 2.63 (m, 2H); 1.21 (m, 3H) |
| II-109 | 2-methyl-thiazole | C=O | CH₂—CHF₂ | Cl | 6-Cl | H | Me | ¹H NMR (400 MHz, CDCl₃): 7.26 (d, 2H); 7.11 (dd, 1H); 6.09 (tt, 1H); 4.07 (td, 2H); 3.91 (s, 3H); 3.90 (s, 2H); 2.70 (s, 3H) |
| II-110 | thiadiazole | C=O | CH₂—CHF₂ | Br | 4-Cl | 6-Et | Me | ¹H NMR (400 MHz, CDCl₃): 7.40 (br s, 1H); 7.14 (br s, 1H); 6.07 (br t, 1H); 4.12 (m, 2H); 4.04 (s, 3H); 3.60 (s, 2H); 2.60 (q, 2H); 1.17 (t, 3H) |
| II-111 | 2-methyl-thiazole | C=O | CH₃ | Cl | 6-Cl | H | Me | ¹H NMR (400 MHz, CDCl₃): 7.26 (d, 2H); 7.10 (t, 1H); 3.90 (s, 3H); 3.84 (s, 2H); 3.28 (s, 3H); 2.71 (s, 3H) |
| II-112 | thiazole | C=O | CH₃ | Br | 4-Br | 6-OCF₃ | Me | ¹H NMR (400 MHz, CDCl₃): 8.87 (s, 1H); 7.65 (d, 1H); 7.35 (br s, 1H); 3.93 (s, 3H); 3.65 (s, 2H); 3.31 (s, 3H) |

TABLE 153-continued

Inventive compounds of the formula (II)

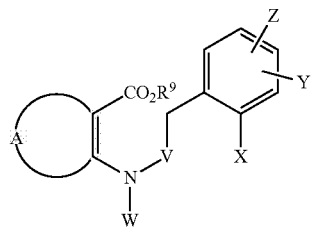

(II)

| No. | A | V | W | X | Y | Z | R⁹ | Analytical data |
|---|---|---|---|---|---|---|---|---|
| II-113 | thiazole | C=O | CH₂—CHF₂ | Br | 4-Br | 6-OCF₃ | Me | $^1$H NMR (400 MHz, CDCl$_3$): 8.87 (s, 1H); 7.66 (d, 1H); 7.35 (m, 1H); 6.07 (tt, 1H); 4.10 (td, 2H); 3.94 (s, 3H); 3.70 (s, 2H) |
| II-114 | thiadiazole | C=O | CH₂—C≡CH | Br | 4-Cl | 6-Et | Me | $^1$H NMR (400 MHz, CDCl$_3$): 7.41 (br s, 1H); 7.15 (br s, 1H); 4.70 (br s, 2H); 3.99 (br s, 3H); 3.61 (br s, 2H); 2.63 (m, 2H); 2.17 (br s, 1H); 1.19 (br s, 3H) |
| II-115 | thiazole | C=O | CH₃ | Cl | 4-Br | 6-OCF₃ | Me | $^1$H NMR (400 MHz, CDCl$_3$): 8.87 (s, 1H); 7.48 (d, 1H); 7.34 (d, 1H); 3.93 (s, 3H); 3.62 (s, 2H); 3.30 (s, 3H) |
| II-116 | thiazole | C=O | CH₂—CHF₂ | Cl | 4-Br | 6-OCF₃ | Me | $^1$H NMR (400 MHz, CDCl$_3$): 8.87 (s, 1H); 7.48 (d, 1H); 7.31 (m, 1H); 6.07 (tt, 1H); 4.09 (td, 2H); 3.94 (s, 3H); 3.67 (s, 2H) |
| II-117 | thiazole | C=O | CH₂—CHF₂ | Br | 4-Cl | 6-OCF₃ | Me | $^1$H NMR (400 MHz, CDCl$_3$): 8.88 (s, 1H); 7.51 (d, 1H); 7.22 (m, 1H); 6.08 (tt, 1H); 4.10 (td, 2H); 3.94 (s, 3H); 3.71 (s, 2H) |
| II-118 | thiazole | C=O | CH₃ | Br | 4-Cl | 6-OCF₃ | Me | $^1$H NMR (400 MHz, CDCl$_3$): 8.88 (s, 1H); 7.51 (d, 1H); 7.21 (br s, 1H); 3.93 (s, 3H); 3.66 (s, 2H); 3.31 (s, 3H) |
| II-119 | thiazole | C=O | CH₂—CHF₂ | F | 6-CF₃ | H | Me | $^1$H NMR (400 MHz, CDCl$_3$): 8.93 (s, 1H); 7.44 (d, 1H); 7.37 (q, 1H); 7.26 (m, 1H); 6.07 (tt, 1H); 4.11 (td, 2H); 3.96 (s, 3H); 3.68 (s, 2H) |
| II-120 | thiazole | C=O | CH₂—C≡CH | F | 6-CF₃ | H | Me | $^1$H NMR (400 MHz, CDCl$_3$): 8.95 (s, 1H); 7.43 (d, 1H); 7.35 (q, 1H); 7.25 (t, 1H); 4.65 (d, 2H); 3.95 (s, 3H); 3.65 (s, 2H); 2.14 (br s, 1H) |
| II-121 | thiazole | C=O | CH₃ | F | 6-CF₃ | H | Me | $^1$H NMR (400 MHz, CDCl$_3$): 8.91 (s, 1H); 7.43 (d, 1H); 7.35 (q, 1H); 7.25 (t, 1H); 3.95 (s, 3H); 3.63 (s, 2H); 3.31 (s, 3H) |

TABLE 153-continued

Inventive compounds of the formula (II)

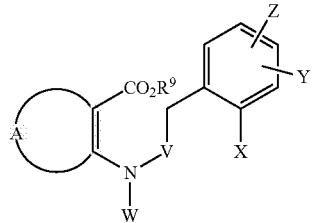

(II)

| No. | A | V | W | X | Y | Z | R⁹ | Analytical data |
|---|---|---|---|---|---|---|---|---|
| II-122 | thiazole | C=O | CH$_2$—CHF$_2$ | Cl | 6-CF$_3$ | H | Me | $^1$H NMR (400 MHz, CDCl$_3$): 8.95 (s, 1H); 7.58 (dd, 2H); 7.33 (t, 1H); 6.07 (tt, 1H); 4.12 (td, 2H); 3.96 (s, 3H); 3.80 (s, 2H) |
| II-123 | 2-Me-thiazole | C=O | CH$_3$ | Cl | 4-Cl | 6-Et | Me | $^1$H NMR (400 MHz, CDCl$_3$): 7.19 (d, 1H); 7.07 (d, 1H); 3.89 (s, 3H); 3.65 (s, 2H); 3.26 (s, 3H); 2.72 (s, 3H); 2.60 (q, 2H); 1.16 (t, 3H) |
| II-124 | 2-Me-thiazole | C=O | CH$_2$—C≡CH | Cl | 4-Cl | 6-Et | Me | $^1$H NMR (400 MHz, CDCl$_3$): 7.19 (d, 1H); 7.08 (d, 1H); 4.61 (d, 1H); 3.89 (s, 3H); 3.68 (s, 2H); 2.75 (s, 3H); 2.60 (q, 2H); 2.14 (br s, 1H); 1.16 (t, 3H) |
| II-125 | 2-Me-thiazole | C=O | CH$_2$—CHF$_2$ | Cl | 4-Cl | 6-Et | Me | $^1$H NMR (400 MHz, CDCl$_3$): 7.20 (d, 1H); 7.08 (d, 1H); 6.06 (tt, 1H); 4.06 (td, 2H); 3.90 (s, 3H); 3.69 (s, 2H); 2.73 (s, 3H); 2.58 (q, 2H); 1.16 (t, 3H) |
| II-126 | thiazole | C=O | CH$_3$ | Cl | 6-CF$_3$ | H | Me | $^1$H NMR (400 MHz, CDCl$_3$): 8.93 (s, 1H); 7.57 (dd, 1H); 7.31 (t, 1H); 3.96 (s, 3H); 3.76 (s, 2H); 3.32 (s, 3H) |
| II-127 | 2-Et-thiazole | C=O | CH$_3$ | Cl | 6-Cl | H | Me | $^1$H NMR (400 MHz, CDCl$_3$): 7.26 (m, 2H); 7.09 (t, 1H); 3.90 (s, 3H); 3.84 (s, 2H); 3.29 (s, 3H); 3.01 (q, 2H); 1.41 (t, 3H) |
| II-128 | 2-Et-thiazole | C=O | CH$_2$—C≡CH | Cl | 6-Cl | H | Me | $^1$H NMR (400 MHz, CDCl$_3$): 7.26 (m, 2H); 7.10 (dd, 1H); 4.64 (d, 2H); 3.90 (s, 3H); 3.87 (s, 2H); 3.04 (q, 2H); 2.13 (br s, 1H); 1.42 (t, 3H) |
| II-129 | 2-Et-thiazole | C=O | CH$_2$—CHF$_2$ | Cl | 4-Cl | 6-Et | Me | $^1$H NMR (400 MHz, CDCl$_3$): 7.20 (d, 1H); 7.08 (d, 1H); 6.06 (tt, 1H); 4.07 (td, 2H); 3.90 (s, 3H); 3.69 (s, 2H); 3.03 (q, 2H); 2.59 (q, 2H); 1.42 (t, 3H); 1.16 (t, 3H) |

TABLE 153-continued

Inventive compounds of the formula (II)

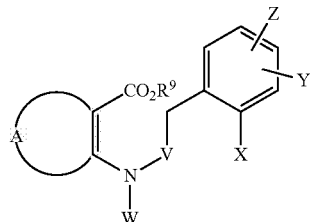

(II)

| No. | A | V | W | X | Y | Z | R⁹ | Analytical data |
|---|---|---|---|---|---|---|---|---|
| II-130 | 2-methylthiazole | C=O | CH₂—C≡CH | Br | 4-Cl | 6-Et | Me | $^1$H NMR (400 MHz, CDCl$_3$): 7.38 (d, 1H); 7.12 (d, 1H); 4.62 (d, 2H); 3.89 (s, 3H); 3.72 (s, 2H); 2.75 (s, 3H); 2.61 (q, 2H); 2.14 (br s, 1H); 1.16 (t, 3H) |
| II-131 | 2-ethylthiazole | C=O | CH₂—CHF₂ | Cl | 6-Cl | H | Me | $^1$H NMR (400 MHz, CDCl$_3$): 7.26 (m, 2H); 7.11 (dd, 1H); 6.09 (tt, 1H); 4.08 (td, 2H); 3.91 (s, 3H); 3.89 (s, 2H); 3.00 (q, 2H); 1.40 (t, 3H) |
| II-132 | 2-methylthiazole | C=O | CH₂—CHF₂ | Br | 4-Cl | 6-Et | Me | $^1$H NMR (400 MHz, CDCl$_3$): 7.38 (d, 1H); 7.12 (d, 1H); 6.06 (tt, 1H); 4.07 (td, 2H); 3.90 (s, 3H); 3.73 (s, 2H); 2.74 (s, 3H); 2.60 (q, 2H); 1.16 (t, 3H) |
| II-133 | 2-methylthiazole | C=O | CH₃ | Br | 4-Cl | 6-Et | Me | $^1$H NMR (400 MHz, CDCl$_3$): 7.38 (d, 1H); 7.11 (d, 1H); 3.89 (s, 3H); 3.69 (s, 2H); 3.27 (s, 3H); 2.73 (s, 3H); 2.61 (q, 2H); 1.16 (t, 3H) |
| II-134 | 2-ethylthiazole | C=O | CH₃ | Cl | 4-Cl | 6-Et | Me | $^1$H NMR (400 MHz, CDCl$_3$): 7.19 (d, 1H); 7.07 (d, 1H); 3.89 (s, 3H); 3.65 (s, 2H); 3.27 (s, 3H); 3.02 (q, 2H); 2.60 (q, 2H); 1.42 (t, 3H); 1.16 (t, 3H) |
| II-135 | 2-ethylthiazole | C=O | CH₂—C≡CH | Br | 4-Cl | 6-Et | Me | $^1$H NMR (400 MHz, CDCl$_3$): 7.38 (d, 1H); 7.12 (d, 1H); 4.63 (d, 2H); 3.90 (s, 3H); 3.71 (s, 2H); 3.05 (q, 2H); 2.62 (q, 2H); 2.13 (br s, 1H); 1.43 (t, 3H); 1.16 (t, 3H) |
| II-136 | 2-ethylthiazole | C=O | CH₃ | Br | 4-Cl | 6-Et | Me | $^1$H NMR (400 MHz, CDCl$_3$): 7.38 (d, 1H); 7.11 (d, 1H); 3.90 (s, 3H); 3.68 (s, 2H); 3.28 (s, 3H); 3.03 (q, 2H); 2.61 (q, 2H); 1.42 (t, 3H); 1.16 (t, 3H) |
| II-137 | 2-propylthiazole | C=O | CH₂—CHF₂ | Cl | 6-Cl | H | Me | $^1$H NMR (400 MHz, CDCl$_3$): 7.26 (m, 2H); 7.11 (dd, 1H); 6.09 (tt, 1H); 4.09 (td, 2H); 3.91 (s, 3H); 3.88 (s, 2H); 2.95 (t, 2H); 1.83 (sxt, 2H); 1.04 (t, 3H) |

TABLE 153-continued

Inventive compounds of the formula (II)

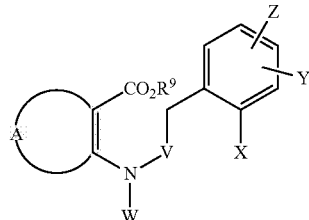
(II)

| No. | A | V | W | X | Y | Z | R⁹ | Analytical data |
|---|---|---|---|---|---|---|---|---|
| II-138 | ![thiazole] | C=O | CH$_3$ | Cl | 6-Cl | H | Me | $^1$H NMR (400 MHz, CDCl$_3$): 7.26 (m, 2H); 7.10 (dd, 1H); 3.90 (s, 3H); 3.83 (s, 2H); 3.29 (s, 3H); 2.96 (t, 2H); 1.85 (sxt, 2H); 1.05 (t, 3H) |
| II-139 | ![thiazole] | C=O | CH$_2$—CHF$_2$ | Cl | 4-Cl | 6-Et | Me | $^1$H NMR (400 MHz, CDCl$_3$): 7.20 (d, 1H); 7.08 (d, 1H); 6.06 (tt, 1H); 4.07 (td, 2H); 3.90 (s, 3H); 3.68 (s, 2H); 2.97 (t, 2H); 2.59 (q, 2H); 1.85 (sxt, 2H); 1.16 (t, 3H); 1.04 (t, 3H) |
| II-140 | ![thiazole] | C=O | CH$_2$—C≡CH | Cl | 6-Cl | H | Me | $^1$H NMR (400 MHz, CDCl$_3$): 7.26 (m, 2H); 7.10 (dd, 1H); 4.64 (d, 2H); 3.90 (s, 3H); 3.86 (s, 2H); 2.98 (t, 2H); 2.12 (br s, 1H); 1.85 (sxt, 2H); 1.04 (t, 3H) |
| II-141 | ![thiazole] | C=O | CH$_2$—C≡CH | Cl | 4-Cl | 6-Et | Me | $^1$H NMR (400 MHz, CDCl$_3$): 7.19 (d, 1H); 7.07 (d, 1H); 4.63 (d, 2H); 3.89 (s, 3H); 3.67 (s, 2H); 2.99 (t, 2H); 2.60 (q, 2H); 2.12 (br s, 1H); 1.86 (sxt, 2H); 1.16 (t, 3H); 1.04 (t, 3H) |
| II-142 | ![thiazole] | C=O | CH$_3$ | BrI | 4-Cl | 6-Et | Me | $^1$H NMR (400 MHz, CDCl$_3$): 7.38 (d, 1H); 7.11 (d, 1H); 3.90 (s, 3H); 3.67 (s, 2H); 3.28 (s, 3H); 2.97 (t, 2H); 2.61 (q, 2H); 1.85 (sxt, 2H); 1.16 (t, 3H); 1.05 (t, 3H) |
| II-143 | ![thiazole] | C=O | CH$_3$ | Cl | 4-Cl | 6-Et | Me | $^1$H NMR (400 MHz, CDCl$_3$): 7.19 (d, 1H); 7.07 (d, 1H); 3.89 (s, 3H); 3.64 (s, 2H); 3.27 (s, 3H); 2.96 (t, 2H); 2.60 (q, 2H); 1.85 (sxt, 2H); 1.16 (t, 3H); 1.05 (t, 3H) |
| II-144 | ![thiazole] | C=O | CH$_2$—CHF$_2$ | Br | 4-Cl | 6-Et | Me | $^1$H NMR (400 MHz, CDCl$_3$): 7.39 (d, 1H); 7.13 (d, 1H); 6.06 (tt, 1H); 4.08 (td, 2H); 3.90 (s, 3H); 3.72 (s, 2H); 2.98 (t, 2H); 2.60 (q, 2H); 1.85 (sxt, 2H); 1.16 (t, 3H); 1.05 (t, 3H) |

TABLE 153-continued

Inventive compounds of the formula (II)

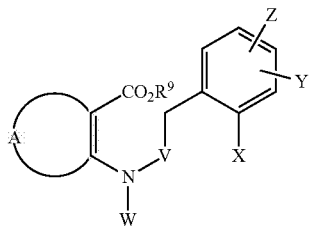

(II)

| No. | A | V | W | X | Y | Z | R⁹ | Analytical data |
|---|---|---|---|---|---|---|---|---|
| II-145 | (propyl-thiazole) | C=O | CH₂—C≡CH | Br | 4-Cl | 6-Et | Me | $^1$H NMR (400 MHz, CDCl$_3$): 7.38 (d, 1H); 7.12 (d, 1H); 4.64 (d, 2H); 3.90 (s, 3H); 3.71 (s, 2H); 2.99 (t, 2H); 2.61 (q, 2H); 2.12 (br s, 1H); 1.84 (sxt, 2H); 1.16 (t, 3H); 1.04 (t, 3H) |
| II-146 | (thiazole) | C=O | CH₂—CH₂—SCH₃ | Cl | 6-Cl | H | Me | $^1$H NMR (400 MHz, CDCl$_3$): 8.87 (s, 1H), 7.26 (d, 2H), 7.11 (t, 1H), 3.95 (m, 5H), 3.79 (s, 2H), 2.76 (t, 2H), 2.11 (s, 3H) |
| II-147 | (thiazole) | C=O | CH₂—CH₂—OCH₃ | Cl | 6-Cl | H | Me | $^1$H NMR (400 MHz, CDCl$_3$): 8.85 (s, 1H), 7.26 (d, 2H), 7.10 (t, 1H), 4.00 (t, 2H), 3.97 (s, 3H), 3.82 (s, 2H), 3.60 (t, 2H), 3.21 (s, 3H) |
| II-148 | (dimethyl-thiophene) | C=O | CH₂—CHF₂ | Cl | 4-Br | 6-Et | Et | $^1$H NMR (400 MHz, CDCl$_3$): 7.37 (d, 1H); 7.23 (d, 1H); 6.05 (tt, 1H); 4.33 (m, 2H); 4.18 (m, 1H); 3.73 (s, 2H); 3.69 (m, 1H); 2.54 (q, 2H); 2.37 (s, 3H); 2.30 (s, 3H); 1.36 (t, 3H); 1.17 (t, 3H) |
| II-149 | (phenyl-thiophene) | C=O | CH₂—CHF₂ | Br | 4-Cl | 6-Et | Et | $^1$H NMR (400 MHz, CDCl$_3$): 7.64 (m, 2H); 7.45 (m, 3H); 7.39 (d, 1H); 7.27 (s, 1H); 7.12 (d, 1H); 6.14 (br tt, 1H); 4.37 (m, 3H); 3.71 (br s, 2H); 3.66 (m, 1H); 2.59 (q, 2H); 1.40 (t, 3H); 1.17 (t, 3H) |
| II-150 | (thiophene) | C=O | CH₂—CHF₂ | Cl | 4-Br | 6-Et | Et | $^1$H NMR (400 MHz, CDCl$_3$): 7.62 (d, 1H); 7.36 (d, 1H); 7.24 (d, 1H); 7.11 (d, 1H); 6.09 (br tt, 1H); 4.25 (m, 1H); 3.92 (s, 3H); 3.63 (m, 1H); 3.55 (d, 2H); 2.55 (q, 2H); 1.16 (t, 3H) |

TABLE 153-continued

Inventive compounds of the formula (II)

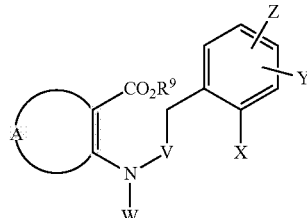

| No. | A | V | W | X | Y | Z | $R^9$ | Analytical data |
|---|---|---|---|---|---|---|---|---|
| II-151 | 5-methylthiophen-2-yl | C=O | $CH_2$—$CHF_2$ | Br | 4-Cl | 6-Et | Me | $^1$H NMR (400 MHz, CDCl$_3$): 7.41 (d, 1H); 7.13 (d, 1H); 7.09 (q, 1H); 6.07 (tt, 1H); 4.15 (m, 1H); 3.87 (s, 3H); 3.76 (m, 3H); 2.56 (q, 2H); 2.49 (d, 3H); 1.16 (t, 3H) |
| II-152 | 1-ethylpyrazol-4-yl | C=O | $CH_2$—$CHF_2$ | Br | 4-Cl | 6-Et | Et | $^1$H NMR (400 MHz, CDCl$_3$): 7.98 (s, 1H); 7.39 (d, 1H); 7.12 (d, 1H); 6.06 (tt, 1H); 4.30 (q, 2H); 4.20 (q, 2H); 4.03 (m, 2H); 3.68 (m, 2H); 2.58 (q, 2H); 1.55 (t, 3H); 1.35 (t, 3H); 1.14 (t, 3H) |

Illustrative preparation of the precursors:

Preparation of methyl 4-{(2,2-difluoroethyl)[(2-iodobenzyl)sulfonyl]amino}-1,3-thiazole-5-carboxylate 2.1 g (4.8 mmol) of methyl 4-{[(2-iodobenzyl)sulfonyl]amino}-1,3-thiazole-5-carboxylate were dissolved in 20 ml of acetonitrile, and 0.9 ml (5.3 mmol) of N,N-diisopropylethylamine was added at RT. The reaction mixture was stirred at RT for 5 min and then a solution of 1.54 g (7.2 mmol) of difluoroethyl trifluoromethane-sulfonate in 5 ml of acetonitrile was added dropwise within 10 min. The reaction mixture was stirred at RT for 12 h and then concentrated to dryness. The residue was purified by means of preparative HPLC ($C_{18}$—$SiO_2$, gradient acetonitrile/water 20:80 to 100:0). This gave 2.09 g of methyl 4-{(2,2-difluoroethyl)[(2-iodobenzyl)-sulfonyl]amino}-1,3-thiazole-5-carboxylate.

$^1$H NMR (400 MHz, CDCl$_3$): 8.82 (s, 1H); 7.90 (br d, 1H); 7.63 (dd, 1H); 7.35 (td, 1H); 7.04 (td, 1H); 5.96 (tt, 1H); 4.81 (s, 2H); 4.14 (td, 1H); 3.92 (s, 3H).

Preparation of methyl 4-{[(2-iodobenzyl)sulfonyl]amino}-1,3-thiazole-5-carboxylate 2 g (12.64 mmol) of methyl 4-amino-1,3-thiazole-5-carboxylate were dissolved together with 5.1 ml (63.2 mmol) NEt$_3$ in 20 ml of dioxane, and 4.4 g (13.9 mmol) of (2-iodophenyl)methanesulfonyl chloride were added at room temperature. The reaction mixture was stirred at RT for 5 h. Then 40 ml of water were added and the mixture was extracted repeatedly with ethyl acetate. The combined organic phases were washed with 2N HCl, dried and concentrated. The residue was purified by means of column chromatography (SiO$_2$, gradient ethyl acetate/n-heptane 10:90 to 75:25). This gave 4.3 g of methyl 4-{[(2-iodobenzyl)sulfonyl]amino}-1,3-thiazole-5-carboxylate.

$^1$H NMR (400 MHz, CDCl$_3$): 9.01 (br s, 1H); 8.81 (s, 1H); 7.87 (d, 1H); 7.51 (d, 1H); 7.36 (t, 1H); 7.04 (td, 1H); 5.06 (s, 2H); 3.88 (s, 3H).

Formulation Examples

Dusting Product

A dusting product is obtained by mixing 10 parts by weight of a compound of the formula (I) and 90 parts by weight of talc as an inert substance and comminuting the mixture in a hammer mill.

Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltauride as a wetting agent and dispersant, and grinding the mixture in a pinned-disk mill.

Dispersion Concentrate

A readily water-dispersible dispersion concentrate is obtained by mixing 20 parts by weight of a compound of the formula (I), 6 parts by weight of alkylphenol polyglycol ether®Triton X 207), 3 parts by weight of isotridecanol polyglycol ether (8 EO) and 71 parts by weight of paraffinic mineral oil (boiling range, for example, about 255 to above 277° C.) and grinding the mixture in a ball mill to a fineness of less than 5 microns.

Emulsifiable Concentrate

An emulsifiable concentrate is obtained from 15 parts by weight of a compound of the formula (I), 75 parts by weight of cyclohexanone as a solvent and 10 parts by weight of oxethylated nonylphenol as an emulsifier.

Water-dispersible Granules

Water-dispersible granules are obtained by mixing
75 parts by weight of a compound of the formula (I),
10" calcium lignosulfonate,
5" sodium laurylsulfate,
3" polyvinyl alcohol and
7" kaolin,
grinding the mixture in a pinned-disk mill and granulating the powder in a fluidized bed by spraying on water as a granulating liquid.

Water-dispersible Granules are also Obtained by Homogenizing and Precomminuting
25 parts by weight of a compound of the formula (I),
5" sodium 2,2'-dinaphthylmethane-6,6'-disulfonate,
2" sodium oleoylmethyltauride,
1" polyvinyl alcohol,
17" calcium carbonate and
50" water
in a colloid mill, then grinding the mixture in a bead mill and atomizing and drying the resulting suspension in a spray tower by means of a one-substance nozzle.

Biological Examples

Pre-emergence Herbicidal Action against Weed Plants and Compatibility with Crop Plants Seeds or rhizome sections of mono- and dicotyledonous weed plants are set out in pots of 9 to 13 cm in diameter in sandy loam soil, and are covered with soil. The herbicides, formulated as emulsifiable concentrates or dusting products, are applied to the surface of the covering earth in different doses in the form of aqueous dispersions or suspensions or emulsions, at a water application rate of 300 to 800 I/ha (converted). The pots are then maintained under glass under optimum conditions for the further cultivation of the plants. After the trial plants have stood for 3 to 4 weeks under glass under optimum growth conditions, the effect of the inventive compounds is scored visually. For example, compounds No. Ia-26, I-c-4, I-a-9, I-a-8, I-a-66, I-g-5, I-a-90, I-a-96 and I-b-13 at an application rate of 1280 grams per hectare each exhibit an at least 80% effect against Veronica persica. Compounds No. I-a-13, I-a-65, I-a-74 and I-b-14 at an application rate of 1280 grams per hectare each exhibit an at least 80% effect against *Echinoa crus galli, Lolium multiflorum* and *Setaria viridis*. Compounds No. I-a-75, I-a-89, I-a-94, I-a-97 and I-c-38 at an application rate of 320 grams per hectare each exhibit an at least 80% effect against *Stellaria media* and *Veronica persica*, and at the same time do not exhibit any damage in corn. Compounds No. I-a-2, I-a-28 and I-a-43 at an application rate of 320 grams per hectare each exhibit an at least 80% effect against *Setaria viridis*, and at the same time do not exhibit any damage in oilseed rape. Compounds No. I-a-36, I-b-22 and I-a-44 at an application rate of 320 grams per hectare each exhibit an at least 80% effect against *Lolium multiflorum*, and at the same time do not exhibit any damage in corn.

Post-emergence herbicidal action against weed plants and compatibility with crop plants Seeds of monocotyledonous and dicotyledonous weed plants are set out in cardboard pots in sandy loam soil, covered with soil, and cultivated under glass under good growth conditions. Two to three weeks after sowing, the trial plants are treated at the three-leaf stage. The inventive compounds, formulated as wettable powders or as emulsifiable concentrates, are sprayed onto the surface of the green parts of the plants, at a water application rate of 600 to 800 I/ha (converted). After the trial plants have stood for 3 to 4 weeks under glass under optimum growth conditions, the effect of the inventive compounds is scored visually. For example, compounds No. Ia-26, I-a-38 and I-b-1 at an application rate of 1280 grams per hectare each exhibit an at least 80% effect against *Amaranthus retroflexus, Lolium multiflorum* and *Stellaria media*.

Compounds No. I-a-26, I-a-9, I-a-75, I-a-88, I-a-89, I-a-94, I-a-8 and I-b-13 at an application rate of 1280 grams per hectare each exhibit an at least 80% effect against *Matricaria inodora* and *Fallopia convolvulus*. Compounds No. I-g-5, I-h-11, I-a-83, I-a-86 and I-a-93 at an application rate of 320 grams per hectare each exhibit an at least 80% effect against *Stellaria media* and *Veronica persica*, and at the same time do not exhibit any damage in corn. Compounds No. I-a-36, I-a-37 and I-a-44 at an application rate of 320 grams per hectare each exhibit an at least 80% effect against *Matricaria inodora, Fallopia convolvulus, Stellaria media* and *Veronica persica*, and at the same time do not exhibit any damage in corn.

The invention claimed is:
1. A compound of formula (I) or a salt thereof

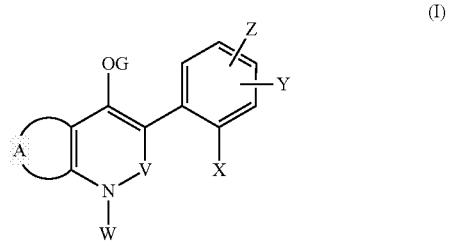

in which
A is one of the five-membered heterocycles A2 or A3 shown below, in which the broken lines mean the bond to the adjacent pyridine ring,

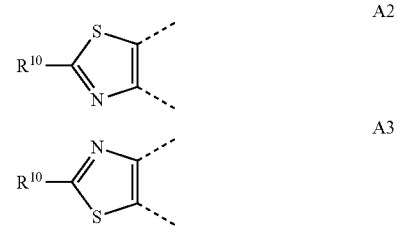

V is C(=O);
n is 0,1,2or 3;
G is hydrogen, $C(=O)R^1$, $C(=L)MR^2$, $SO_2R^3$, $P(=L)R^4R^5$, $C(=L)NR^6R^7$, E or R8;
E is a metal ion or an ammonium ion;
L is oxygen or sulfur;
M is oxygen or sulfur
$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl each substituted by n halogen atoms,
a fully saturated 3- to 6-membered ring consisting of 3 to 5 carbon atoms and 1 to 3 heteroatoms from the group of oxygen, sulfur and nitrogen and substituted by n radicals from the group consisting of halogen, $(C_1-C_4)$-alkyl and $(C_1-C_4)$-alkoxy, ($C_3$-$C_6$)-cycloalkyl, phenyl, phenyl-($C_1$-$C_4$)-alkyl, heteroaryl, phenoxy-($C_1$-$C_4$)-alkyl or heteroaryloxy-($C_1$-$C_4$)-alkyl substituted by n radicals from the group consisting of halogen, ($C_1$-$C_4$)-alkyl and ($C_1$-$C_4$)-alkoxy;

$R^2$ is ($C_1$-$C_6$)-alkyl, ($C_2$-$C_6$)-alkenyl, ($C_1$-$C_4$)-alkoxy-($C_1$-$C_6$)-alkyl or di-($C_1$-$C_4$)-alkoxy-($C_1$-$C_6$)-alkyl each substituted by n halogen atoms, or ($C_3$-$C_6$)-cycloalkyl, phenyl or benzyl substituted by n radicals in each case from the group consisting of halogen, ($C_1$-$C_4$)-alkyl and ($C_1$-$C_4$)-alkoxy;

$R^3$, $R^4$ and $R^5$ are each independently ($C_1$-$C_6$)-alkyl, ($C_1$-$C_4$)-alkoxy, N-($C_1$-$C_6$)-alkylamino, N,N-di-($C_1$-$C_6$)-alkylamino, ($C_1$-$C_4$)-alkylthio, ($C_2$-$C_4$)-alkenyl or ($C_3$-$C_6$)-cycloalkylthio each substituted by n halogen atoms, or phenyl, benzyl, phenoxy or phenylthio substituted by n radicals from the group consisting of halogen, ($C_1$-$C_4$)-alkyl and ($C_1$-$C_4$)-alkoxy;

$R^6$ and $R^7$ are each independently hydrogen, ($C_1$-$C_6$)-alkyl, ($C_3$-$C_6$)-cycloalkyl, ($C_2$-$C_6$)-alkenyl, ($C_1$-$C_6$)-alkoxy or ($C_1$-$C_4$)-alkoxy-($C_1$-$C_6$)-alkyl substituted by n halogen atoms, phenyl or benzyl substituted by in each case n radicals from the group consisting of halogen, ($C_1$-$C_4$)-alkyl and ($C_1$-$C_4$)-alkoxy, or $R^6$ and $R^7$ form, together with the nitrogen atom to which they are bonded, a 3- to 6-membered ring containing 2 to 5 carbon atoms and 0 or 1 oxygen or sulfur atom;

$R^8$ is ($C_1$-$C_6$)-alkyl, ($C_2$-$C_6$)-alkenyl, ($C_2$-$C_6$)-alkynyl, ($C_1$-$C_4$)-alkoxy-($C_1$-$C_6$)-alkyl, ($C_1$-$C_4$)-alkylthio-($C_1$-$C_4$)-alkyl or di-($C_1$-$C_4$)-alkoxy-($C_1$-$C_6$)-alkyl substituted by n halogen atoms, ($C_3$-$C_6$)-cycloalkyl substituted by n radicals from the group consisting of halogen, ($C_1$-$C_4$)-alkyl and ($C_1$-$C_4$)-alkoxy, a fully saturated 3- to 6-membered ring consisting of 3 to 5 carbon atoms and 1 to 3 heteroatoms from the group of oxygen, sulfur and nitrogen and substituted by n radicals from the group consisting of halogen, ($C_1$-$C_4$)-alkyl and ($C_1$-$C_4$)-alkoxy, phenyl, phenyl-($C_1$-$C_4$)-alkyl, heteroaryl, phenoxy-($C_1$-$C_4$)-alkyl or heteroaryloxy-($C_1$-$C_4$)-alkyl substituted by n radicals from the group consisting of halogen, ($C_1$-$C_4$)-alkyl and ($C_1$-$C_4$)-alkoxy;

$R^{10}$ is hydrogen, or ($C_1$-$C_6$)-alkyl, ($C_1$-$C_4$)-alkoxy, ($C_1$-$C_4$)-alkylthio, ($C_1$-$C_4$)-alkylsulfinyl or ($C_1$-$C_4$)-alkylsulfonyl substituted by n halogen atoms;

W is ($C_1$-$C_6$)-alkyl, ($C_2$-$C_6$)-alkenyl, ($C_3$-$C_6$)-alkenyl, ($C_3$-$C_6$)-cycloalkyl, ($C_{1-C4}$)-alkoxy-($C_1$-$C_6$)-alkyl, di-($C_1$-$C_4$)-alkoxy-($C_{1-C6}$)-alkyl, ($C_{1-C4}$)-alkylthio-($C_{1-C6}$)-alkyl, ($C_{1-C4}$)-alkylsulfinyl-($C_{1-C6}$)-alkyl, ($C_{1-C4}$)-alkylsulfonyl-($C_{1-C6}$)-alkyl or ($C_3$-$C_6$)-cycloalkyl-($C_{1-C6}$)-alkyl each substituted by n halogen atoms, and X, Y and Z are each independently hydrogen, ($C_1$-$C_6$)-alkyl, halogen, cyano, nitro, halo-($C_1$-$C_6$)-alkyl, halo-($C_1$-$C_6$)-alkoxy, ($C_3$-$C_6$)-cycloalkyl, ($C_1$-$C_6$)-alkoxy, ($C_1$-$C_6$)-alkoxy-($C_1$-$C_6$)-alkyl, halo-($C_1$-$C_6$)-alkoxy-($C_1$-$C_6$)-alkyl.

2. A compound as claimed in claim 1, in which

A is one of the five-membered heterocycles A2 to A3 shown below, in which the broken lines mean the bond to the adjacent pyridine or ketosultam ring,

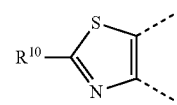

A2

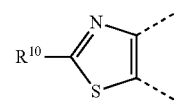

A3

V is C(=O);

n is 0,1,2 or 3;

G is hydrogen;

W is ($C_1$-$C_6$)-alkyl, ($C_2$-$C_6$)-alkenyl, ($C_3$-$C_6$)-alkynyl, ($C_3$-$C_6$)-cycloalkyl, ($C_1$-$C_4$)-alkoxy-($C_1$-$C_6$)-alkyl, di-($C_1$-$C_4$)-alkoxy-($C_1$-$C_6$)-alkyl, ($C_1$-$C_4$)-alkylthio-($C_1$-$C_6$)-alkyl, ($C_1$-$C_4$)-alkylsulfinyl-($C_1$-$C_6$)-alkyl, ($C_1$-$C_4$)-alkylsulfonyl-($C_1$-$C_6$)-alkyl or ($C_3$-$C_6$)-cycloalkyl-($C_1$-$C_6$)-alkyl each substituted by n halogen atoms;

X, Y and Z are each independently hydrogen, ($C_1$-$C_6$)-alkyl, ($C_3$-$C_6$)-cycloalkyl, halogen, cyano, nitro, halo-($C_1$-$C_6$)-alkyl, halo-($C_1$-$C_6$)-alkoxy, ($C_1$-$C_6$)-alkoxy, ($C_1$-$C_6$)-alkoxy-($C_1$-$C_6$)-alkyl, halo-($C_1$-$C_6$)-alkoxy-($C_1$-$C_6$)-alkyl; and $R^{10}$ is hydrogen, or ($C_1$-$C_6$)-alkyl, ($C_1$-$C_4$)-alkoxy, ($C_1$-$C_4$)-alkylthio, ($C_1$-$C_4$)-alkylsulfinyl or ($C_1$-$C_4$)-alkylsulfonyl substituted by n halogen atoms.

3. A compound as claimed in claim 1, in which

A is one of the five-membered heterocycles A2 or A3 shown below, in which the broken lines mean the bond to the adjacent pyridine ring,

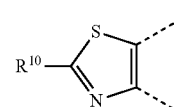

A2

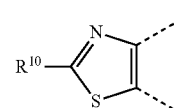

A3

V is C(=O)

n is 0, 1, 2 or 3;

G is C(=O)$R^1$;

$R^1$ is ($C_1$-$C_6$)-alkyl each substituted by n halogen atoms;

W is ($C_1$-$C_6$)-alkyl, ($C_2$-$C_6$)-alkenyl, ($C_3$-$C_6$)-alkynyl, ($C_3$-$C_6$)-cycloalkyl, ($C_1$-$C_4$)-alkoxy- ($C_1$-$C_6$)-alkyl, di-($C_1$-$C_4$)-alkoxy-($C_1$-$C_6$)-alkyl, ($C_1$-$C_4$)-alkylthio-($C_1$-$C_6$)-alkyl, ($C_1$-$C_4$)-alkylsulfinyl-($C_1$-$C_6$)-alkyl, ($C_1$-$C_4$)-alkylsulfonyl-($C_1$-$C_6$)-alkyl or ($C_3$-$C_6$)-cycloalkyl-($C_1$-$C_6$)-alkyl each substituted by n halogen atoms; and $R^{10}$ is hydrogen, or ($C_1$-$C_6$)-alkyl, ($C_1$-$C_4$)-alkoxy, ($C_1$-$C_4$)-alkylthio, ($C_1$-$C_4$)-alkylsulfinyl or ($C_1$-$C_4$)-alkylsulfonyl substituted by n halogen atoms.

4. A compound as claimed in claim 1, in which

A is one of the five-membered heterocycles A2 or A3 shown below, in which the broken lines mean the bond to the adjacent pyridine ring,

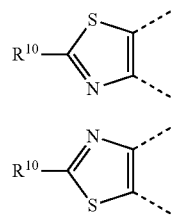

A2

A3

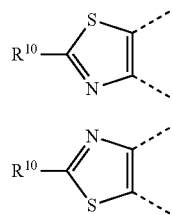

A2

A3

V is C(=O);
n is 0,1,2 or 3;
G is C(=L)MR$^2$;
L is oxygen;
M is oxygen or sulfur;
R$^2$ is (C$_1$-C$_6$)-alkyl each substituted by n halogen atoms;
W is (C$_1$-C$_6$)-alkyl, (C$_2$-C$_6$)-alkenyl, (C$_3$-C$_6$)-alkynyl, (C$_3$-C$_6$)-cycloalkyl, (C$_1$-C$_4$)-alkoxy-(C$_1$-C$_6$)-alkyl, di-(C$_1$-C$_4$)-alkoxy-(C$_1$-C$_6$)-alkyl, (C$_1$-C$_4$)-alkylthio-(C$_1$-C$_6$)-alkyl, (C$_1$-C$_4$)-alkylsulfinyl-(C$_1$-C$_6$)-alkyl, (C$_1$-C$_4$)-alkylsulfonyl-(C$_1$-C$_6$)-alkyl or (C$_3$-C$_6$)-cycloalkyl-(C$_1$-C$_6$)-alkyl each substituted by n halogen atoms and
X, Y and Z are each independently hydrogen, (C$_1$-C$_6$)-alkyl, (C$_3$-C$_6$)-cycloalkyl, halogen, cyano, nitro, halo-(C$_1$-C$_6$)-alkyl, halo-(C$_1$-C$_6$)-alkoxy, (C$_1$-C$_6$)-alkoxy, (C$_1$-C$_6$)-alkoxy-(C$_1$-C$_6$)-alkyl, halo-(C$_1$-C$_6$)-alkoxy-(C$_1$-C$_6$)-alkyl; and
R$^{10}$ is hydrogen, or (C$_1$-C$_6$)-alkyl, (C$_1$-C$_4$)-alkoxy, (C$_1$-C$_4$)-alkylthio, (C$_1$-C$_4$)-alkylsulfinyl or (C$_1$-C$_4$)-alkylsulfonyl substituted by n halogen atoms.

5. A compound as claimed in claim 1, in which
A is one of the five-membered heterocycles A2 or A3 shown below, in which the broken lines mean the bond to the adjacent pyridine ring, V is C(=O);
n is 0,1,2 or 3;
G is R$^8$;
R$^8$ is (C$_1$-C$_6$)-alkyl, (C$_2$-C$_6$)-alkenyl, (C$_2$-C$_6$)-alkynyl substituted by n halogen atoms;
W is (C$_1$-C$_6$)-alkyl, (C$_2$-C$_6$)-alkenyl, (C$_3$-C$_6$)-alkynyl, (C$_3$-C$_6$)-cycloalkyl, (C$_1$-C$_4$)-alkoxy-(C$_1$-C$_6$)-alkyl, di-(C$_1$-C$_4$)-alkoxy-(C$_1$-C$_6$)-alkyl, (C$_1$-C$_4$)-alkylthio-(C$_1$-C$_6$)-alkyl, (C$_1$-C$_4$)-alkylsulfinyl-(C$_1$-C$_6$)-alkyl, (C$_1$-C$_4$)-alkylsulfonyl-(C$_1$-C$_6$)-alkyl or (C$_3$-C$_6$)-cycloalkyl-(C$_1$-C$_6$)-alkyl each substituted by n halogen atoms;
X, Y and Z are each independently hydrogen, (C$_1$-C$_6$)-alkyl, (C$_3$-C$_6$)-cycloalkyl, halogen, cyano, nitro, halo-(C$_1$-C$_6$)-alkyl, halo-(C$_1$-C$_6$)-alkoxy, (C$_1$-C$_6$)-alkoxy, (C$_1$-C$_6$)-alkoxy-(C$_1$-C$_6$)-alkyl, halo-(C$_1$-C$_6$)-alkoxy-(C$_1$-C$_6$)-alkyl; and
R$^{10}$ is hydrogen, or (C$_1$-C$_6$)-alkyl, (C$_1$-C$_4$)-alkoxy, (C$_1$-C$_4$)-alkylthio, (C$_1$-C$_4$)-alkylsulfinyl or (C$_1$-C$_4$)-alkylsulfonyl substituted by n halogen atoms.

6. A herbicidal composition comprising a herbicidally active content of at least one compound as claimed in claim 1.

7. The herbicidal composition as claimed in claim 6 in a mixture with one or more formulation assistants.

\* \* \* \* \*